US012672812B2

(12) United States Patent
Hatakeyama et al.

(10) Patent No.: US 12,672,812 B2
(45) Date of Patent: Jul. 7, 2026

(54) BIO-ELECTRODE COMPOSITION, BIO-ELECTRODE, AND METHOD FOR MANUFACTURING THE SAME

(71) Applicant: SHIN-ETSU CHEMICAL CO., LTD., Tokyo (JP)

(72) Inventors: Jun Hatakeyama, Joetsu (JP); Osamu Watanabe, Joetsu (JP); Joe Ikeda, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 365 days.

(21) Appl. No.: 18/346,213

(22) Filed: Jul. 1, 2023

(65) Prior Publication Data

US 2024/0032838 A1 Feb. 1, 2024

(30) Foreign Application Priority Data

Jul. 21, 2022 (JP) ................................ 2022-116590

(51) Int. Cl.
*A61B 5/268* (2021.01)
*A61B 5/257* (2021.01)
(Continued)

(52) U.S. Cl.
CPC .............. *A61B 5/268* (2021.01); *A61B 5/257* (2021.01); *A61B 5/265* (2021.01); *C08F 112/30* (2020.02);
(Continued)

(58) Field of Classification Search
CPC ......... A61B 5/268; A61B 5/257; A61B 5/265; A61B 2562/125; A61B 5/263;
(Continued)

(56) References Cited

U.S. PATENT DOCUMENTS 5,981,680 A 11/1999 Petroff et al.
10,005,868 B2 * 6/2018 Hatakeyama ......... G03F 7/0395
(Continued)

FOREIGN PATENT DOCUMENTS

CN 101218281 A 7/2008
JP H05-095924 A 4/1993
(Continued)

OTHER PUBLICATIONS

Extended Search Report mailed Dec. 14, 2023, in corresponding European Application No. 23181615.8.
(Continued)

*Primary Examiner* — Joanne M Rodden
*Assistant Examiner* — Dana Stumpfoll
(74) *Attorney, Agent, or Firm* — Harness, Dickey & Pierce, P.L.C.

(57) ABSTRACT

The present invention is a bio-electrode composition containing an ionic polymer material as a component (A), where the component (A) includes a polymer having: a repeating unit-a having a structure selected from the group consisting of salts of ammonium, sodium, potassium, and silver formed with any of fluorosulfonic acid, fluorosulfonimide, and N-carbonyl-fluorosulfonamide; and a repeating unit-b having a nitro group. This provides: a bio-electrode composition capable of forming a living body contact layer for a bio-electrode that is excellent in electric conductivity and biocompatibility, is light-weight, can be manufactured at low cost, can control significant reduction in conductivity either when the bio-electrode is soaked in water or dried, and is soft and has excellent stretchability and adhesiveness; a bio-electrode including a living body contact layer formed of the bio-electrode composition; and a method for manufacturing the bio-electrode.

16 Claims, 3 Drawing Sheets

(51) Int. Cl.

| | |
|---|---|
| ***A61B 5/265*** | (2021.01) |
| ***C08F 112/14*** | (2006.01) |
| ***C08F 120/18*** | (2006.01) |
| ***C08F 120/36*** | (2006.01) |
| ***C08F 120/38*** | (2006.01) |
| ***C08F 120/58*** | (2006.01) |

(52) U.S. Cl.

CPC .......... *C08F 120/18* (2013.01); *C08F 120/36* (2013.01); *C08F 120/38* (2013.01); *C08F 120/58* (2013.01); *A61B 2562/125* (2013.01); *C08F 2800/10* (2013.01)

(58) Field of Classification Search

CPC ............ A61B 5/259; A61B 2562/0209; A61B 2562/0215; A61B 5/256; A61B 5/28; A61B 2562/164; C08F 112/30; C08F 120/18; C08F 120/36; C08F 120/38; C08F 120/58; C08F 2800/10; C08F 220/1808; C08F 220/387; C08F 212/30; C08F 220/36; C08F 220/585; C08F 220/12; C08F 220/382; Y02E 60/50; C08G 77/14; C08G 77/20; C08G 77/445; C08G 77/458; C08G 77/46; C08G 77/70; C08L 33/14; C08L 43/04; C08L 83/08; C08L 83/10; C08L 25/18; C08L 33/06; C08L 75/04; C08L 83/04; C08K 3/04; C08K 3/041; C08K 3/08; C08K 2003/0806

See application file for complete search history.

(56) References Cited

U.S. PATENT DOCUMENTS

| | | | | |
|---|---|---|---|---|
| 11,643,492 | B2 * | 5/2023 | Hatakeyama .......... | A61B 5/053 600/396 |
| 2002/0177039 | A1 | 11/2002 | Lu et al. | |
| 2020/0317840 | A1 | 10/2020 | Hatakeyama et al. | |

FOREIGN PATENT DOCUMENTS

| | | | |
|---|---|---|---|
| JP | 2002-332305 | A | 11/2002 |
| JP | 2003-225217 | A | 8/2003 |
| JP | 2004-033468 | A | 2/2004 |
| JP | 2004-527902 | A | 9/2004 |
| JP | 2005-320418 | A | 11/2005 |
| JP | 2007-298373 | A | 11/2007 |
| JP | 2011-079946 | A | 4/2011 |
| JP | 2015-019806 | A | 2/2015 |
| JP | 2015-100673 | A | 6/2015 |
| JP | 2015-193803 | A | 11/2015 |
| JP | 2016-011338 | A | 1/2016 |
| JP | 2016-065238 | A | 4/2016 |
| JP | 2018-044147 | A | 3/2018 |
| JP | 2018-059050 | A | 4/2018 |
| JP | 2018-059052 | A | 4/2018 |
| JP | 2018-123304 | A | 8/2018 |
| JP | 2018-130534 | A | 8/2018 |
| JP | 2019-503406 | A | 2/2019 |
| JP | 2019-070109 | A | 5/2019 |
| TW | 202100580 | A | 1/2021 |
| WO | 2013039151 | A1 | 3/2013 |

OTHER PUBLICATIONS

Long, et al.; Polymer electrolytes for lithium polymer batteries; Journal of Materials Chemistry A, 4, 10038-10069; published May 25, 2016.

Office Action and Search Report mailed May 24, 2024, in corresponding Taiwanese Application No. 112127099.

Snyder, et al.; Ion Conductivity of Comb Polysiloxane Polyelectrolytes Containing Oligoether and Perfluoroether Sidechains; Journal of the Electrochemical Society, 150 (8) A1090-AI094; published Jun. 23, 2003.

* cited by examiner

[FIG. 1]
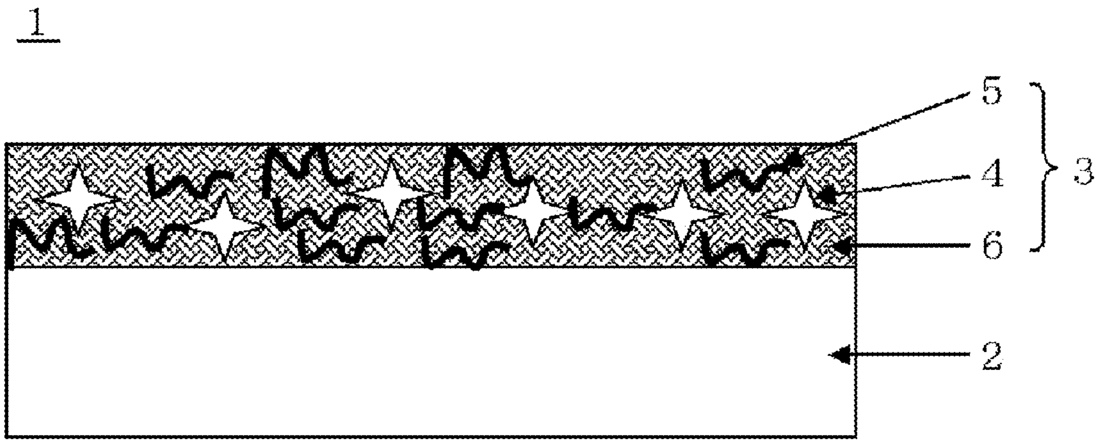
[FIG. 2]
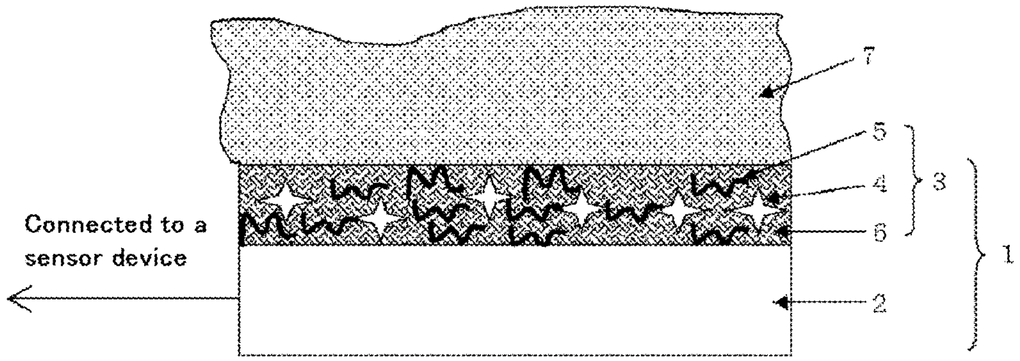

[FIG. 3]
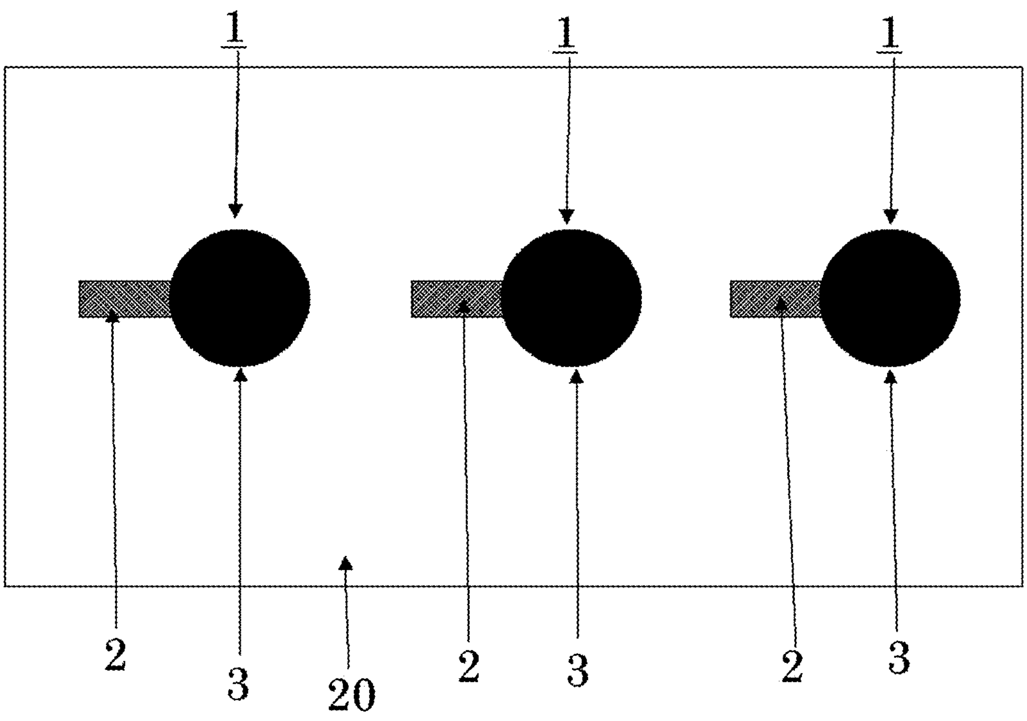
[FIG. 4]
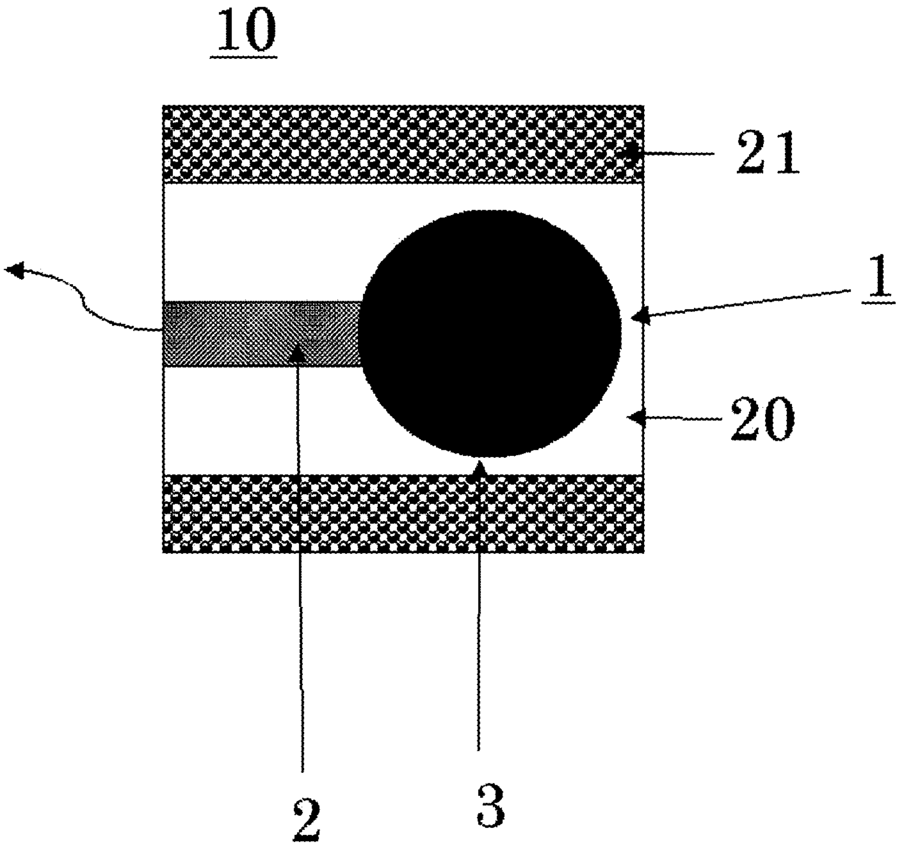

[FIG. 5]
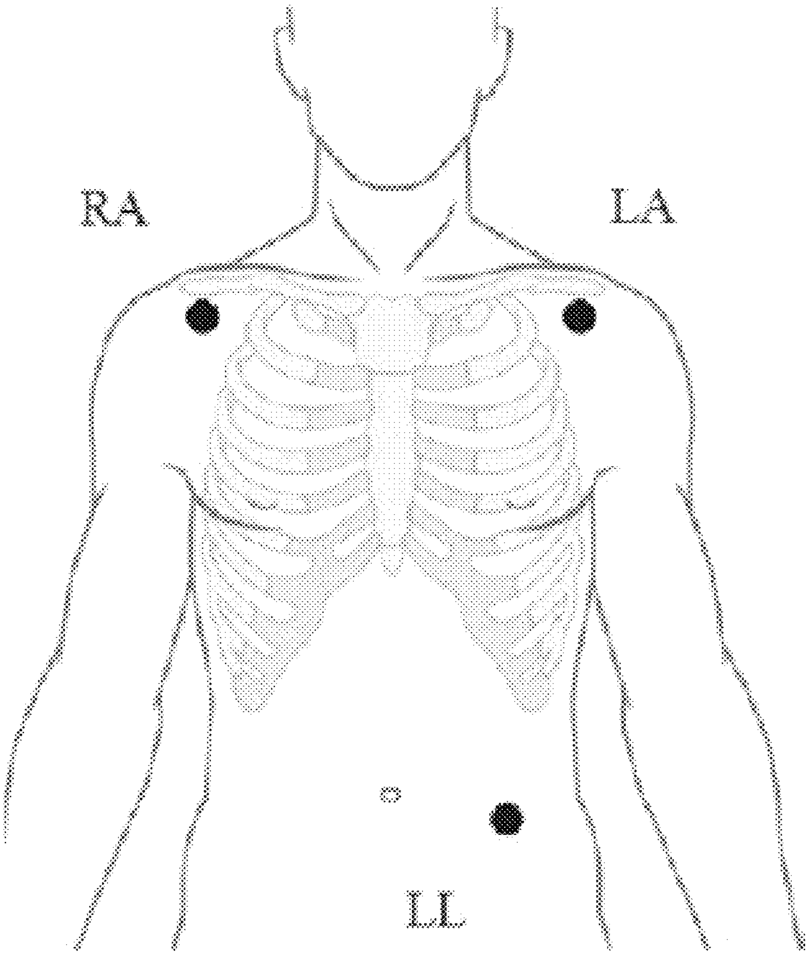
[FIG. 6]
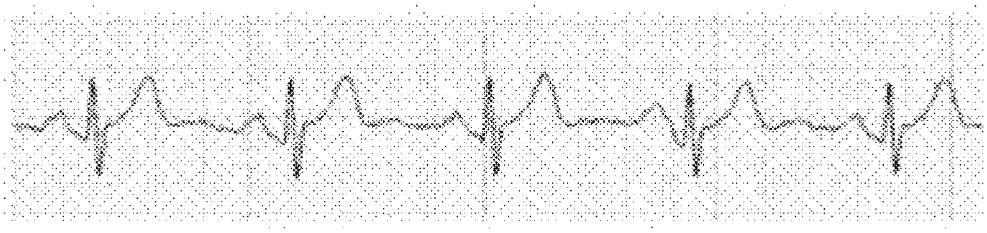

BIO-ELECTRODE COMPOSITION, BIO-ELECTRODE, AND METHOD FOR MANUFACTURING THE SAME

TECHNICAL FIELD

The present invention relates to: a bio-electrode; a method for manufacturing the same; and a bio-electrode composition desirably used for a bio-electrode.

BACKGROUND ART

A recent growing popularity of Internet of Things (IoT) has accelerated the development of wearable devices, such as watches and eye-glasses that allow for Internet access. Even in the fields of medicine and sports, wearable devices for constantly monitoring the user's physical state are increasingly demanded, and such technological development is expected to be further encouraged.

In the field of medicine, the use of wearable devices has been examined for monitoring the state of human organs by sensing extremely weak current, such as an electrocardiogram which detects an electric signal to measure the motion of the heart. The electrocardiogram measurement is conducted by attaching an electrode coated with an electro-conductive paste to a body, but this is a single (not continuous), short-time measurement. On the other hand, development of the above medical wearable device is aimed at devices for continuously monitoring the health condition for a few weeks. Accordingly, a bio-electrode used in a medical wearable device is required to make no changes in electric conductivity even in long-time use and cause no skin allergy. In addition to these, it is also required that a bio-electrode is light-weight and can be produced at low cost.

Medical wearable devices are classified into two types: a type which is directly attached to the body and a type which is incorporated into clothes. As the type which is attached to the body, there has been proposed a bio-electrode using water-soluble gel containing water and electrolyte, which are materials of the foregoing electro-conductive paste (Patent Document 1). The water-soluble gel contains sodium, potassium, or calcium as the electrolyte in a water-soluble polymer for retaining water, and converts changes of ion concentration from skin into electricity. On the other hand, as the type which is incorporated into clothes, there has been proposed a means to use cloth in which an electro-conductive polymer such as PEDOT-PSS (poly-3,4-ethylenedioxythiophene-polystyrenesulfonate) or silver paste is incorporated into the fibers for electrodes (Patent Document 2).

However, the use of the hydrophilic gel containing water and electrolytes unfortunately brings about loss of electric conductivity due to water evaporation in drying process. Meanwhile, the use of a higher-ionization-tendency metal such as copper can cause some users to suffer from skin allergy. The use of an electro-conductive polymer such as PEDOT-PSS can also cause skin allergy due to the strong acidity of the electro-conductive polymer, and further cause peeling of the electro-conductive polymer from fibers during washing.

By taking advantage of excellent electric conductivity, the use of metal nanowire, carbon black, carbon nanotube, and the like as electrode materials has been examined (Patent Documents 3, 4, and 5). With higher contact probability among metal nanowires, the wires can conduct electricity even when added in small quantities. The metal nanowire, however, can cause skin allergies since they are thin materials with sharp tips. Even if these electrode materials themselves cause no allergic reaction in the manners described above, the biocompatibility may be degraded depending on the shape of a material and its inherent stimulation, thereby making it hard to satisfy both electric conductivity and biocompatibility.

Although metal films seem to function as excellent bio-electrodes thanks to extremely high electric conductivity, this is not always the case. Upon heartbeat, the human skin releases not only extremely weak current, but also sodium ion, potassium ion, and calcium ion. It is thus necessary to convert changes in ion concentration into current. Noble metals, however, are difficult to ionize and are inefficient in converting ions from skin to current. Therefore, the resulting bio-electrode using a noble metal is characterized by high impedance and high resistance to the skin during electrical conduction.

Meanwhile, the use of a battery containing an ionic liquid has been examined (Patent Document 6). Advantageously, the ionic liquid is thermally and chemically stable, and the conductivity is excellent, providing more various battery applications. However, an ionic liquid having smaller molecular weight shown in Patent Document 6 unfortunately dissolves into water. A bio-electrode containing such an ionic liquid in use allows the ionic liquid to be extracted from the electrode by sweating, which not only lowers the conductivity, but also causes rough skin by the liquid soaking into the skin.

Batteries using a lithium salt of polymer type sulfonimide have also been examined (Non Patent Document 1). Lithium has been applied to batteries because of their high ionic mobility. However, this is not a bio-compatible material. Additionally, lithium salts of fluorosulfonate have been examined in a form of a pendant on silicone (Non Patent Document 2).

There is proposal of a material for a biosensing device, the base material of the material being a polymer obtained by copolymerizing a repeating unit of a betaine-type ammonium salt and a repeating unit having a nitro group (Patent Document 7). A betaine that makes use of the polarization of nitro groups has high ionic conductivity, and an excellent biosensor may be obtained using the betaine. However, since such a betaine is a water-soluble polymer, the betaine cannot be used as a dry bio-electrode.

Any bio-electrode fails to get biological information when it is apart from the skin. The detection of even changes in contact area can vary quantities of electricity traveling through the electrode, allowing the baseline of an electrocardiogram (electric signal) to fluctuate. Accordingly, in order to stably detect electric signals from the body, the bio-electrode is required to be in constant contact with the skin and make no changes in contact area. This requirement is satisfied, preferably by use of adhesive biomedical electrodes. Moreover, elastic and flexible biomedical electrodes are needed to follow changes in skin expansion and flexion.

There has been examined a bio-electrode composed of: silver chloride at a portion which comes into contact with skin; and silver deposited at a portion through which electricity is conducted to a device. Solid silver chloride has neither adhesive strength to skin nor stretchability, so that the ability to collect biological signals is lowered particularly when the user moves. For this reason, a laminate film of silver chloride and silver is used as a bio-electrode with a water-soluble gel deposited between the bio-electrode and the skin. In this case, the aforementioned degradation occurs when the gel is dried.

CITATION LIST

Patent Literature

Patent Document 1: WO 2013/039151 A1
Patent Document 2: JP 2015-100673 A
Patent Document 3: JP H05-095924 A
Patent Document 4: JP 2003-225217 A
Patent Document 5: JP 2015-019806 A
Patent Document 6: JP 2004-527902 A
Patent Document 7: JP 2007-298373 A

Non Patent Literature

Non Patent Document 1: J. Mater. Chem. A, 2016, 4, p 10038-10069
Non Patent Document 2: J. of the Electrochemical Society, 150(8) A1090-A1094 (2003)

SUMMARY OF INVENTION

Technical Problem

The present invention has been made to solve the problems, and has an object to provide a bio-electrode composition capable of forming a living body contact layer for a bio-electrode that is excellent in electric conductivity and biocompatibility, is light-weight, can be manufactured at low cost, can control significant reduction in conductivity either when the bio-electrode is soaked in water or dried, and is soft and has excellent stretchability and adhesiveness; a bio-electrode including a living body contact layer formed of the bio-electrode composition; and a method for manufacturing the bio-electrode.

Solution to Problem

To achieve the object, the present invention provides a bio-electrode composition comprising an ionic polymer material as a component (A), wherein the component (A) comprises a polymer having: a repeating unit-a having a structure selected from the group consisting of salts of ammonium, sodium, potassium, and silver formed with any of fluorosulfonic acid, fluorosulfonimide, and N-carbonyl-fluorosulfonamide; and a repeating unit-b having a nitro group.

Such a bio-electrode composition is capable of forming a living body contact layer for a bio-electrode which is excellent in electric conductivity and biocompatibility, light-weight, and manufacturable at low cost, prevents significant reduction in the electric conductivity either when wetted with water or dried, and is soft and has excellent stretchability and adhesiveness.

Furthermore, in the present invention, the repeating unit-a preferably has a structure shown by any of the following general formulae (1)-1 to (1)-4, (1)-1

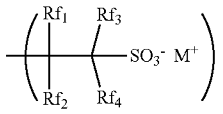

(1)-2

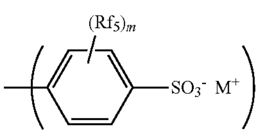

-continued (1)-3

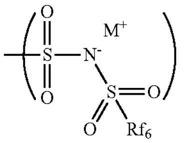

(1)-4

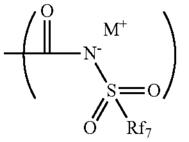

wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom or a linear or branched alkyl group having 1 to 4 carbon atoms, and have at least one fluorine atom; $M^+$ represents an ion selected from the group consisting of an ammonium ion, a sodium ion, a potassium ion, and a silver ion; and "m" represents an integer of 1 to 4.

The repeating unit-a having such structures enables the bio-electrode composition to form a living body contact layer for a bio-electrode that is more excellent in electric conductivity and biocompatibility.

Furthermore, in the present invention, the repeating unit-a preferably comprises at least one repeating unit selected from the group consisting of repeating units-a1 to -a7 shown by the following general formula (2), (2)

a1

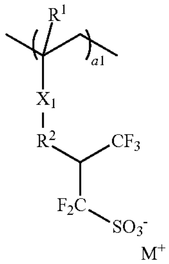

a2

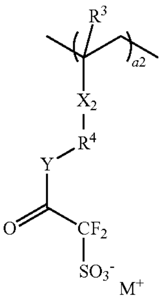

-continued a3

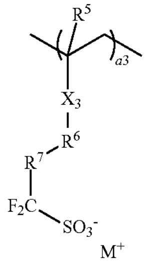

a4

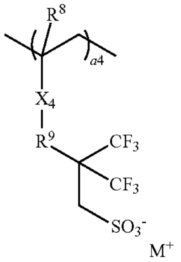

a5

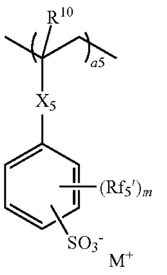

a6

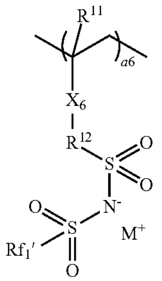

a7

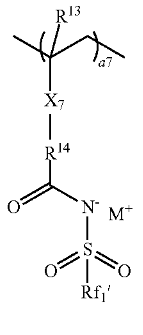

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, $R^{12}$, and $R^{14}$ each independently represent a single bond or a linear, branched, or cyclic hydrocarbon group having 1 to 13 carbon atoms, the hydrocarbon group optionally having either or both of an ester group and an ether group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_3$ represents any of a single bond, an ether group, and an ester group; Y represents an oxygen atom or a —$NR^{19}$— group; $R^{19}$ represents a hydrogen atom or a linear or branched alkyl group having 1 to 4 carbon atoms, and optionally forms a ring together with $R^4$; $Rf_1'$ and $Rf_5'$ each represent a fluorine atom, a trifluoromethyl group, or a linear or branched alkyl group having 1 to 4 carbon atoms, and have at least one fluorine atom; "m" represents an integer of 1 to 4; a1, a2, a3, a4, a5, a6, and a7 satisfy $0 \le a1 < 1.0$, $0 \le a2 < 1.0$, $0 \le a3 < 1.0$, $0 \le a4 < 1.0$, $0 \le a5 < 1.0$, $0 \le a6 < 1.0$, $0 \le a7 < 1.0$, and $0 < a1+a2+a3+a4+a5+a6+a7 < 1.0$; and $M^+$ represents an ion selected from the group consisting of an ammonium ion, a sodium ion, a potassium ion, and a silver ion.

The repeating unit-a having such structures enables the bio-electrode composition to form a living body contact layer for a bio-electrode that is further excellent in electric conductivity and biocompatibility.

In this event, the bio-electrode composition preferably comprises a polymer having a repeating unit-b1 having a nitro group shown by the following general formula (4) copolymerized in addition to the at least one repeating unit selected from the group consisting of the repeating units-a1 to -a7 shown by the general formula (2), (4)

b1

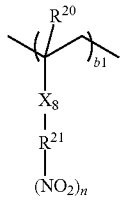

wherein $R^{20}$ represents a hydrogen atom or a methyl group; $X_8$ represents any of a single bond, a phenylene group, a naphthylene group, an ether group, an ester group, and an amide group; $R^{21}$ represents a single bond, a linear, branched, or cyclic alkylene group having 1 to 20 carbon atoms, or a phenylene group, the alkylene group optionally having a hydroxy group, a carboxy group, an ether group, an ester group, a urethane group, a thiourethane group, a carbonate group, an amide group, or a urea bond, and the phenylene group is optionally substituted with a linear or branched alkyl group having 1 to 4 carbon atoms, an alkoxy group, a halogen atom, or a cyano group; and "n" represents 1 or 2 and b1 satisfies $0 < b1 < 1.0$.

The repeating unit-b1 having such a structure enables further improvement of polarizability.

Furthermore, in the present invention, the component (A) preferably comprises an ammonium ion shown by the following general formula (3) as an ammonium ion for forming the ammonium salts, (3)

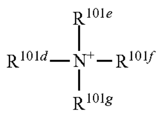

wherein $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the general formula (3) within the ring.

Incorporating the polymer compound (A) containing such an ammonium ion enables the bio-electrode composition to form a living body contact layer for a bio-electrode that is further excellent in electric conductivity and biocompatibility.

The present invention preferably further comprises a resin as a component (B).

Such a bio-electrode composition is made compatible with the component (A), and can prevent elution of the salt.

In this event, the component (B) is preferably at least one resin selected from the group consisting of a silicone resin, a (meth)acrylate resin, and a urethane resin.

The component (B) to be contained in the bio-electrode composition can be selected depending on the properties to be imparted to the living body contact layer.

In this event, the component (B) is preferably adhesive.

Such a component (B) enables further improvement of the adhesiveness of the bio-electrode composition.

In this event, the component (B) preferably comprises a silicone resin having an $SiO_{4/2}$ unit and an $R_xSiO_{(4-x)/2}$ unit, wherein R represents a substituted or unsubstituted monovalent hydrocarbon group having 1 to 10 carbon atoms, and "x" represents a number in a range of 2.5 to 3.5.

Such a component (B) is made compatible with the component (A) and can prevent elution of the salt, and can also impart higher adhesiveness to the bio-electrode composition.

The present invention preferably further comprises a carbon material and/or a metal powder as a component (C).

The carbon material and the metal powder function as electric conductivity improvers, and can impart better electric conductivity to the living body contact layer formed from the bio-electrode composition.

In this event, the carbon material is preferably one or both of carbon black and carbon nanotube.

When such a carbon material is contained, higher electric conductivity can be provided.

In this event, the metal powder is preferably one or more metal powders selected from the group consisting of gold, silver, platinum, copper, tin, titanium, nickel, aluminum, tungsten, molybdenum, ruthenium, chromium, and indium.

As described, various metal powders can be used in the inventive bio-electrode composition.

In this event, the metal powder is preferably a silver powder.

In the inventive bio-electrode composition, silver powder is comprehensively the most preferable in view of electric conductivity, costs, and biocompatibility.

Furthermore, the present invention preferably further comprises an organic solvent as a component (D).

A bio-electrode composition containing an organic solvent can exhibit high coating property.

In addition, the present invention provides a bio-electrode comprising an electro-conductive base material and a living body contact layer formed on the electro-conductive base material, wherein the living body contact layer is a cured product of the above-described bio-electrode composition.

Since the inventive bio-electrode has the living body contact layer containing the cured material of the above-described bio-electrode composition, the inventive bio-electrode is excellent in electric conductivity and biocompatibility, light-weight, manufacturable at low cost, prevents significant reduction in the electric conductivity either when wetted with water or dried, is soft, and is excellent in stretchability and adhesiveness.

In this event, the electro-conductive base material preferably comprises one or more selected from the group consisting of gold, silver, silver chloride, platinum, aluminum, magnesium, tin, tungsten, iron, copper, nickel, stainless steel, chromium, titanium, carbon, and an electro-conductive polymer.

As described, various electro-conductive base materials can be used in the inventive bio-electrode.

The present invention also provides a method for manufacturing a bio-electrode having an electro-conductive base material and a living body contact layer formed on the electro-conductive base material, the method comprising:

applying the above-described bio-electrode composition onto the electro-conductive base material; and curing the bio-electrode composition to form the living body contact layer.

According to such a manufacturing method, it is possible to easily manufacture, at low costs, a bio-electrode which is excellent in electric conductivity and biocompatibility, light-weight, prevents significant reduction in the electric conductivity even when the bio-electrode is wetted with water or dried, is soft, and is excellent in stretchability and adhesiveness.

In this event, the electro-conductive base material preferably comprises one or more selected from the group consisting of gold, silver, silver chloride, platinum, aluminum, magnesium, tin, tungsten, iron, copper, nickel, stainless steel, chromium, titanium, carbon, and an electro-conductive polymer.

As described, various electro-conductive base materials can be used in the inventive method for manufacturing a bio-electrode.

Advantageous Effects of Invention

As described above, the inventive bio-electrode composition, bio-electrode having a living body contact layer formed with the bio-electrode composition, and method for manufacturing the bio-electrode make it possible to provide: a bio-electrode composition with which it is possible to form a living body contact layer for a bio-electrode that is excellent in electric conductivity and biocompatibility, light-weight, manufacturable at low cost, free from significant reduction in electric conductivity even when the bio-electrode is attached to the skin for a long time and wetted with water while bathing and so forth or when dried so that biological signals can be collected stably, soft, excellent in stretchability and adhesiveness, and leaves no residue on the skin after detaching from the skin; a bio-electrode having a living body contact layer formed using the bio-electrode composition; and a method for manufacturing the bio-electrode.

BRIEF DESCRIPTION OF DRAWINGS

FIG. 1 is a schematic sectional view showing an example of the inventive bio-electrode;

FIG. 2 is a schematic sectional view showing an example of the inventive bio-electrode worn on a living body;

FIG. 3 is a schematic view of printed bio-electrodes prepared in Examples of the present invention;

FIG. 4 is a schematic view of one of the bio-electrodes prepared in Examples of the present invention, the bio-electrode being cut out and provided with an adhesive layer and an electric wire;

FIG. 5 is a view showing locations where electrodes and earth are attached on a human body in measuring biological signals in Examples of the present invention; and FIG. 6 shows one of electrocardiogram waveforms obtained using the bio-electrodes in Examples of the present invention.

DESCRIPTION OF EMBODIMENTS

As noted above, it has been desired to develop: a bio-electrode composition that can form a living body contact layer for a bio-electrode which is excellent in electric conductivity and biocompatibility, light-weight, manufacturable at low cost, soft, has excellent stretchability and adhesive strength, and which prevents significant reduction in the electric conductivity even when attached to the skin for a long time and wetted with water due to bathing and so forth or when dried; a bio-electrode including a living body contact layer formed of the bio-electrode composition; and a method for manufacturing the bio-electrode.

The surface of skin releases ions of sodium, potassium, and calcium in accordance with heartbeat. A bio-electrode has to convert the increase and decrease of ions released from skin to electric signals. Accordingly, the bio-electrode requires a material that is excellent in ionic conductivity to transmit the increase and decrease of ions.

For the bio-electrode to be attached to the skin and obtain biological signals stably, softness, stretchability, and adhesiveness as a bio-electrode film are necessary. The keratin of the outer layer of the skin is regenerated daily, and old keratin (dirt) accumulates between the attached bio-electrode film and the skin. Old keratin easily peels from the outer surface of the skin, so that the bio-electrode becomes detached, making it impossible to collect biological signals. Therefore, it is necessary for the adhesiveness of the bio-electrode not to decrease even when the bio-electrode is attached for a long time. Meanwhile, if a residue is left on the skin when the bio-electrode is detached after keeping attached for a long time, the residue may cause a rash or rough skin.

In neutralized salts formed from highly acidic acids, the ions are strongly polarized to improve the ionic conductivity. This is why lithium salts of bis(trifluoromethanesulfonyl)imidic acid and tris(trifluoromethanesulfonyl)methide acid show high ionic conductivity as a lithium ion battery. On the other hand, the higher acidity of the acid before the neutral salt formation results in a problem that the salt has stronger irritation to the body. That is, ionic conductivity and irritation to the body are in relation of trade-off. However, a salt applied to a bio-electrode has to achieve both high ionic conductivity and low irritation to the body.

Ion compound having higher molecular weight have such natures that the permeability and the stimulus to skin are decreased. Accordingly, the ion compound is preferably a polymer type with higher molecular weight. Thus, the present inventors have solved the problem of irritation to the skin by polymerizing the ionic compound to form an ionic compound having a polymerizable double bond.

Irritation to the skin has been avoided by polymerizing the ions, but a problem of decreased ionic conductivity occurs. In order to increase ionic conductivity, it is effective to increase the polarizability of the polymer itself. According to the published patent related to a biosensing device mentioned above, a polymer containing a nitro group is effective for increasing polarizability. Thus, the present inventors have conceived the present invention, in which highly polarizable nitro groups are introduced into the ionic polymer of the bio-electrode.

That is, the present invention is a bio-electrode composition comprising an ionic polymer material as a component (A), wherein the component (A) comprises a polymer having: a repeating unit-a having a structure selected from the group consisting of salts of ammonium, sodium, potassium, and silver formed with any of fluorosulfonic acid, fluorosulfonimide, and N-carbonyl-fluorosulfonamide; and a repeating unit-b having a nitro group.

Hereinafter, the present invention will be described in detail, but the present invention is not limited thereto.

<Bio-Electrode Composition>

The inventive bio-electrode composition contains an ionic polymer material as a component (A). Besides this, the composition may contain a resin or the like as a component (B). Below, each component will be described in further detail.

[(A) Ionic Polymer Material]

The inventive bio-electrode composition has a characteristic that it contains, as a component (A), an ionic polymer material. The component (A) contains a polymer having: a repeating unit-a having a structure selected from the group consisting of salts of ammonium, sodium, potassium, and silver formed with any of fluorosulfonic acid, fluorosulfonimide, and N-carbonyl-fluorosulfonamide; and a repeating unit-b having a nitro group.

The repeating unit-a preferably has a structure shown by any of the following general formulae (1)-1 to (1)-4.

(1)-1

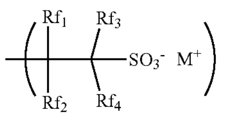

(1)-2

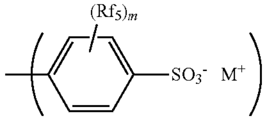

(1)-3

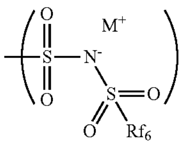

-continued (1)-4

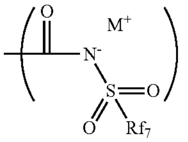

In the general formula (1)-1, $Rf_1$ and $Rf_2$ each represent a hydrogen atom, a fluorine atom, an oxygen atom, a methyl group, or a trifluoromethyl group. When $Rf_1$ and $Rf_2$ represent an oxygen atom, the single oxygen atom represented by $Rf_1$ and $Rf_2$ bonds to a single carbon atom to form a carbonyl group. $Rf_3$ and $Rf_4$ each represent a hydrogen atom, a fluorine atom, or a trifluoromethyl group. At least one of $Rf_1$ to $Rf_4$ is a fluorine atom or a trifluoromethyl group. In the general formulae (1)-2, (1)-3, and (1)-4, $Rf_5$, $Rf_6$, and $Rf_7$ each represent a fluorine atom or a linear or branched alkyl group having 1 to 4 carbon atoms, and have at least one fluorine atom. In the general formulae (1)-1 to (1)-4, $M^+$ represents an ion selected from the group consisting of an ammonium ion, a sodium ion, a potassium ion, and a silver ion. In the general formula (1)-2, "m" represents an integer of 1 to 4.

The repeating unit-a preferably includes at least one repeating unit selected from the group consisting of repeating units-a1 to -a7 shown by the following general formula (2).

(2)

a1

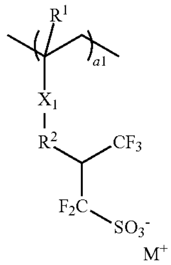

a2

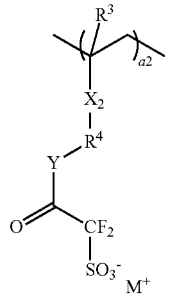

a3

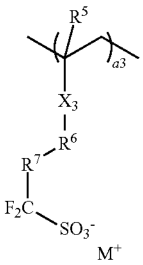

-continued a4

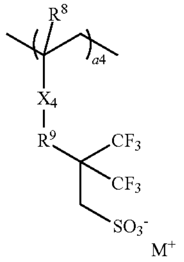

a5

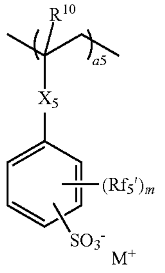

a6

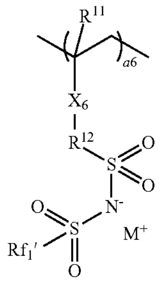

a7

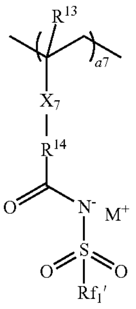

In the general formula (2), $R^1$, $R^3$, $R^5$, $R^8$, $R^{10}$, $R^{11}$, and $R^{13}$ each independently represent a hydrogen atom or a methyl group. $R^2$, $R^4$, $R^6$, $R^9$, $R^{12}$, and $R^{14}$ each independently represent a single bond or a linear, branched, or cyclic hydrocarbon group having 1 to 13 carbon atoms. The hydrocarbon group optionally has either or both of an ester group and an ether group. $R^7$ represents a linear or branched alkylene group having 1 to 4 carbon atoms. One or two hydrogen atoms in $R^7$ are optionally substituted with a fluorine atom. $X_1$, $X_2$, $X_3$, $X_4$, $X_6$, and $X_7$ each independently represent any of a single bond, a phenylene group, a naphthylene group, an ether group, an ester group, and an amide group. X represents any of a single bond, an ether group, and an ester group. Y represents an oxygen atom or a —$NR^{19}$— group. $R^{19}$ represents a hydrogen atom or a linear or branched alkyl group having 1 to 4 carbon atoms, and optionally forms a ring together with $R^4$. $Rf_1'$ and $Rf_5'$ each represent a fluorine atom, a trifluoromethyl group, or a linear or branched alkyl group having 1 to 4 carbon atoms, and have at least one fluorine atom. "m" represents an integer of 1 to 4. a1, a2, a3, a4, a5, a6, and a7 satisfy $0 \leq a1 < 1.0$, $0 \leq a2 < 1.0$, $0 \leq a3 < 1.0$, $0 \leq a4 < 1.0$, $0 \leq a5 < 1.0$, $0 \leq a6 < 1.0$, $0 \leq a7 < 1.0$, and $0 < a1+a2+a3+a4+a5+a6+a7 < 1.0$. $M^+$ represents an ion selected from the group consisting of an ammonium ion, a sodium ion, a potassium ion, and a silver ion.

Among the repeating units-a1 to -a7 shown by the general formula (2), the repeating units-a1 to -a5 can be obtained from fluorosulfonic acid salt monomers specifically exemplified below.

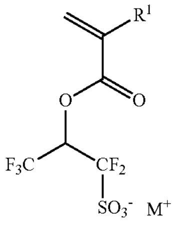

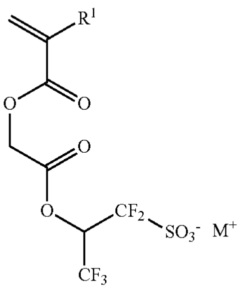

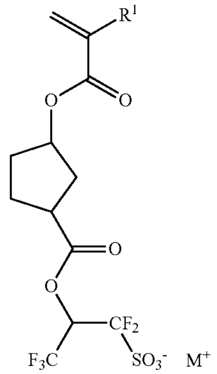

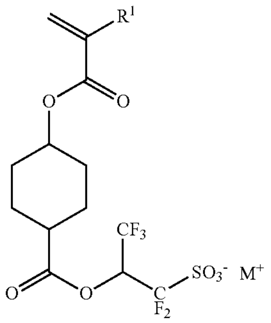

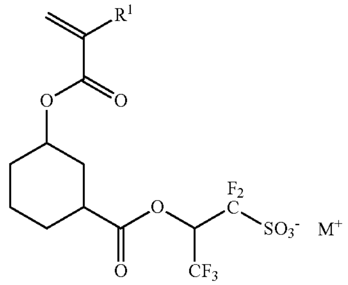

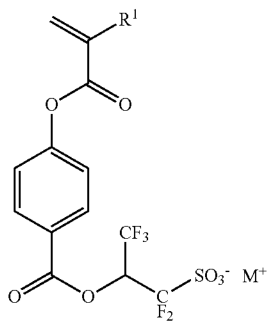

-continued

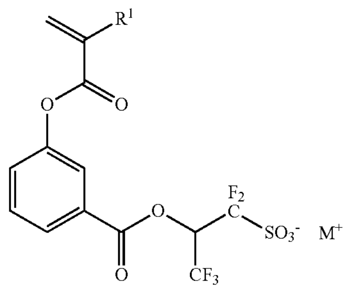

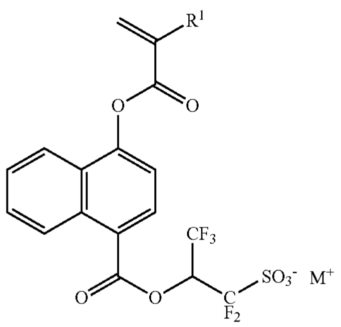

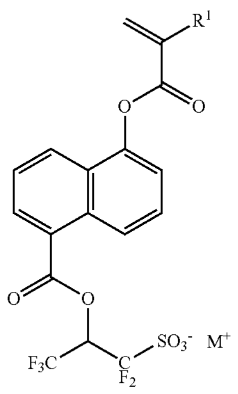

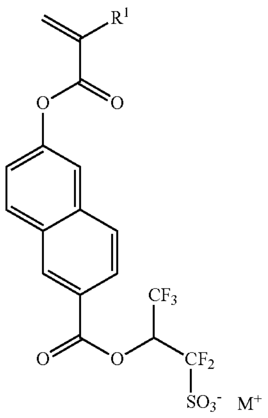

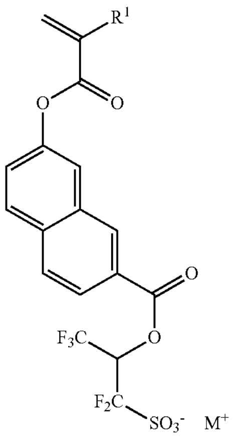

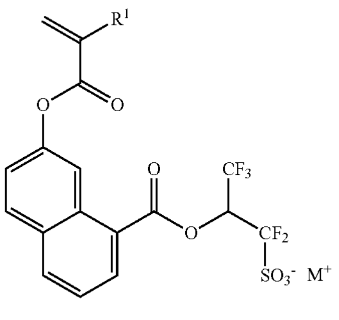

-continued
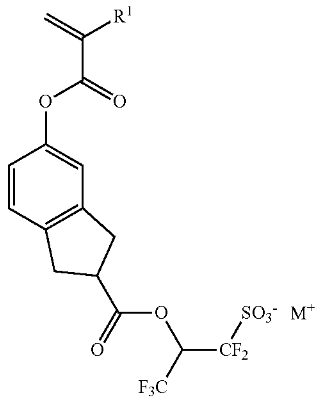
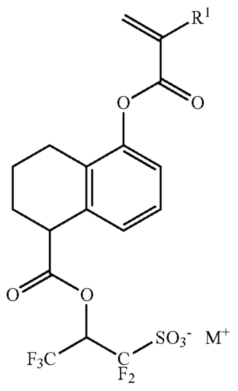
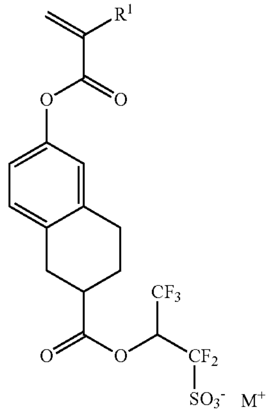
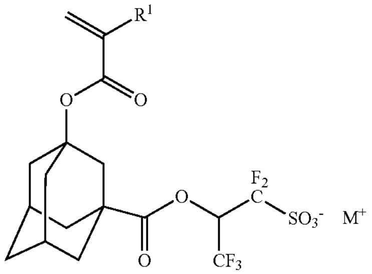
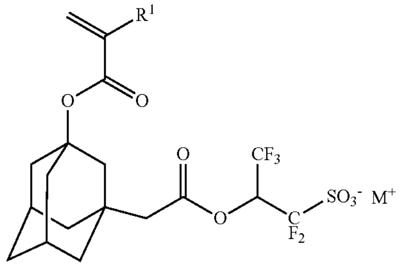
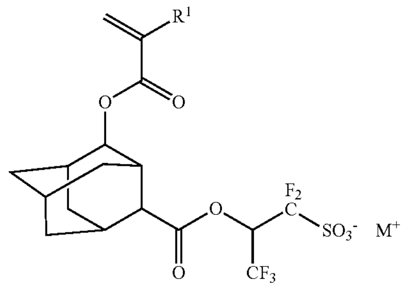
-continued
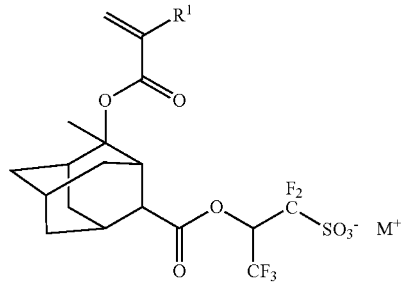
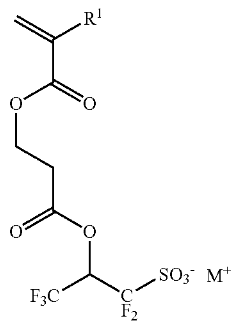
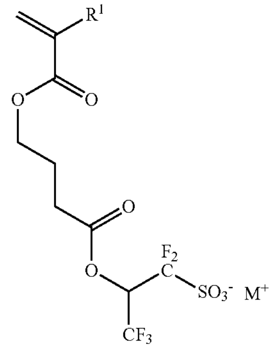
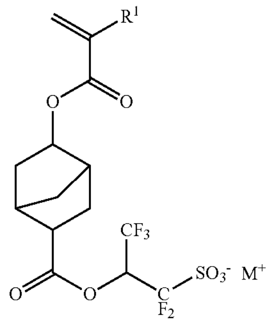
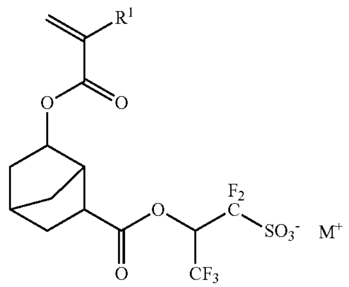
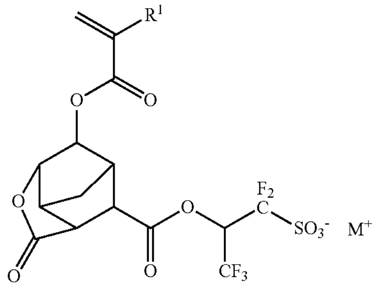

-continued
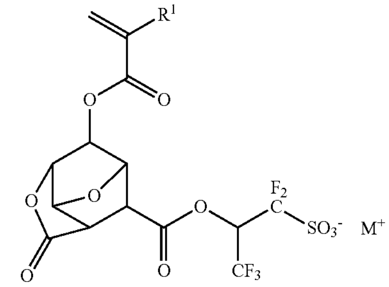
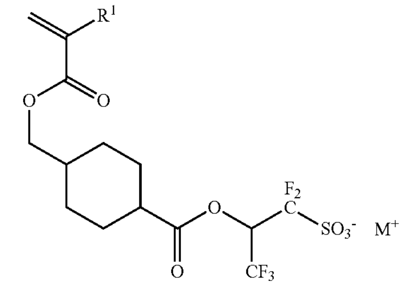
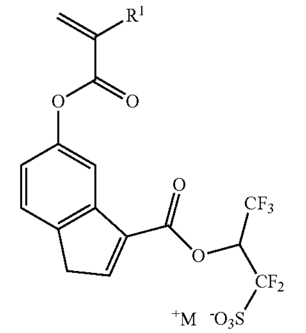
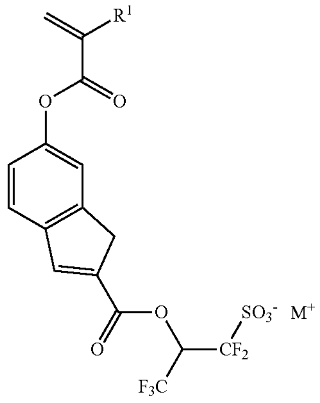
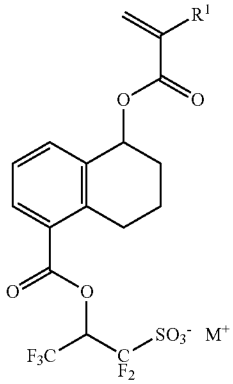
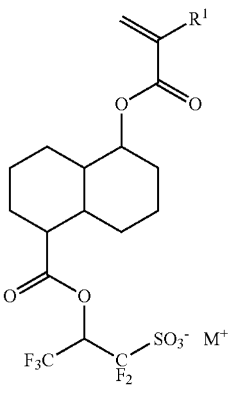
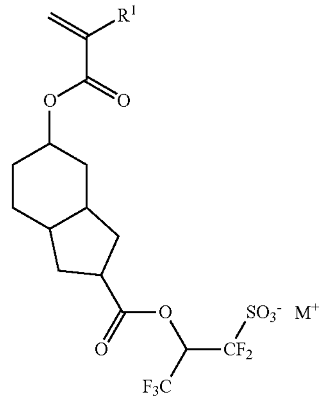
-continued
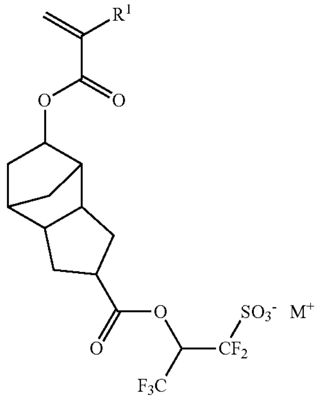
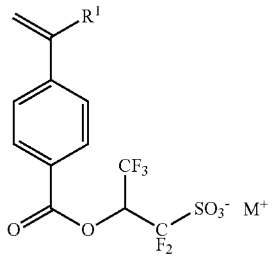
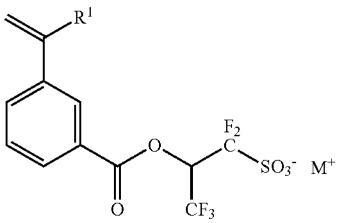
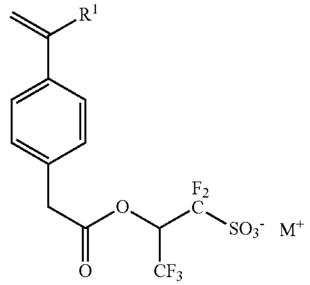
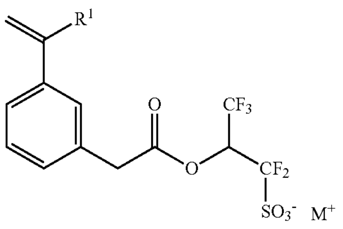
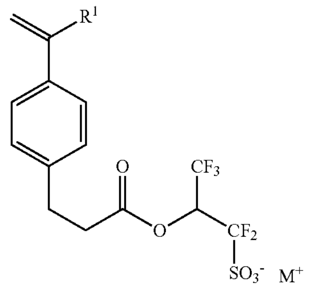

-continued
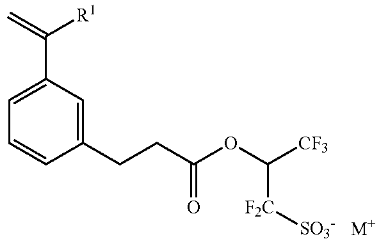
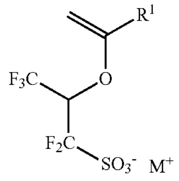
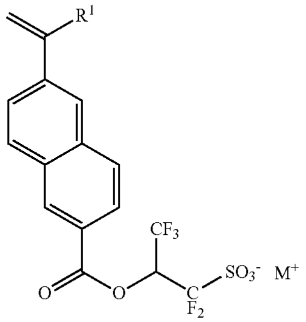
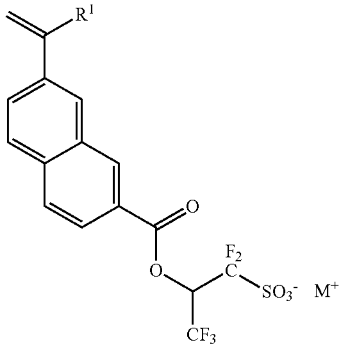
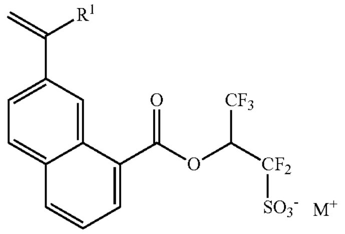
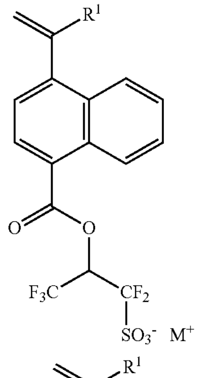
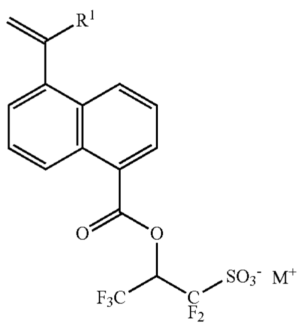
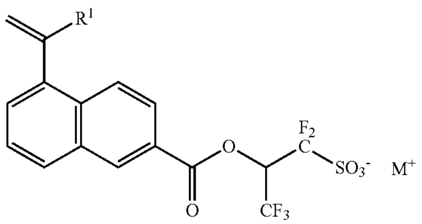
-continued
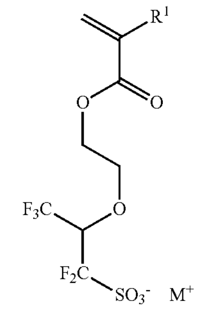
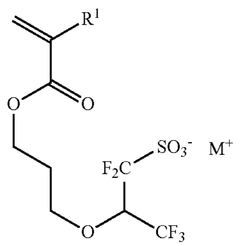
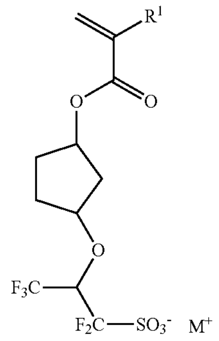
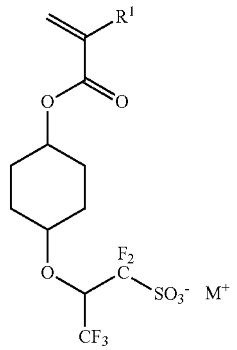
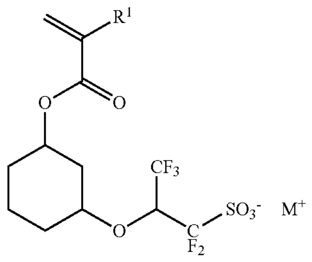
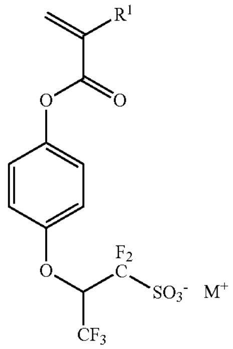
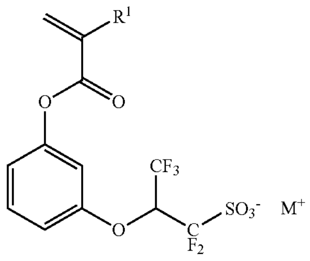
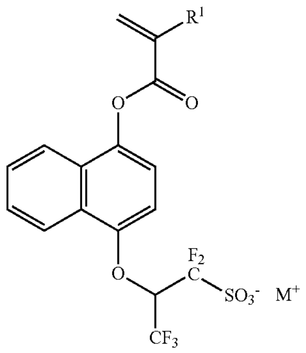
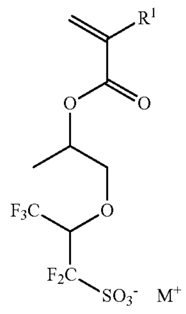

-continued
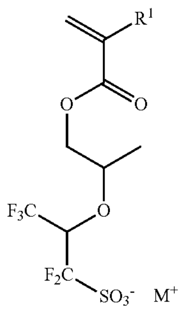
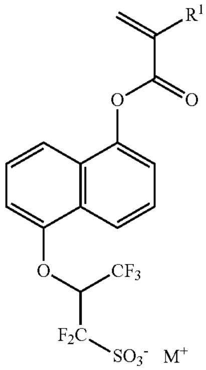
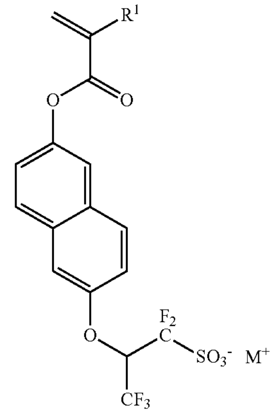
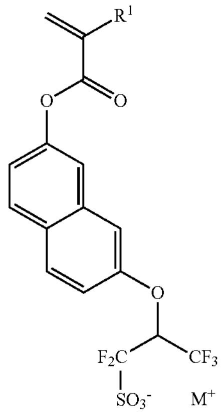
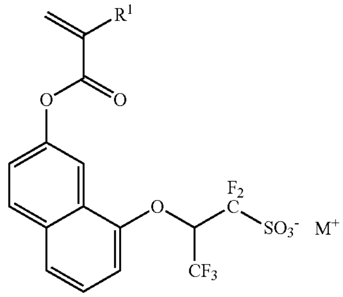
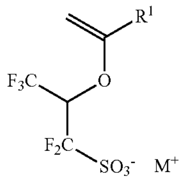
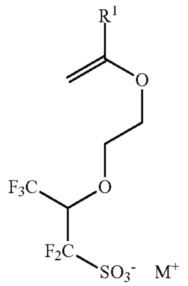
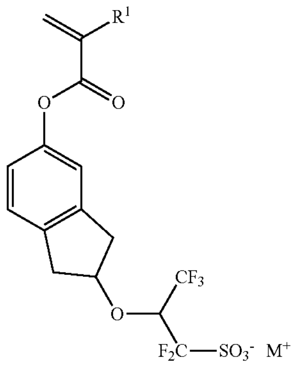
-continued
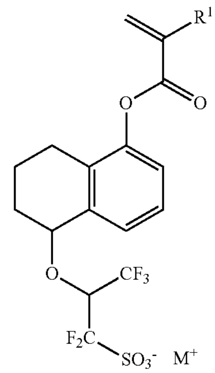
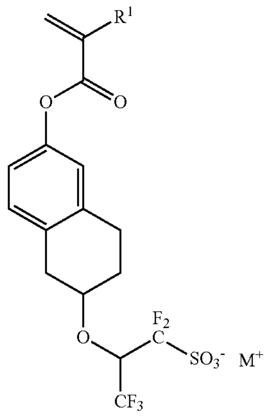
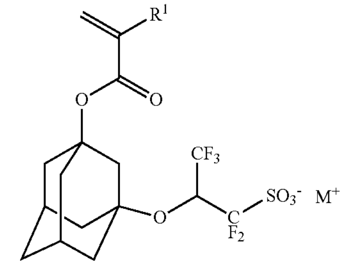
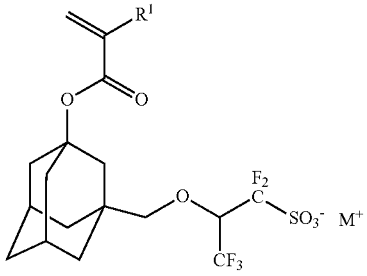
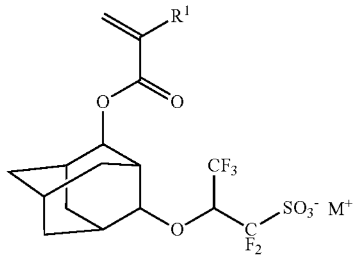
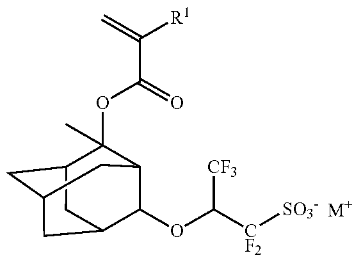

-continued
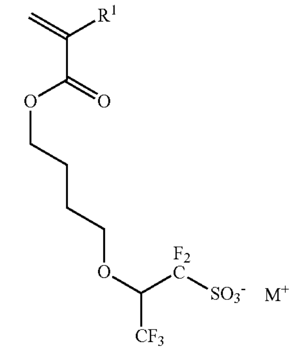
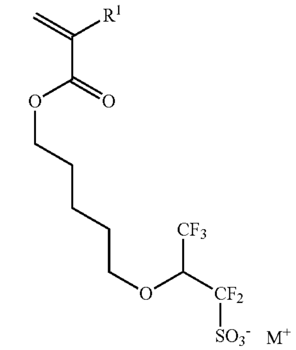
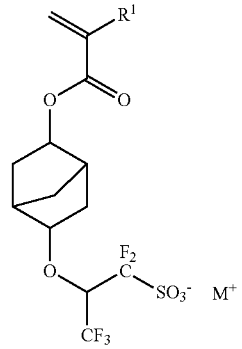
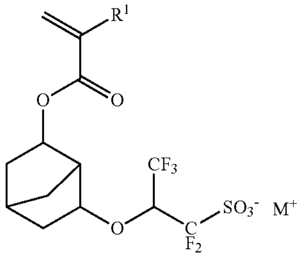
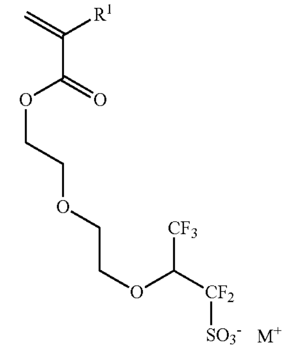
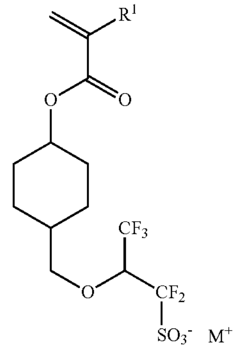
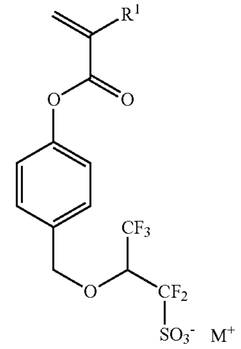
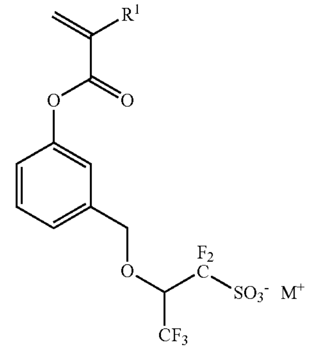
-continued
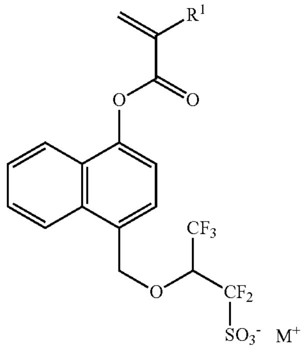
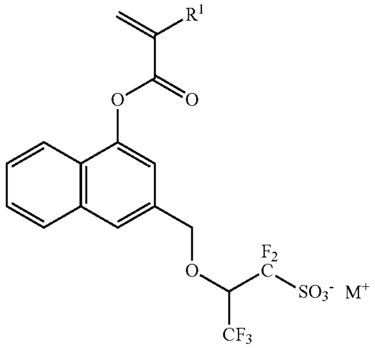
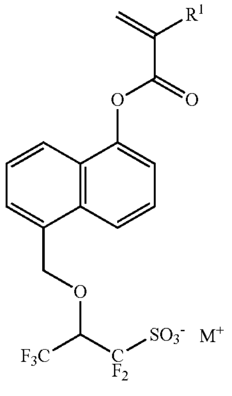
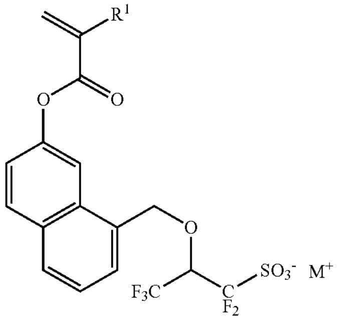
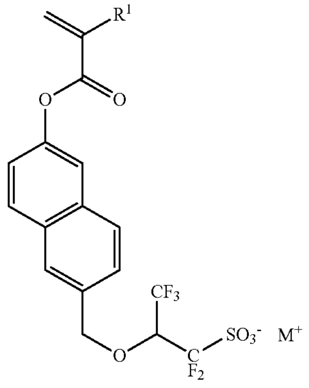
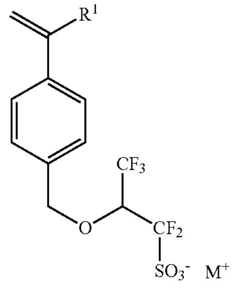

-continued
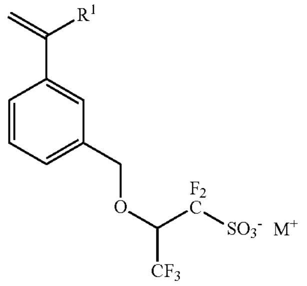
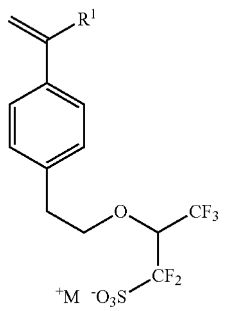
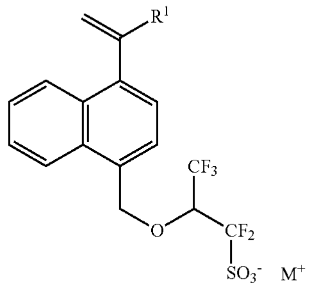
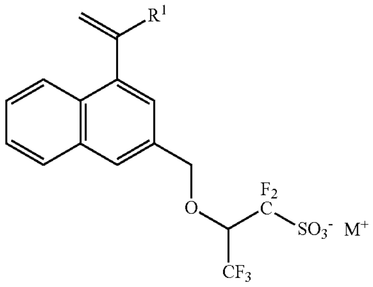
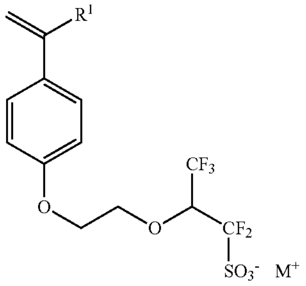
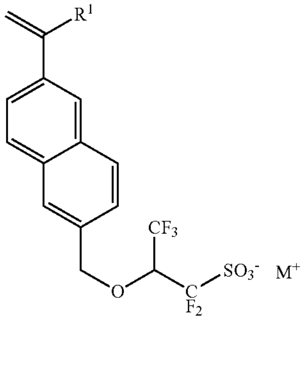
-continued
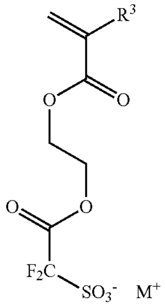
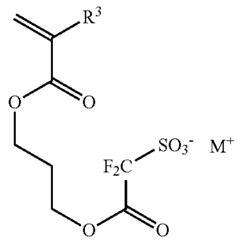
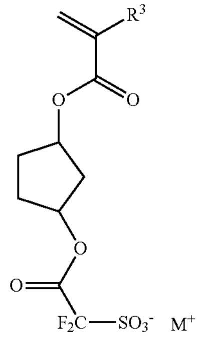
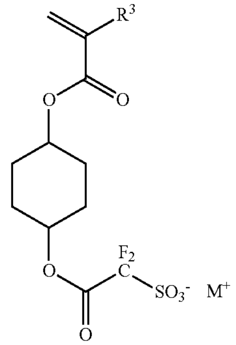
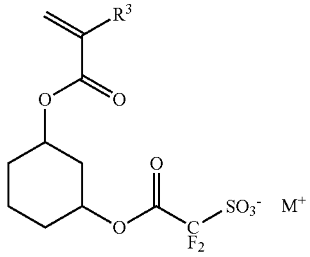
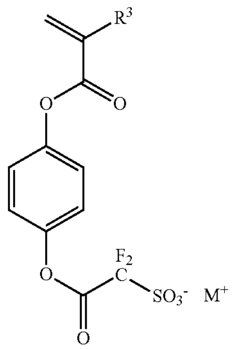
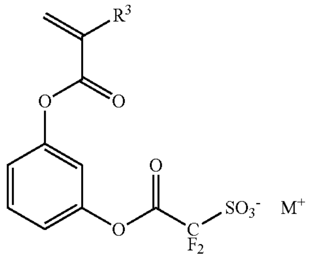
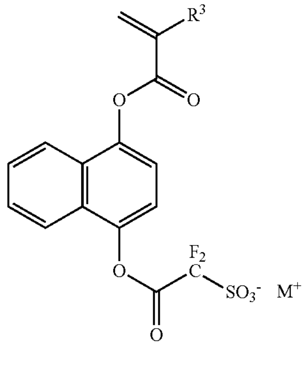
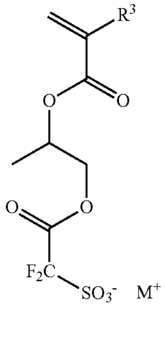

-continued
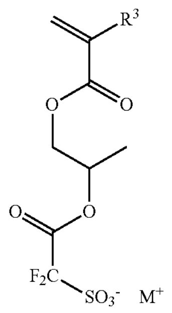
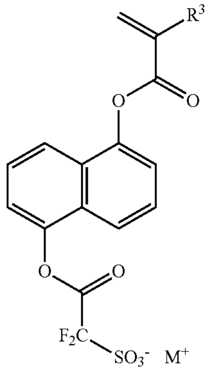
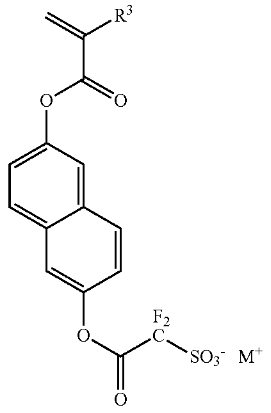
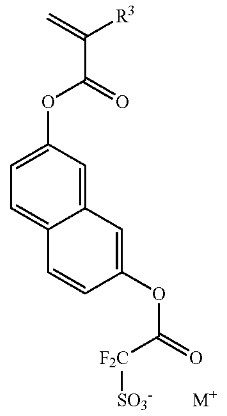
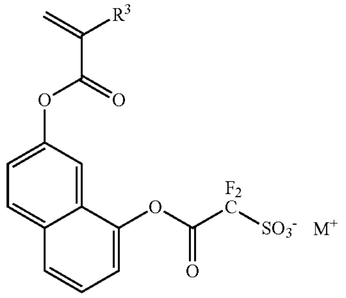
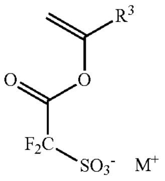
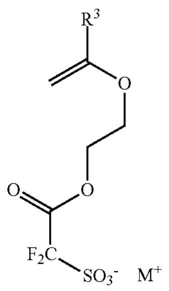
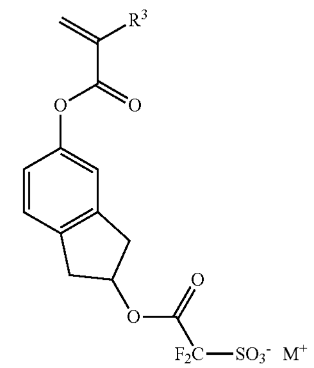
-continued
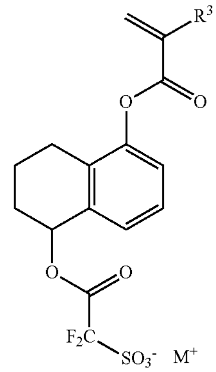
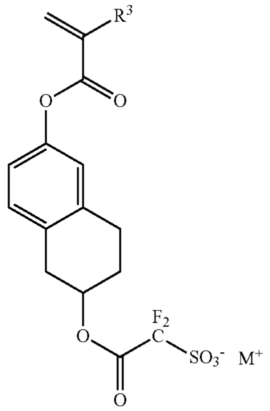
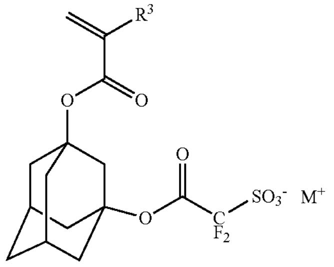
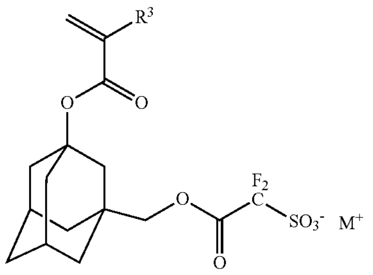
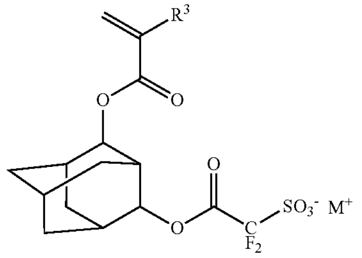
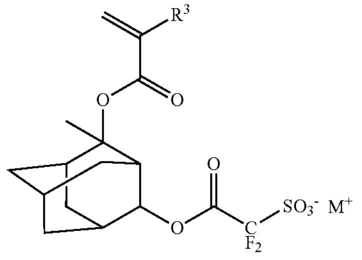

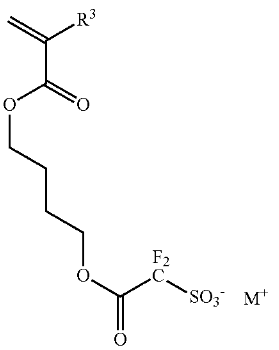
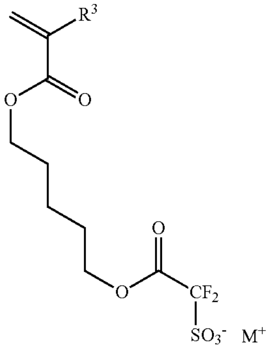
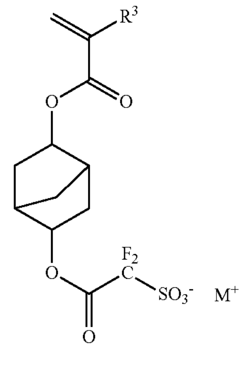
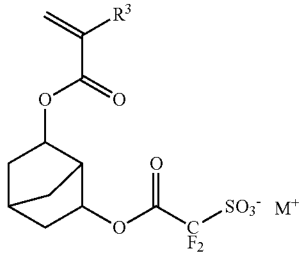
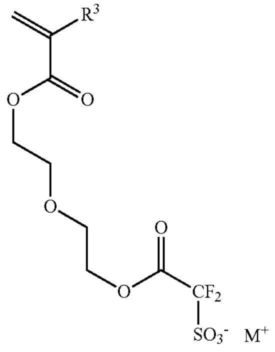
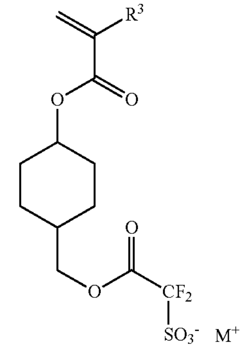
-continued
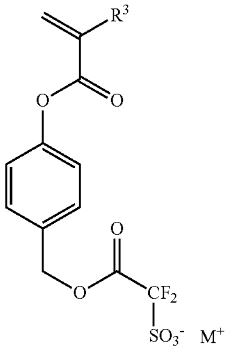
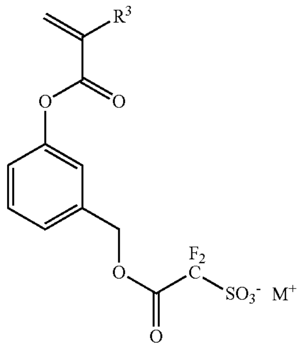
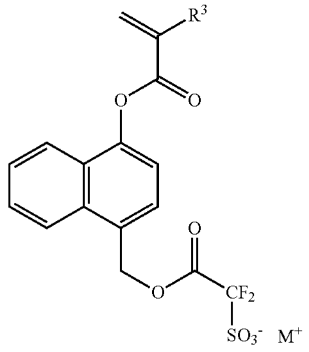
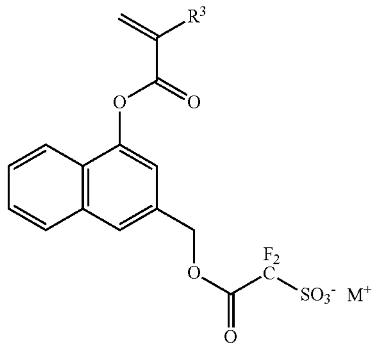
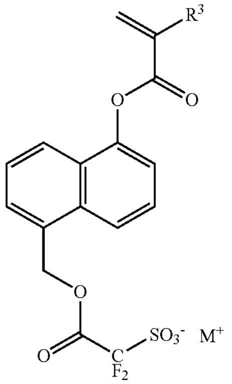
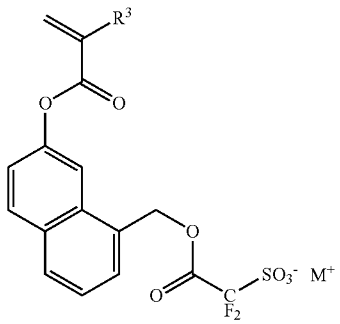

-continued
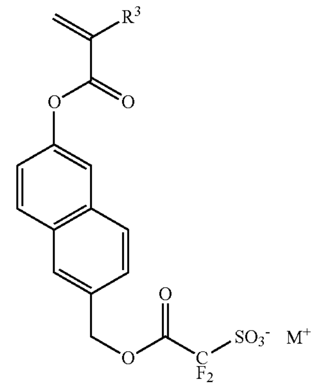
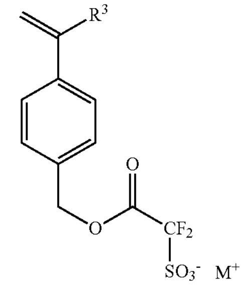
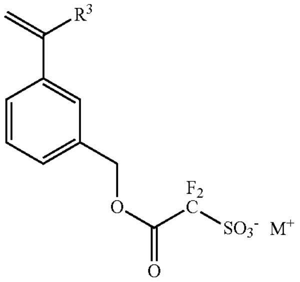
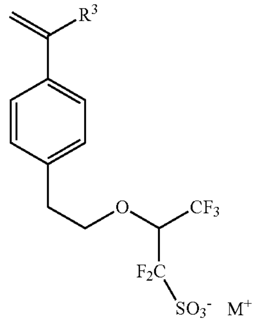
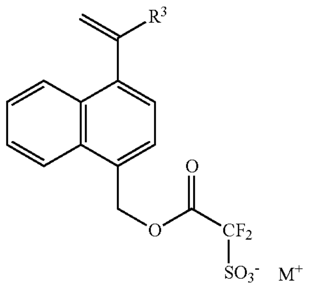
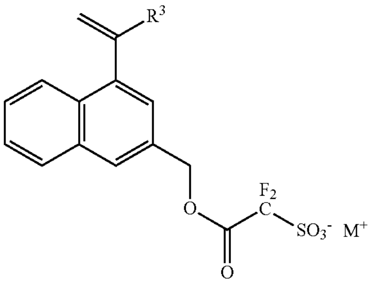
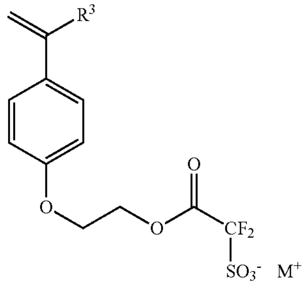
-continued
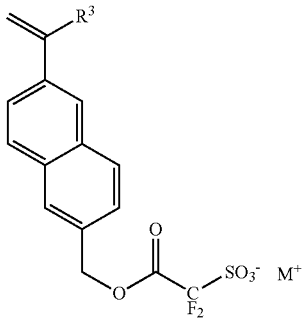
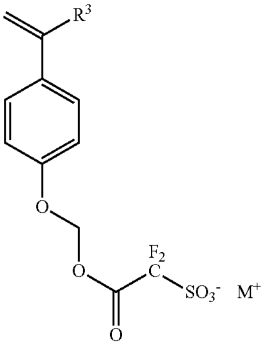
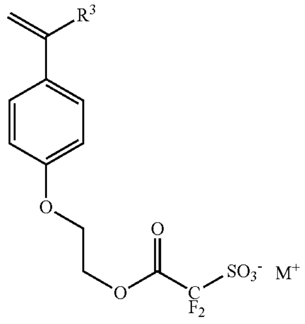
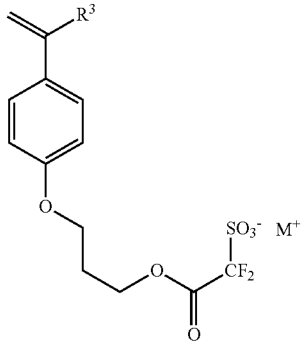
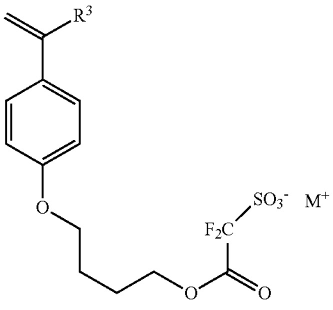
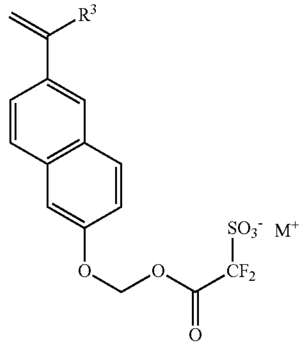

-continued
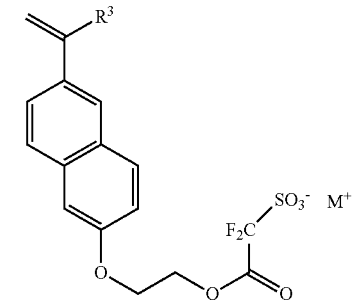
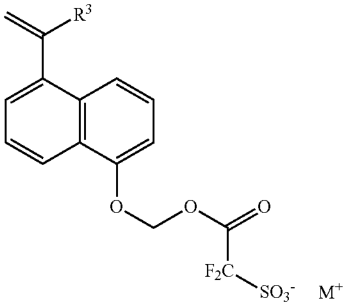
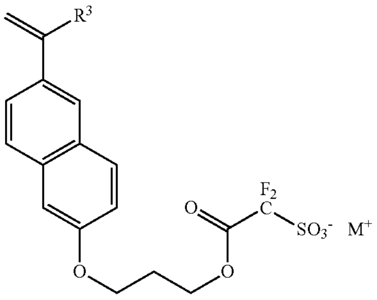
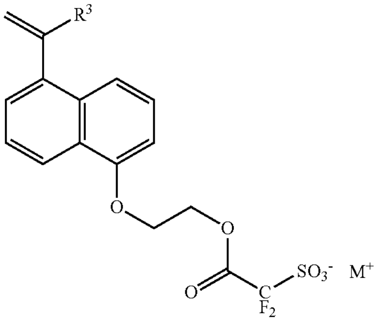
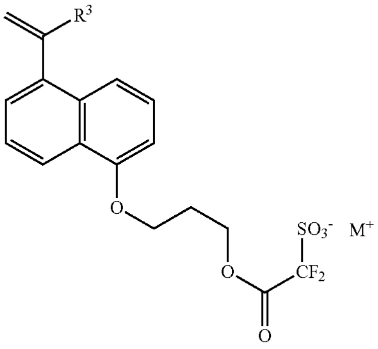
-continued
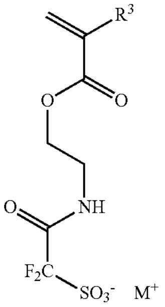
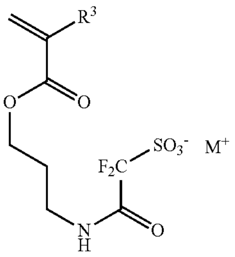
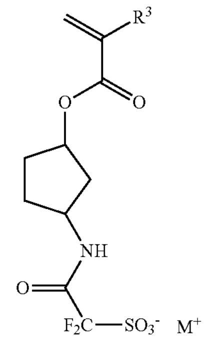
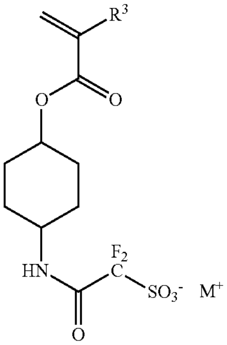
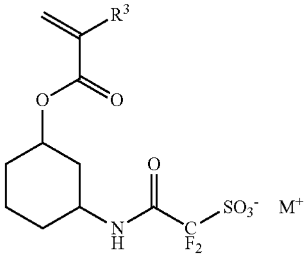
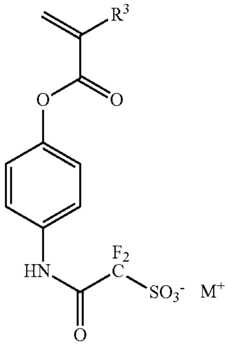
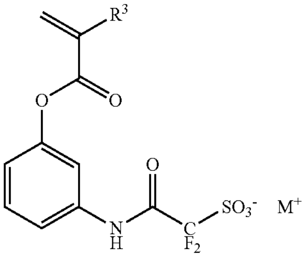
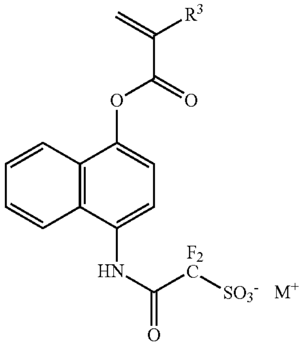
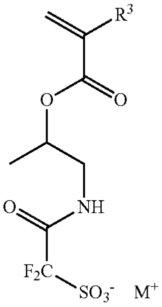

-continued
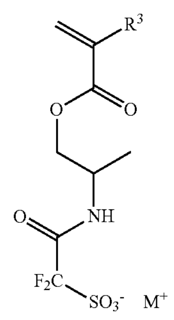
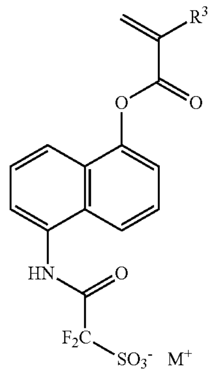
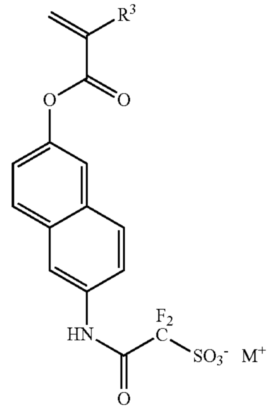
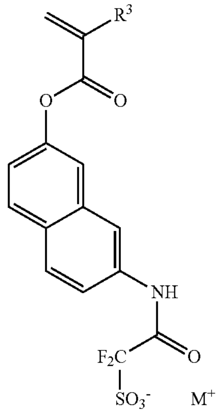
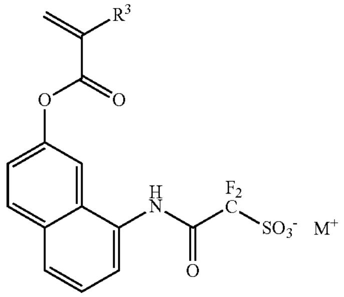
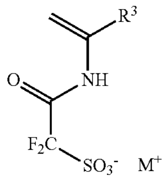
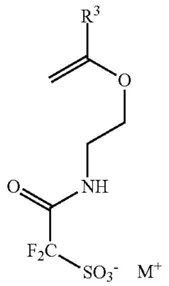
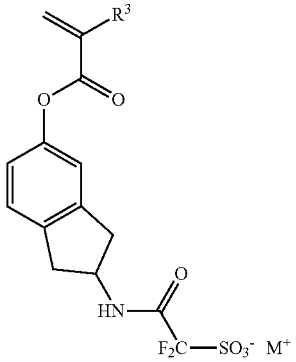
-continued
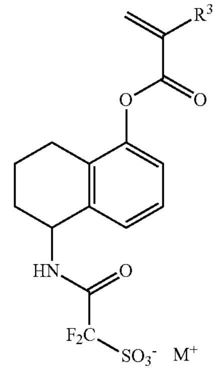
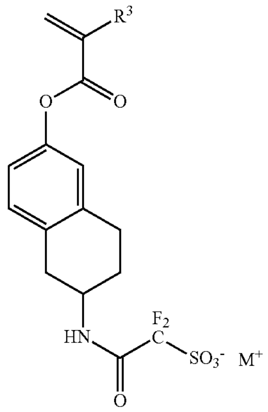
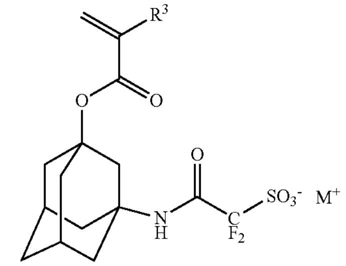
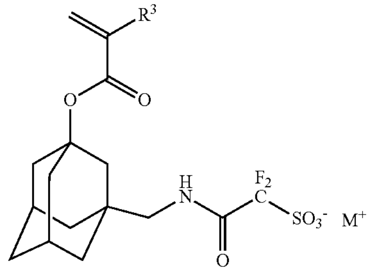
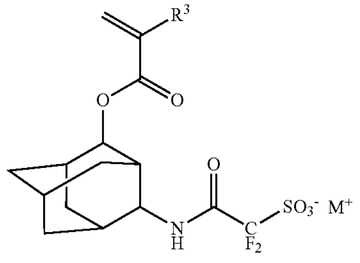
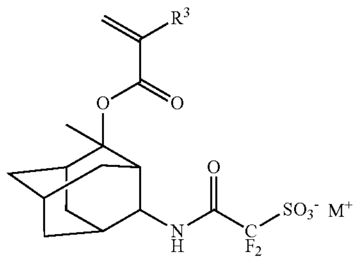

-continued
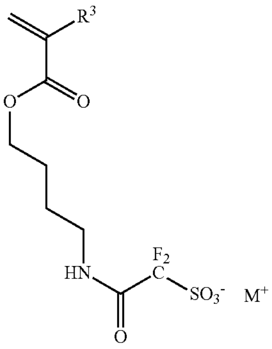
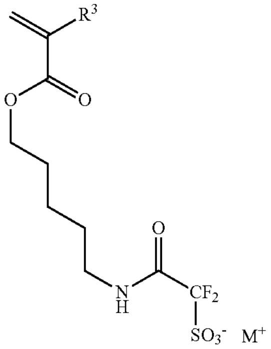
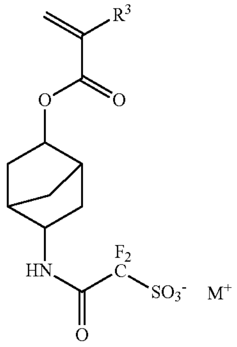
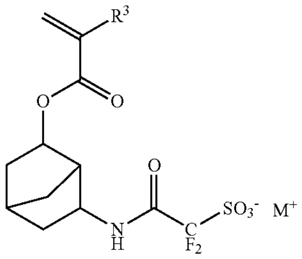
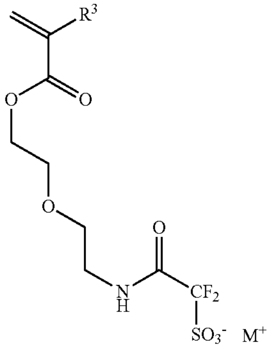
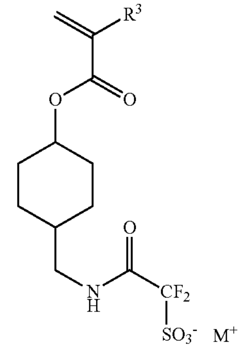
-continued
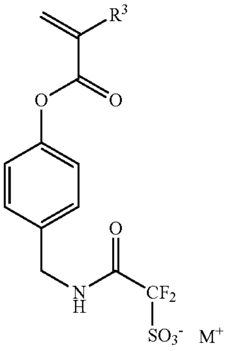
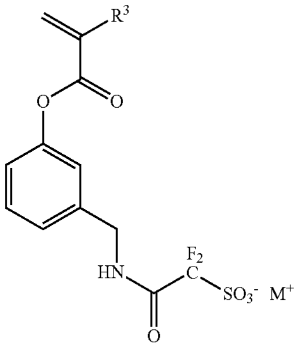
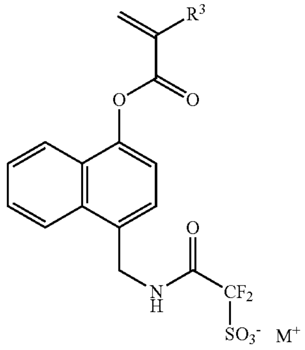
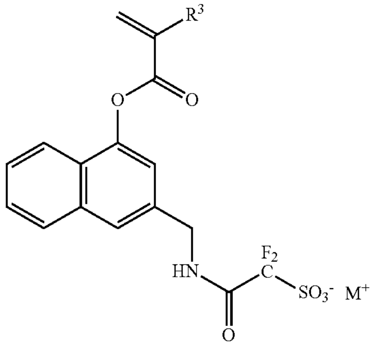
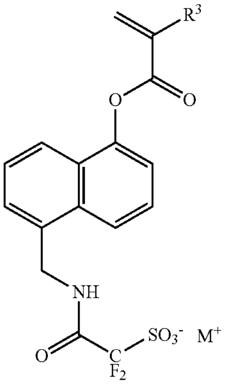
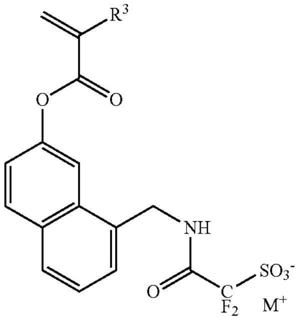

-continued
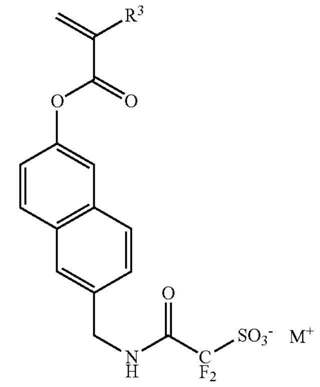
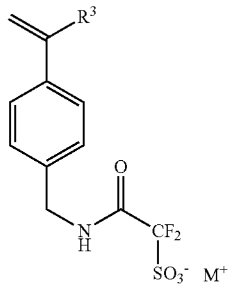
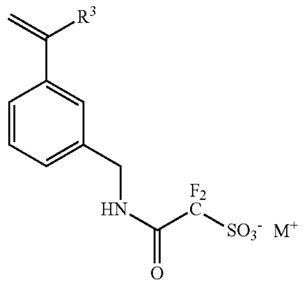
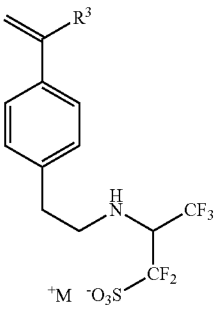
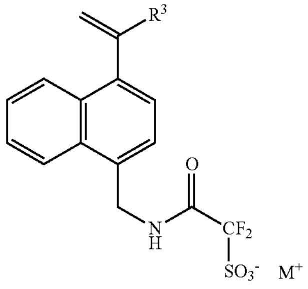
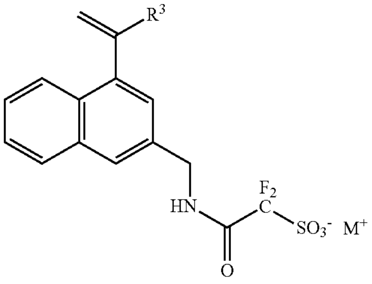
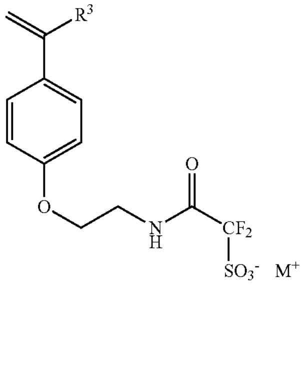
-continued
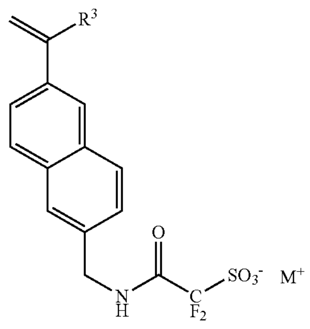
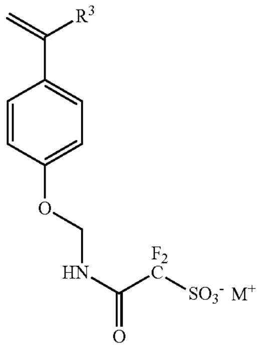
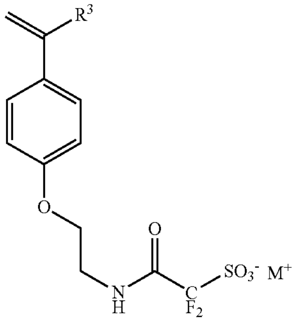
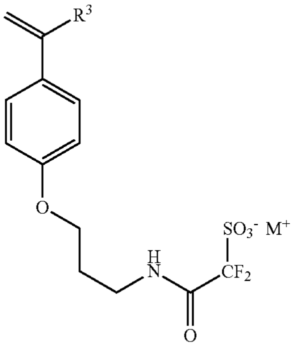
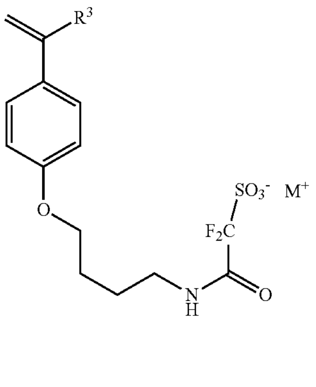

-continued
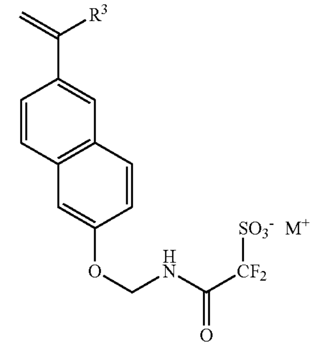
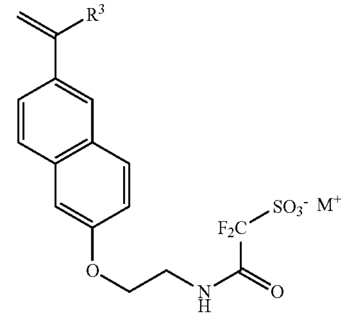
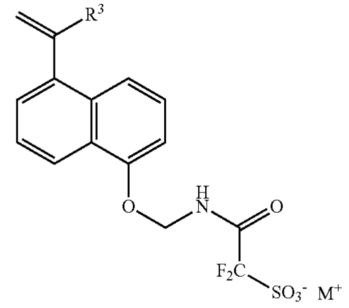
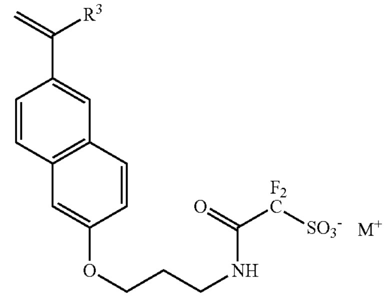
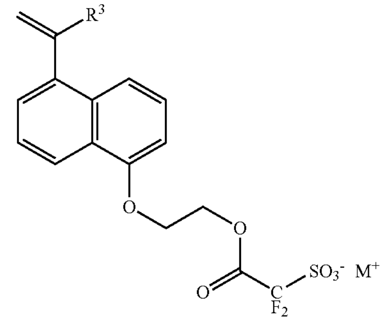
-continued
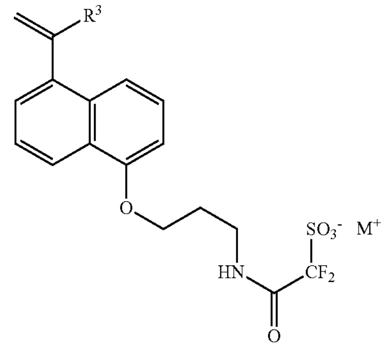
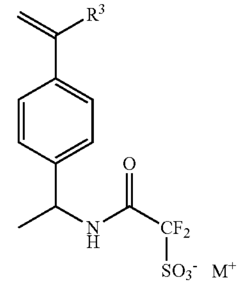
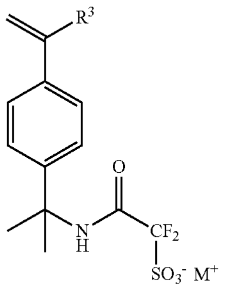
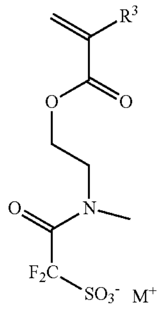
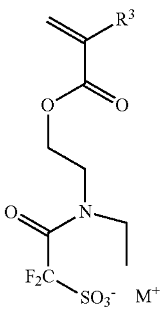
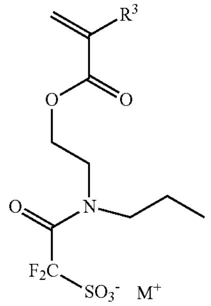
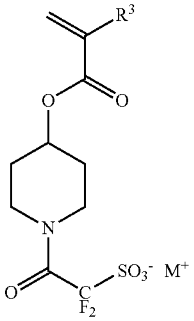
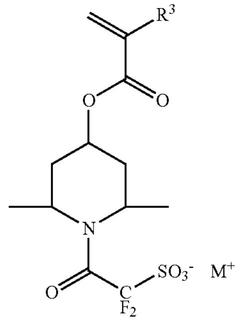
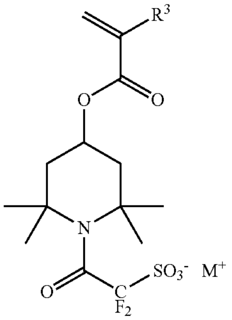

-continued
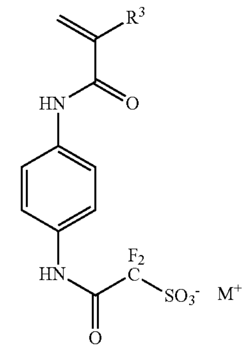
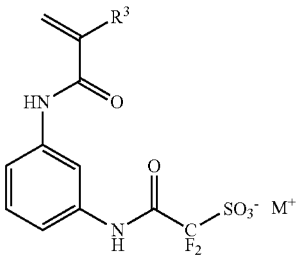
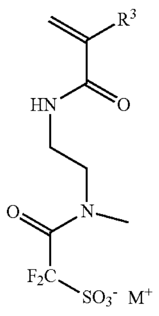
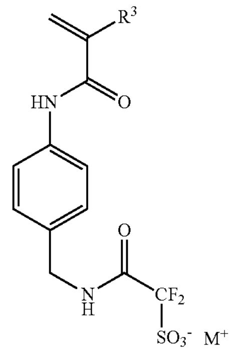
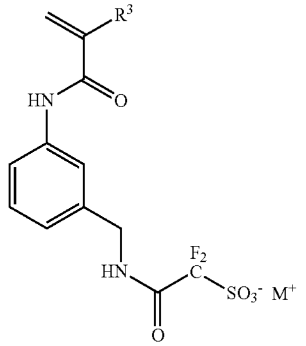
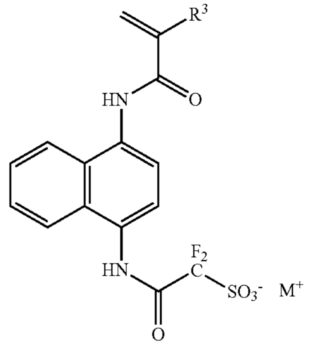
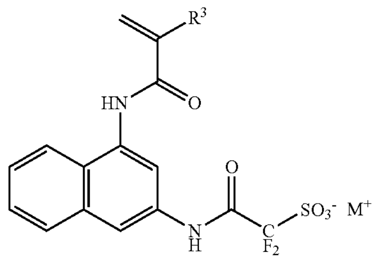
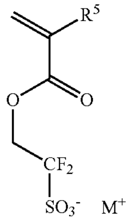
-continued
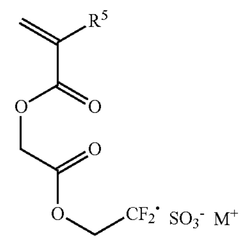
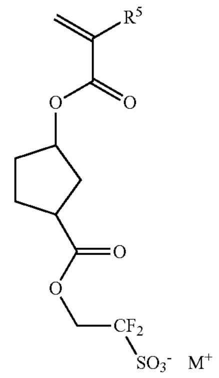
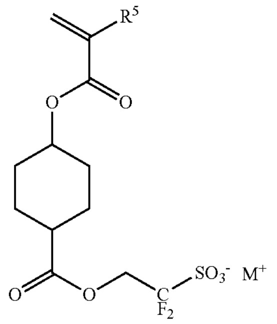
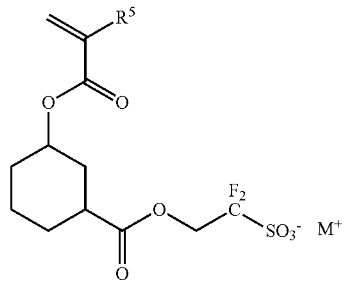
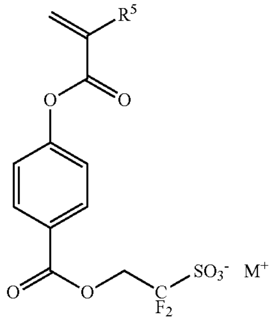
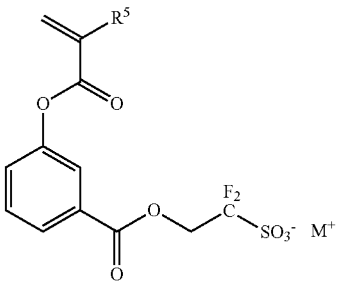

-continued
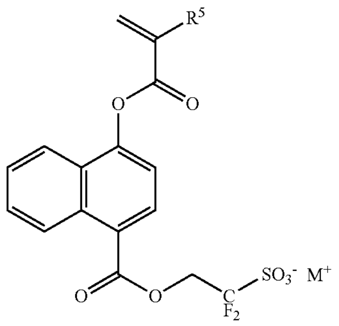
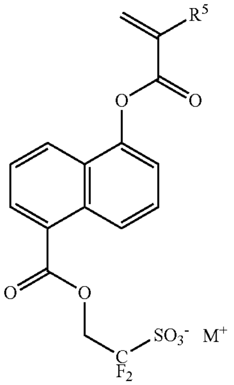
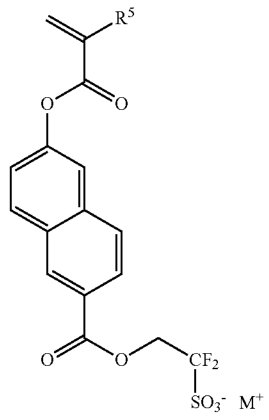
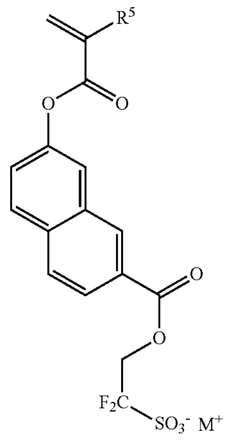
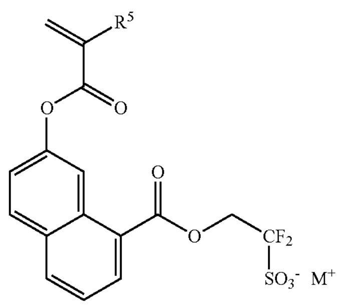
-continued
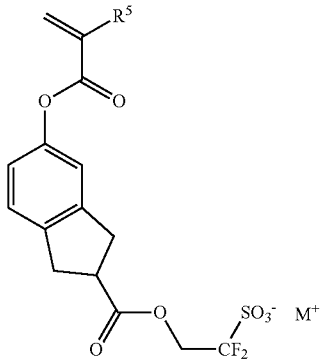
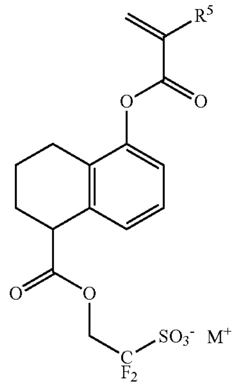
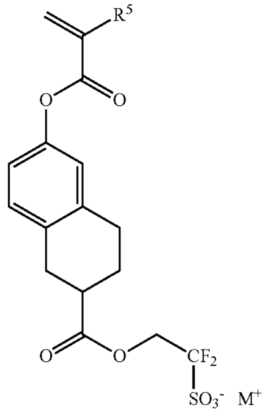
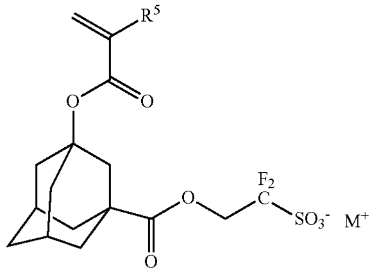
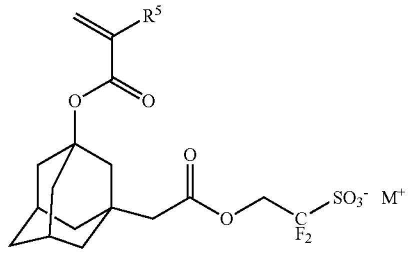
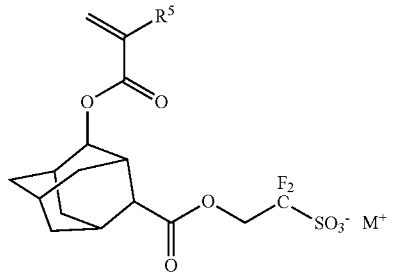

-continued
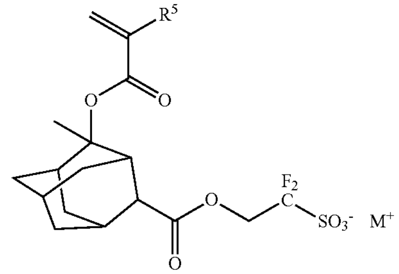
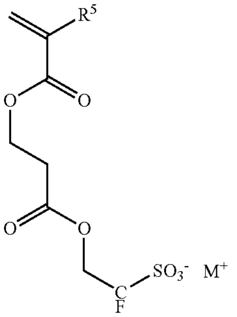
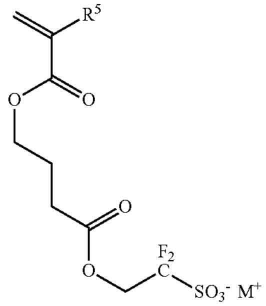
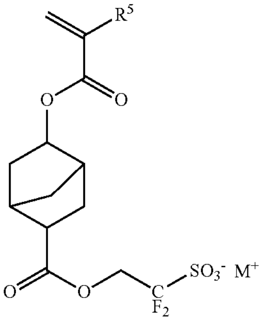
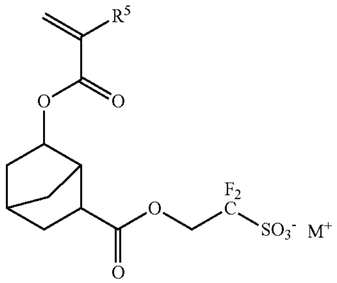
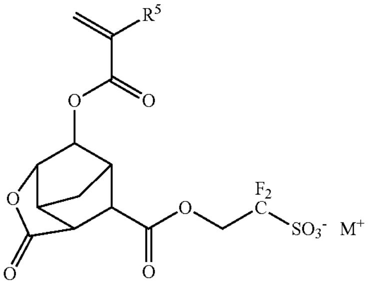
-continued
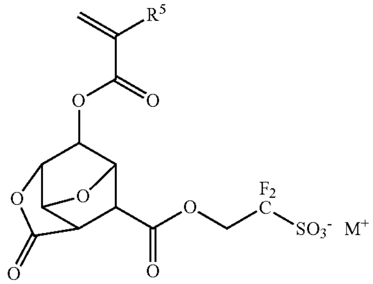
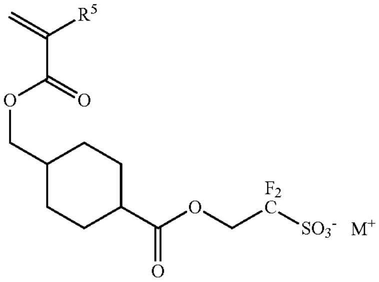
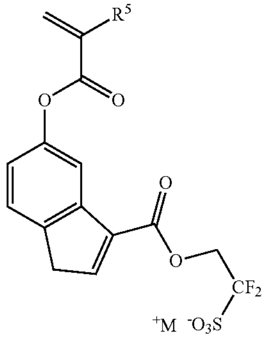
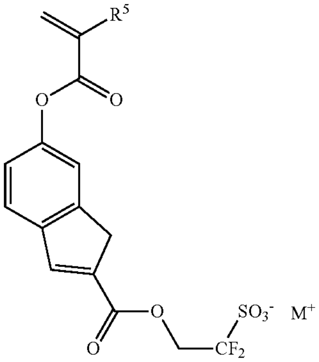
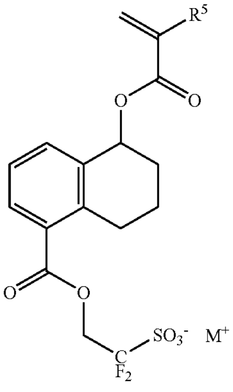
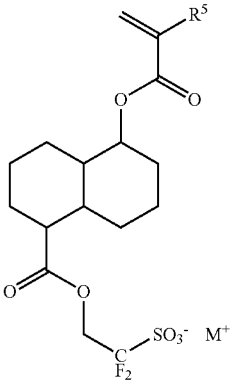

-continued
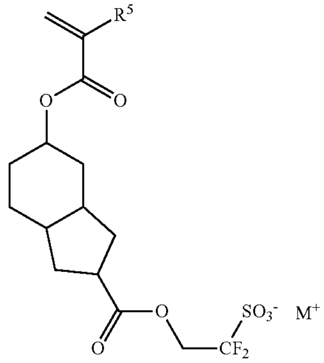
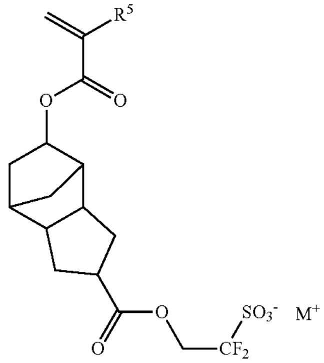
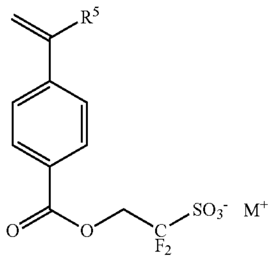
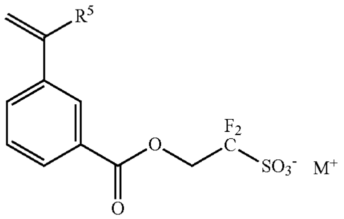
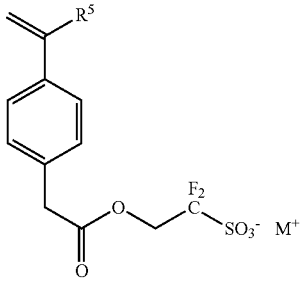
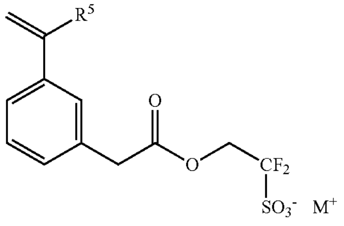
-continued
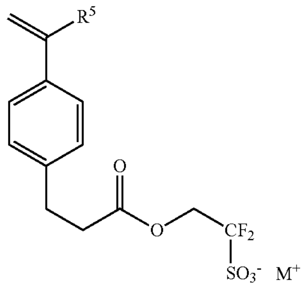
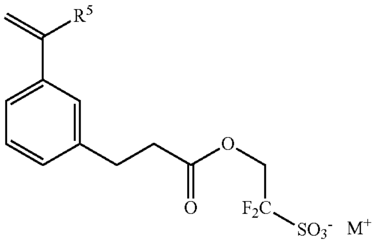
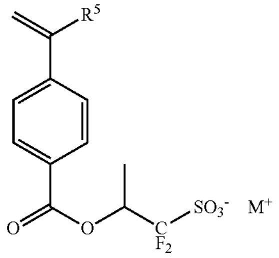
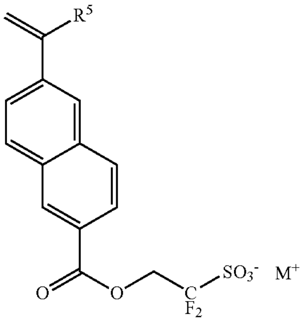
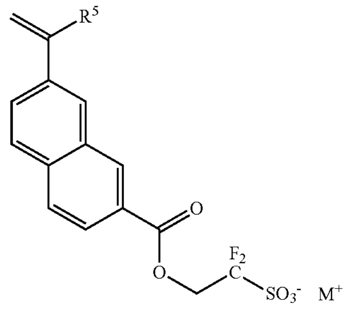
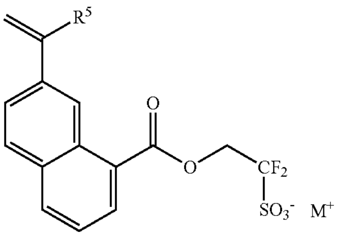
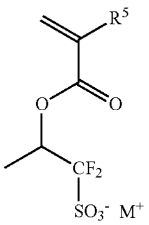

-continued
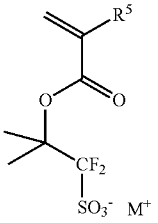
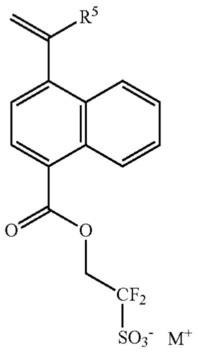
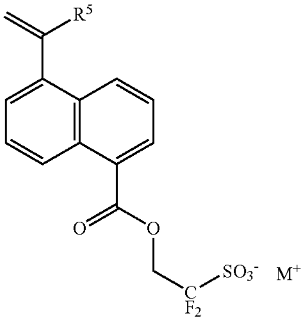
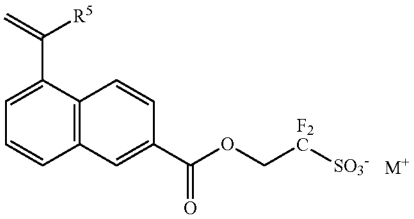
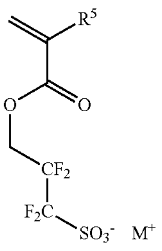
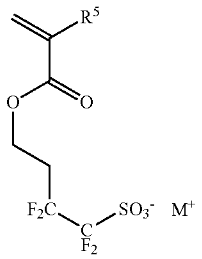
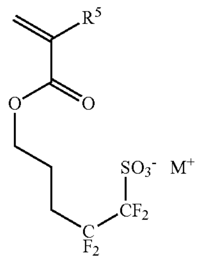
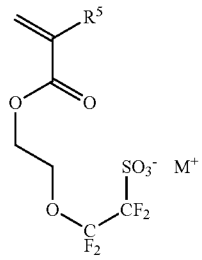
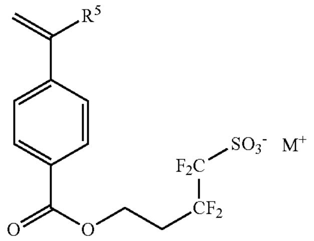
-continued
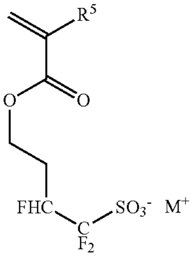
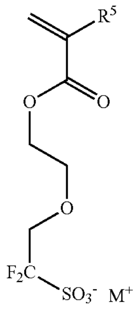
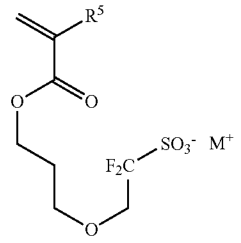
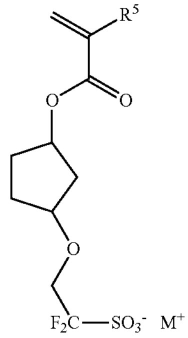
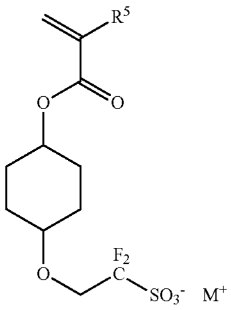
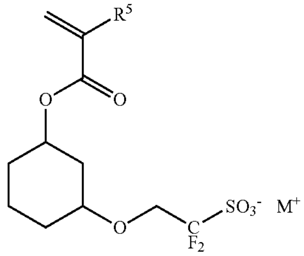
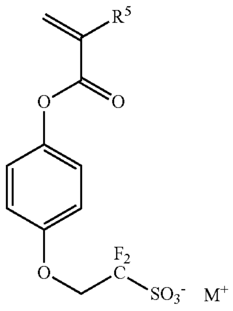
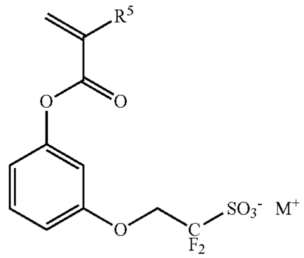
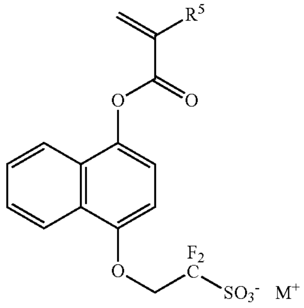
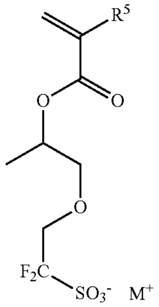

-continued
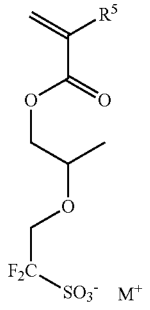
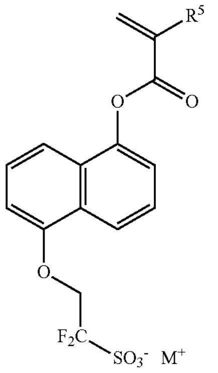
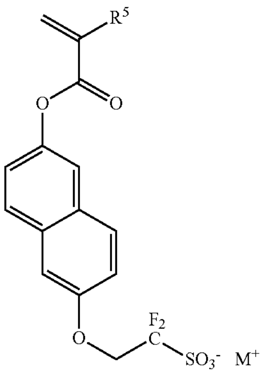
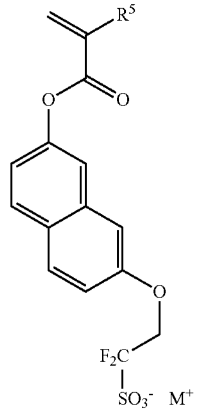
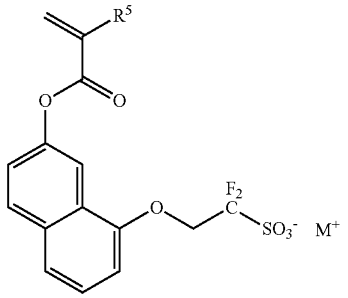
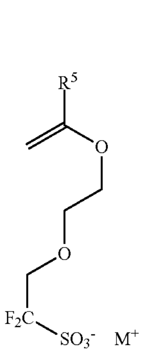
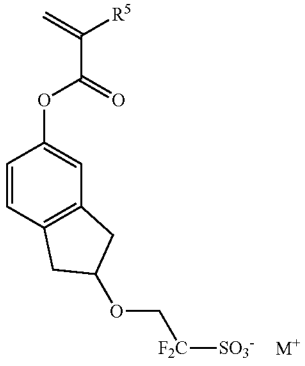
-continued
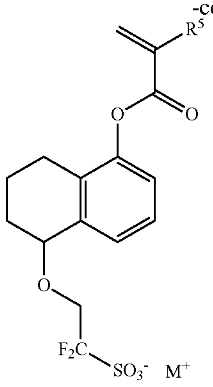
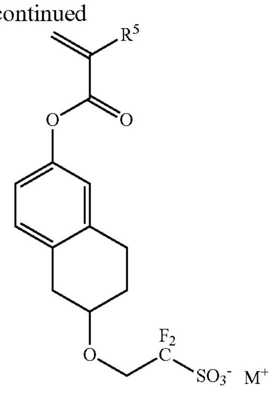
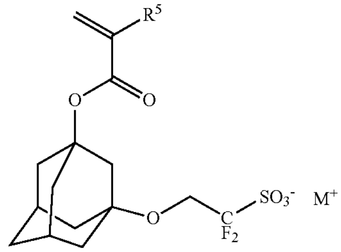
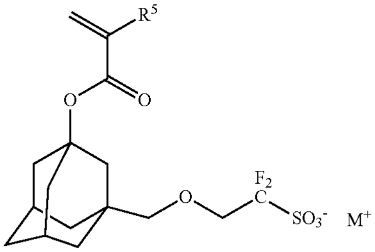
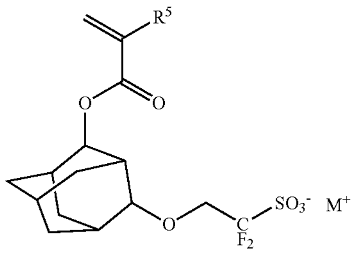
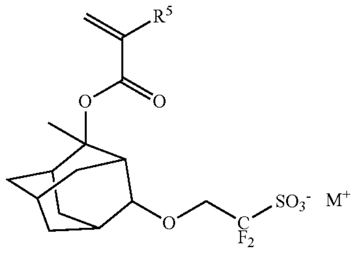

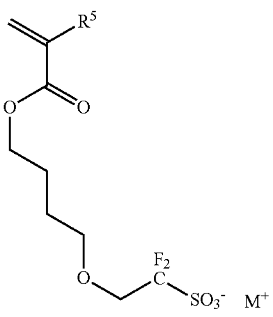
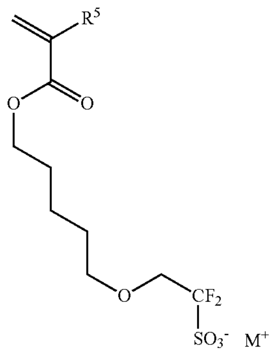
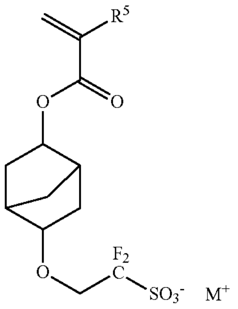
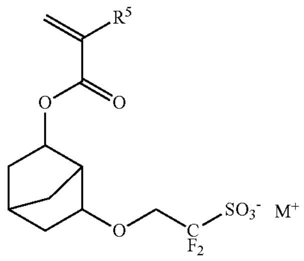
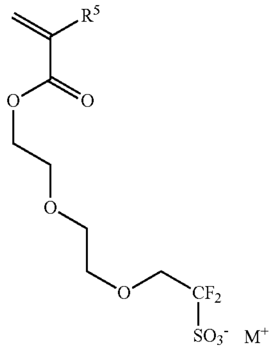
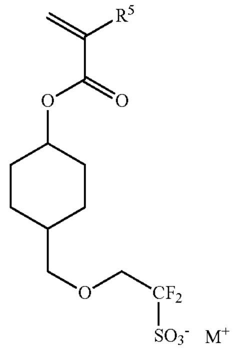
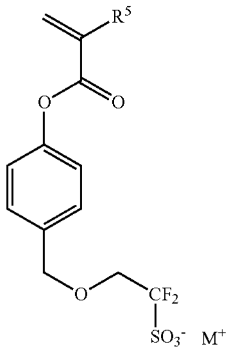
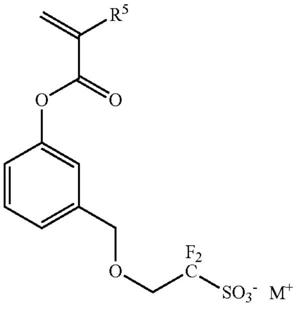
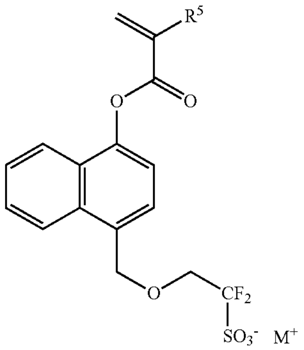
-continued
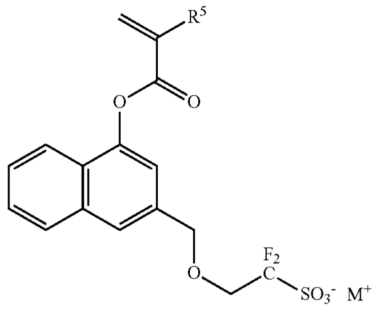
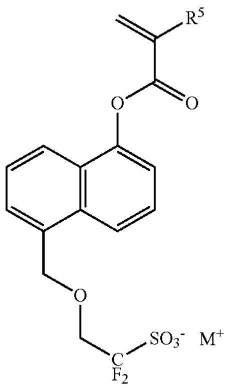
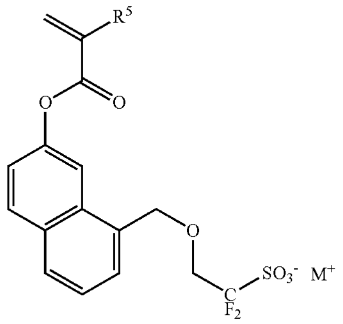
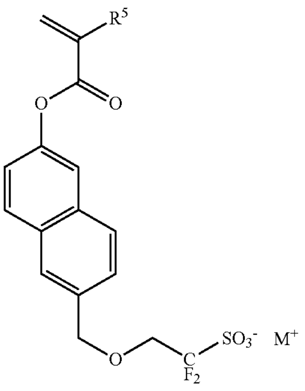
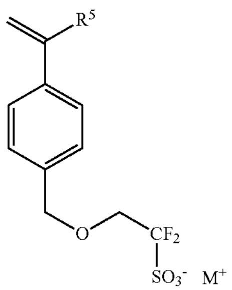
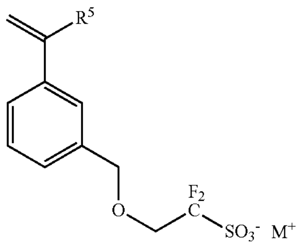
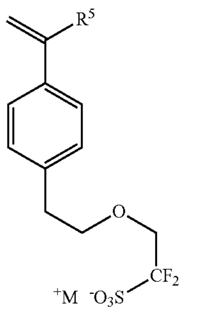
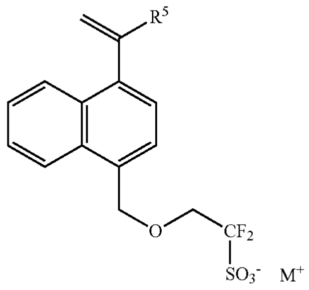

-continued
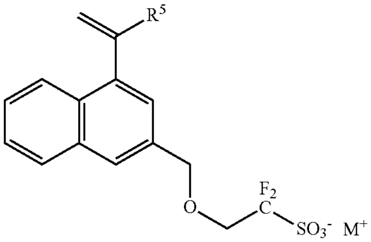
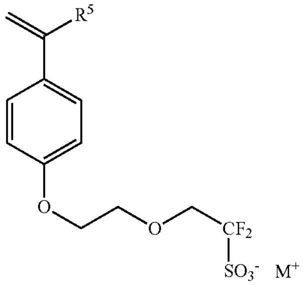
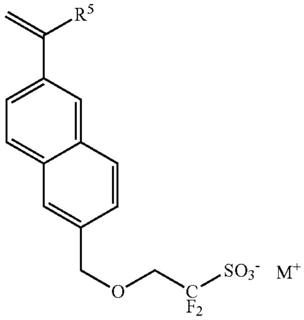
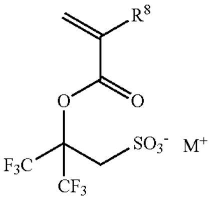
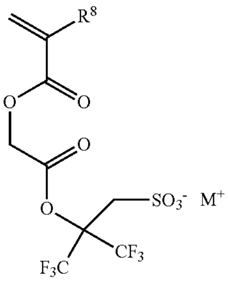
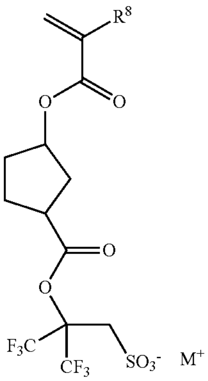
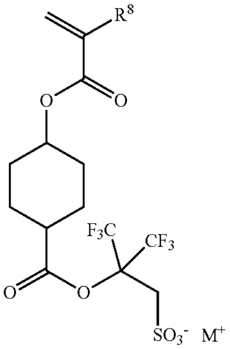
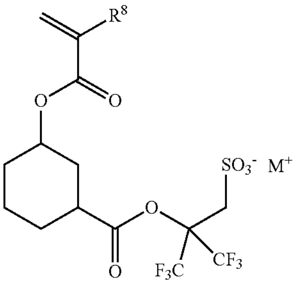
-continued
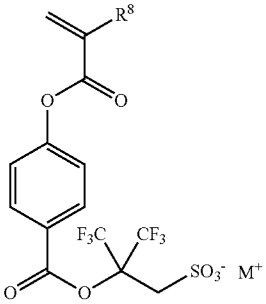
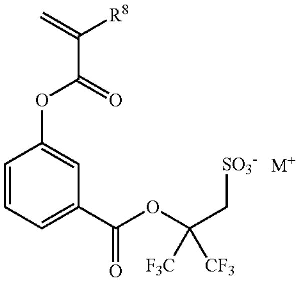
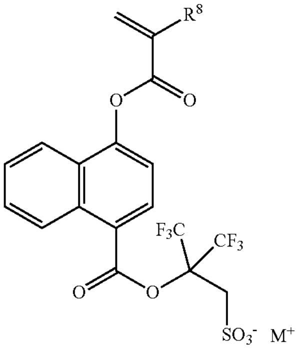
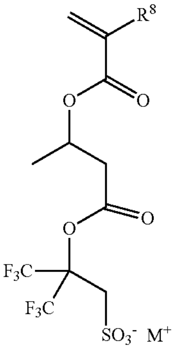
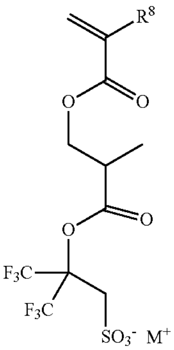
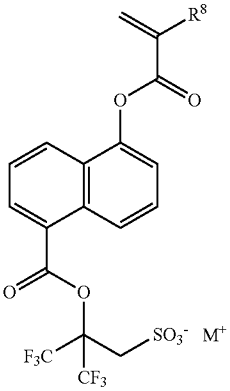
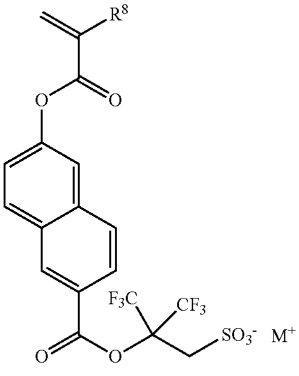
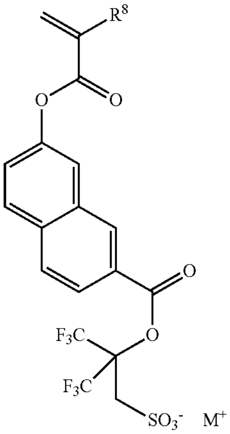

-continued
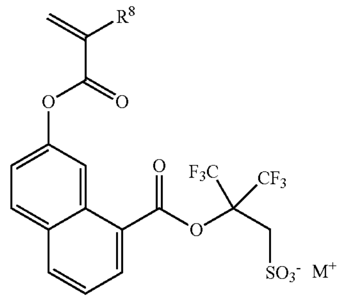
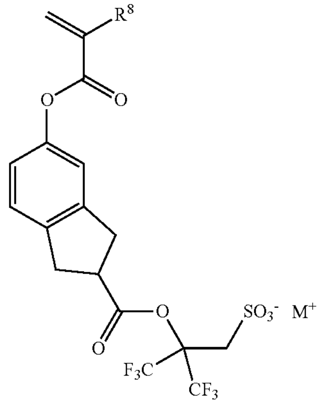
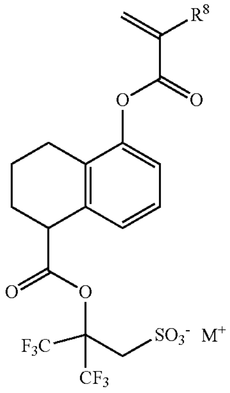
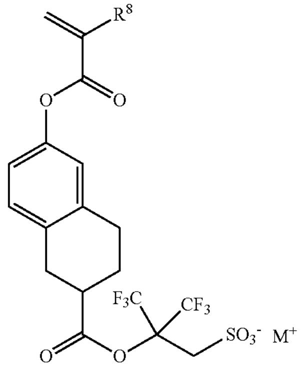
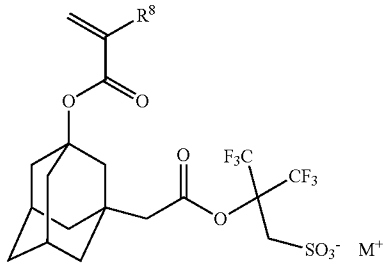
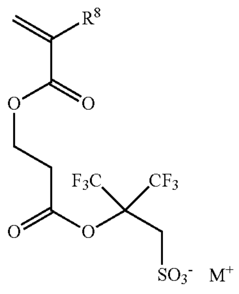
-continued
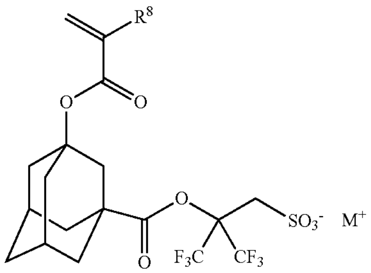
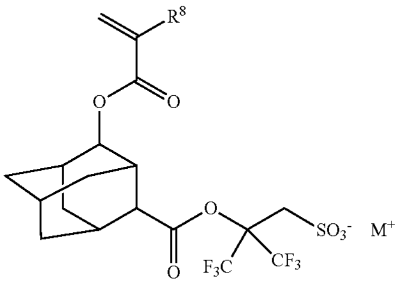
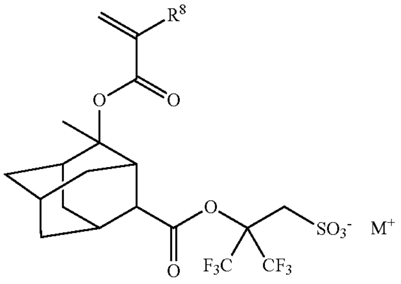
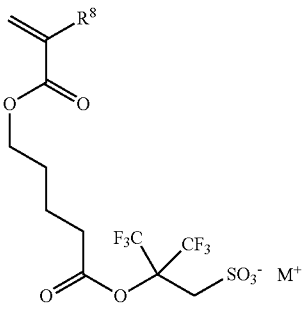
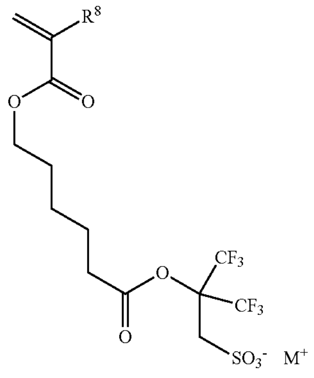
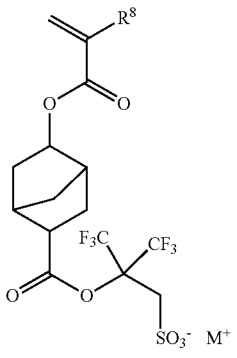

-continued
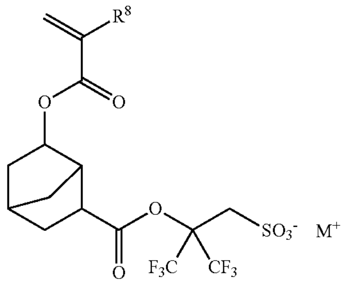
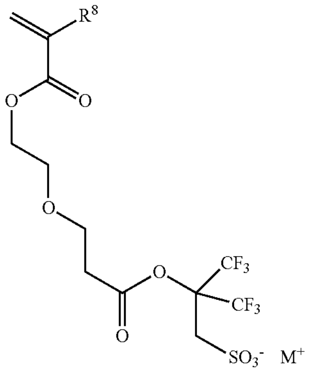
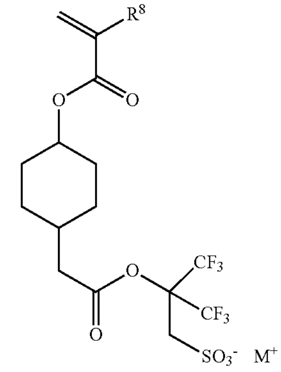
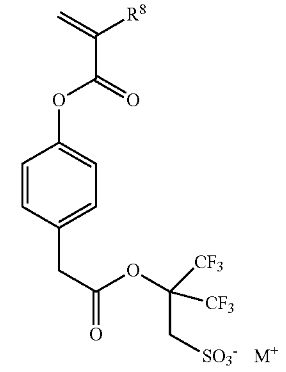
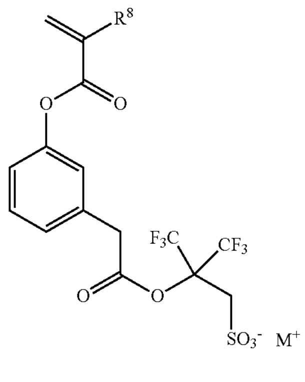
-continued
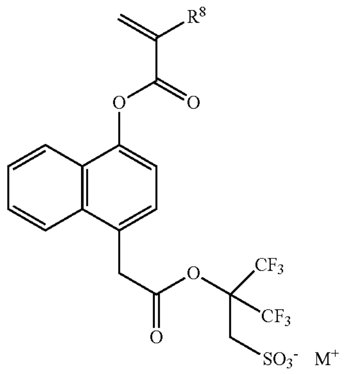
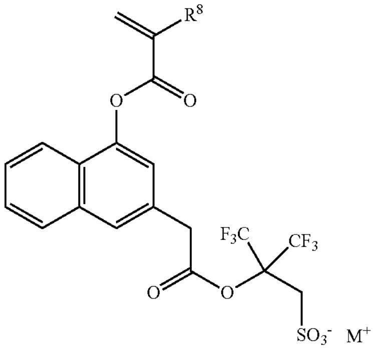
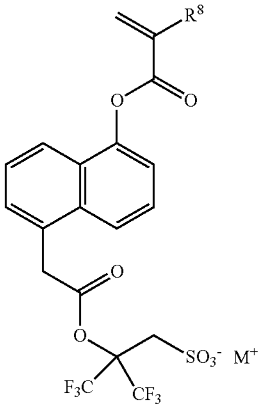
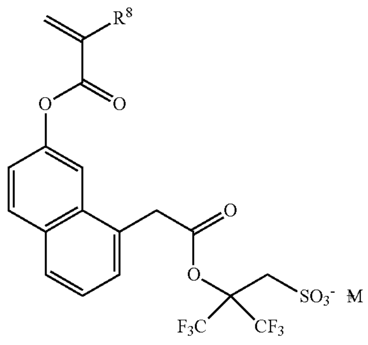

-continued
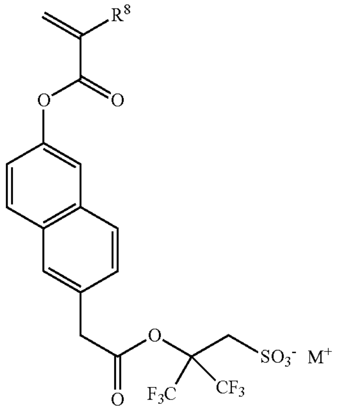
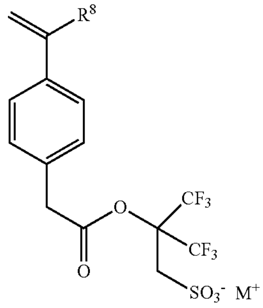
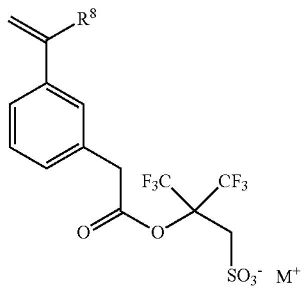
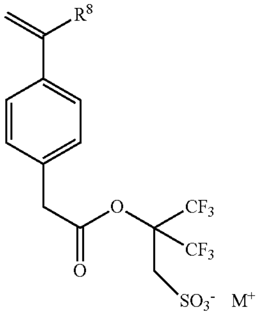
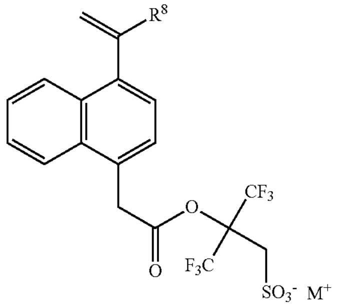
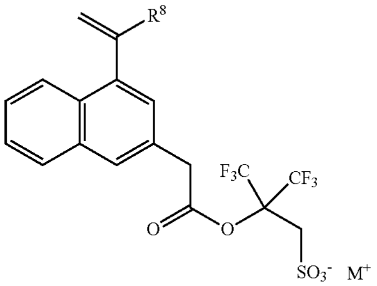
-continued
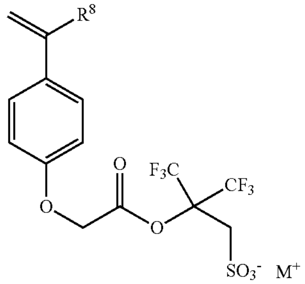
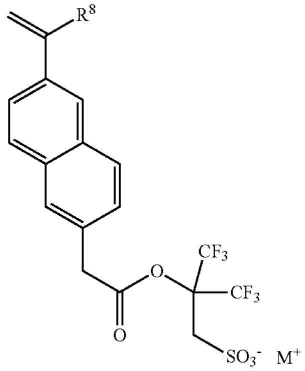
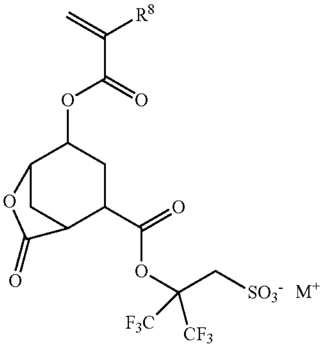
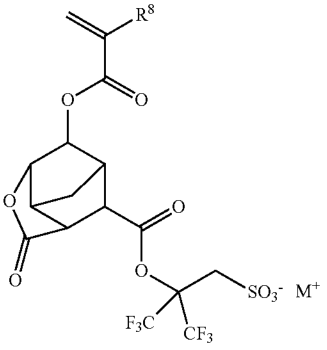
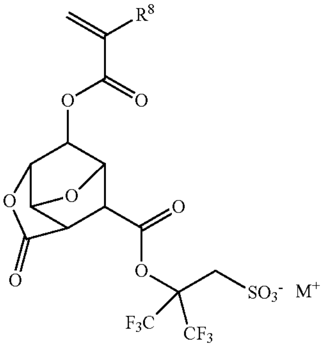

-continued
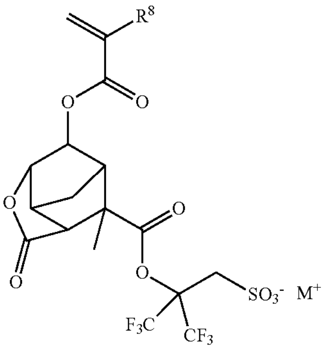
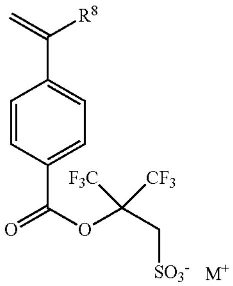
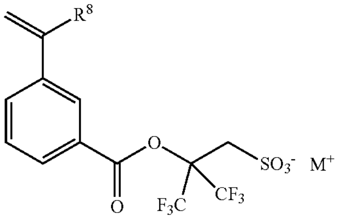
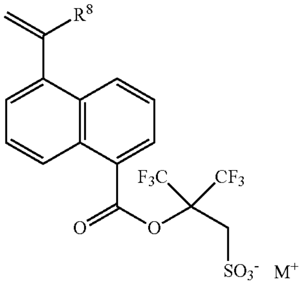
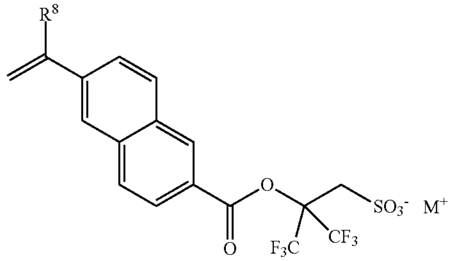
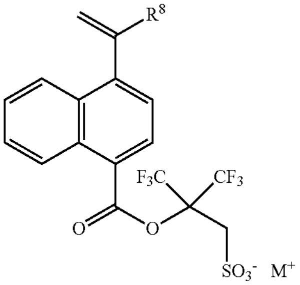
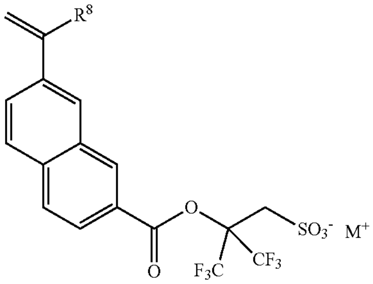
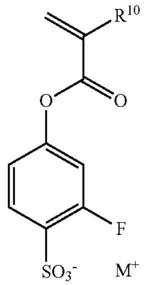
-continued
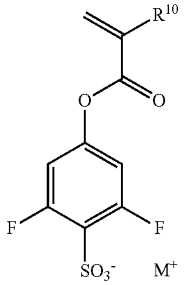
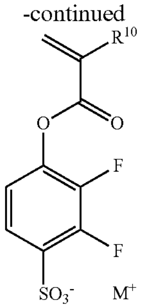
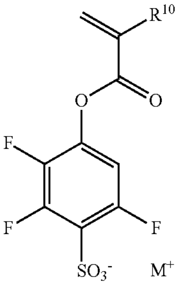
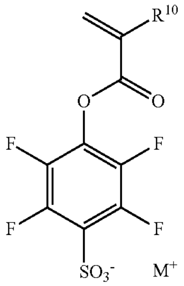
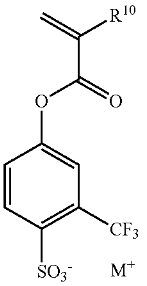
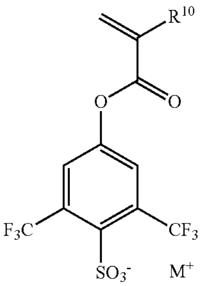
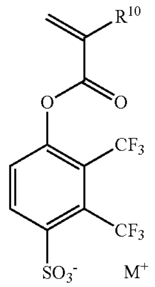
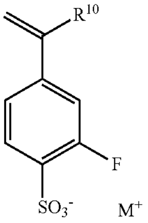
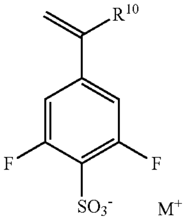
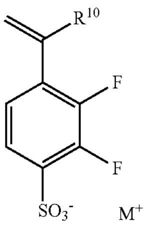
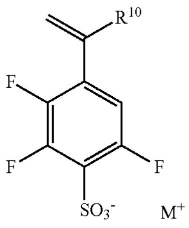
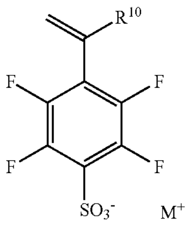
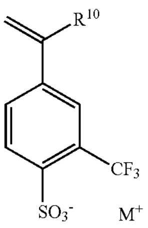
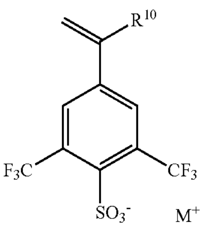
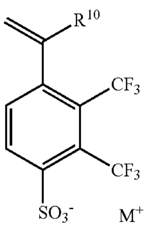
The repeating unit-a6 shown by the general formula (2) can be obtained from fluorosulfonimide salt monomers specifically exemplified below.

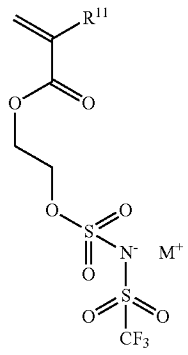
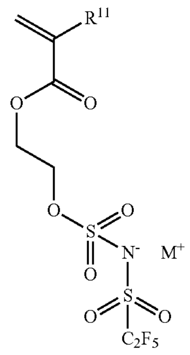
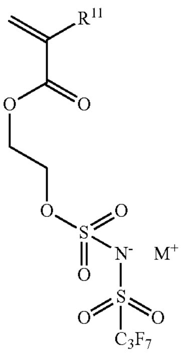
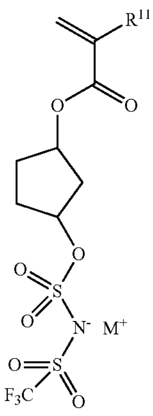
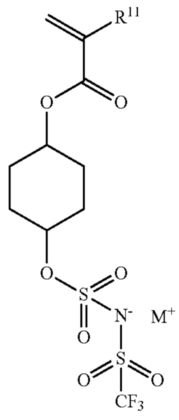
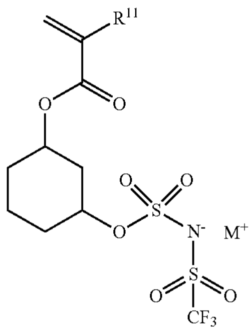
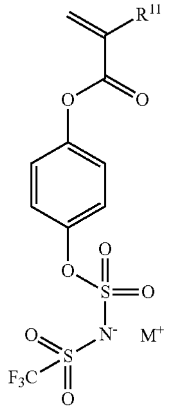
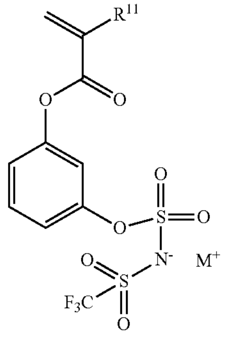
-continued
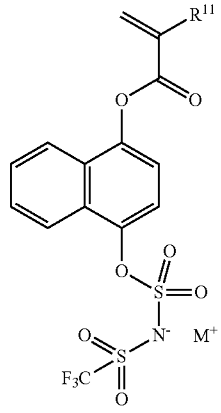
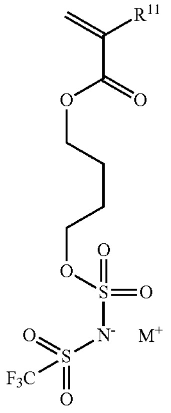
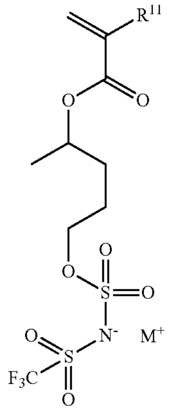
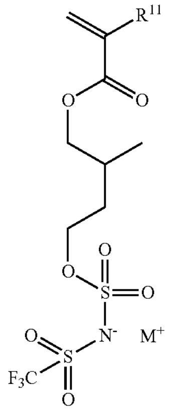
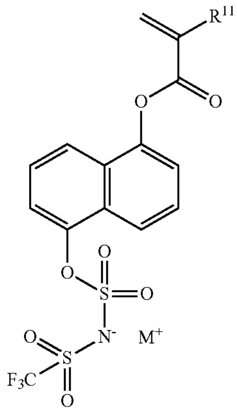
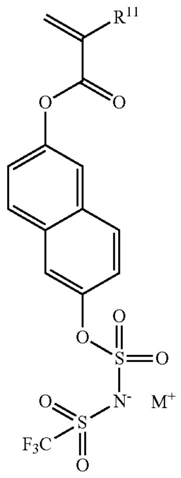
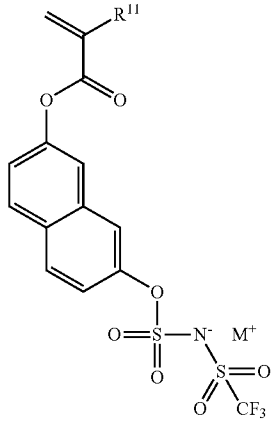
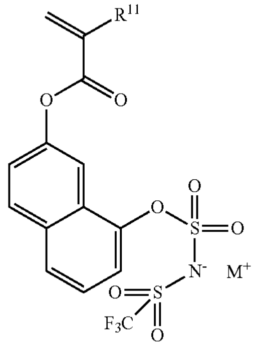

-continued
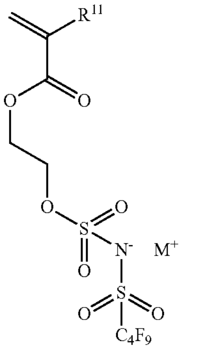
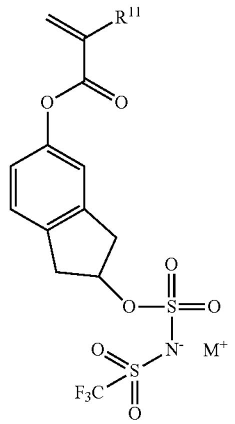
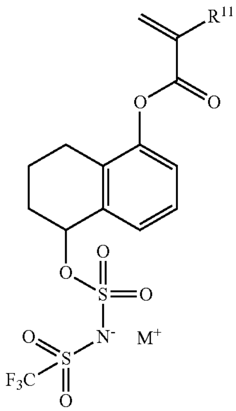
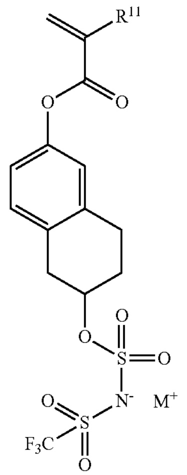
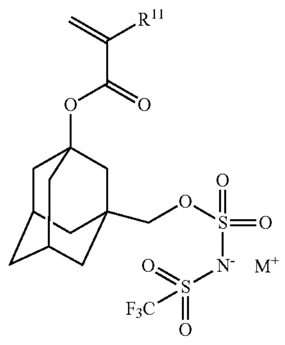
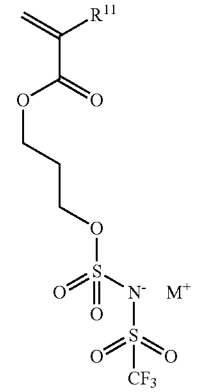
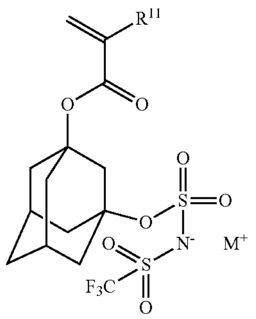
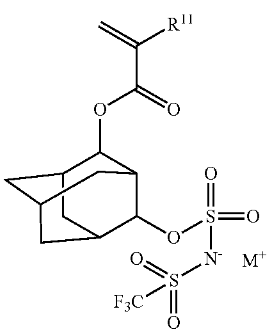
-continued
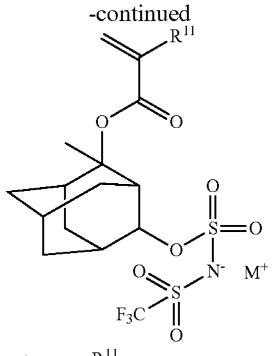
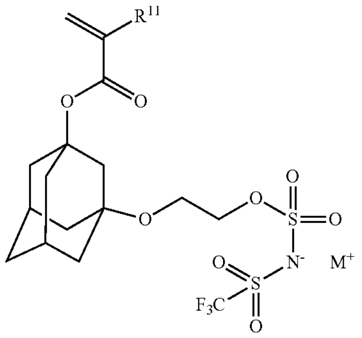
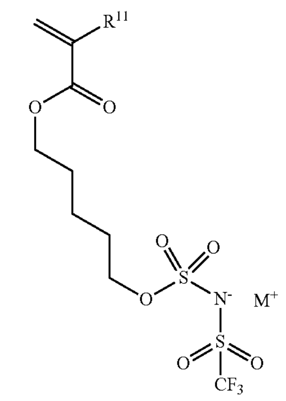
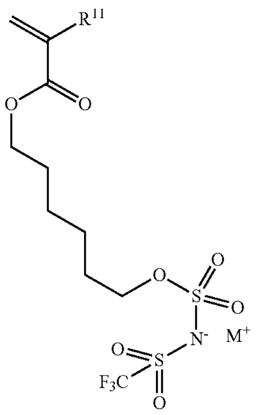
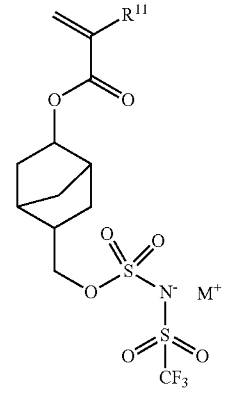
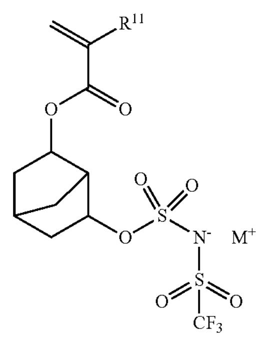

-continued
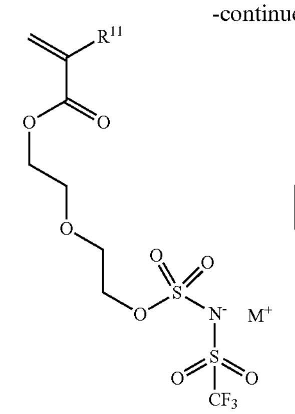
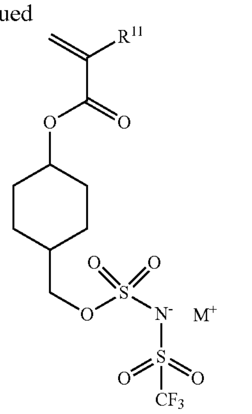
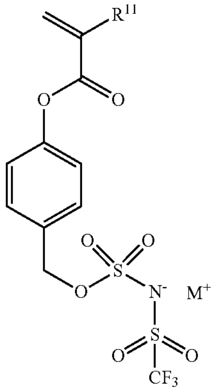
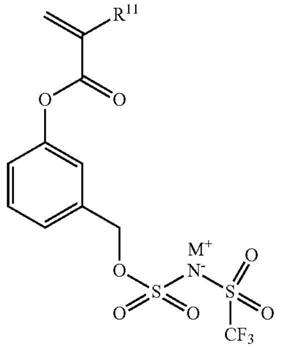
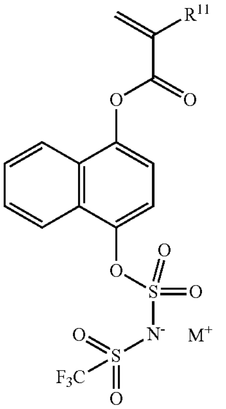
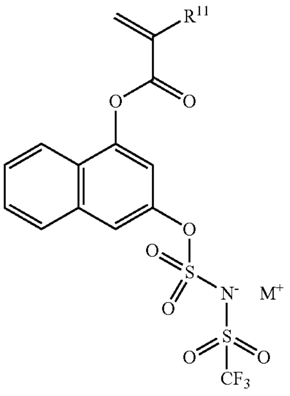
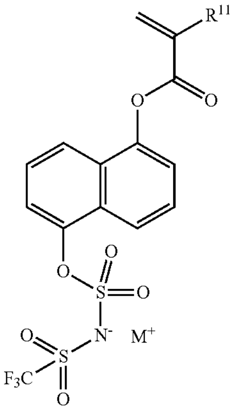
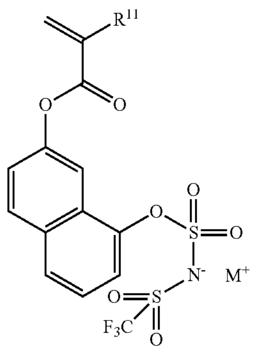
-continued
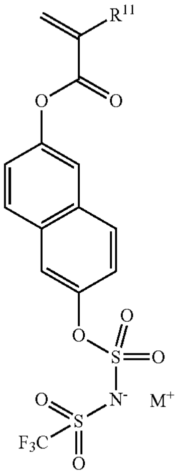
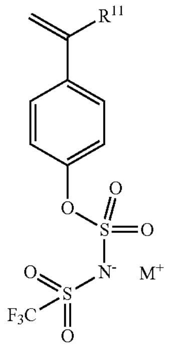
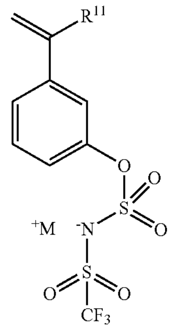
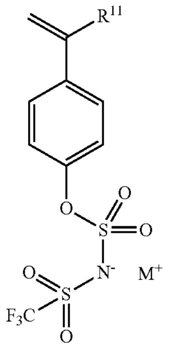
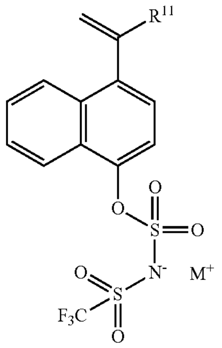
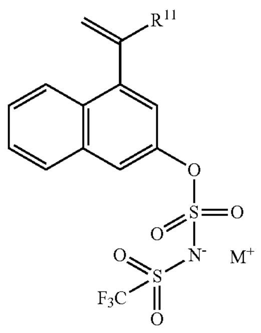
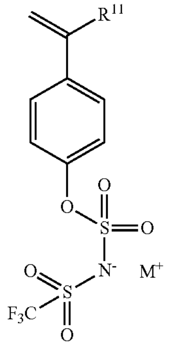
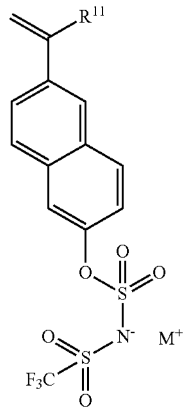
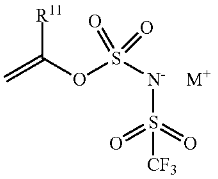

-continued
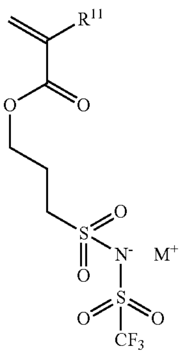
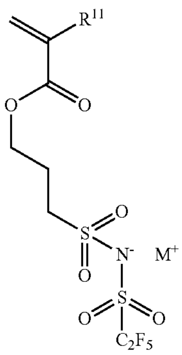
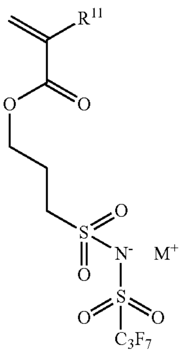
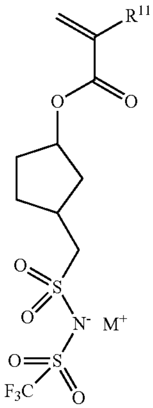
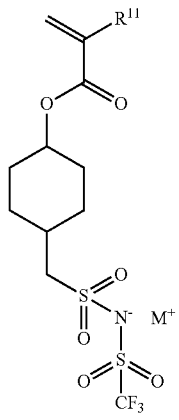
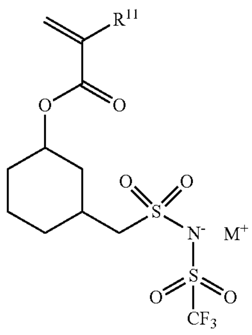
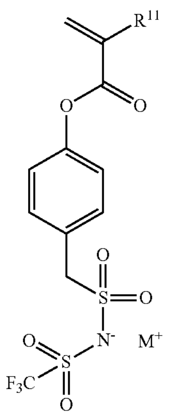
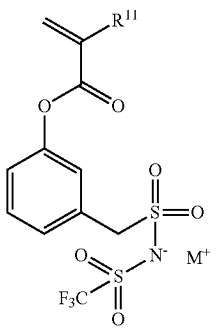
-continued
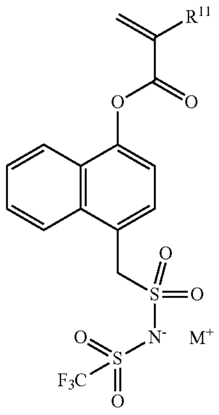
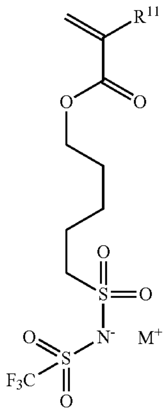
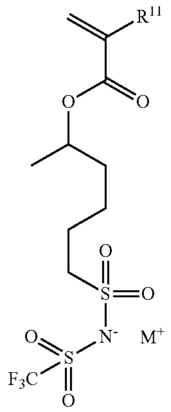
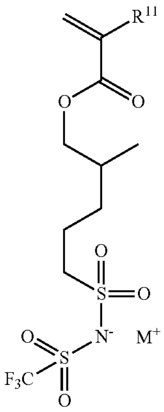
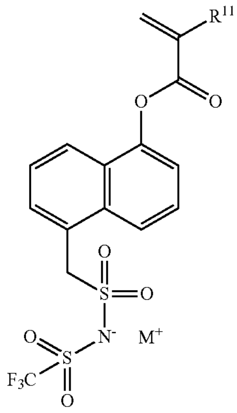
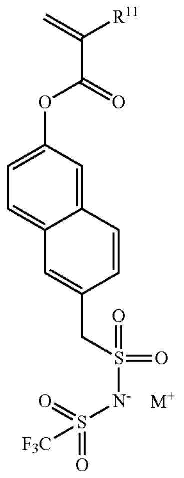
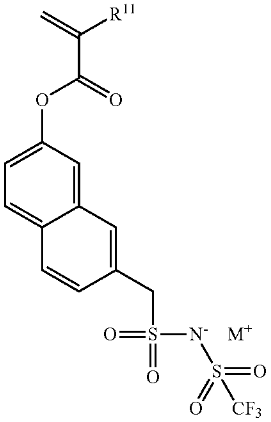
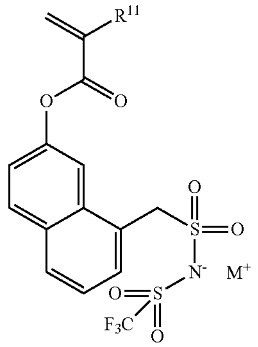

-continued
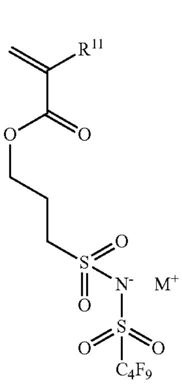
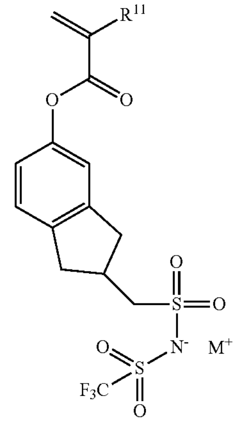
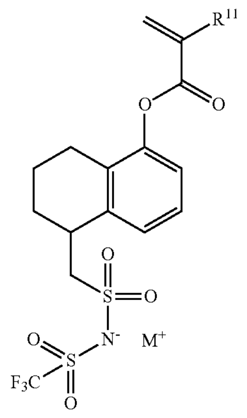
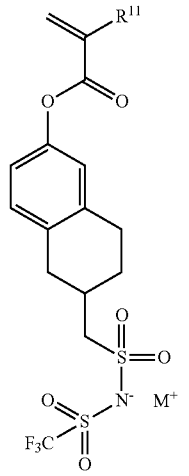
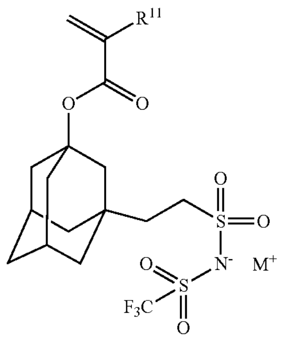
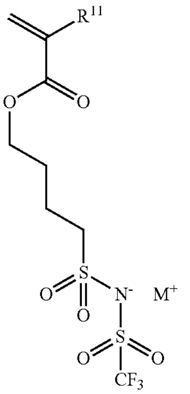
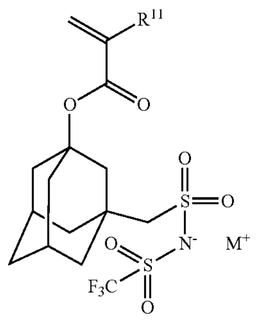
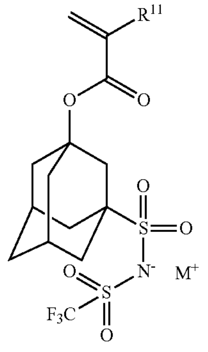
-continued
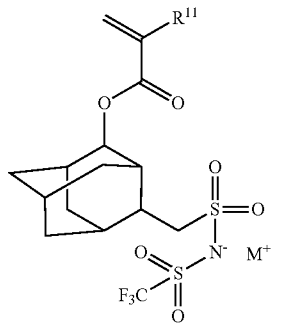
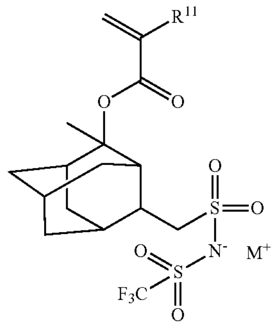
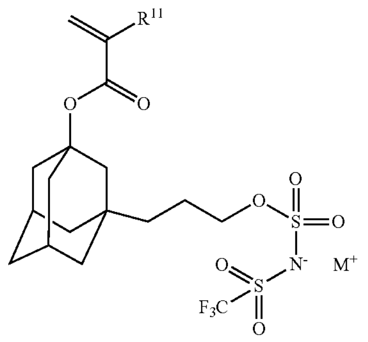
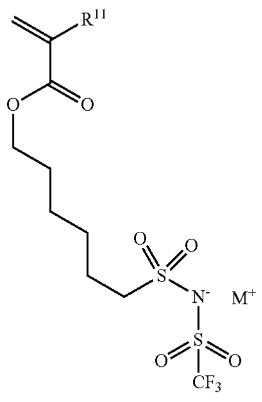
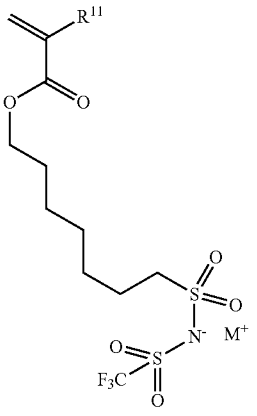
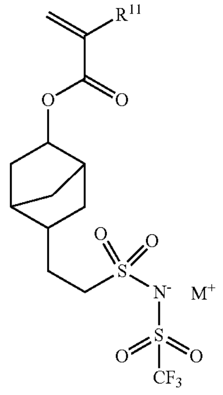
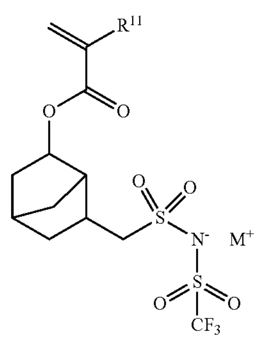

-continued
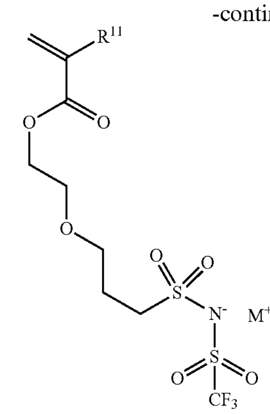
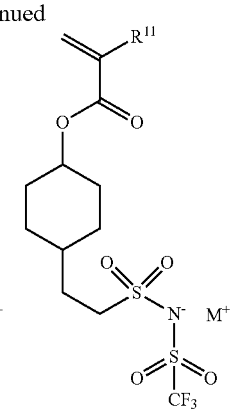
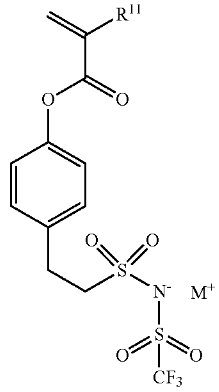
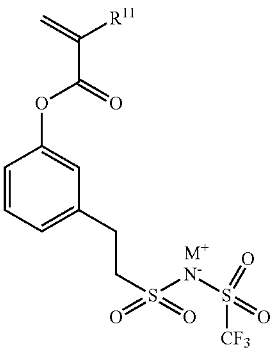
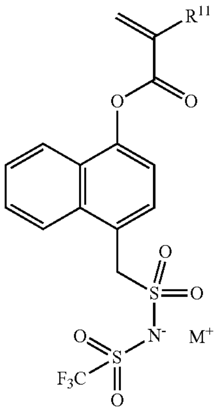
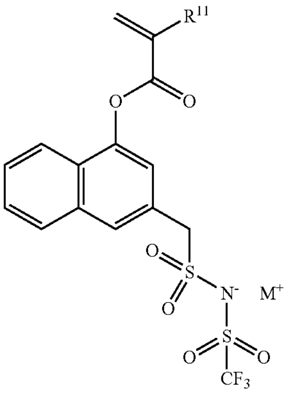
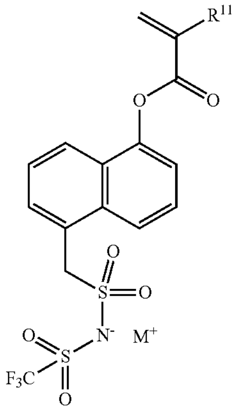
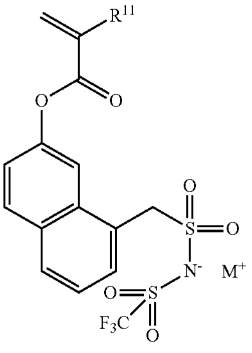
-continued
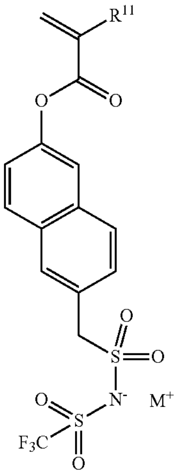
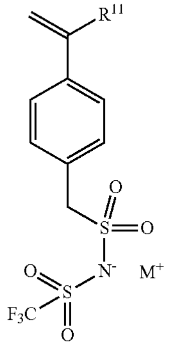
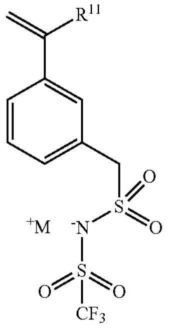
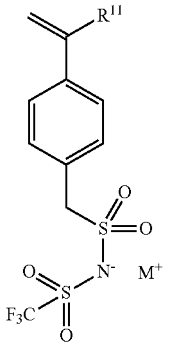
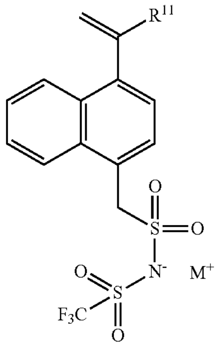
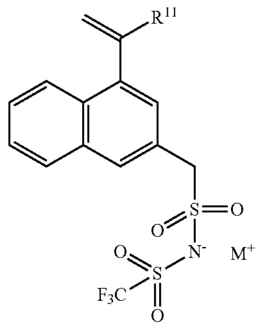
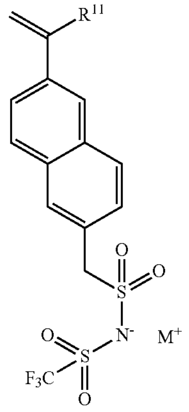
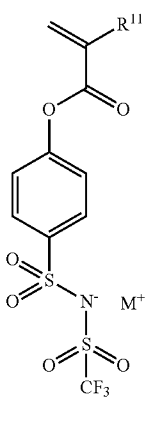
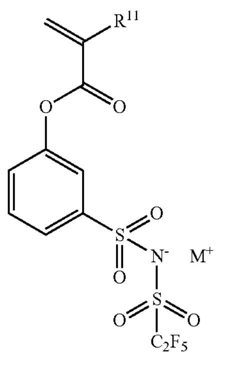

-continued
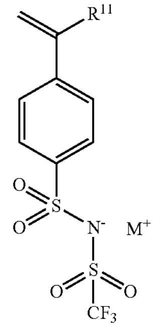
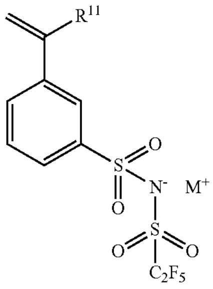
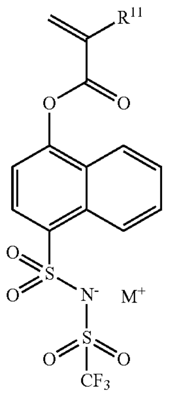
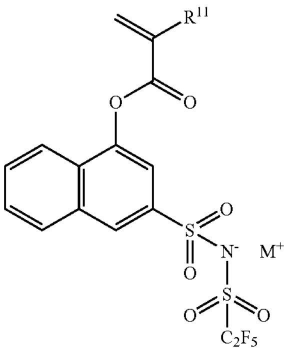
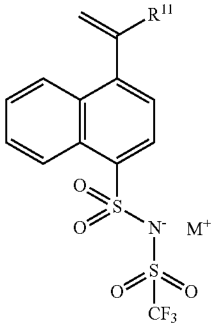
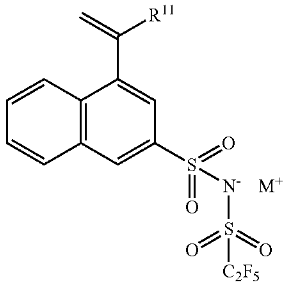
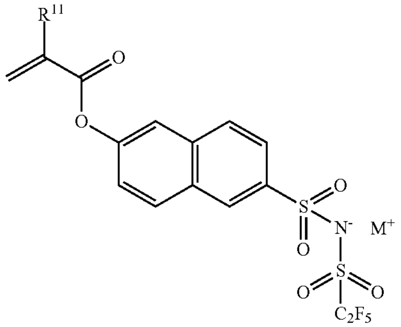
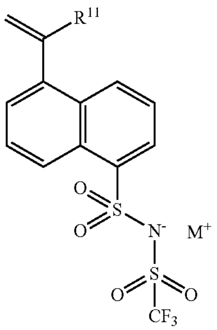
-continued
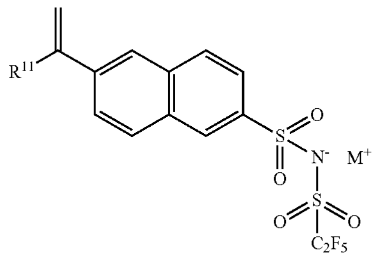
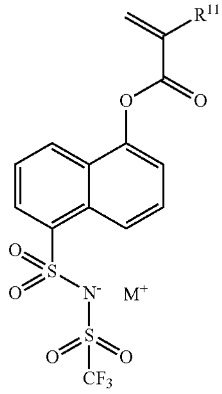
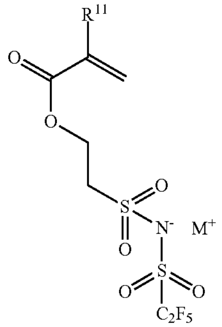
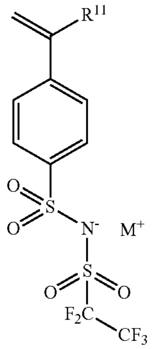
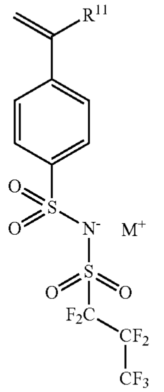
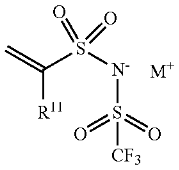
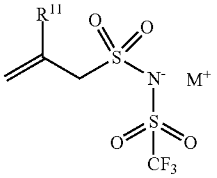
The repeating unit-a7 shown by the general formula (2) can be obtained from N-carbonyl-fluorosulfonamide salt monomers specifically exemplified below.
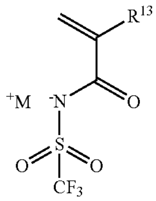
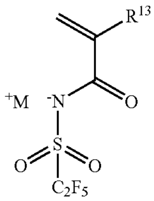
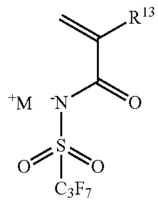

-continued
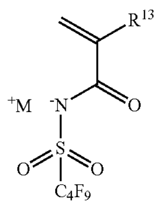
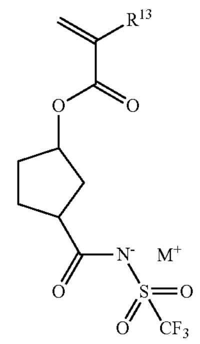
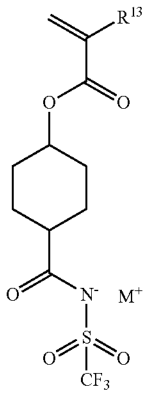
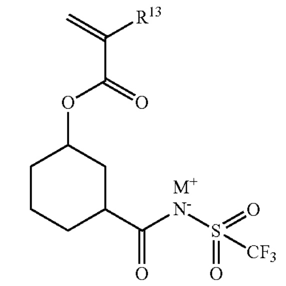
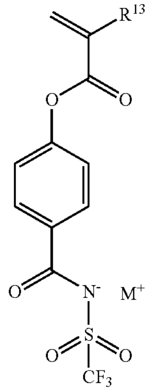
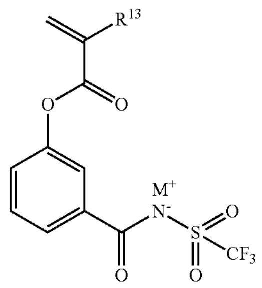
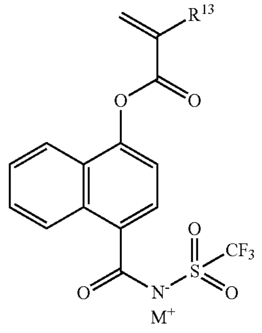
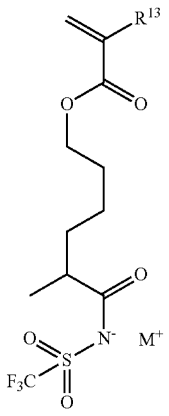
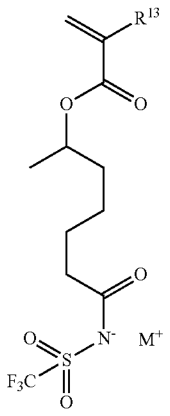
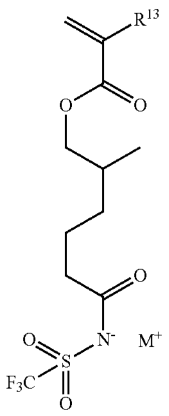
-continued
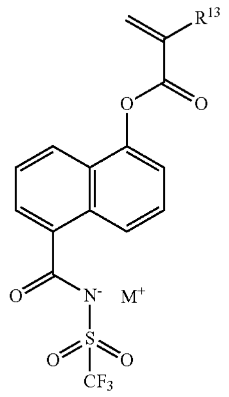
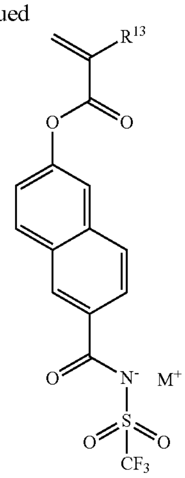
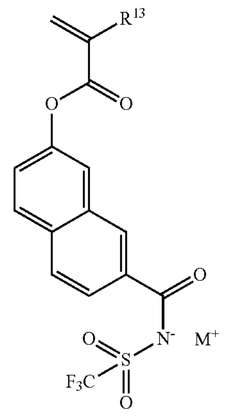
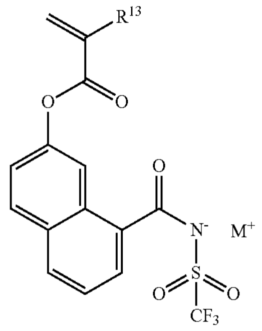
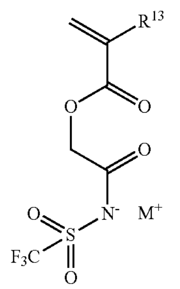
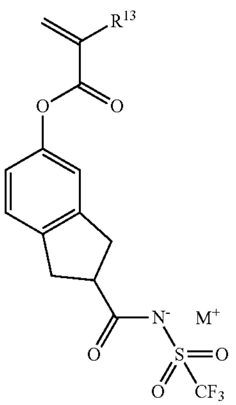
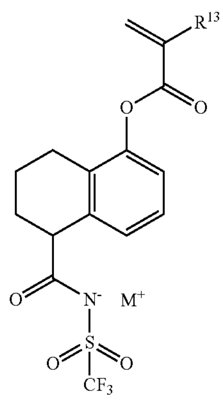
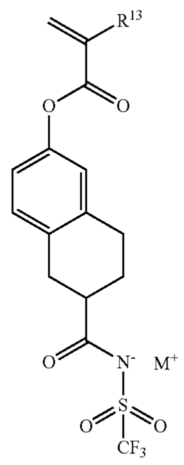

-continued
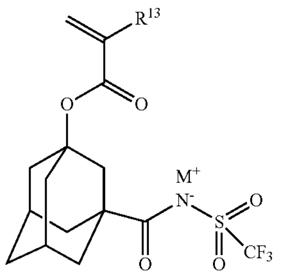
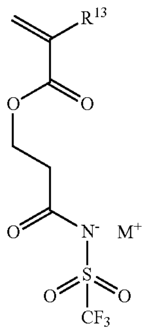
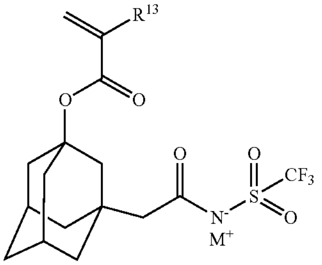
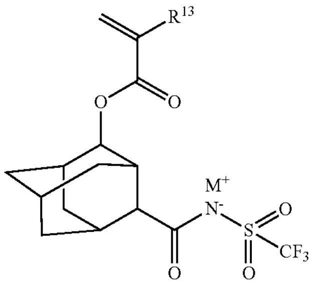
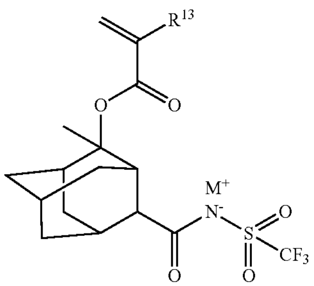
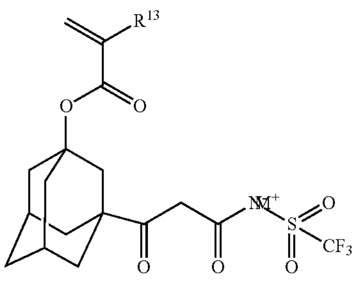
-continued
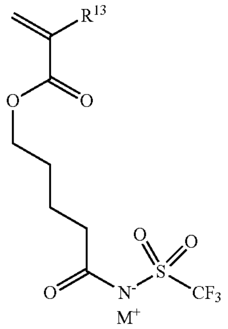
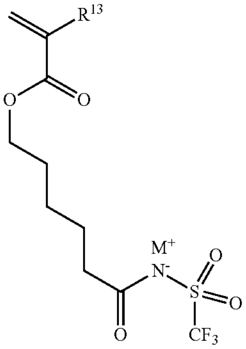
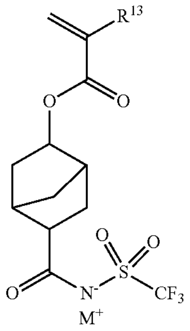
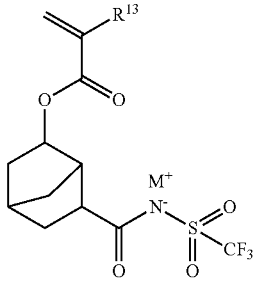
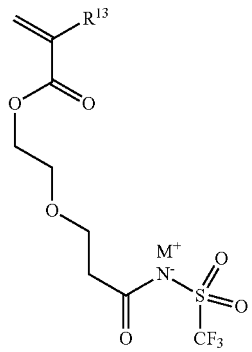
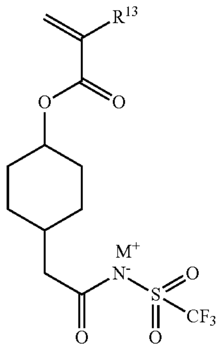
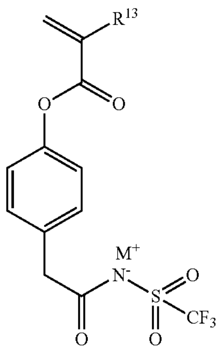
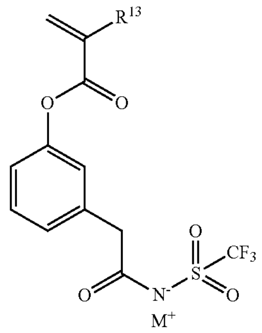
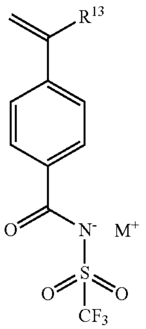
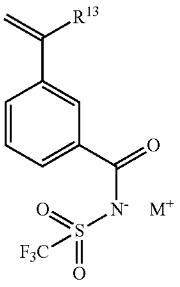

-continued

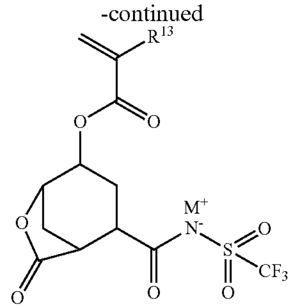

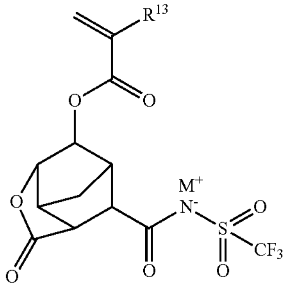

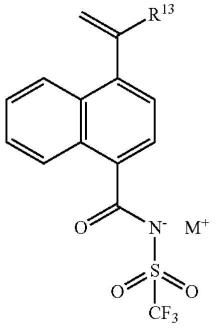

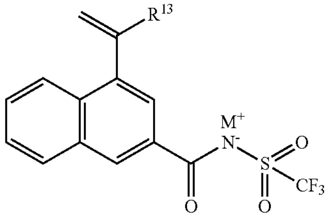

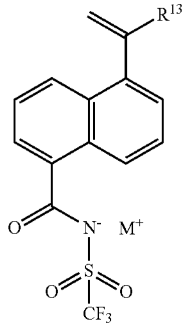

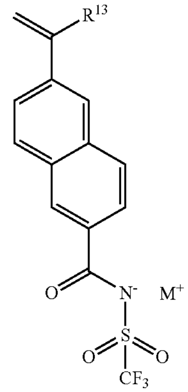

In the formulae, $R^1$, $R^3$, $R^5$, $R^8$, $R^{10}$, $R^{11}$, and $R^{13}$ are as defined above.

Furthermore, the component (A) preferably contains an ammonium ion (ammonium cation) shown by the following general formula (3) as an ammonium ion for forming the ammonium salts.

(3)

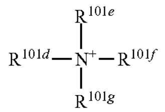

In the general formula (3), $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom. $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the general formula (3) within the ring.

Specific examples of the ammonium ion shown by the general formula (3) include the following.

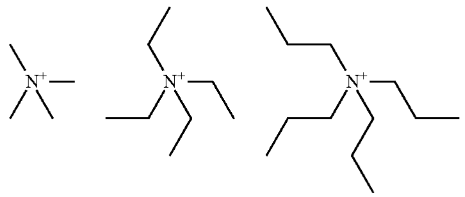

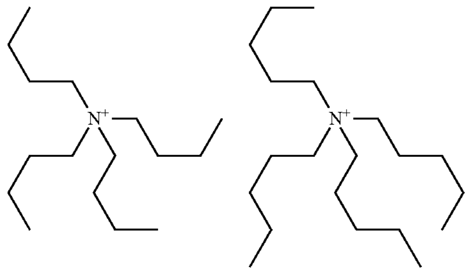

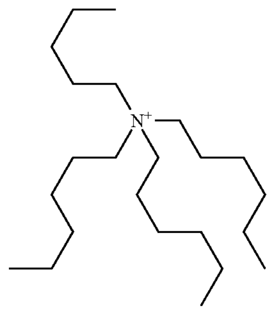

-continued
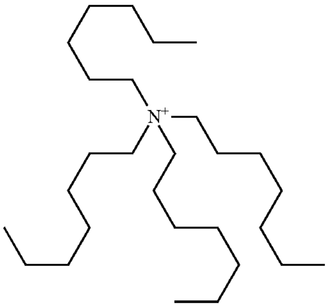
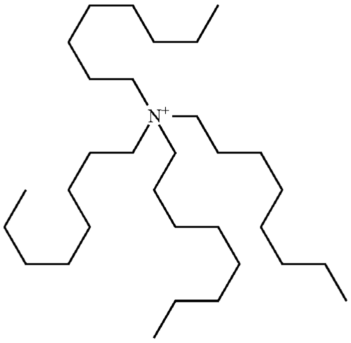
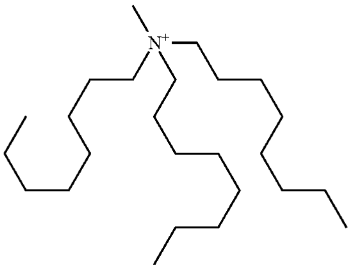
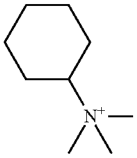
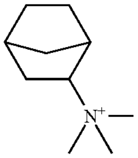
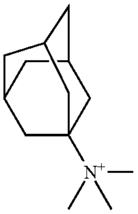
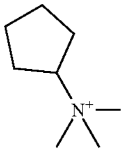
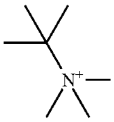
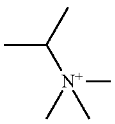
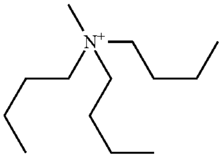
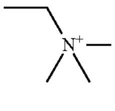
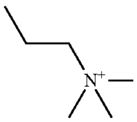
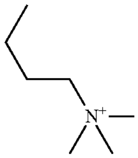
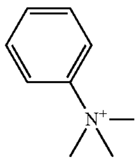
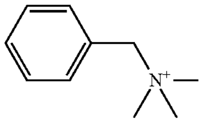
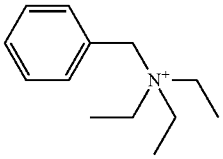
-continued
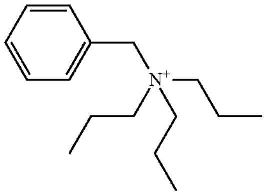
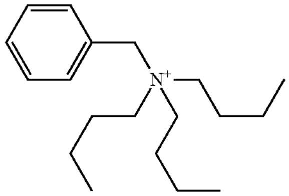
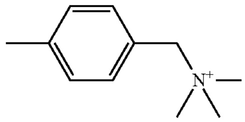
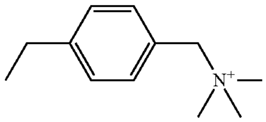
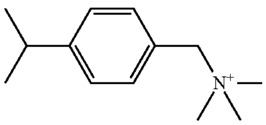
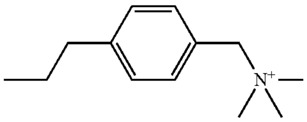
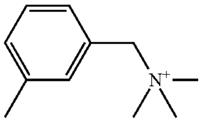
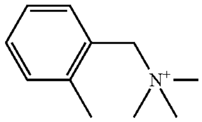
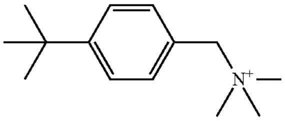
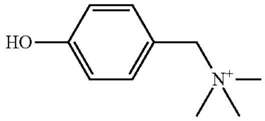
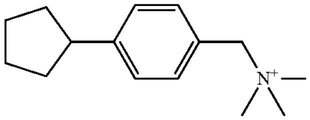
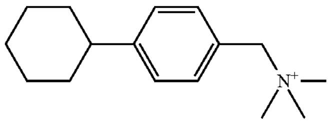
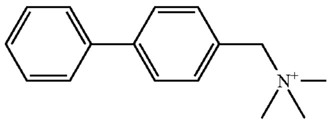
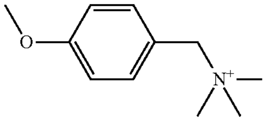
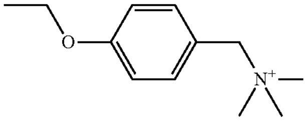
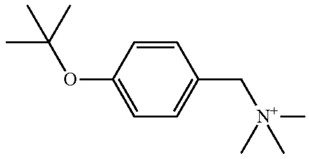
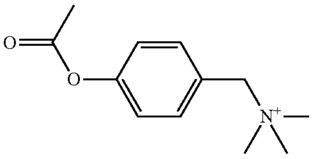
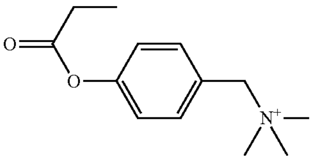

-continued
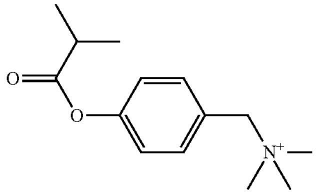
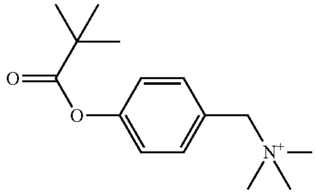
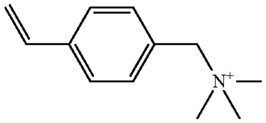
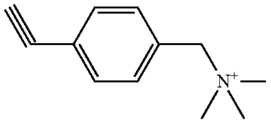
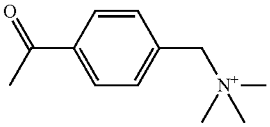
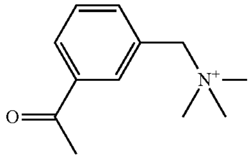
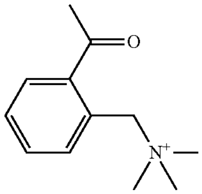
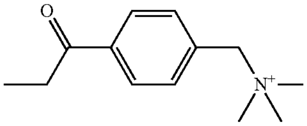
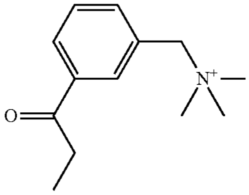
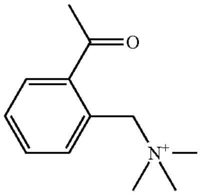
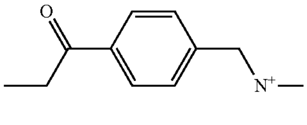
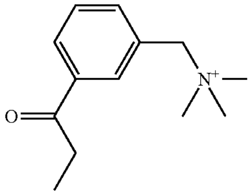
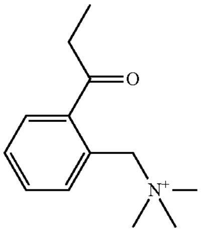
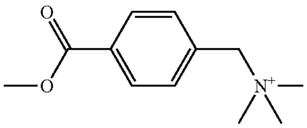
-continued
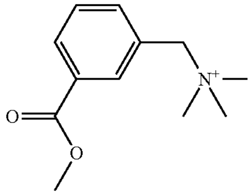
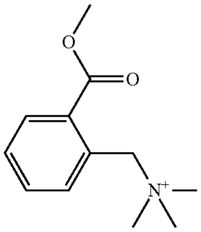
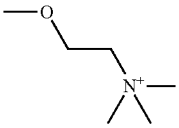
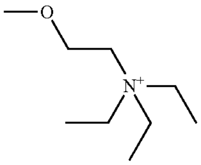
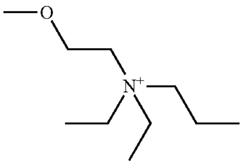
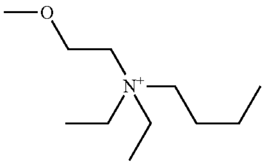
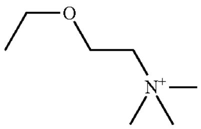
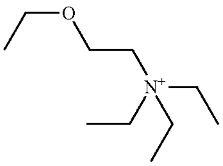
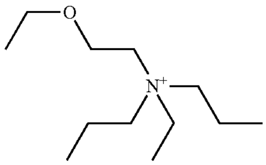
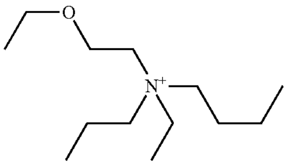
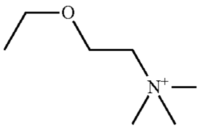
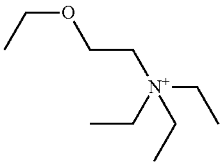
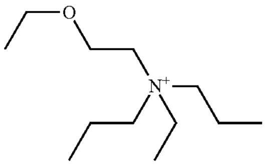
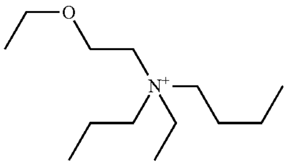
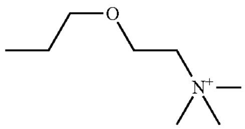
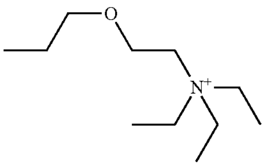
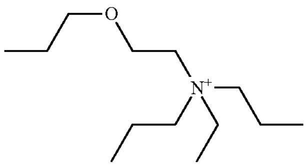
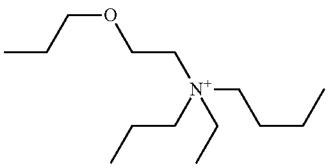

-continued
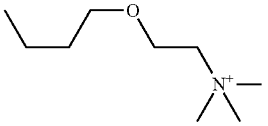
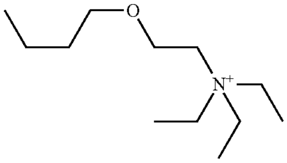
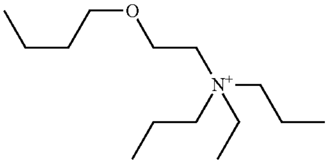
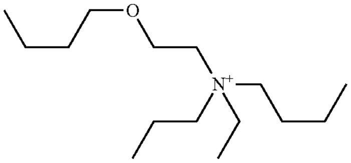
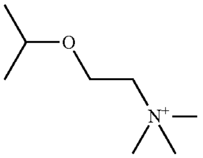
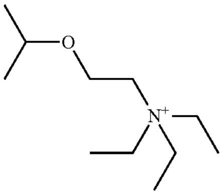
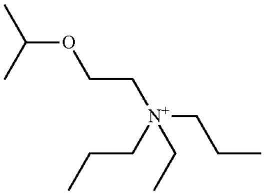
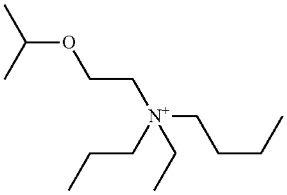
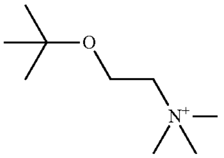
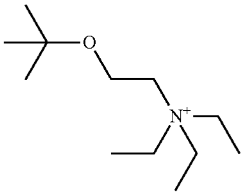
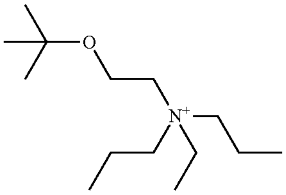
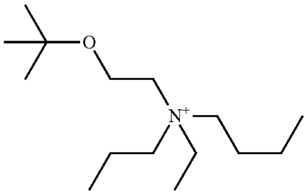
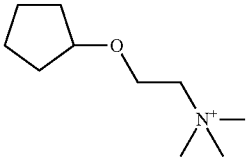
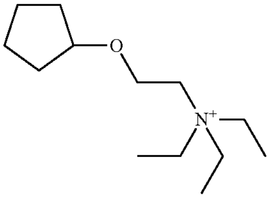
-continued
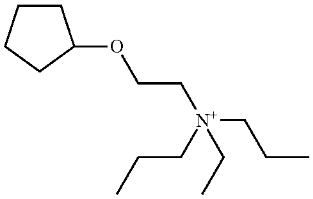
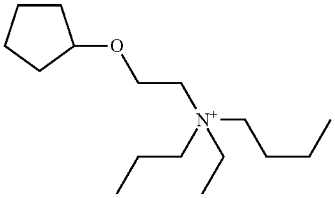
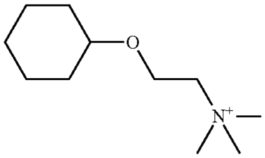
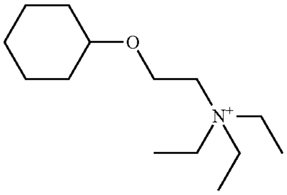
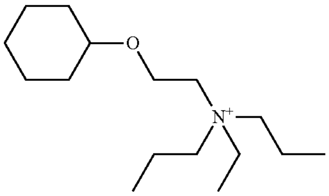
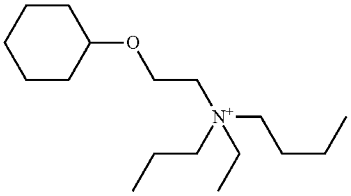
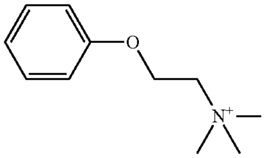
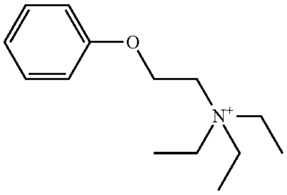
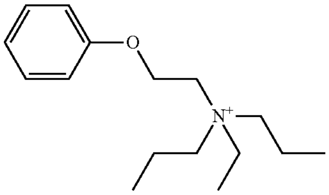
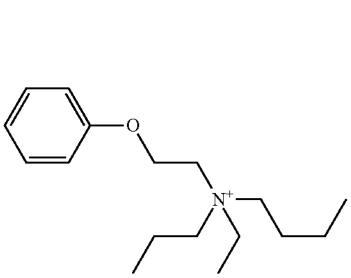

-continued
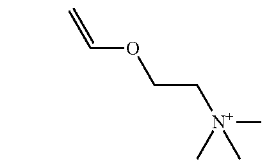
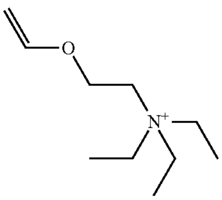
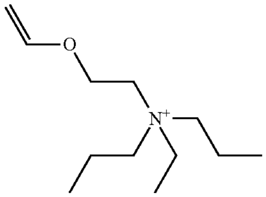
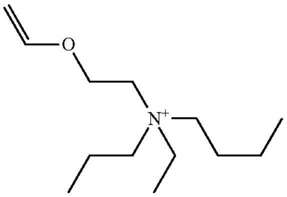
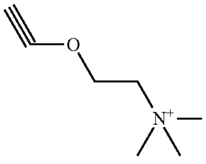
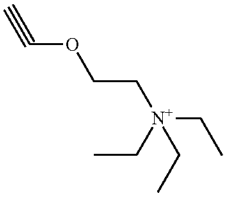
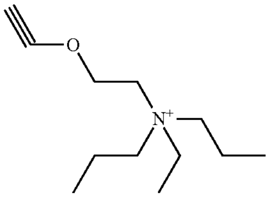
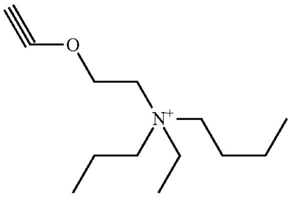
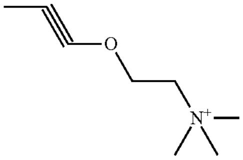
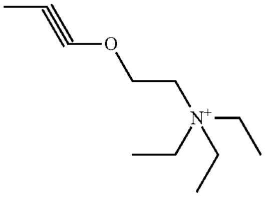
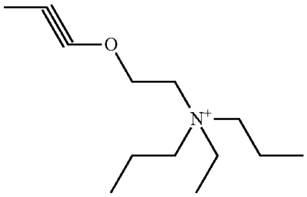
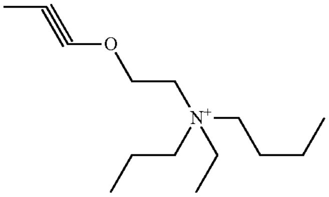
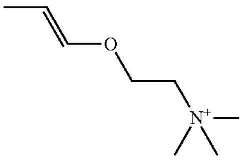
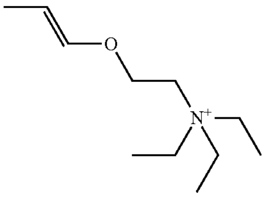
-continued
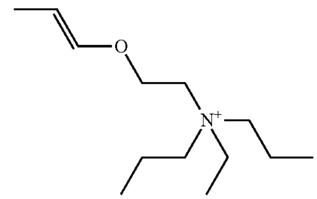
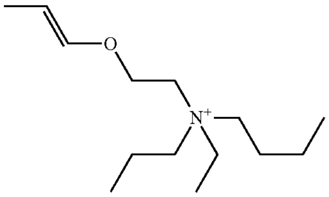
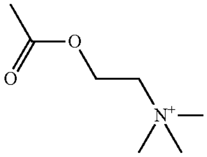
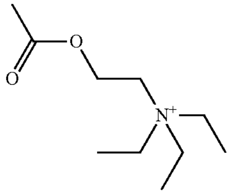
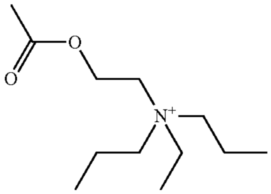
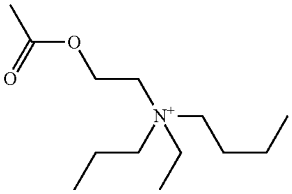
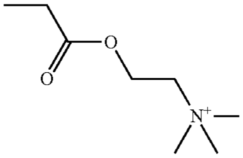
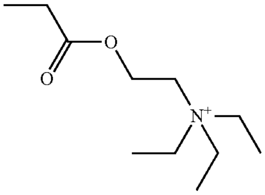
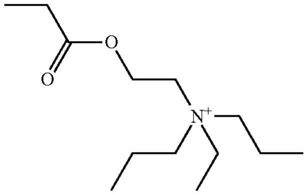
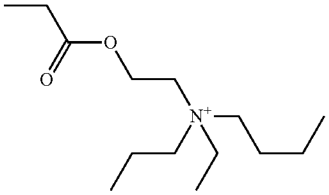
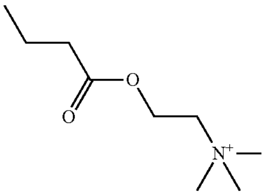
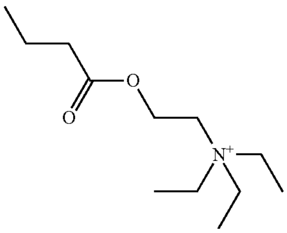

-continued
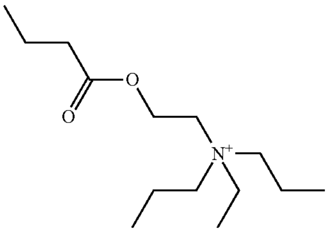
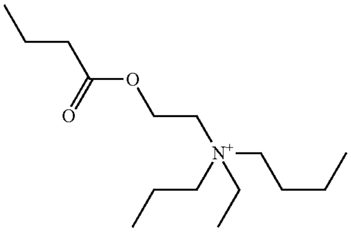
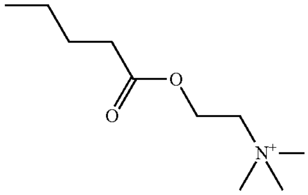
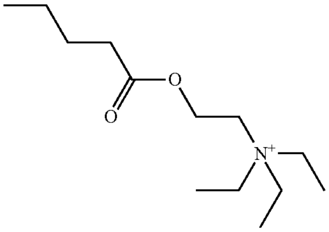
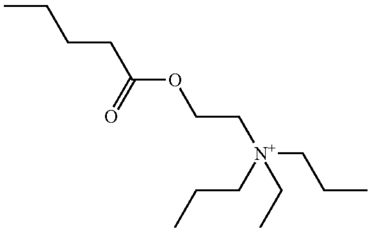
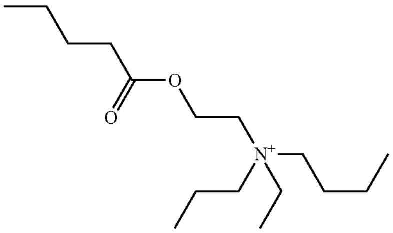
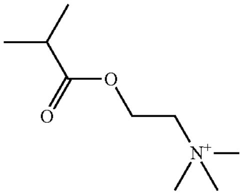
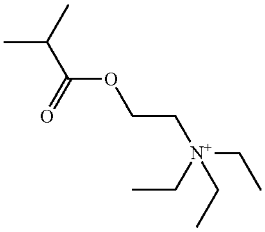
-continued
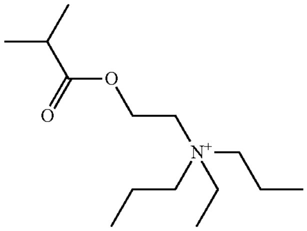
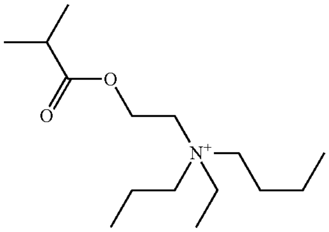
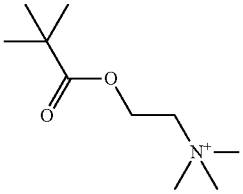
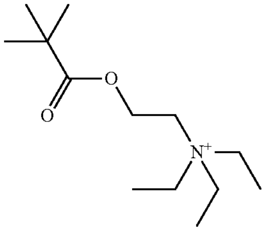
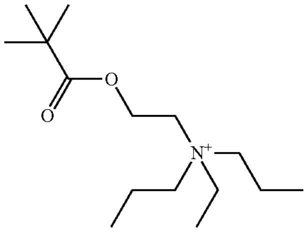
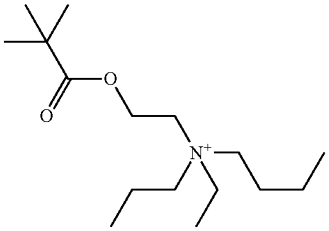
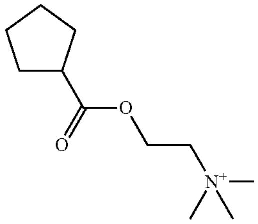
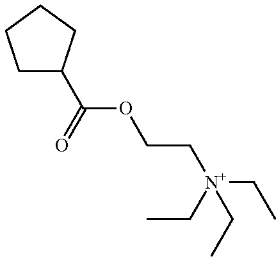
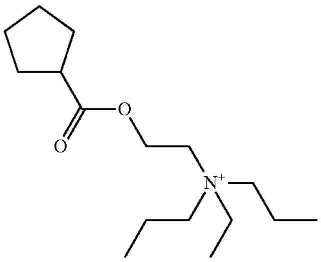

-continued
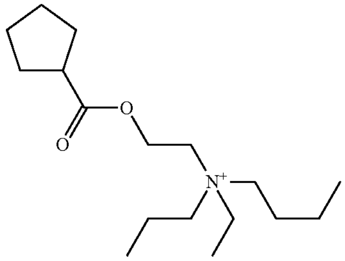
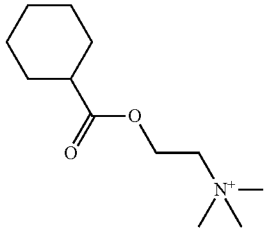
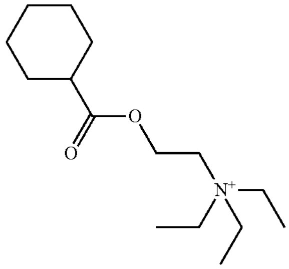
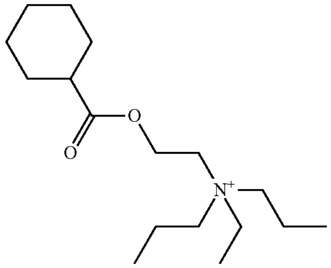
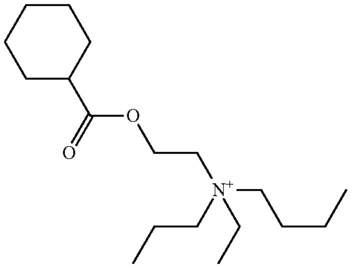
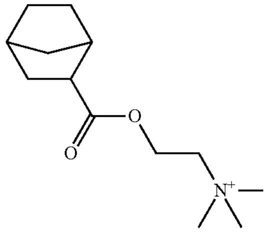
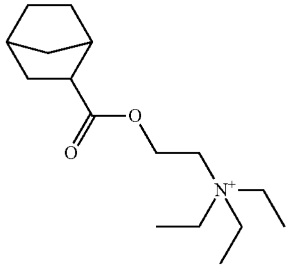
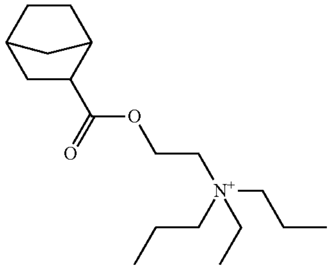
-continued
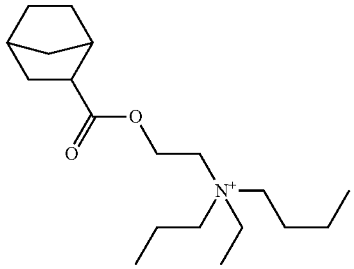
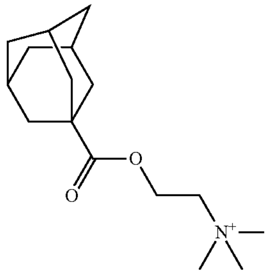
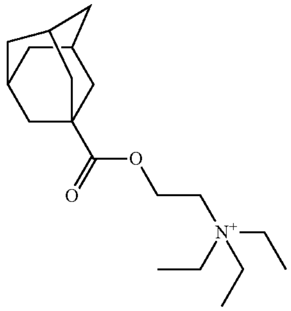
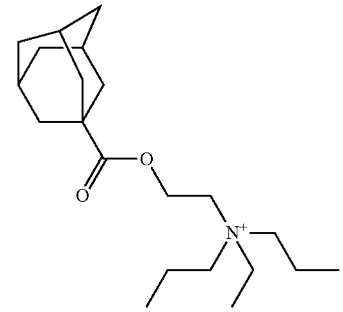
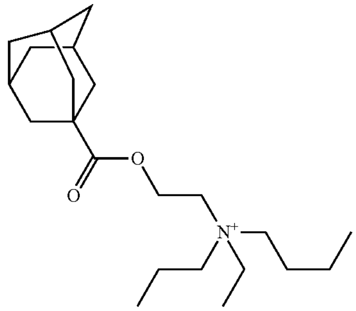
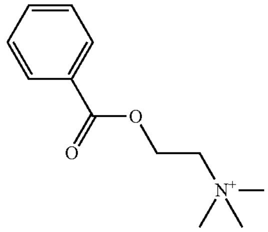
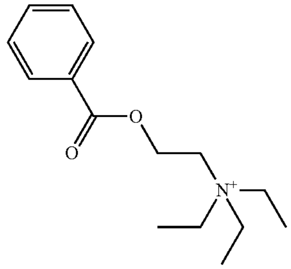

-continued
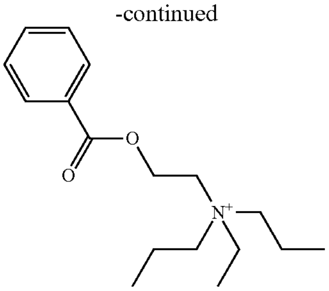
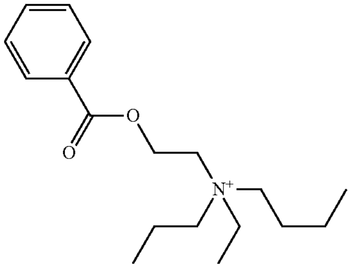
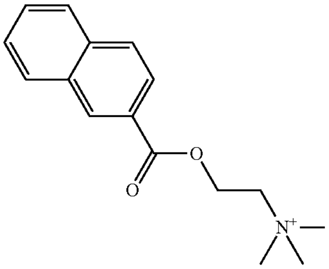
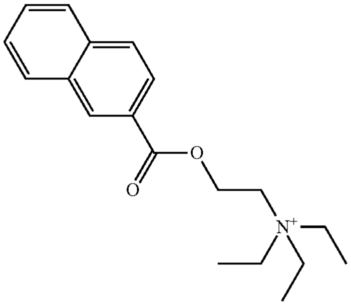
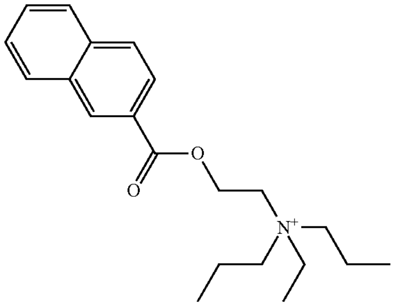
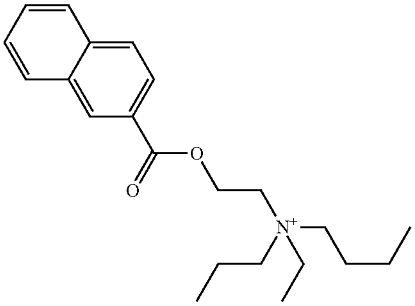
-continued
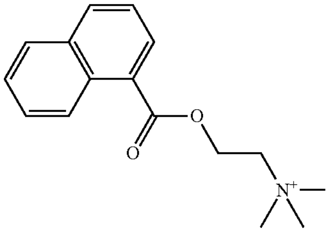
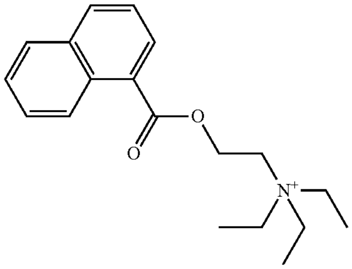
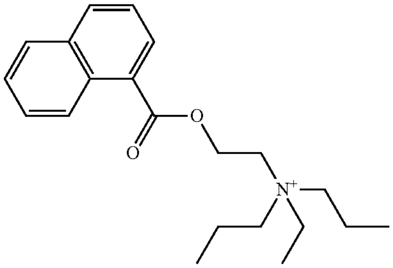
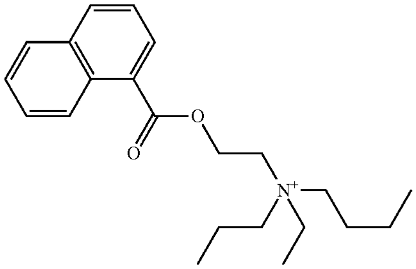
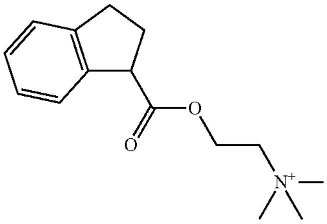
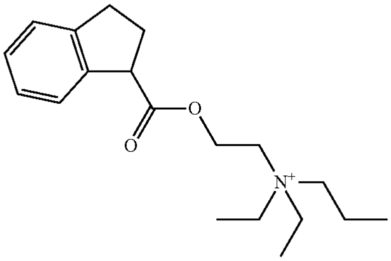

-continued
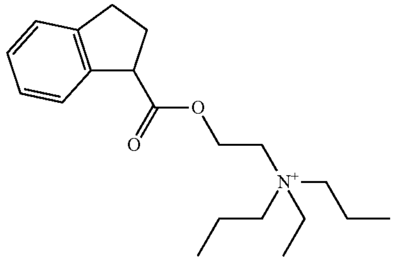
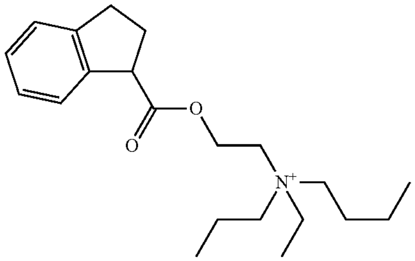
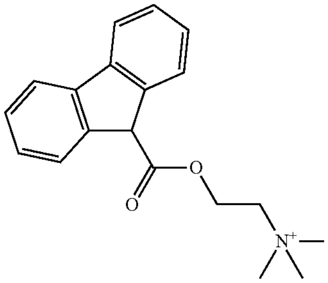
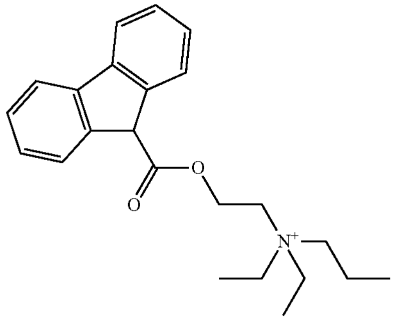
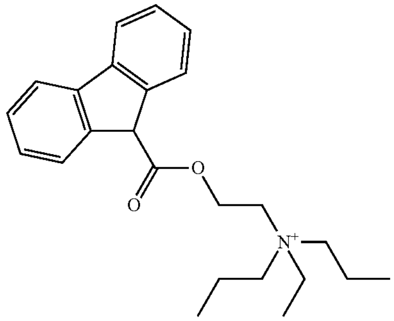
-continued
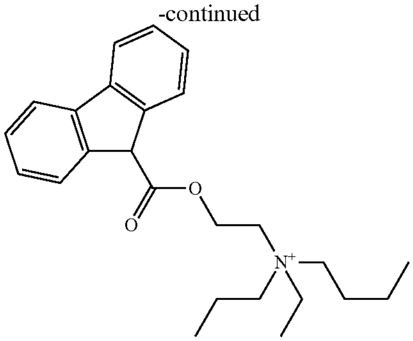
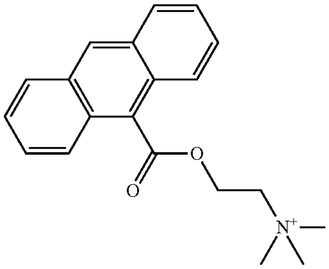
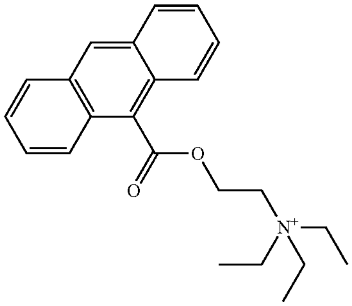
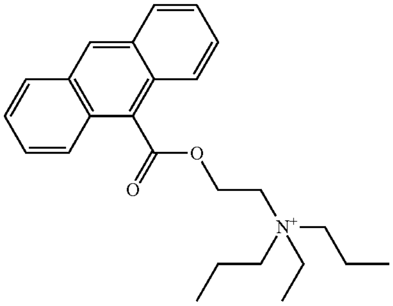
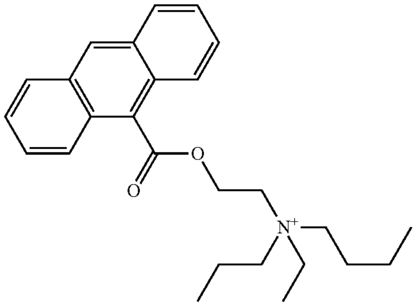
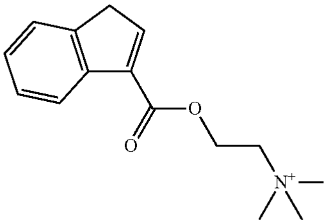

-continued
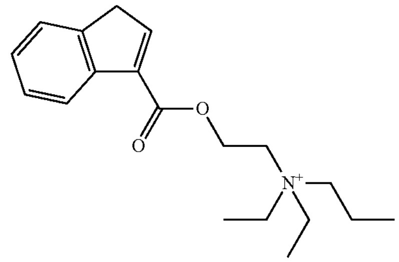
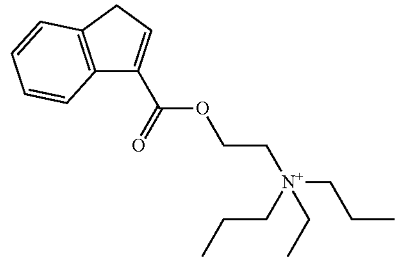
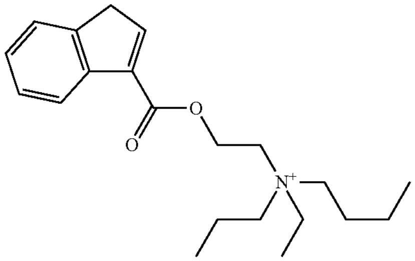
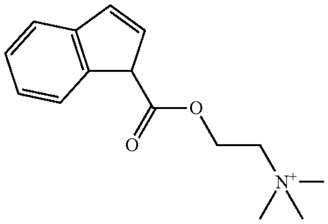
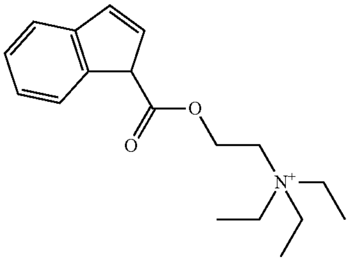
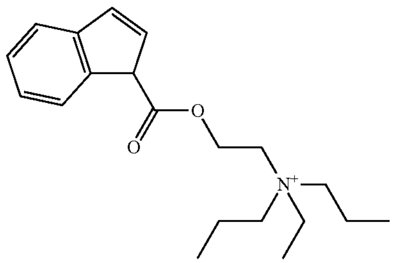
-continued
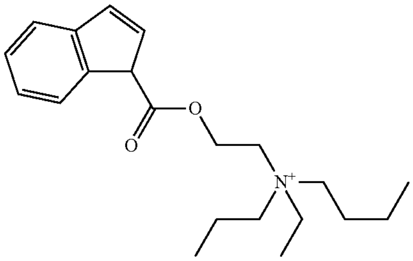
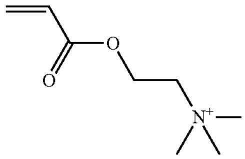
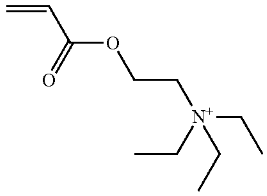
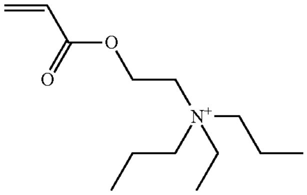
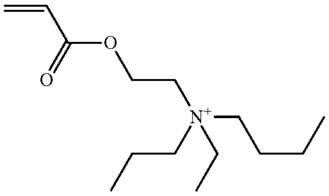
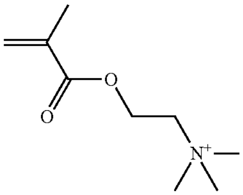
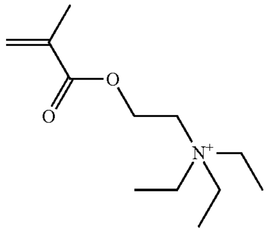
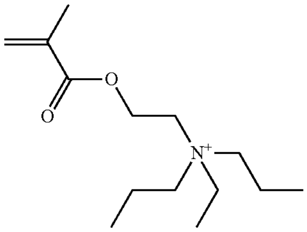
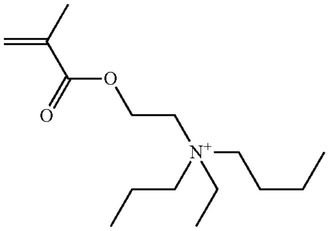

-continued
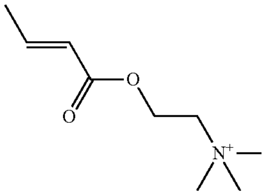
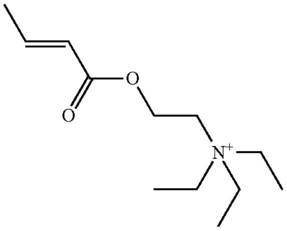
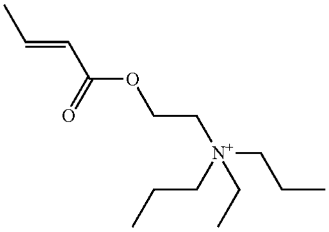
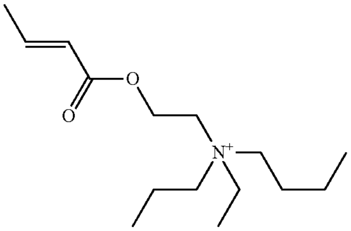
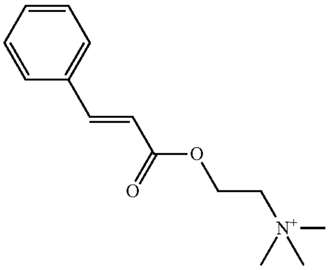
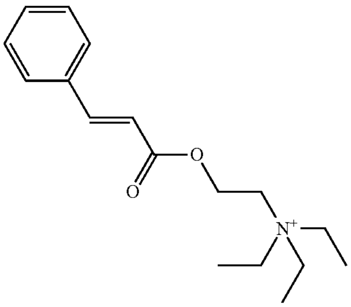
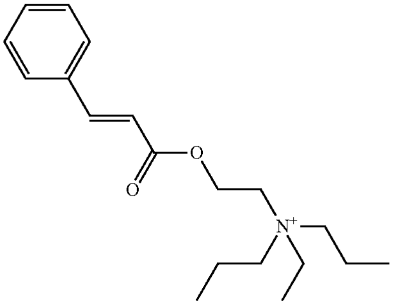
-continued
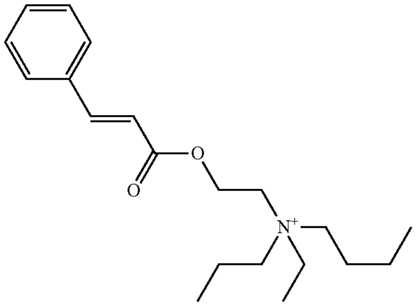
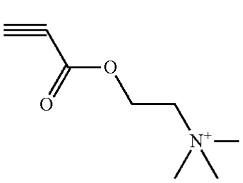
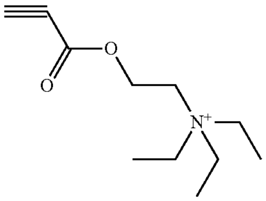
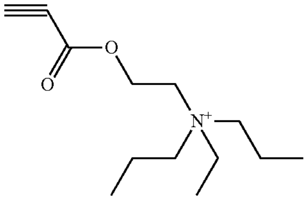
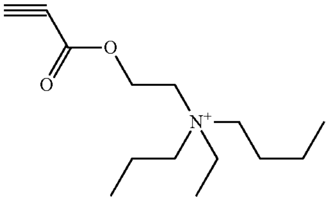
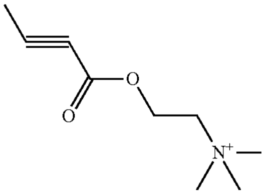
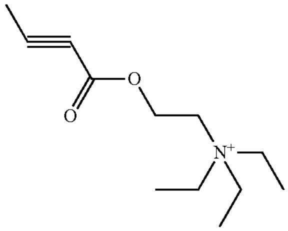
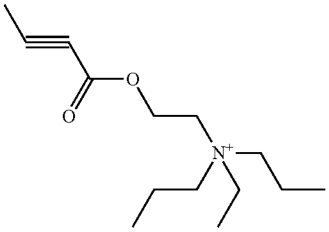
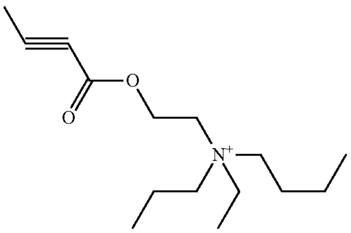

-continued
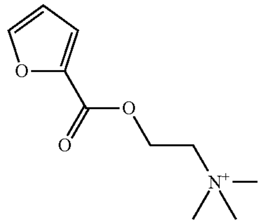
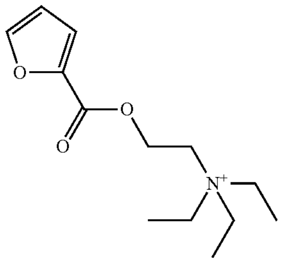
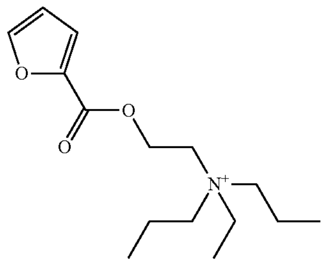
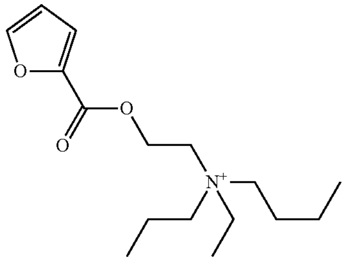
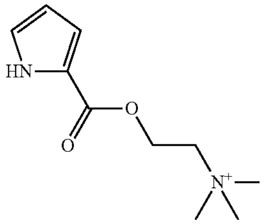
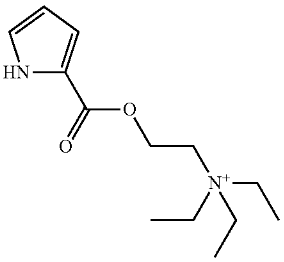
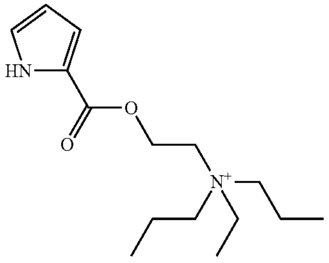
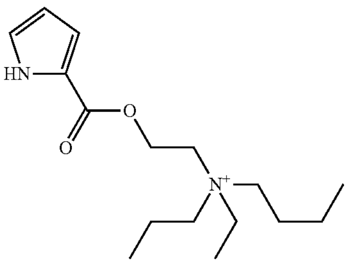
-continued
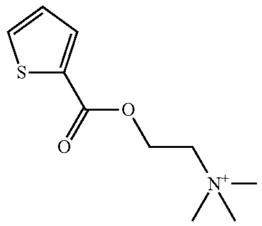
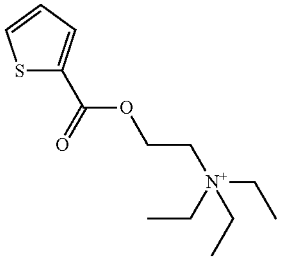
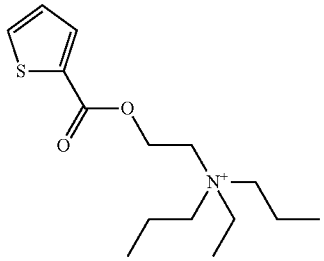
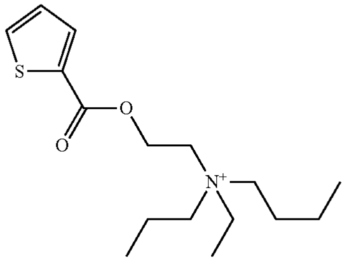
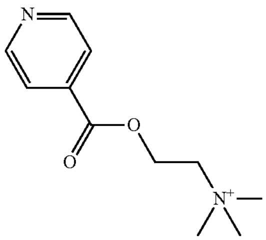
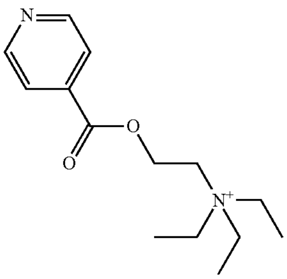
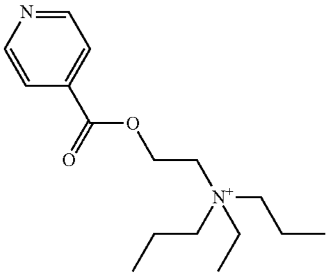
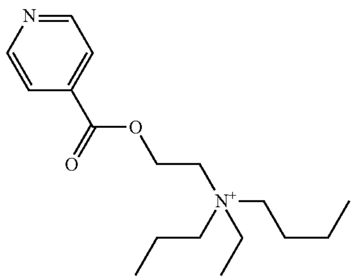

-continued
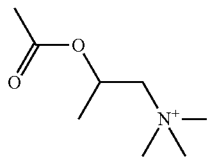
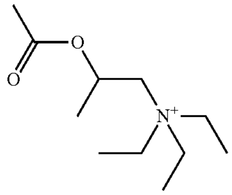
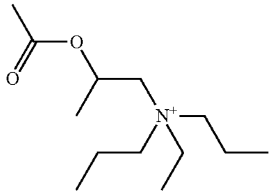
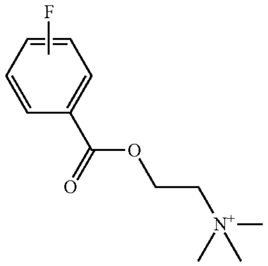
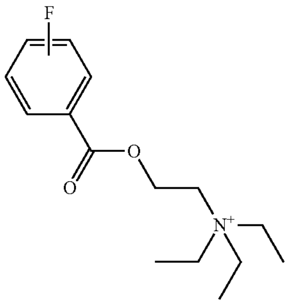
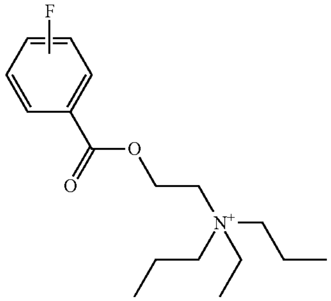
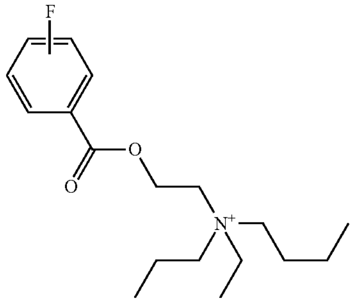
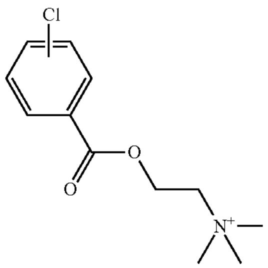
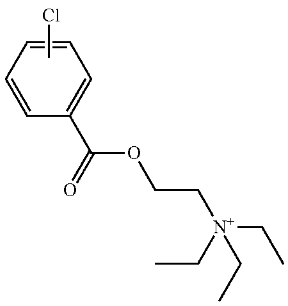
-continued
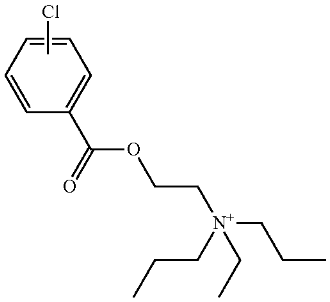
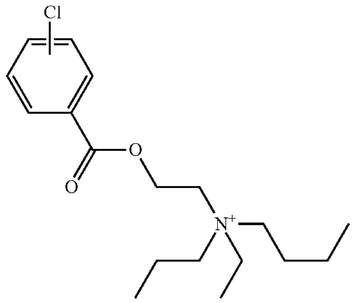
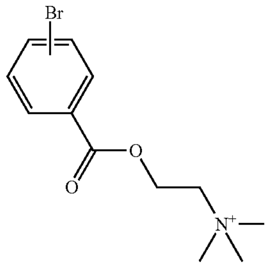
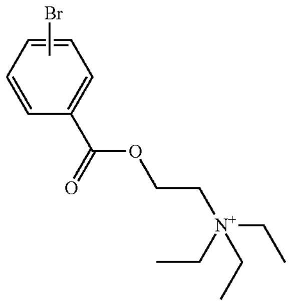
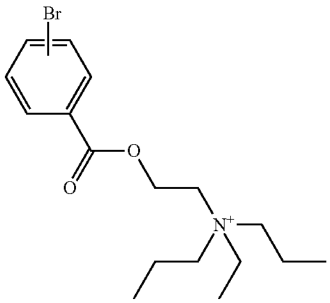
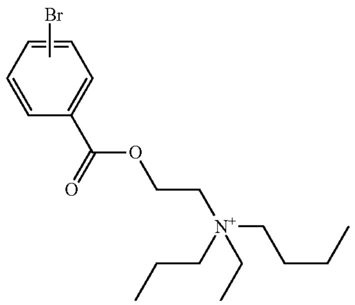

-continued
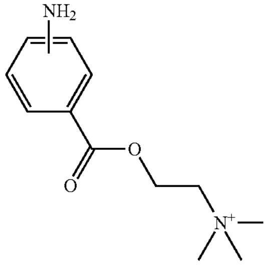
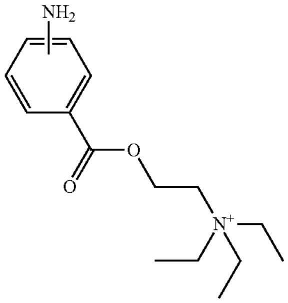
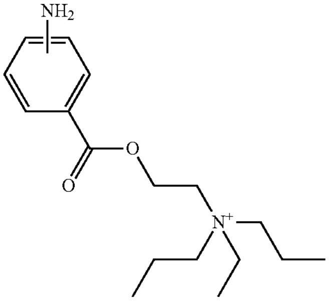
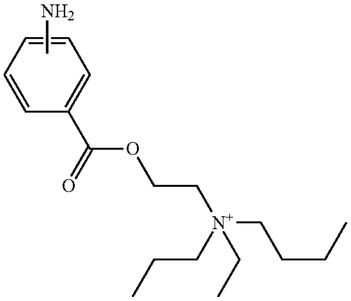
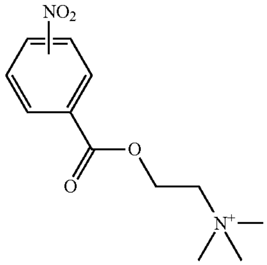
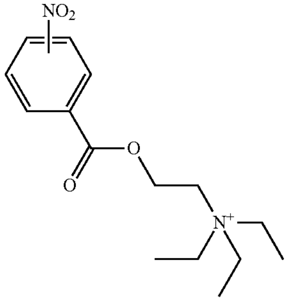
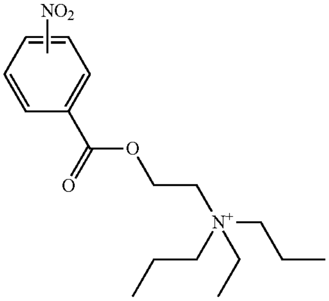
-continued
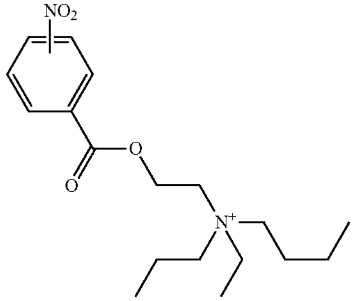
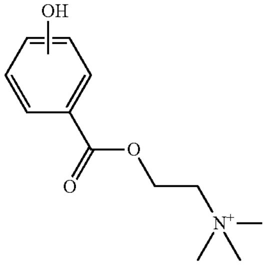
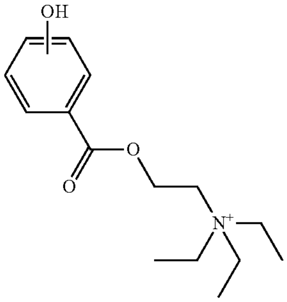
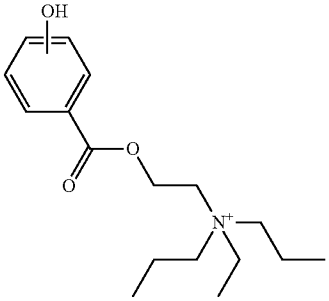
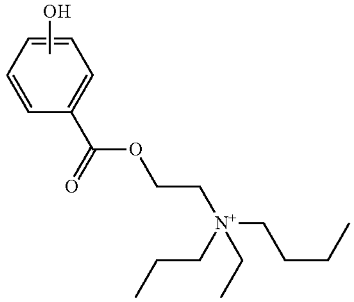
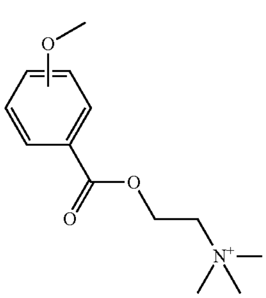
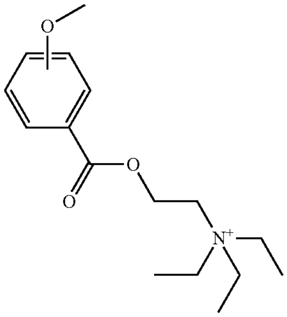

-continued
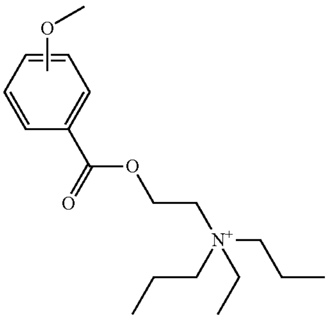
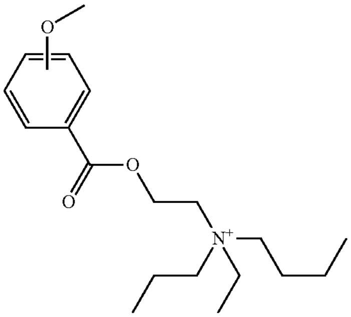
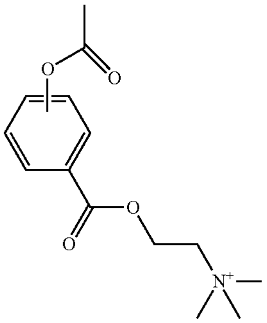
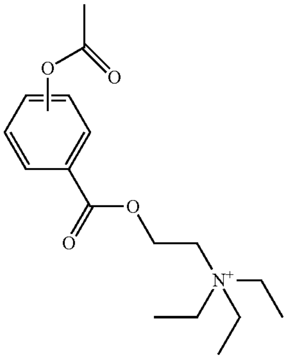
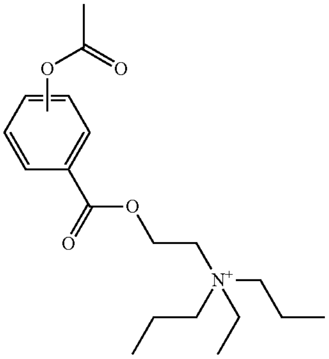
-continued
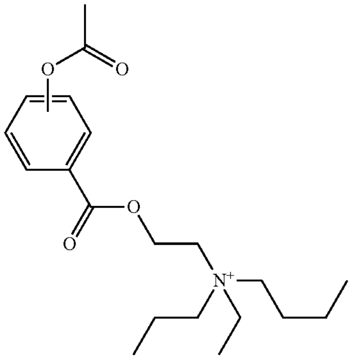
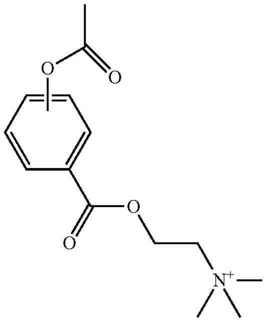
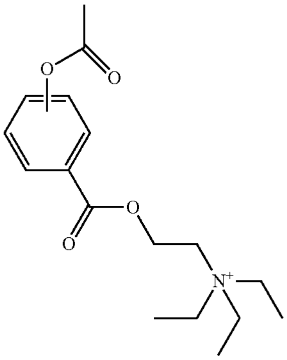
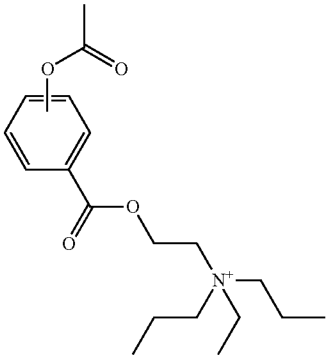
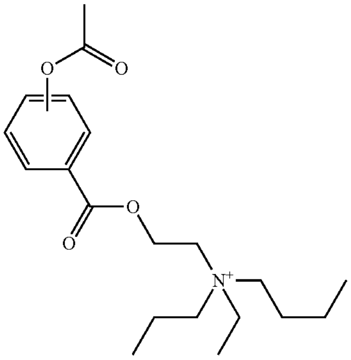
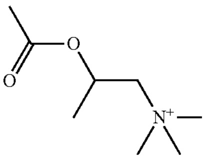
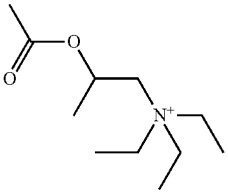

-continued
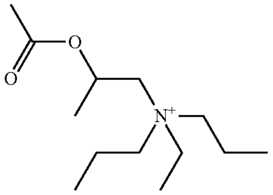
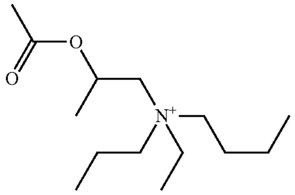
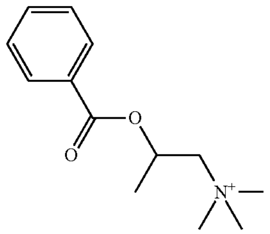
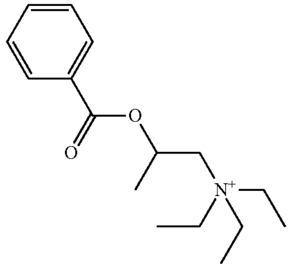
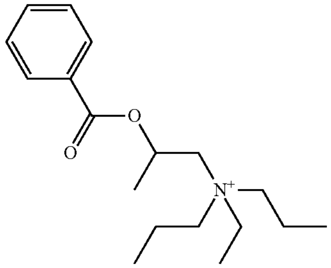
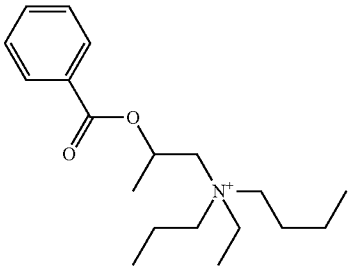
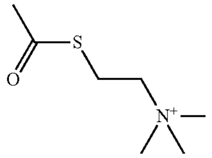
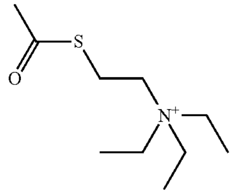
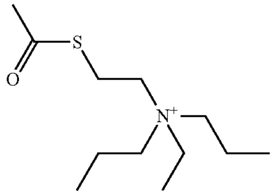
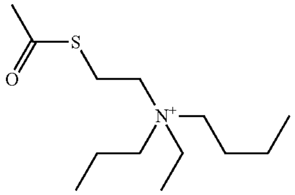
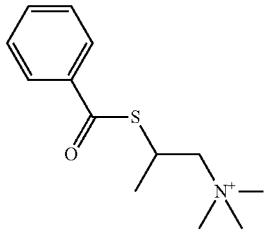
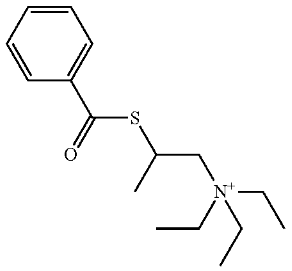
-continued
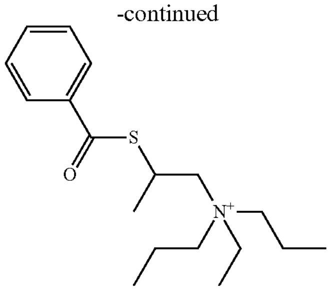
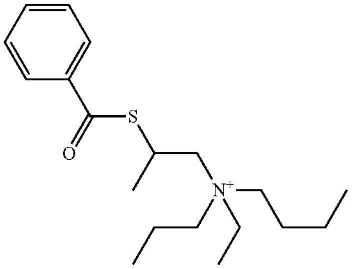
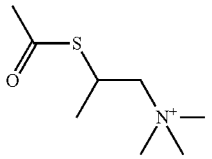
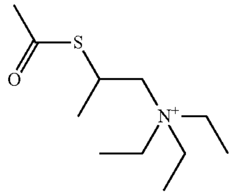
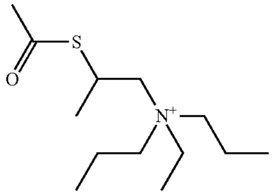
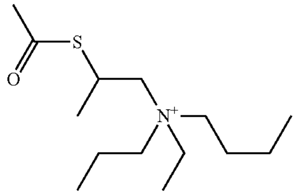
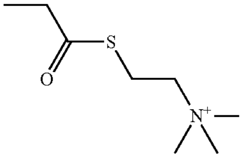
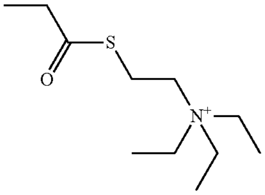
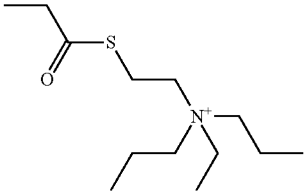
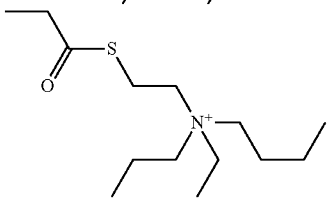
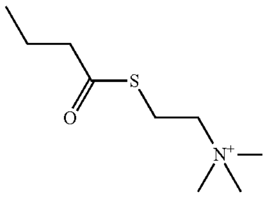
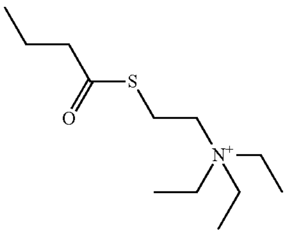

-continued
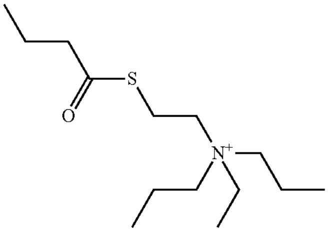
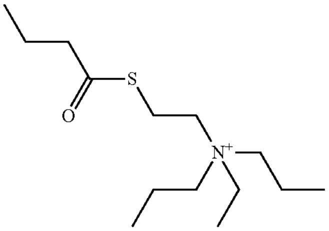
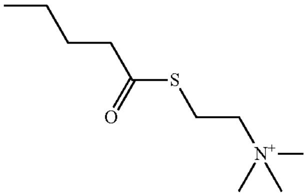
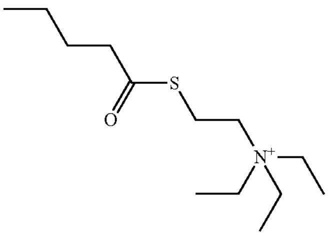
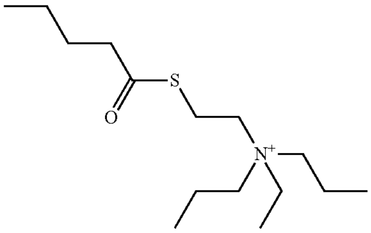
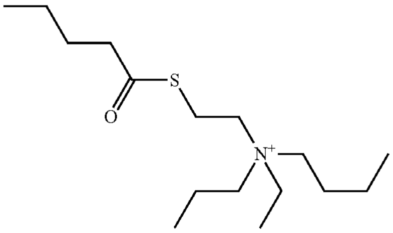
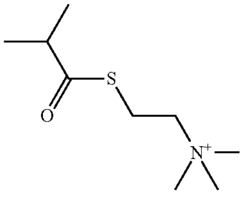
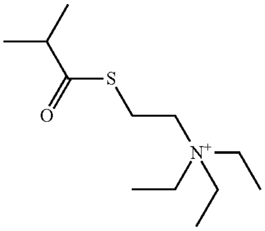
-continued
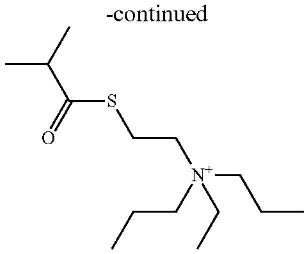
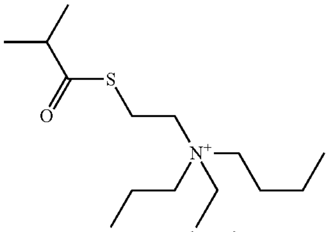
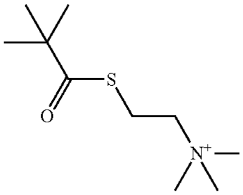
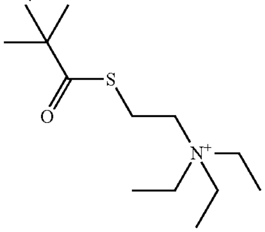
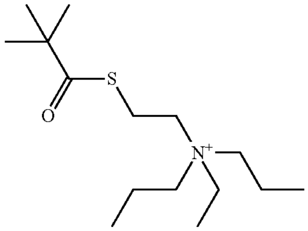
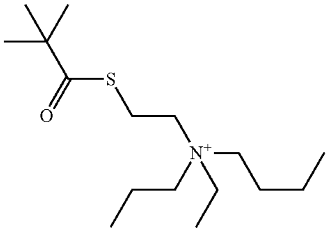
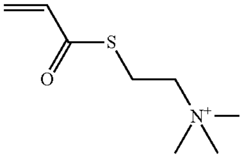
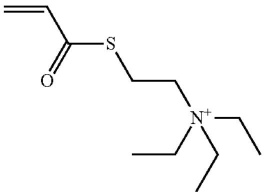
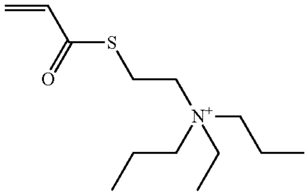
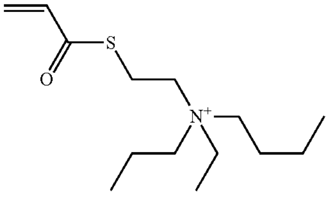

-continued
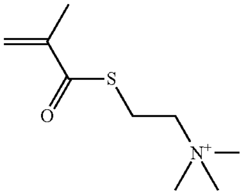
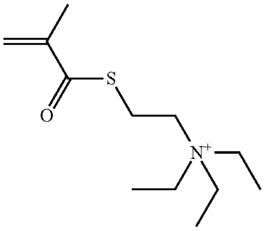
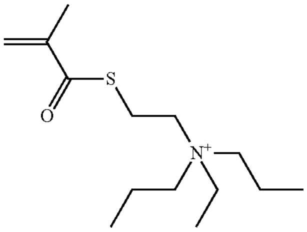
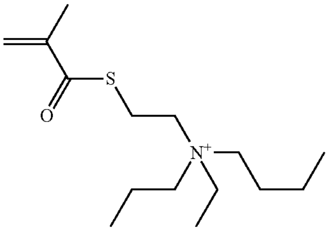
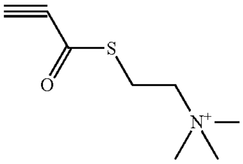
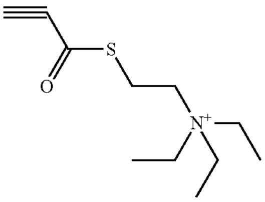
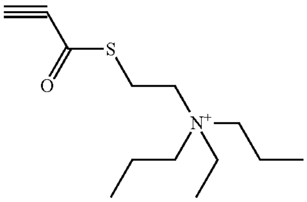
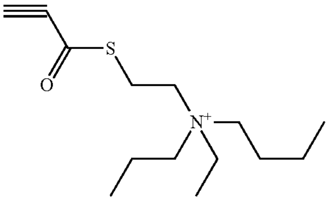
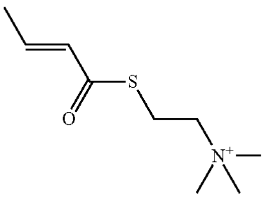
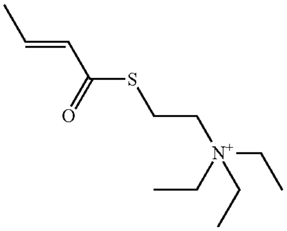
-continued
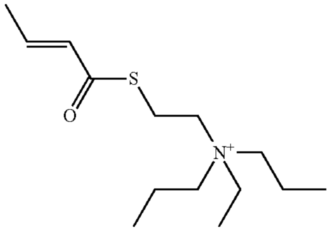
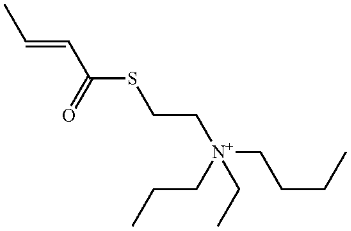
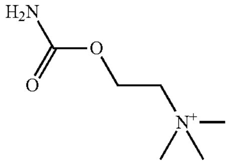
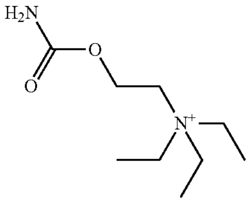
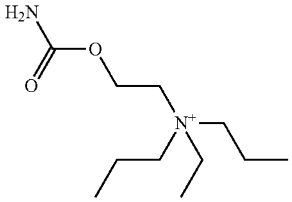
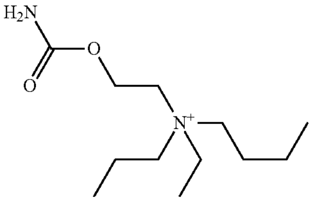
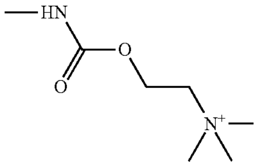
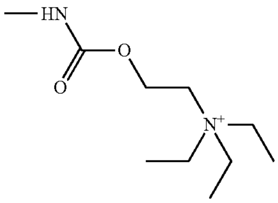
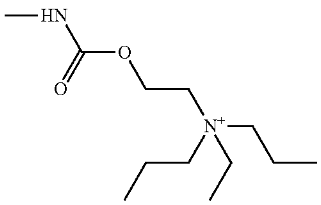
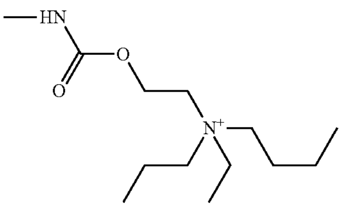

-continued
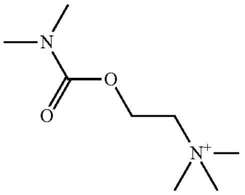
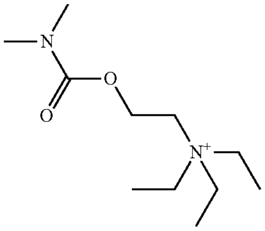
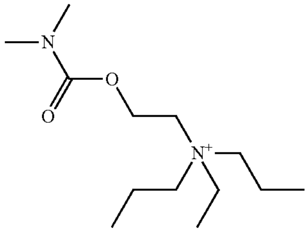
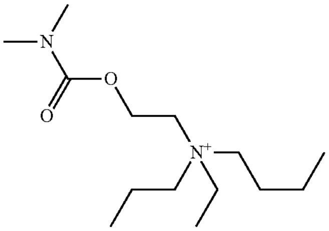
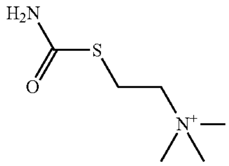
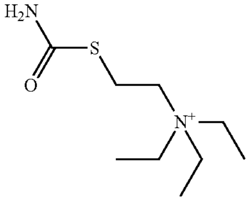
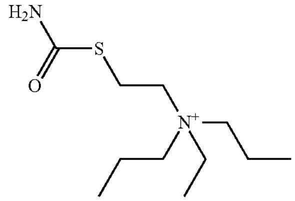
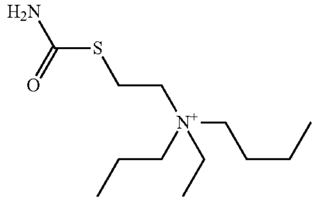
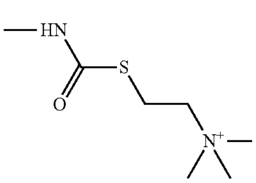
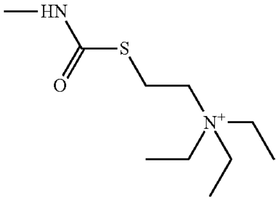
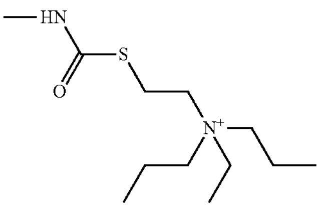
-continued
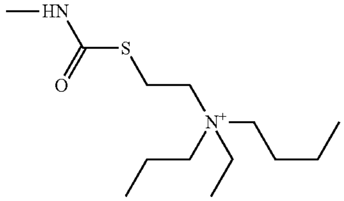
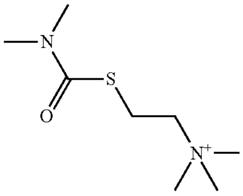
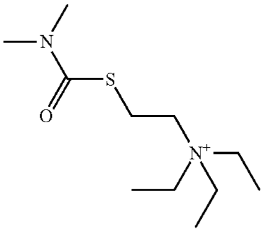
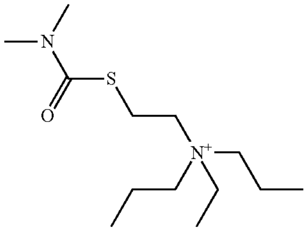
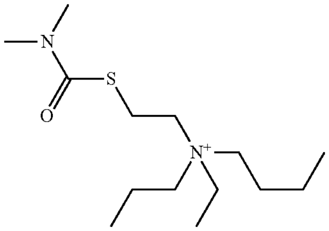
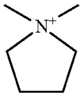
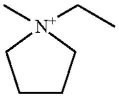
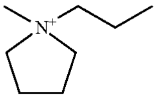
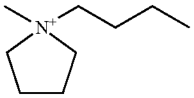
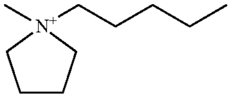
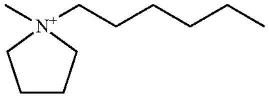
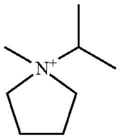
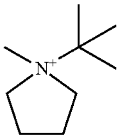
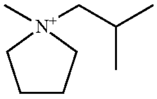
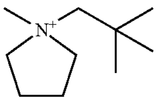
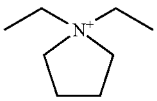
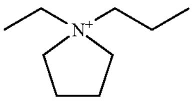
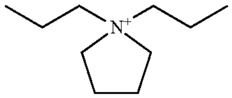
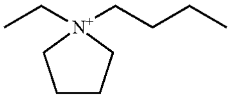
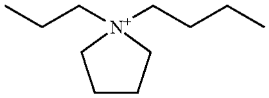
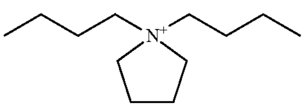
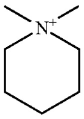
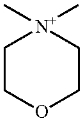

-continued
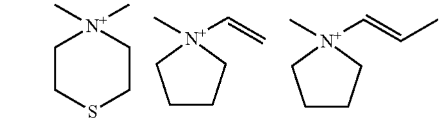
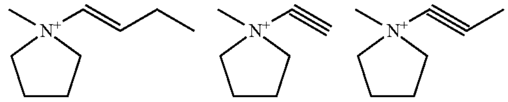
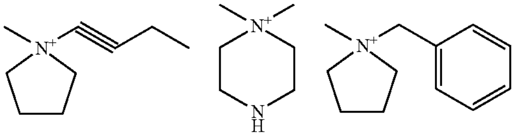
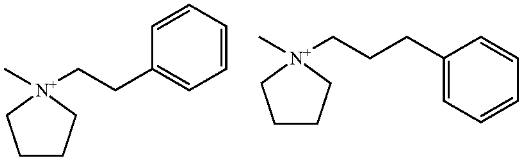
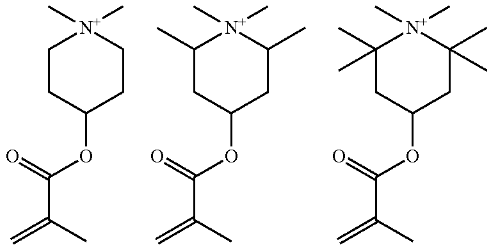
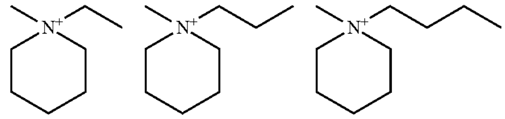
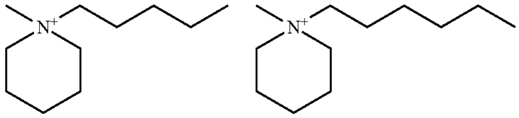
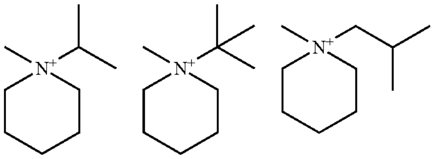
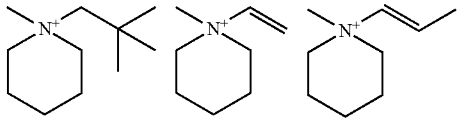
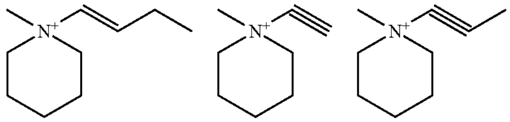
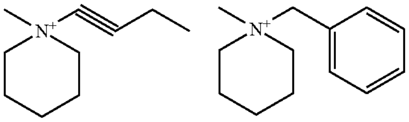
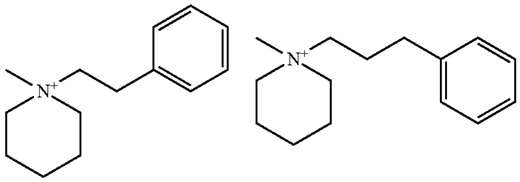
-continued
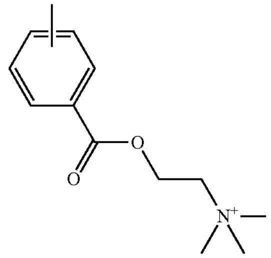
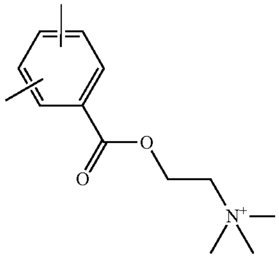
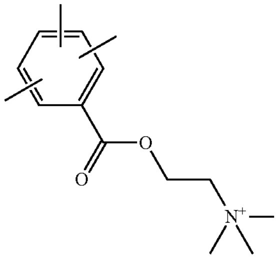
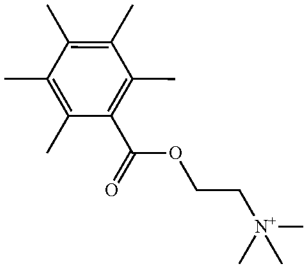
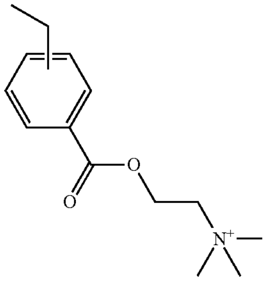
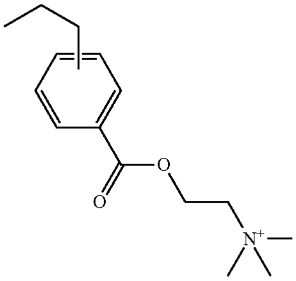
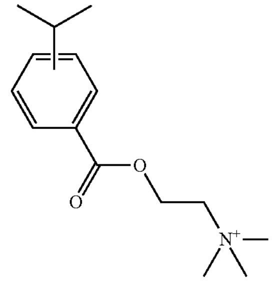
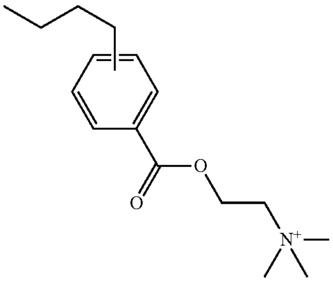

-continued
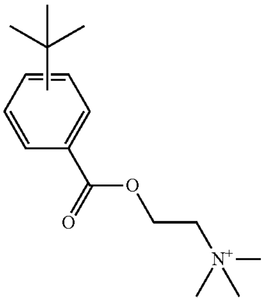
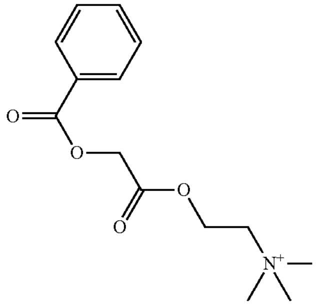
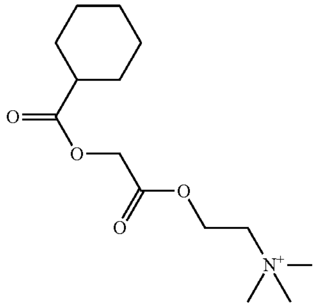
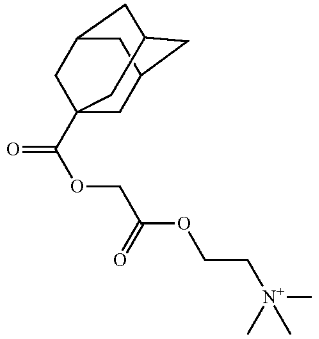
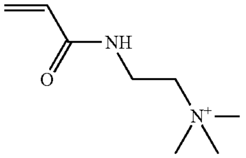
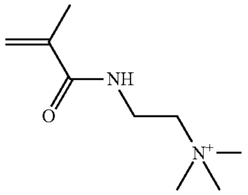
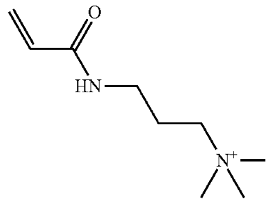
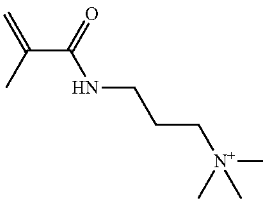
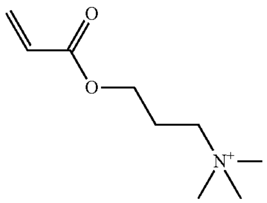
-continued
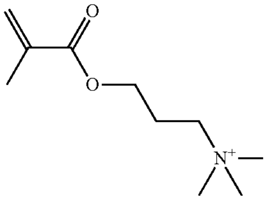
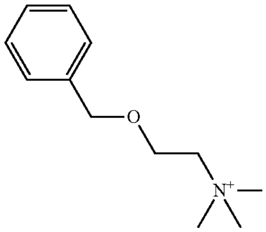
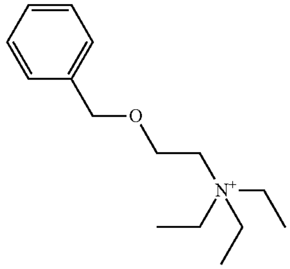
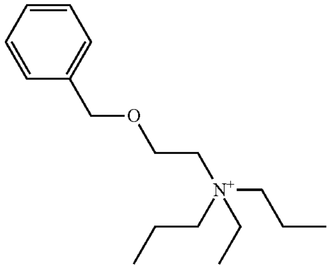
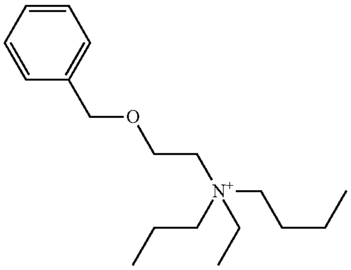
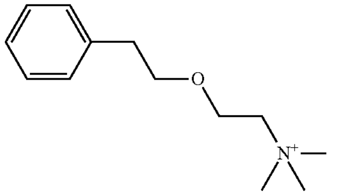
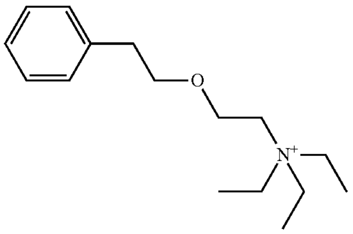
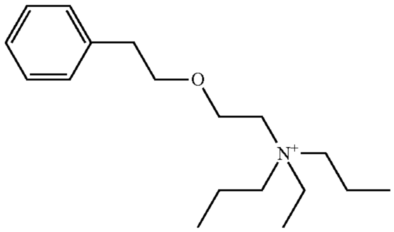

-continued
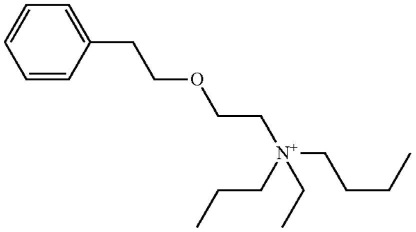
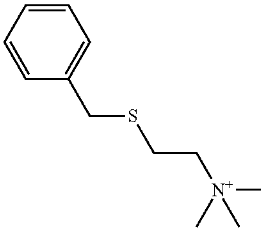
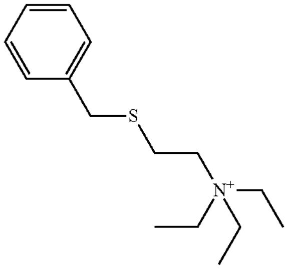
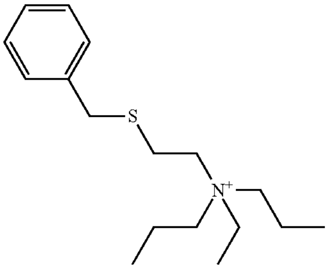
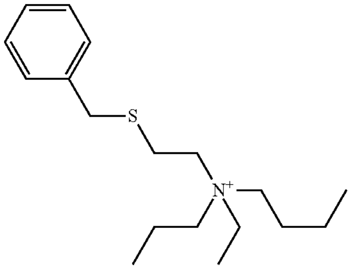
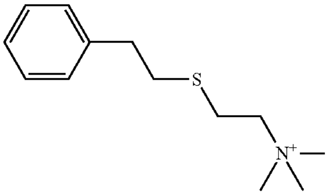
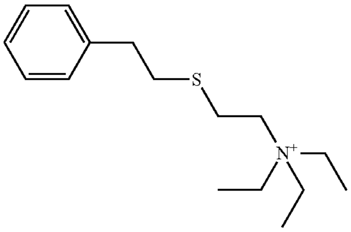
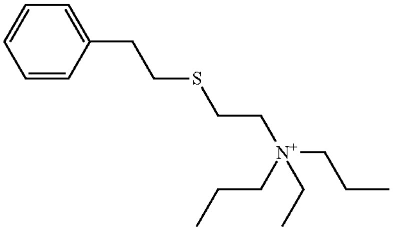
-continued
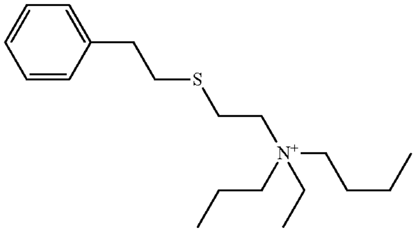
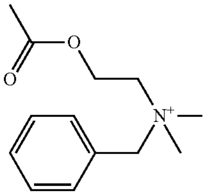
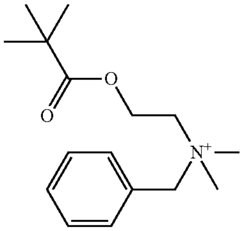
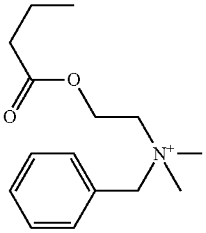
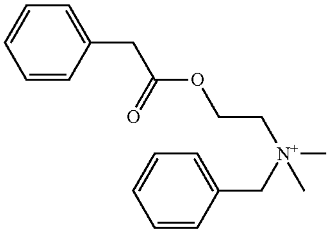
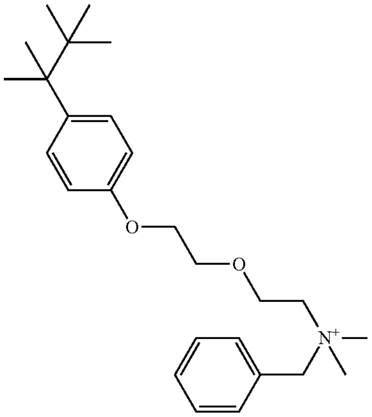
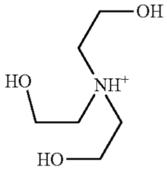
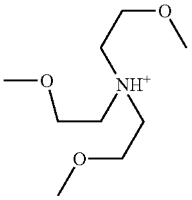
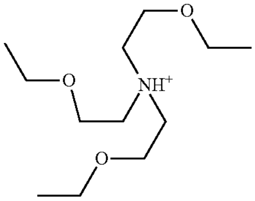
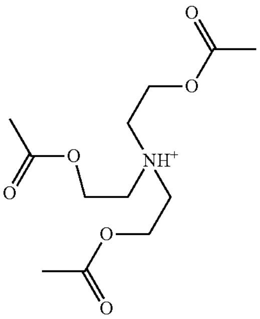

-continued
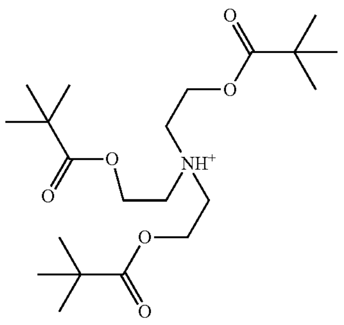
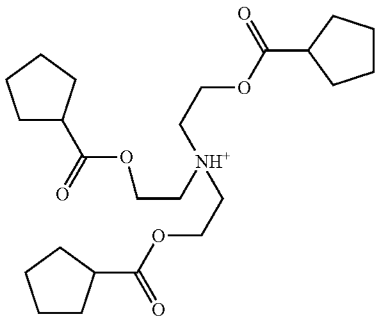
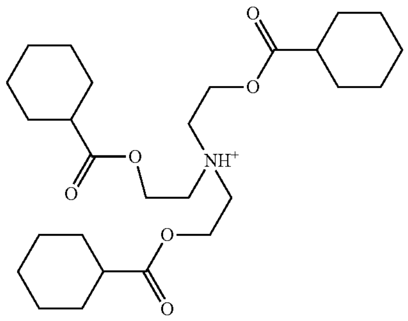
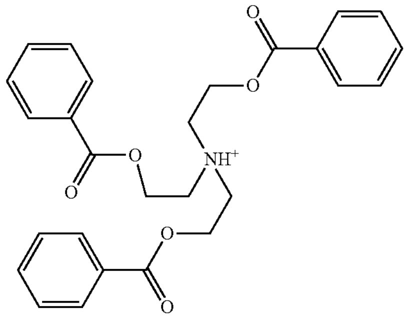
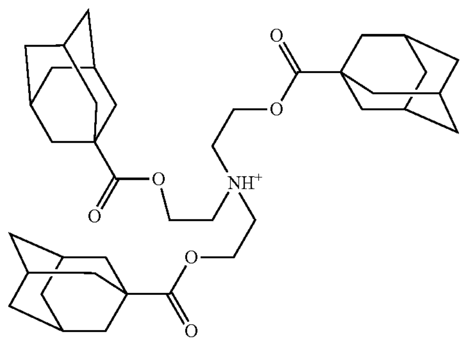
-continued
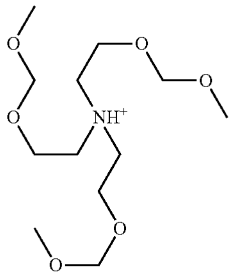
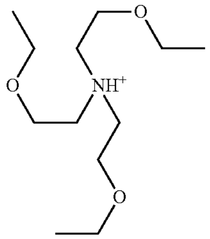
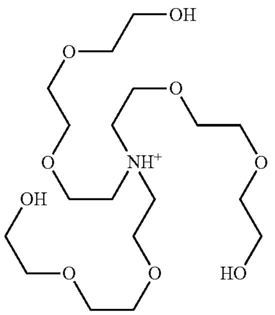
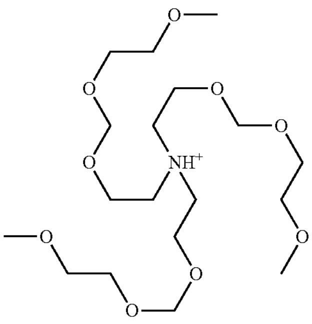
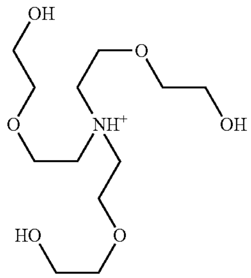
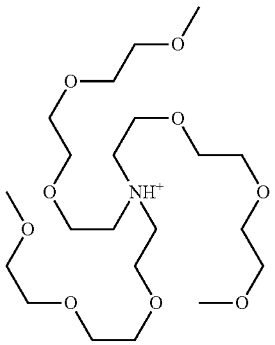
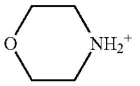
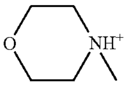
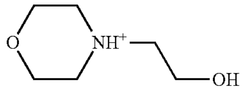
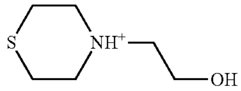
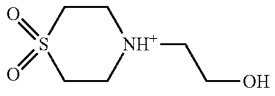
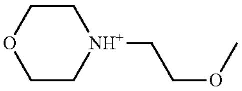
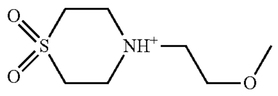
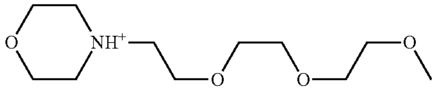
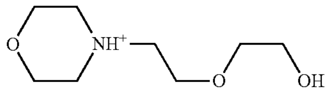

-continued

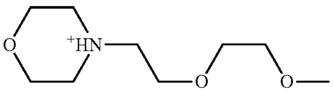

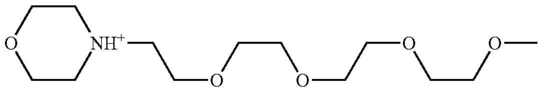

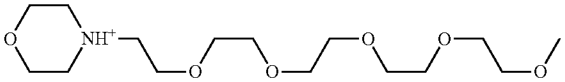

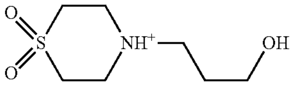 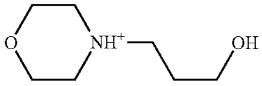

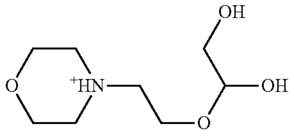

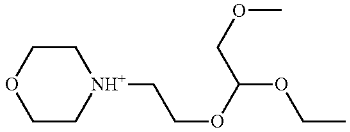

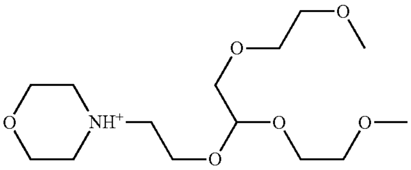

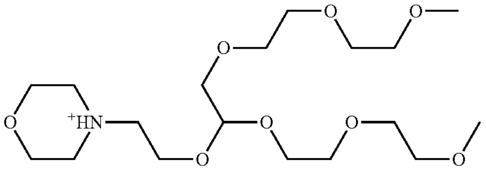

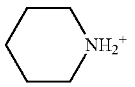 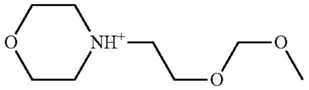

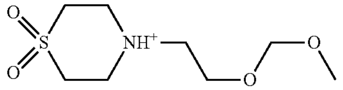

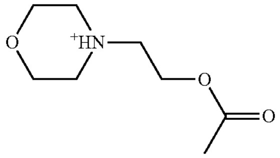 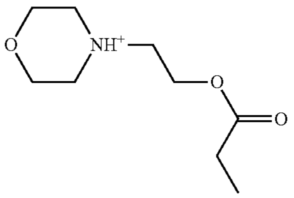

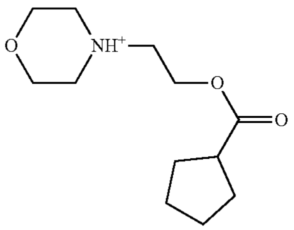

-continued

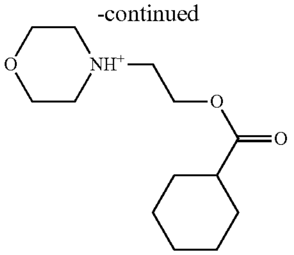

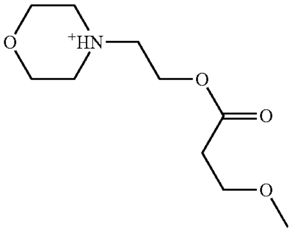

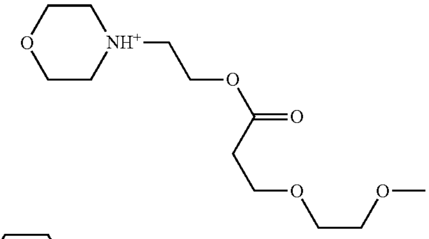

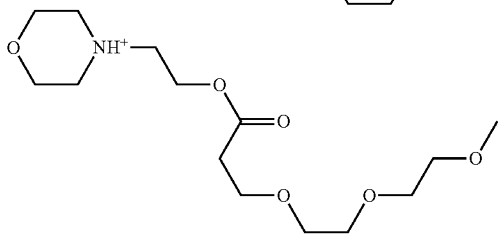

The ammonium ion shown by the general formula (3) is particularly preferably a tertiary or quaternary ammonium ion.

(Repeating Unit-b1)

The inventive bio-electrode composition contains a polymer having a repeating unit-b having a nitro group in addition to the repeating unit-a. As the repeating unit-b, a repeating unit-b1 having a nitro group shown by the following general formula (4) is preferable.

(4)

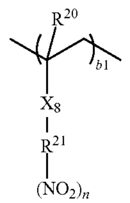

b1

In the general formula (4), $R^{20}$ represents a hydrogen atom or a methyl group. $X_8$ represents any of a single bond, a phenylene group, a naphthylene group, an ether group, an ester group, and an amide group. $R^{21}$ represents a single bond, a linear, branched, or cyclic alkylene group having 1 to 20 carbon atoms, or a phenylene group. The alkylene group optionally has a hydroxy group, a carboxy group, an ether group, an ester group, a urethane group, a thiourethane group, a carbonate group, an amide group, or a urea bond, and the phenylene group is optionally substituted with a linear or branched alkyl group having 1 to 4 carbon atoms, an alkoxy group, a halogen atom, or a cyano group. "n" represents 1 or 2 and b1 satisfies 0<b1<1.0.

The repeating unit-b1 shown by the general formula (4) can be obtained from the monomers specifically exemplified below.

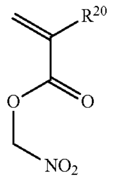
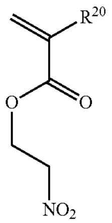
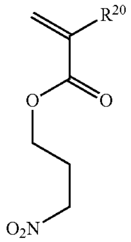
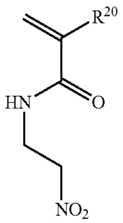
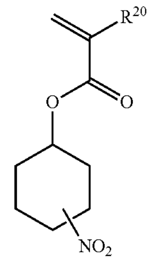
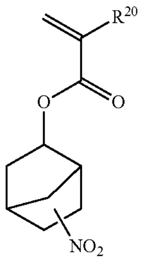
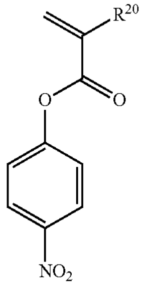
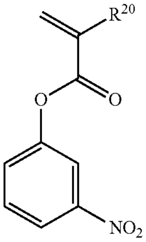
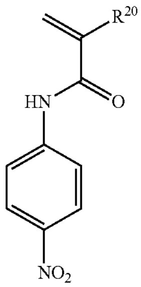
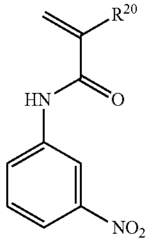
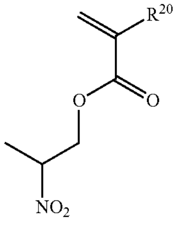
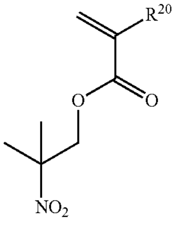
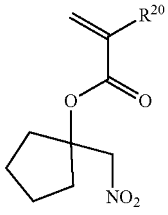
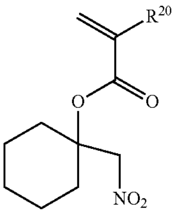
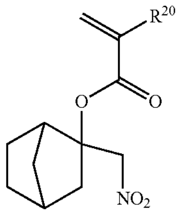

-continued

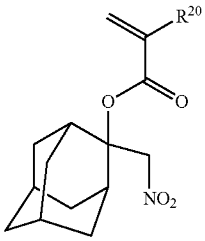
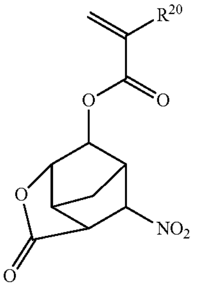
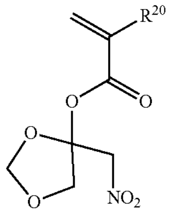
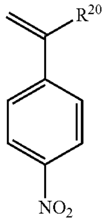
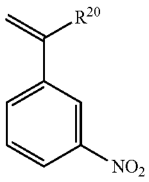
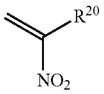
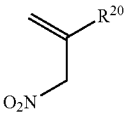
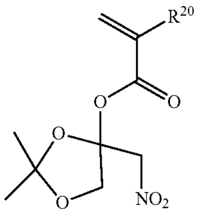
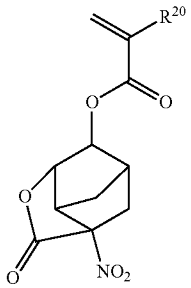
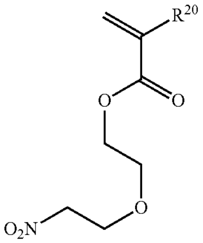
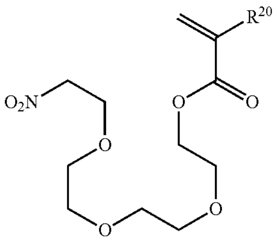
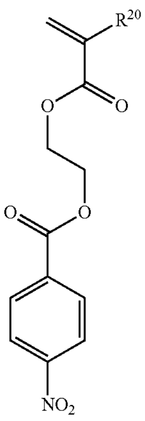

-continued
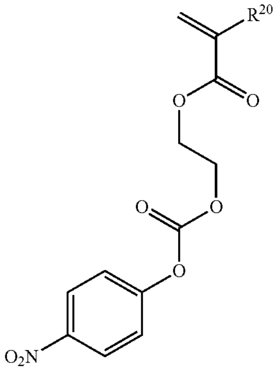
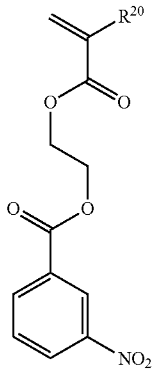
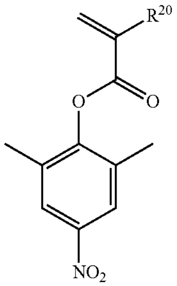
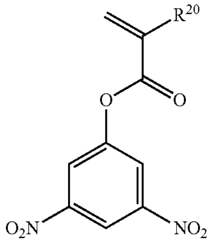
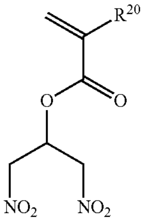
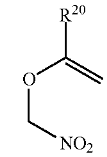
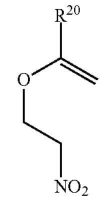
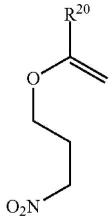
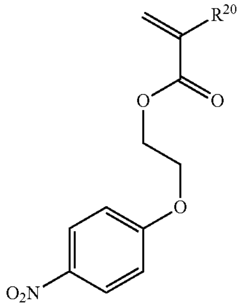
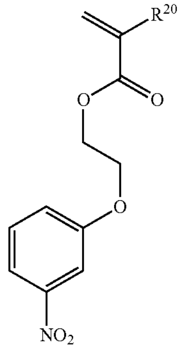
-continued
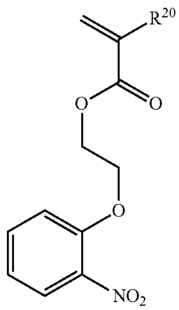
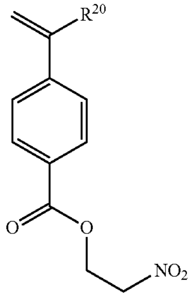
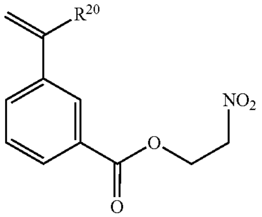
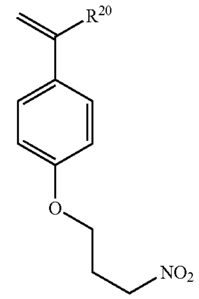
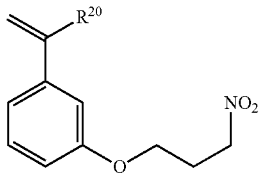
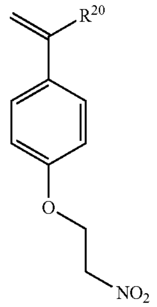
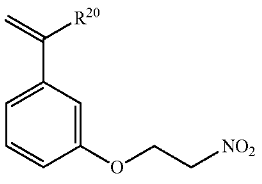
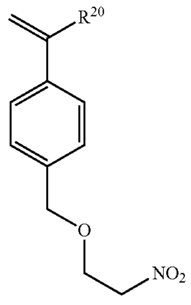
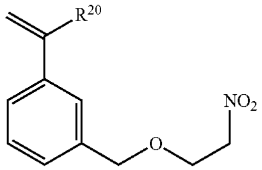
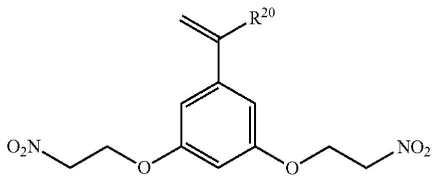

-continued
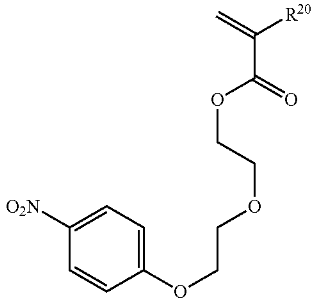
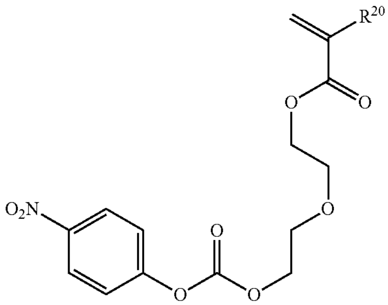
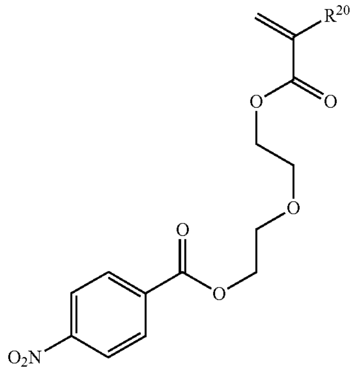
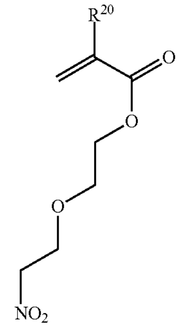
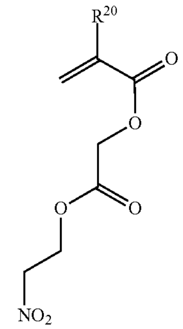
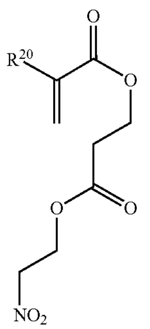
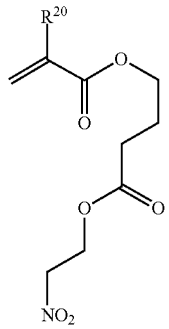
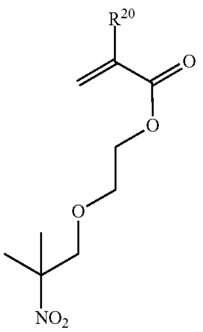
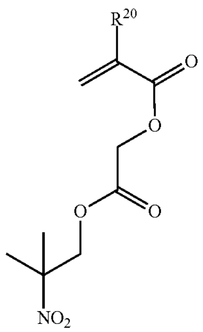
-continued
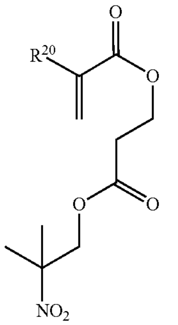
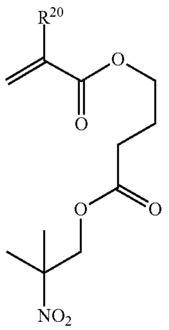
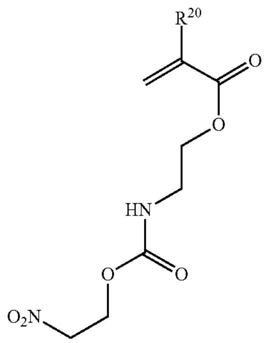
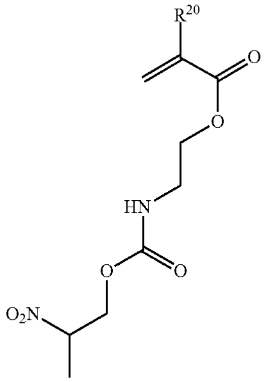
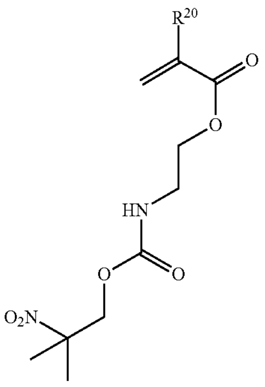
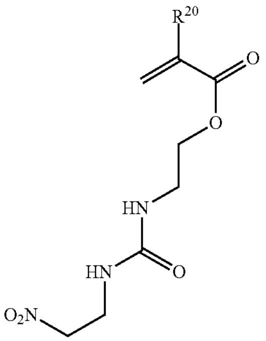
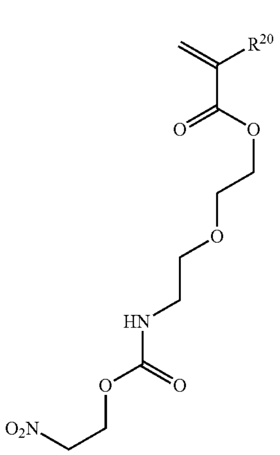
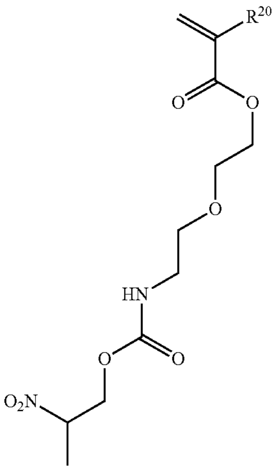

-continued
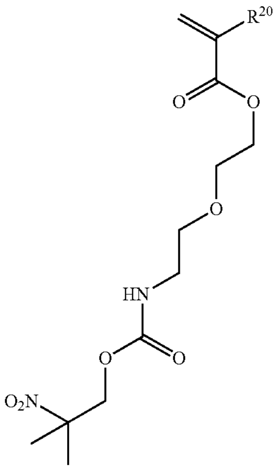
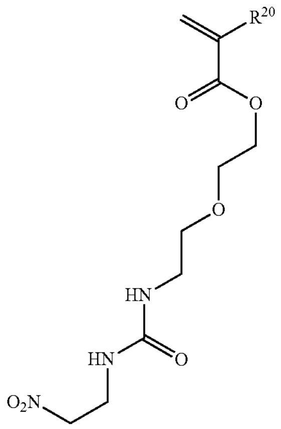
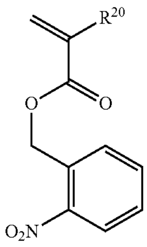
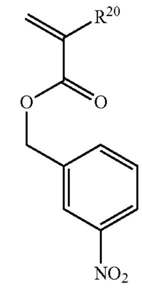
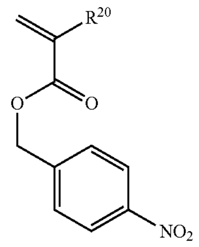
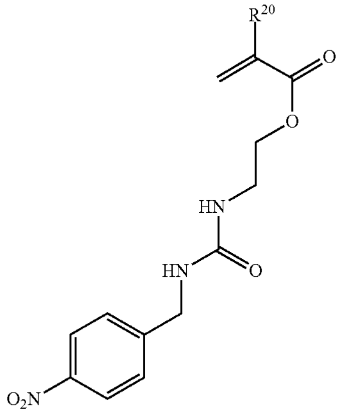
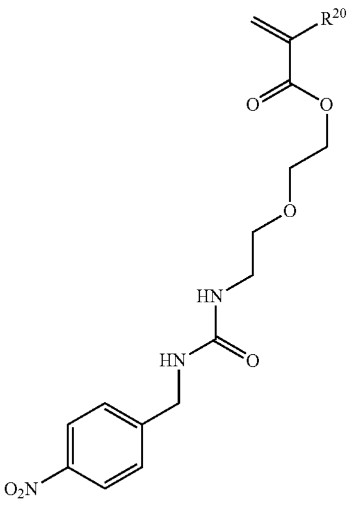
-continued
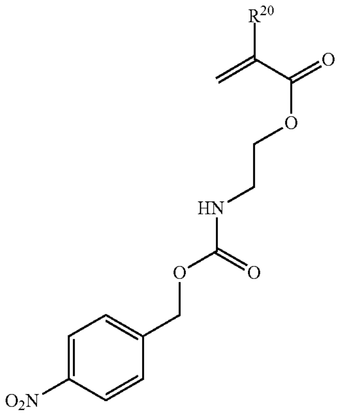
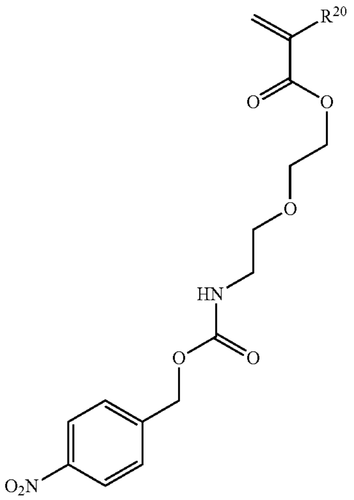
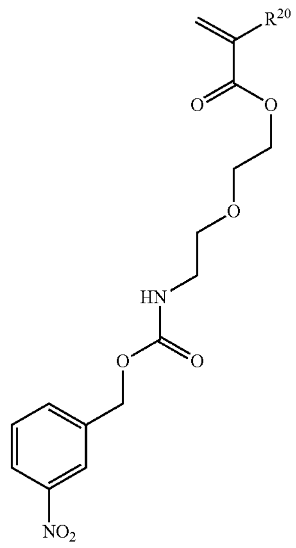

-continued
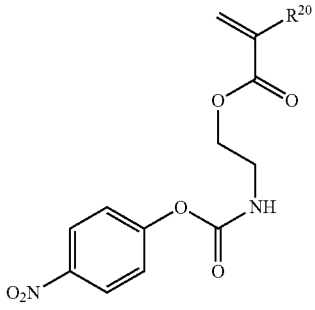
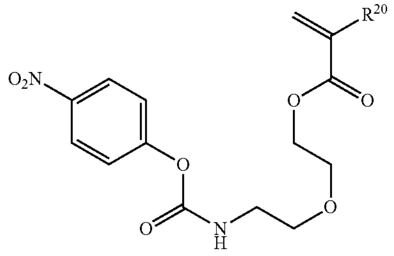
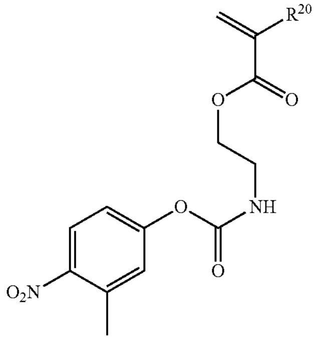
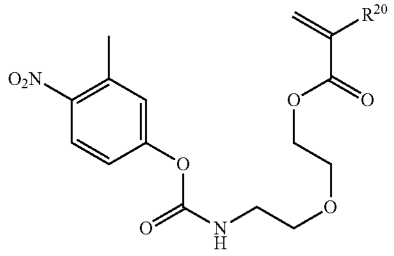
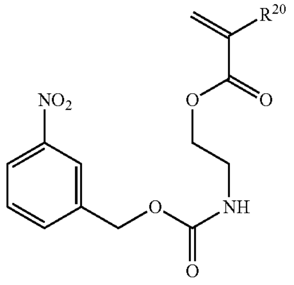
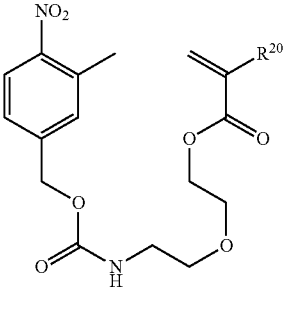
-continued
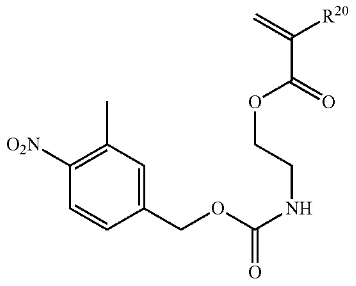
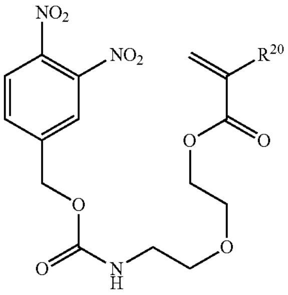
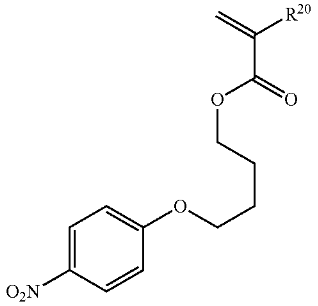
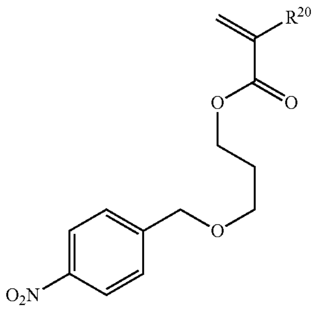
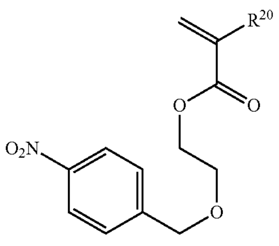
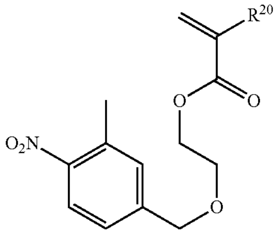

-continued
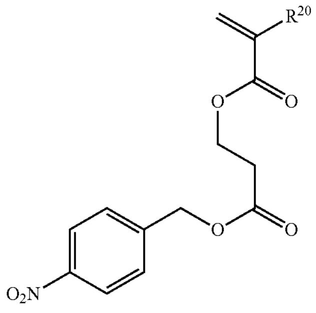
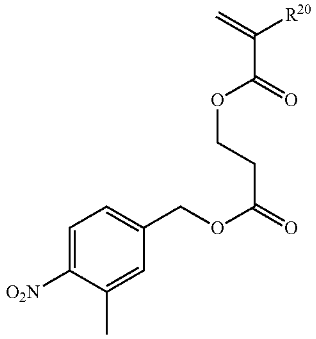
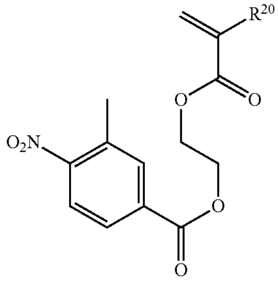
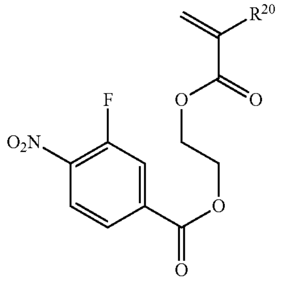
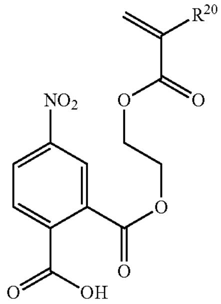
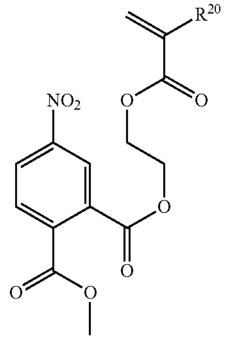
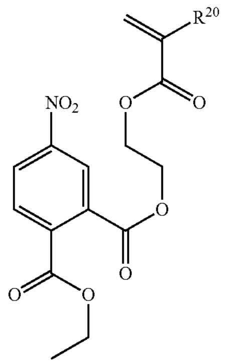
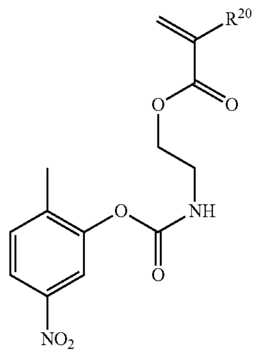
-continued
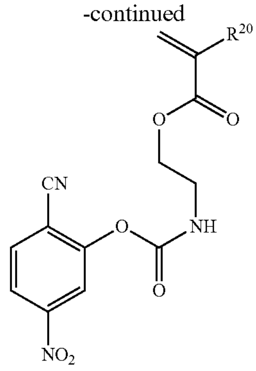
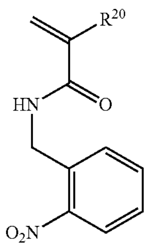
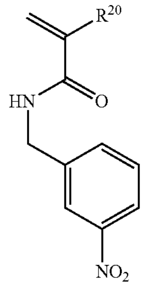
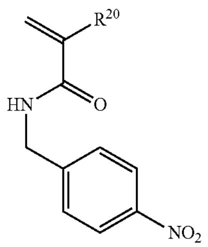
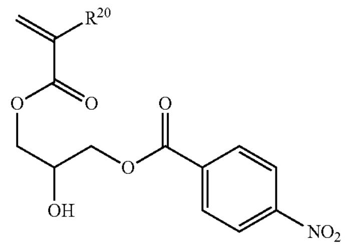
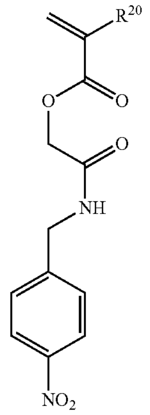
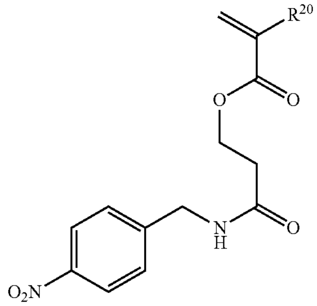
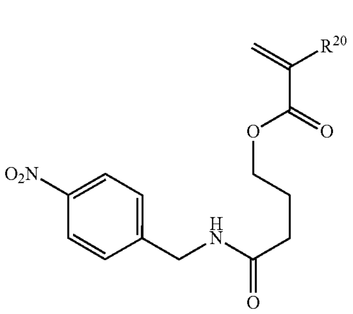

-continued
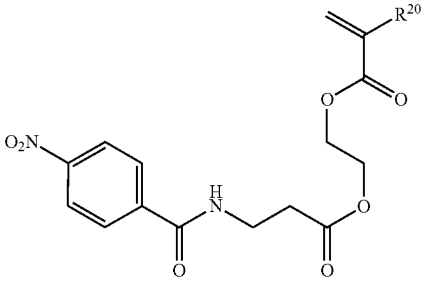
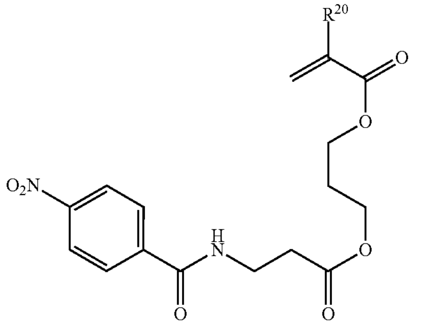
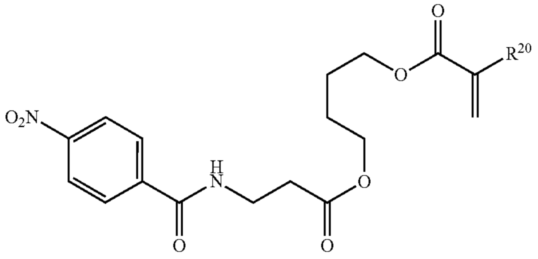
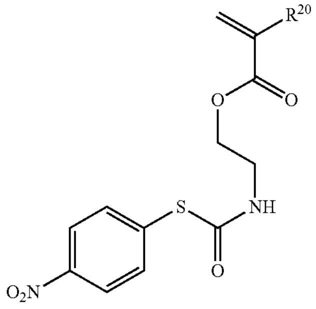
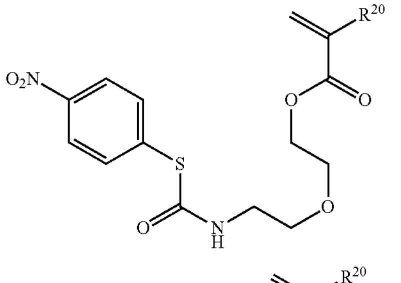
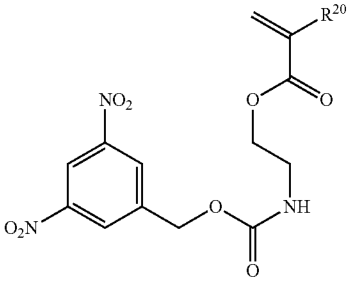
-continued
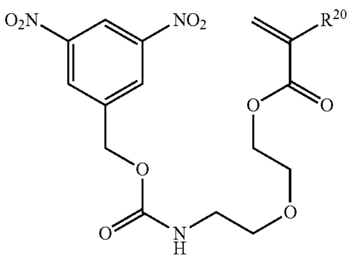
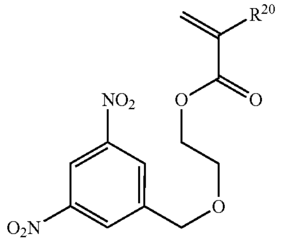
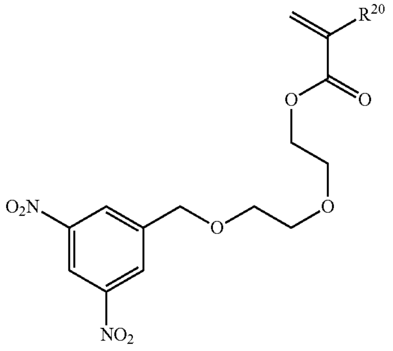
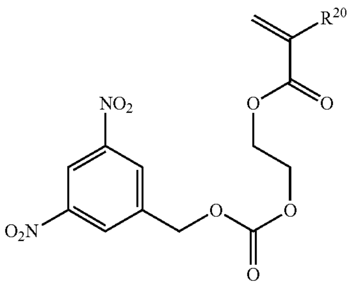
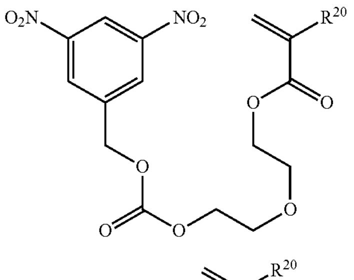
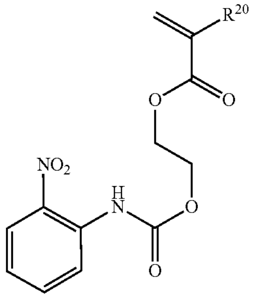

-continued

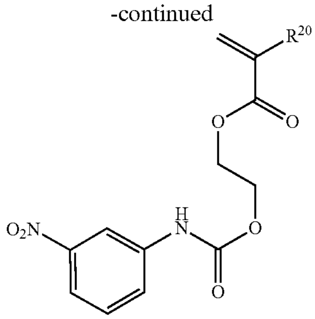

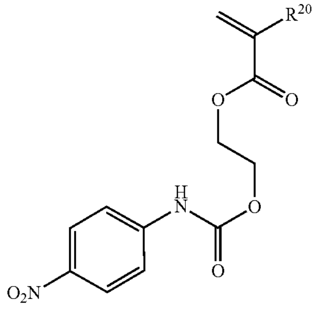

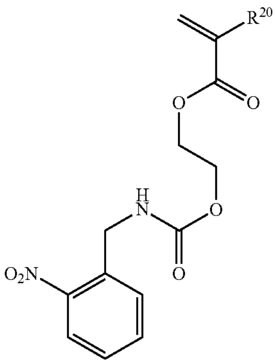

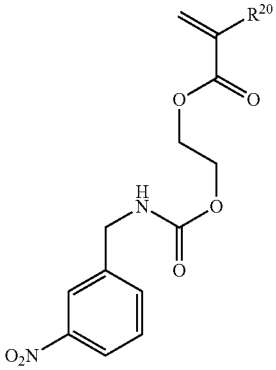

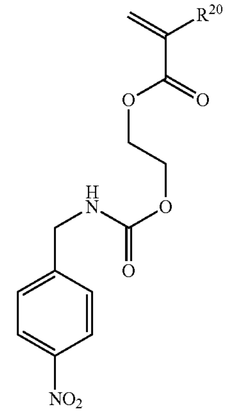

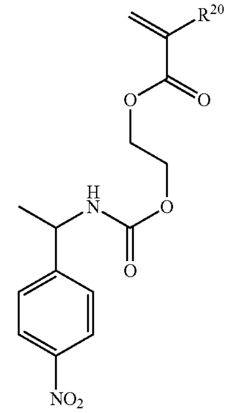

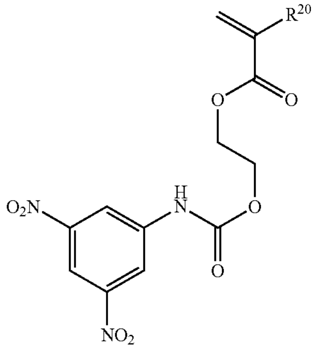

-continued

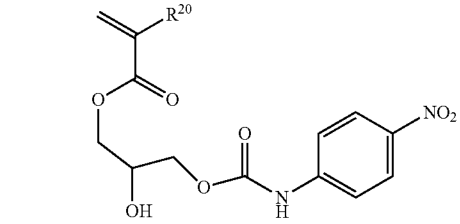

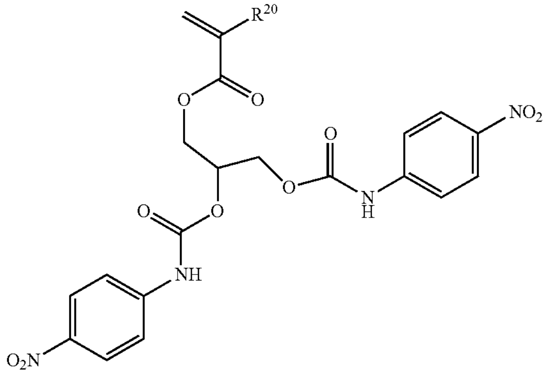

In the formulae, $R^{20}$ is as defined above.

(Repeating Unit-c)

In addition to the repeating units-a1 to -a7 and -b1, a repeating unit-c having a glyme chain can also be copolymerized in the component (A) of the inventive bio-electrode composition in order to enhance the electric conductivity. Specific examples of a monomer to give the repeating unit-c having a glyme chain includes the following. The copolymerization with the repeating unit-c having a glyme chain facilitates the movement of ions released from the skin in a dry electrode film, and thus can increase the sensitivity of a dry electrode.

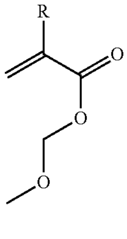

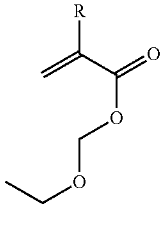

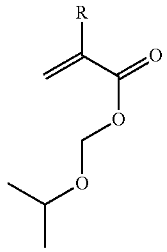

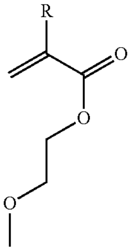

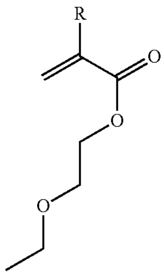

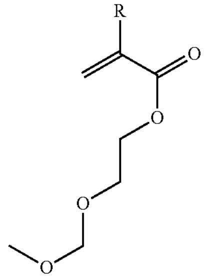

-continued
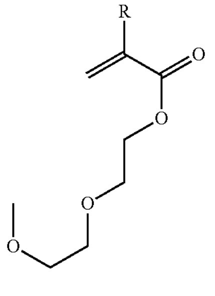
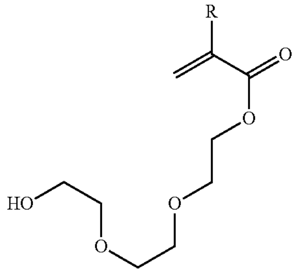
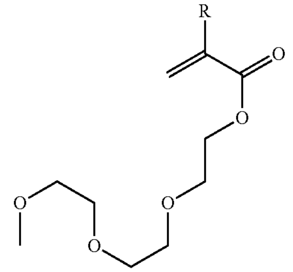
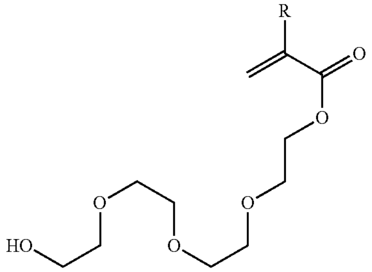
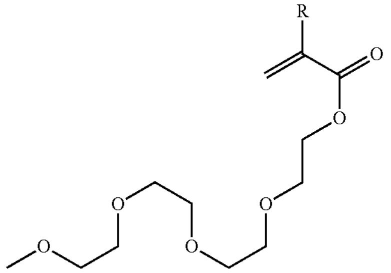
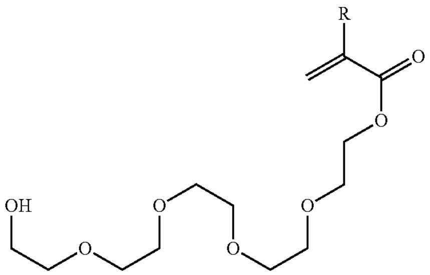
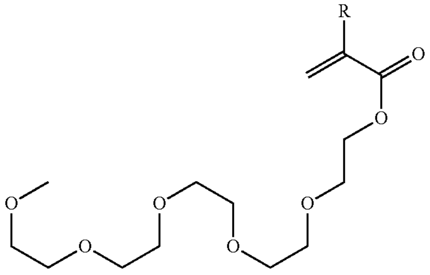
-continued
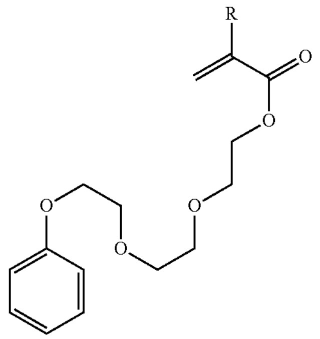
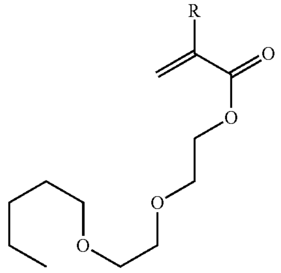
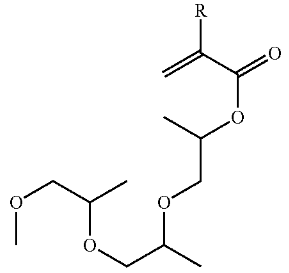
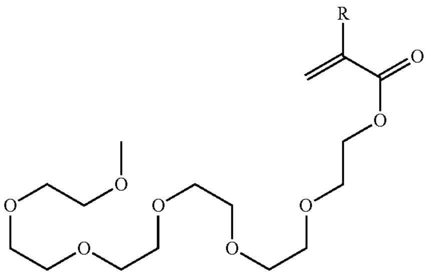
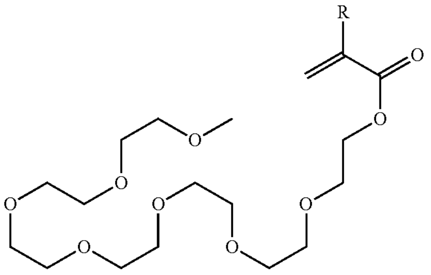
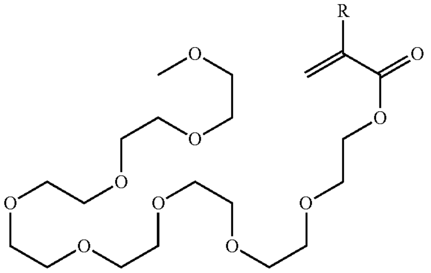
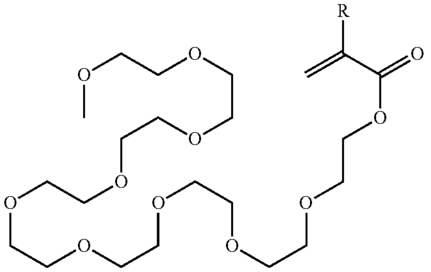

-continued
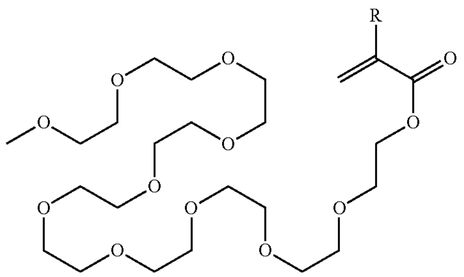
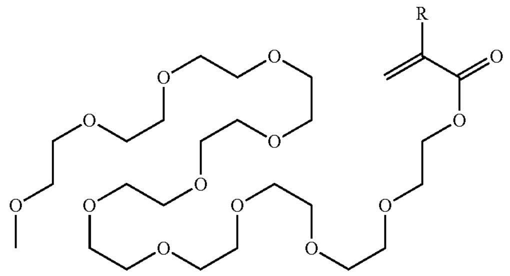
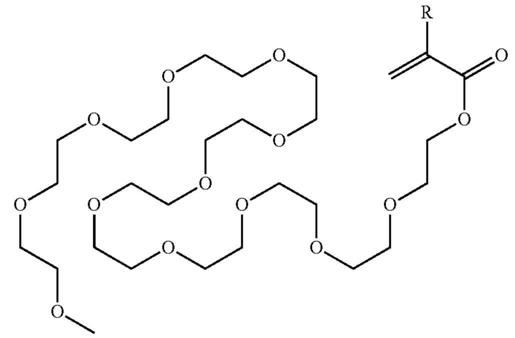
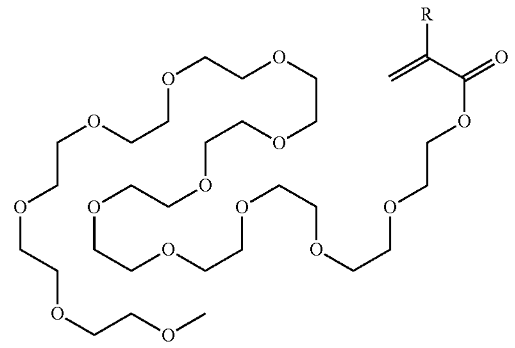
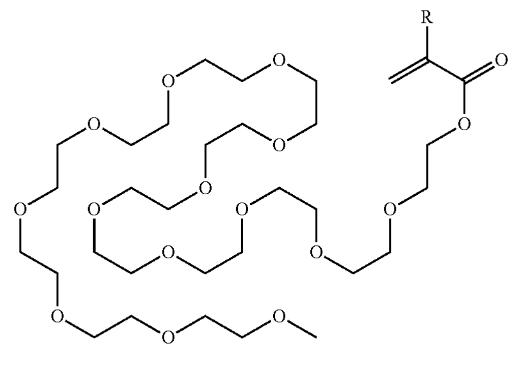
-continued
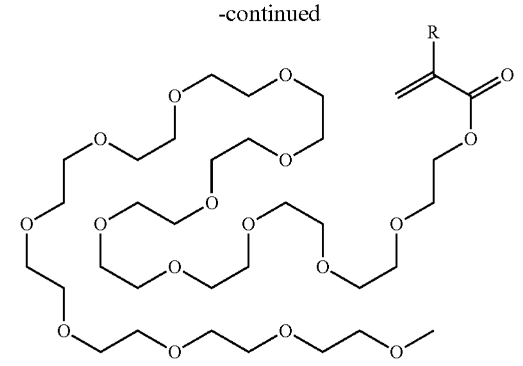
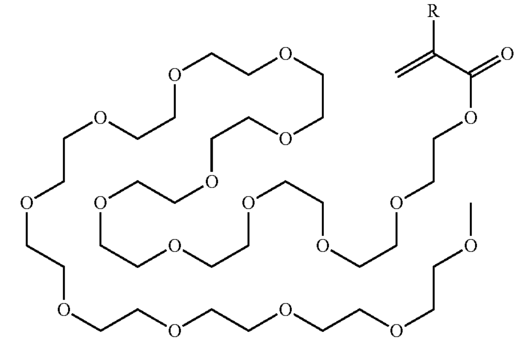
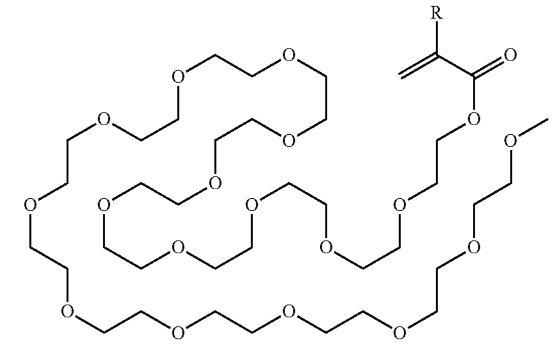
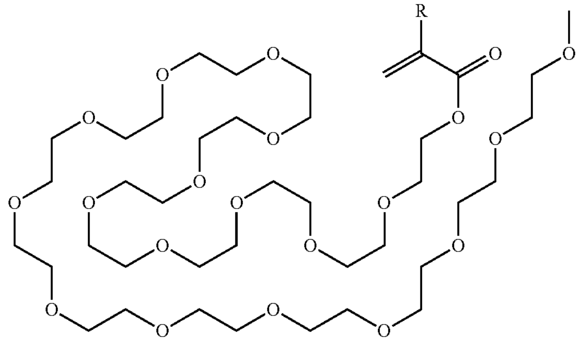
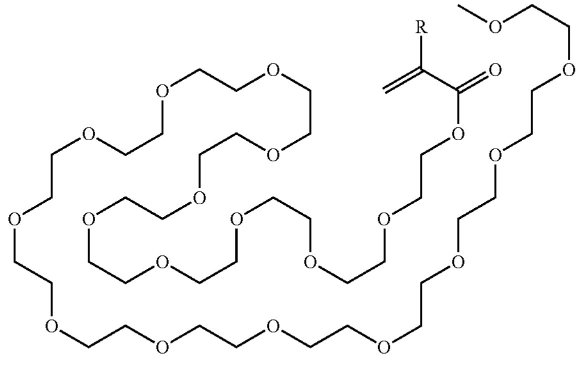

-continued
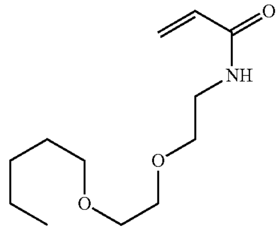
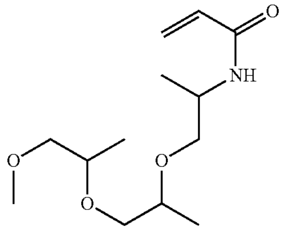
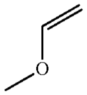
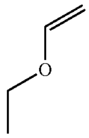
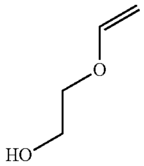
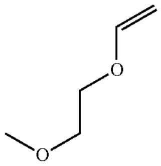
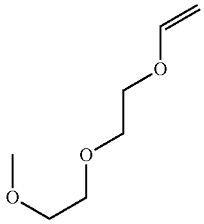
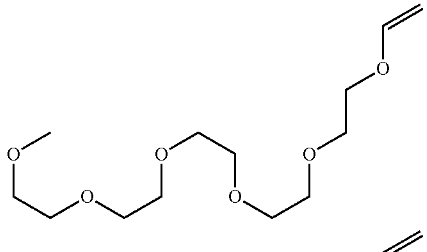
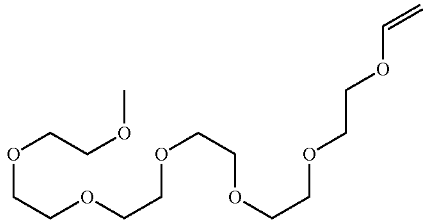
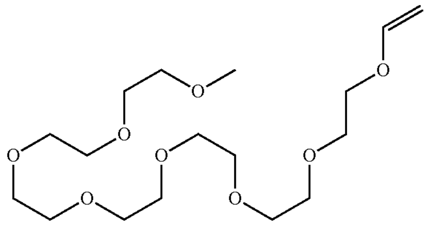
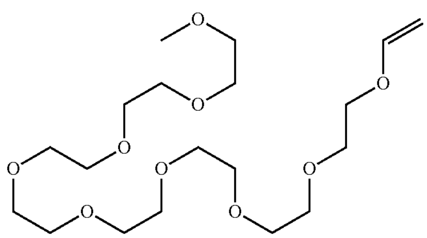
-continued
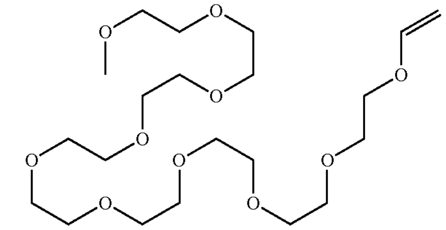
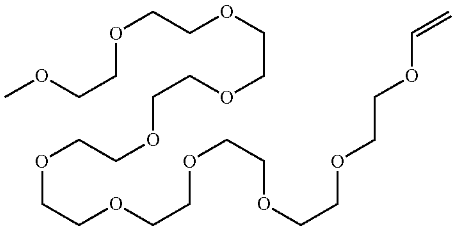
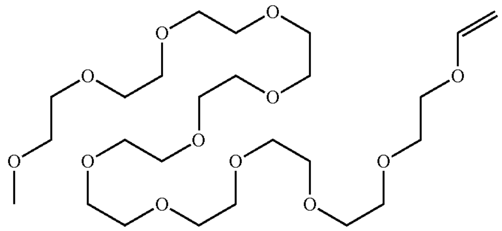
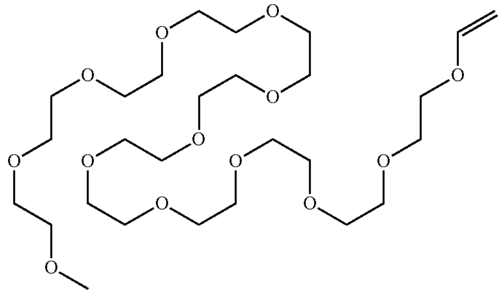
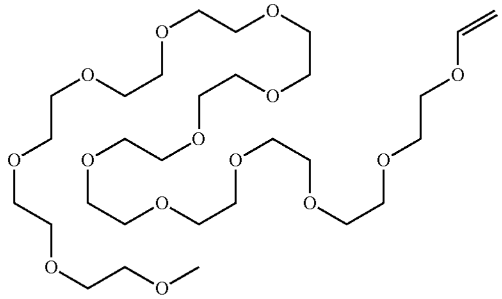
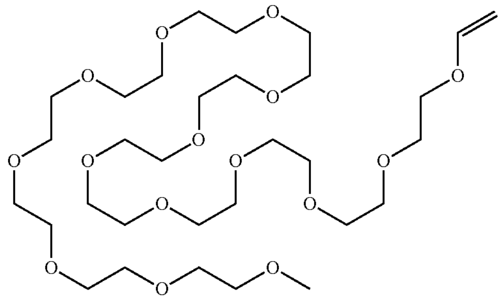

-continued
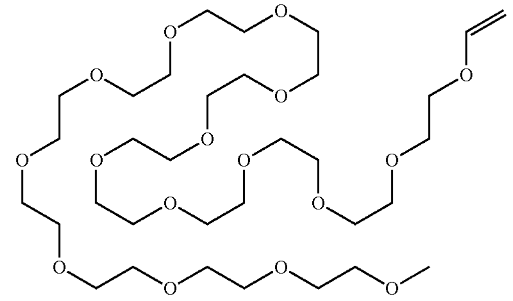
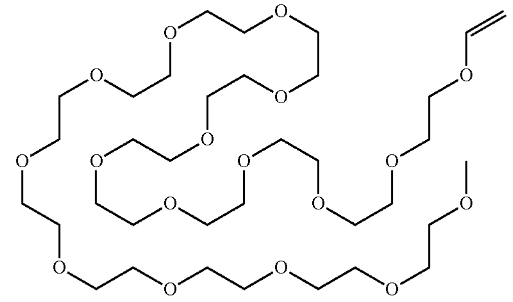
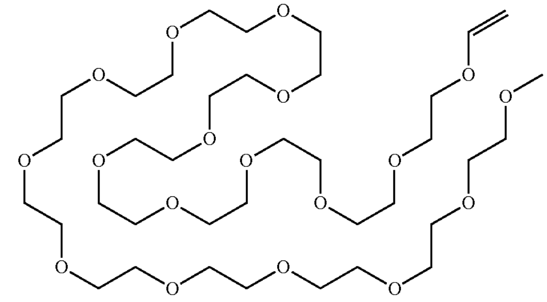
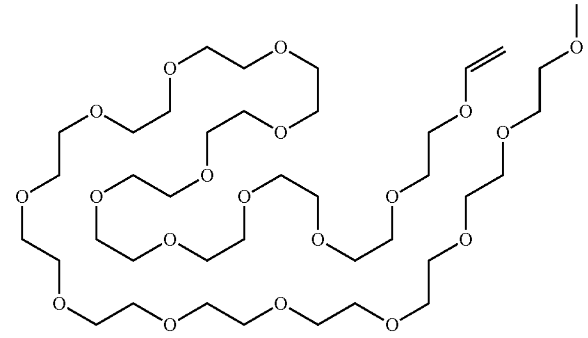
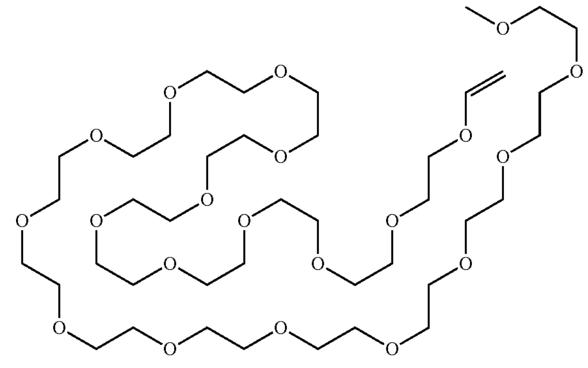
-continued
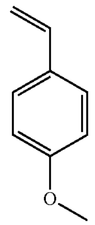
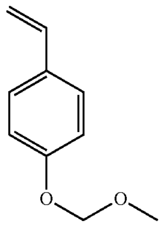
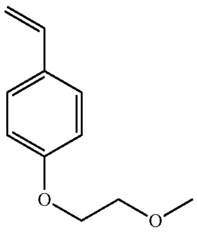
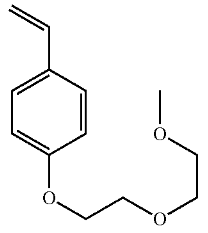
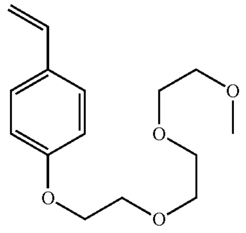
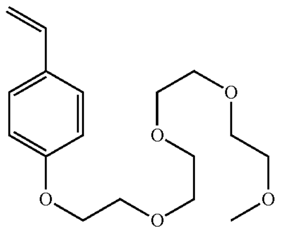
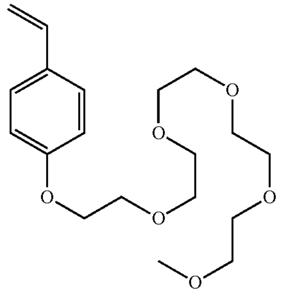
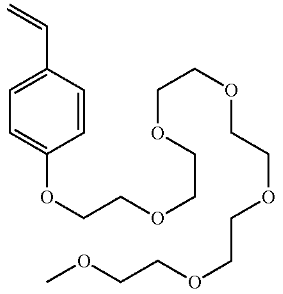
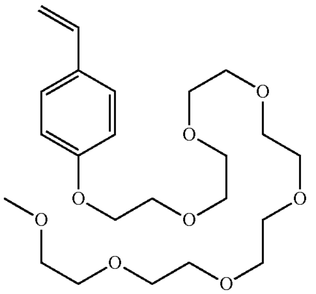
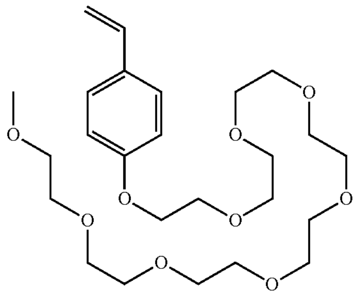

-continued

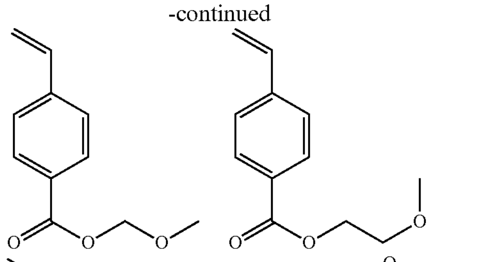

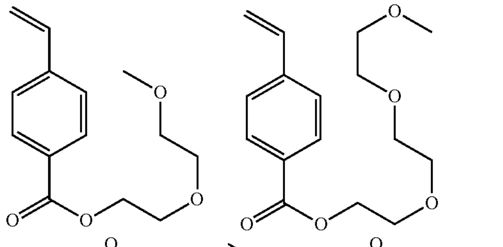

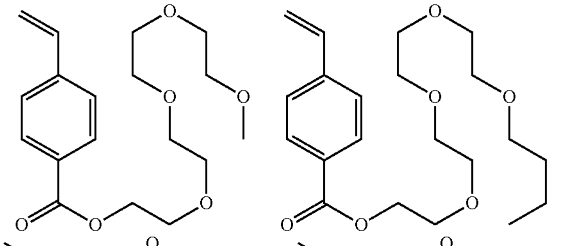

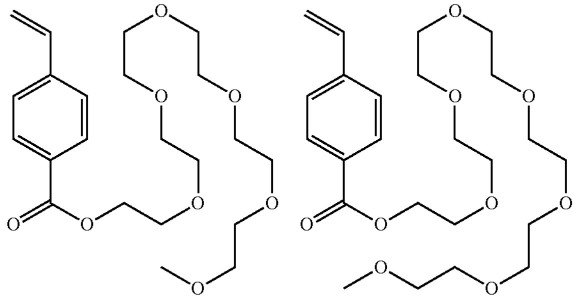

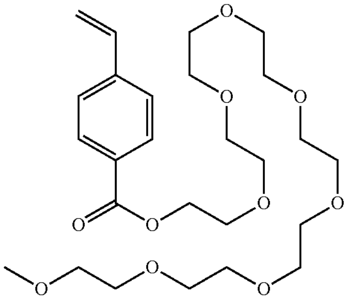

In the formulae, R represents a hydrogen atom or a methyl group.

(Repeating Unit-d)

In addition to the repeating units-a1 to -a7, -b1, and -c, it is also possible to copolymerize, in the component (A) of the inventive bio-electrode composition, a hydrophilic repeating unit-d having a hydroxy group, a carboxy group, an ammonium salt, a betaine, an amide group, pyrrolidone, a lactone ring, a lactam ring, a sultone ring, a sodium salt of sulfonic acid, or a potassium salt of sulfonic acid in order to enhance electric conductivity. Specific examples of a monomer to give the hydrophilic repeating unit-d include the following. The copolymerization with the repeating unit-d containing such hydrophilic groups can increase the sensitivity of the dry electrode by increasing the sensitivity to ions released from the skin.

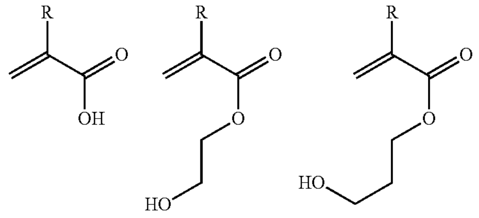

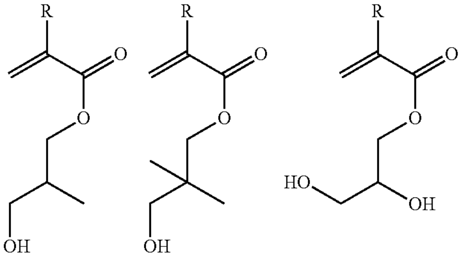

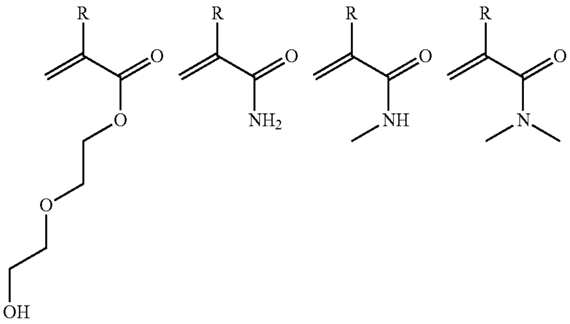

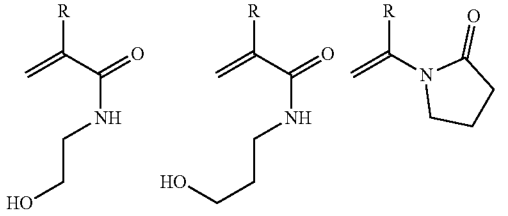

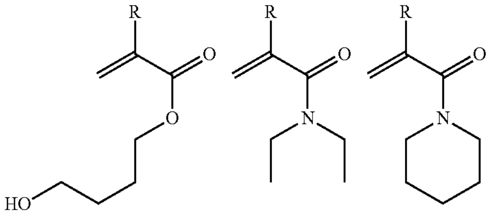

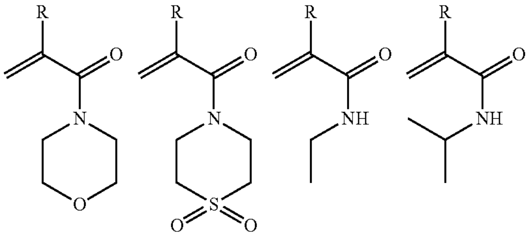

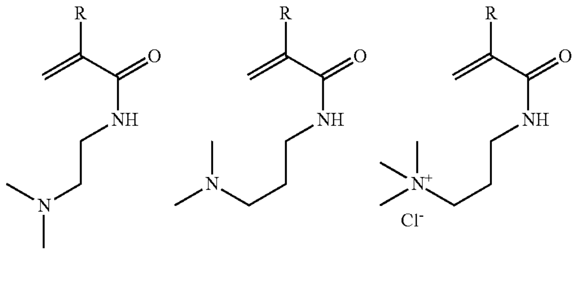

-continued
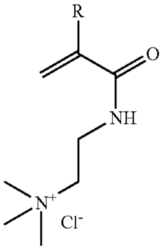
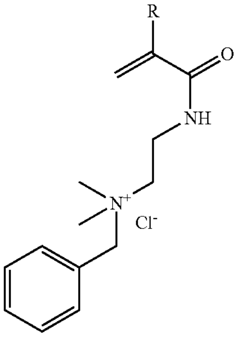
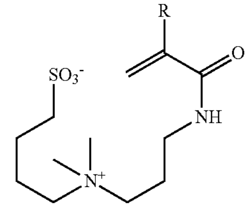
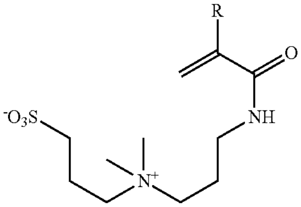
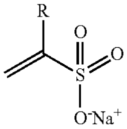
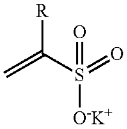
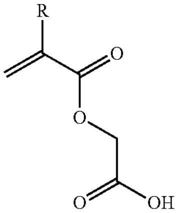
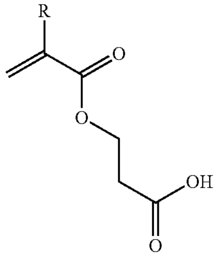
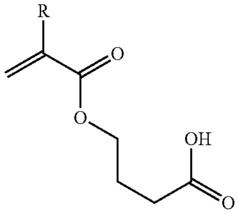
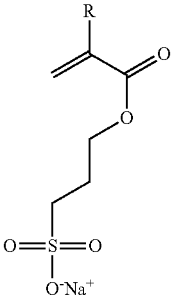
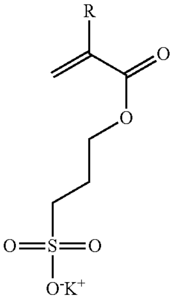
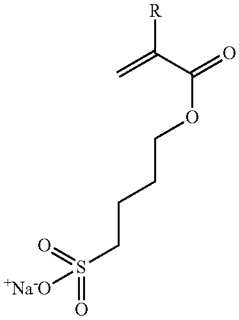
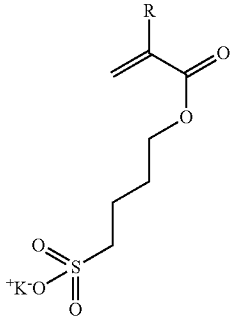
-continued
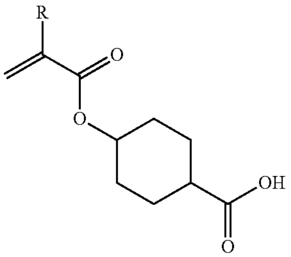
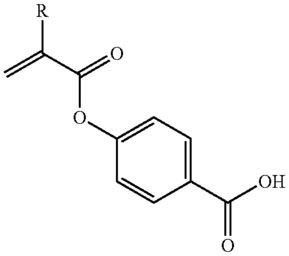
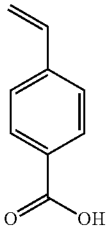
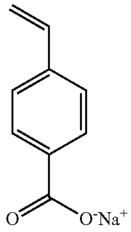
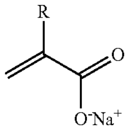
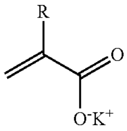
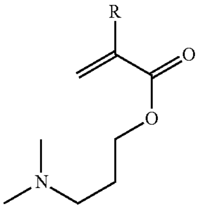
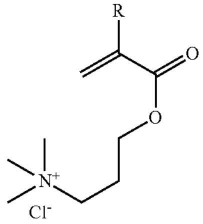
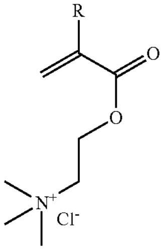
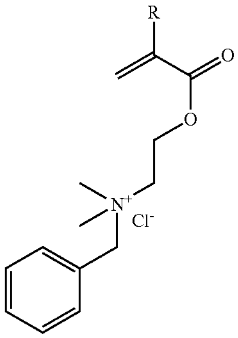
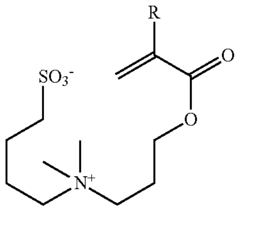
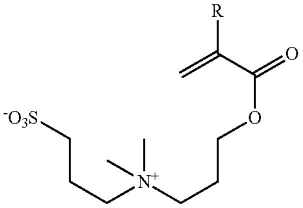
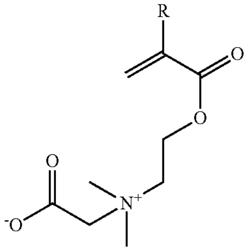

-continued
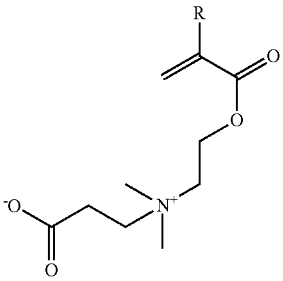
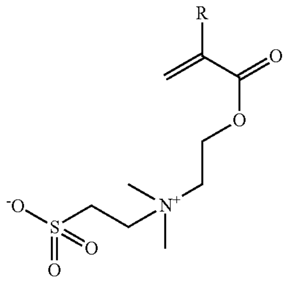
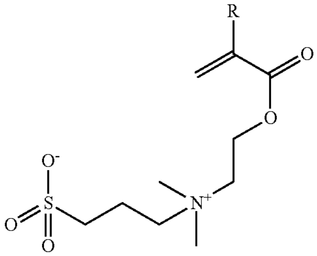
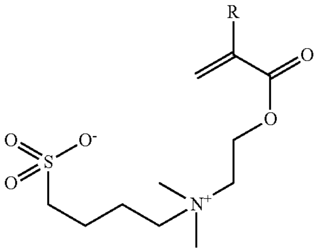
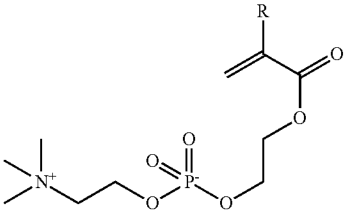
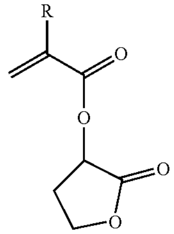
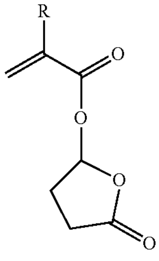
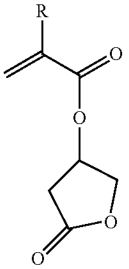
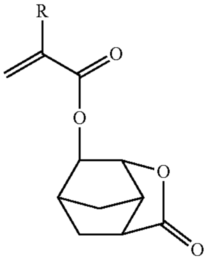
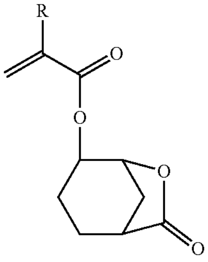
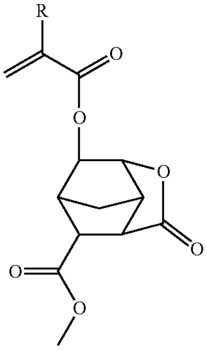
-continued
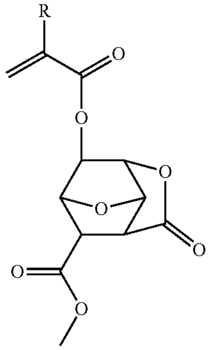
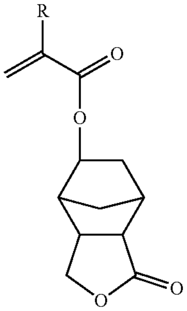
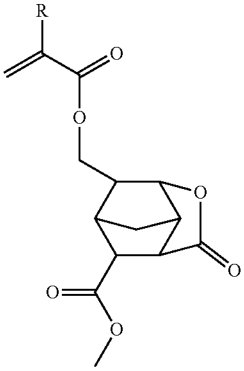
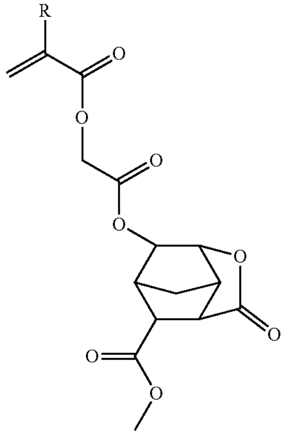
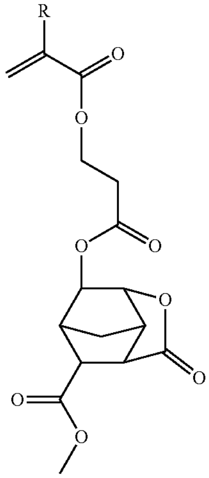
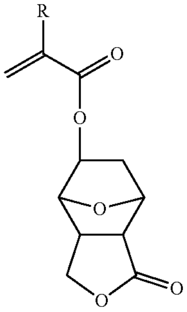
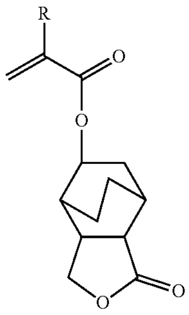
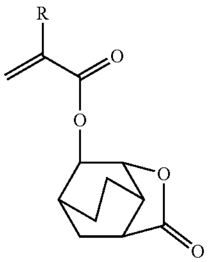

-continued
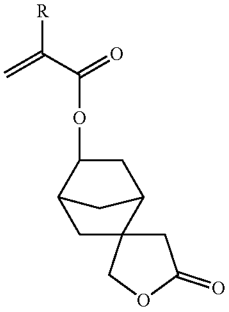
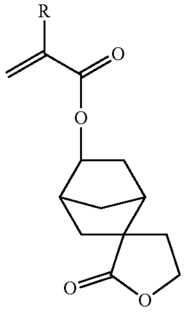
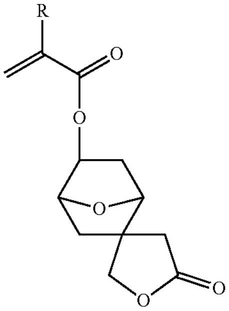
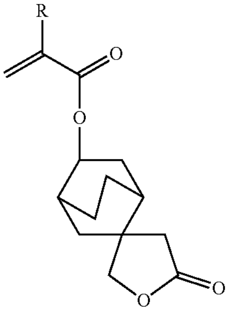
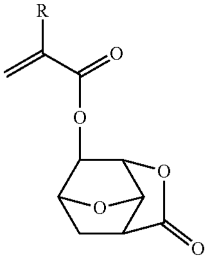
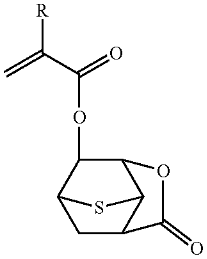
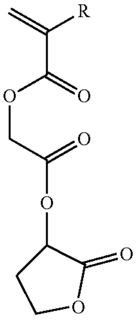
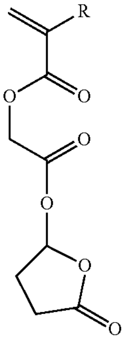
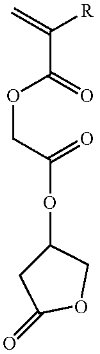
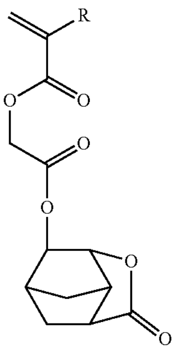
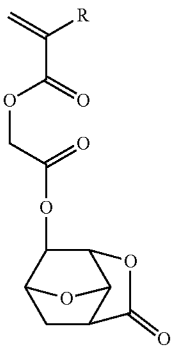
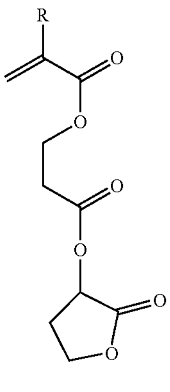
-continued
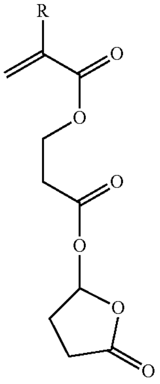
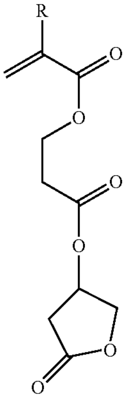
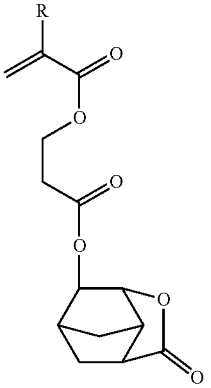
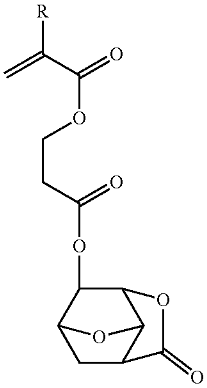
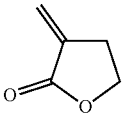
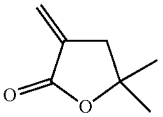
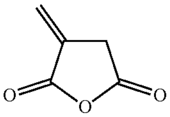
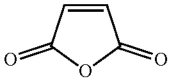
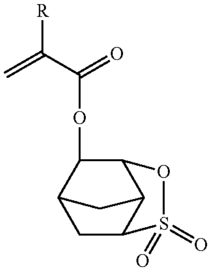
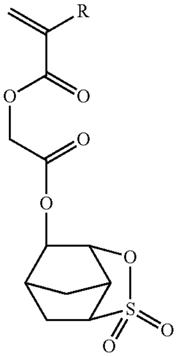
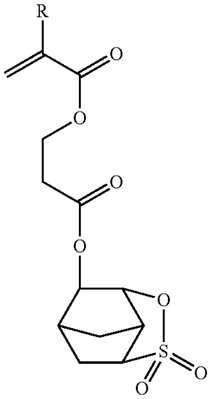
In the formulae, R represents a hydrogen atom or a methyl group.
(Repeating Unit-e)
In addition to the repeating units-a1 to -a7, -b1, -c, and -d, the component (A) of the inventive bio-electrode composition can have a repeating unit-e to impart adhesion properties. Specific examples of a monomer to give the repeating unit-e include the following.

-continued
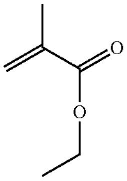
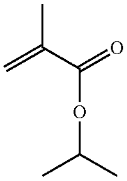
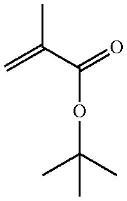
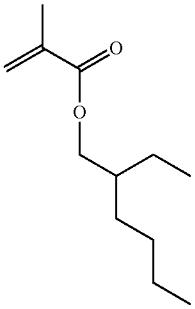
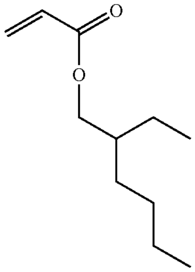
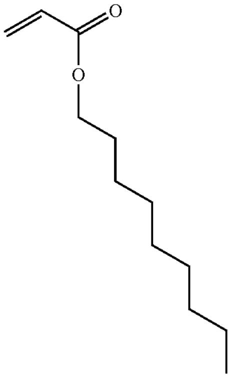
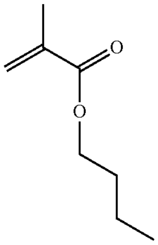
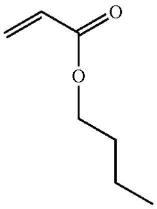
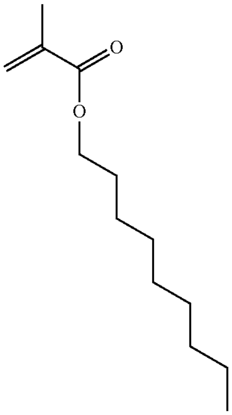
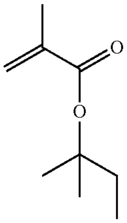
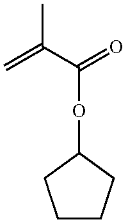
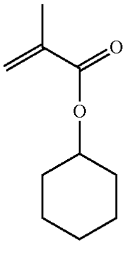
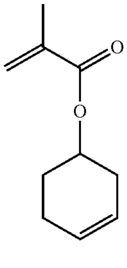
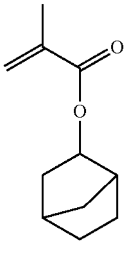
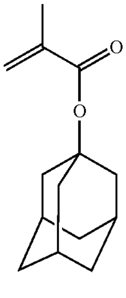
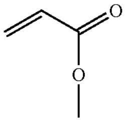
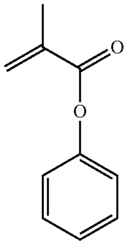
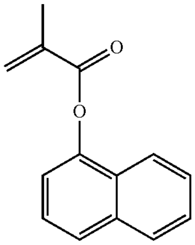
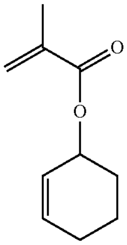
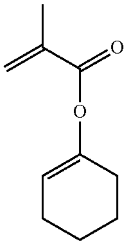
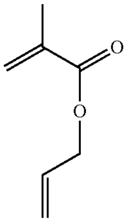
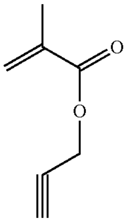
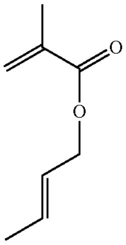
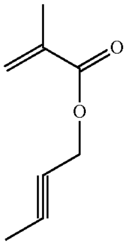
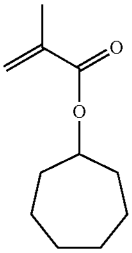
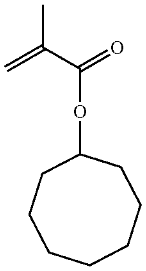
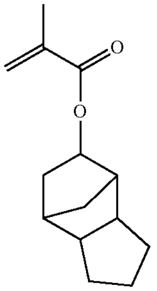
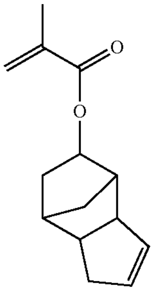
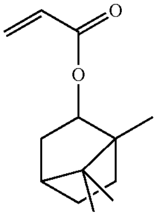
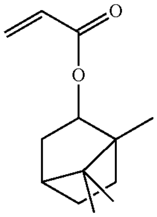
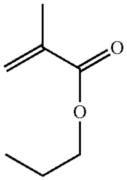
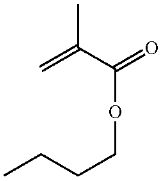
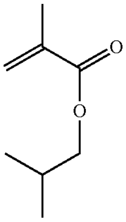
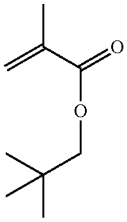
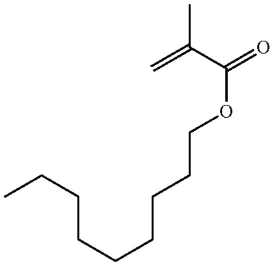

-continued
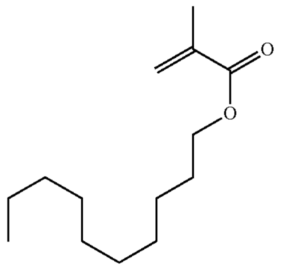
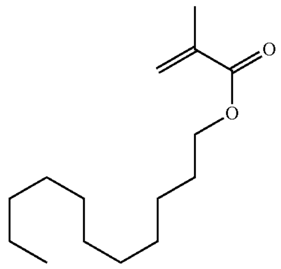
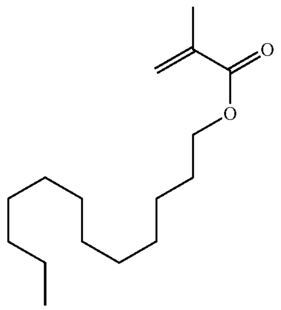
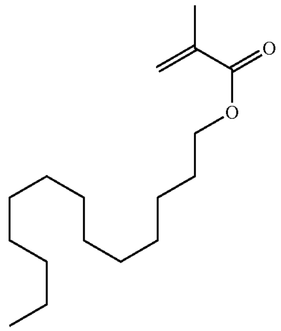
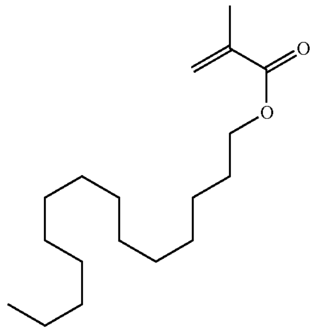
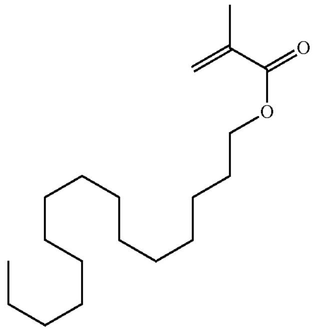
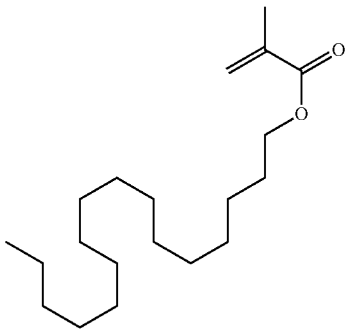
-continued
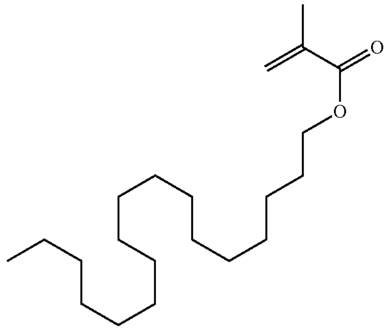
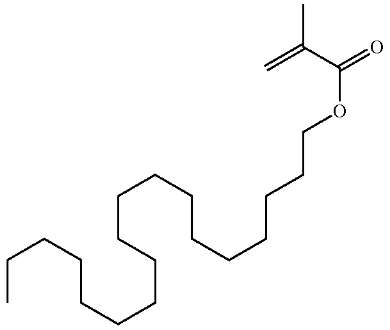
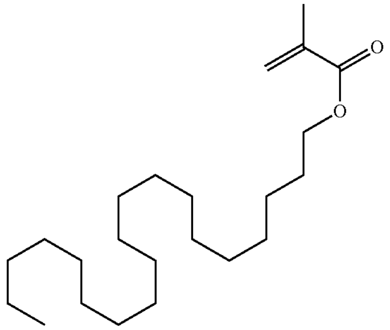
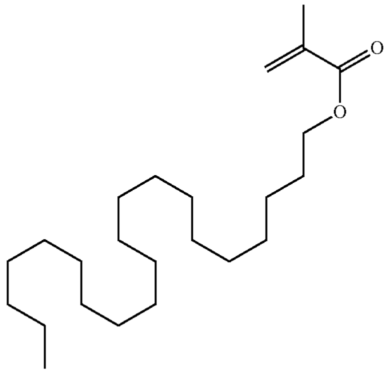

-continued
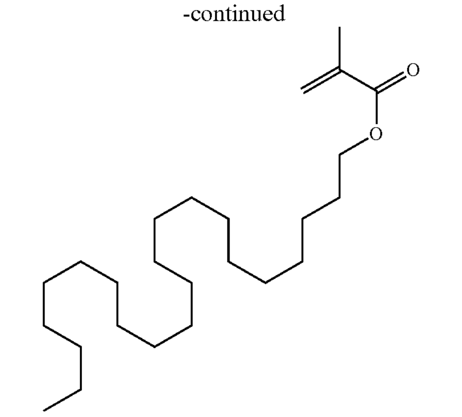
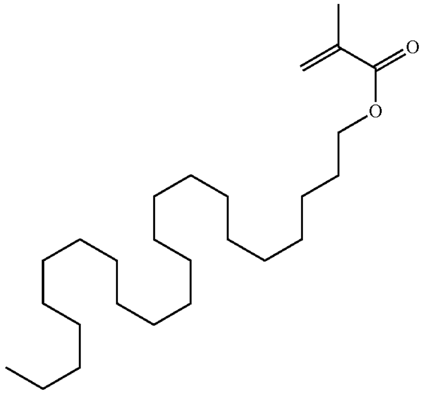
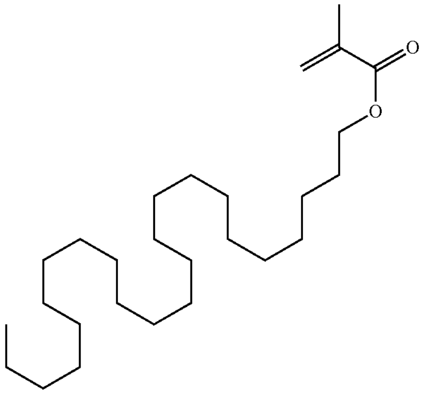
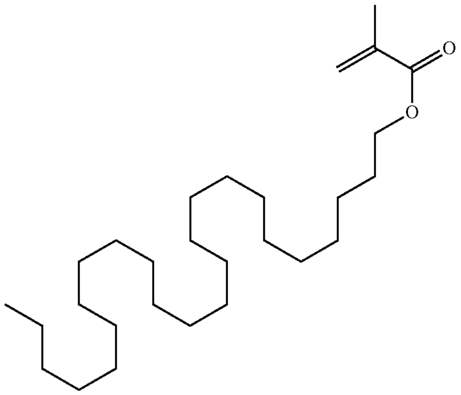
-continued
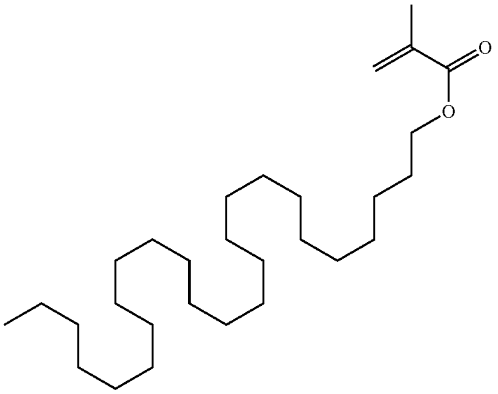
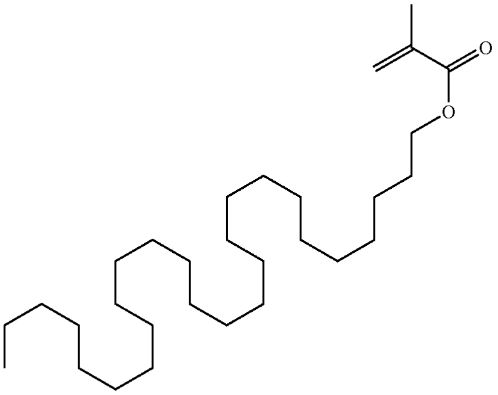
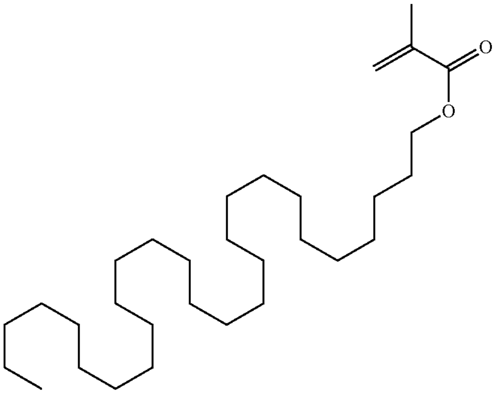
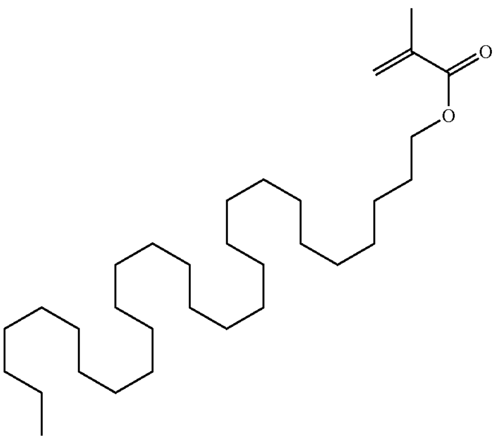

-continued
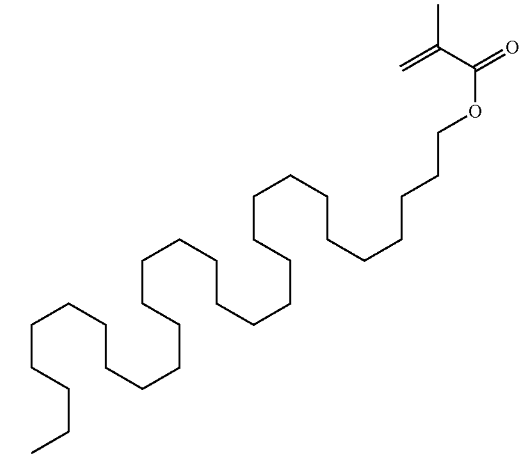
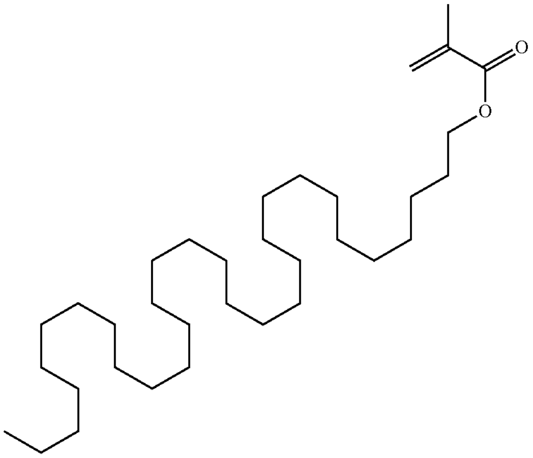
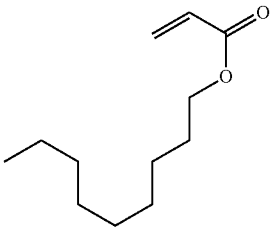
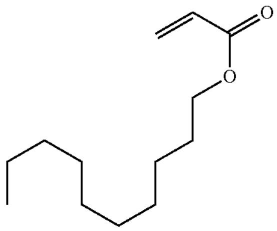
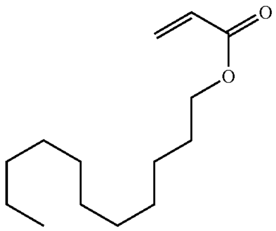
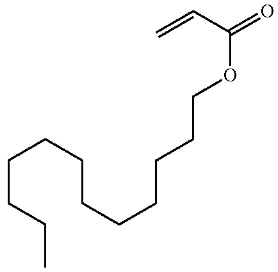
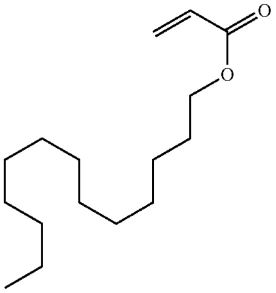
-continued
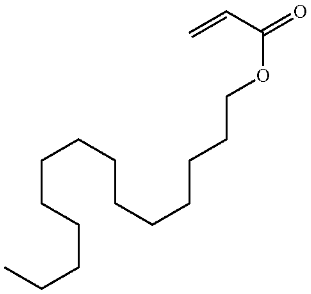
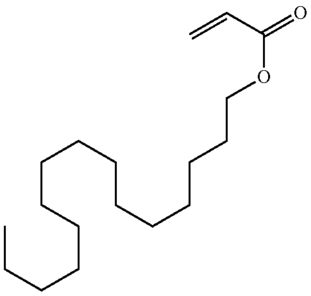
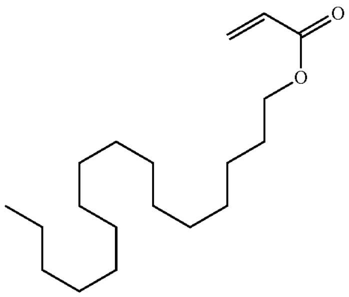
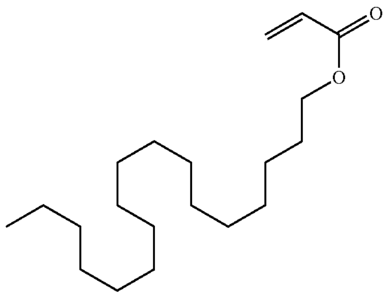
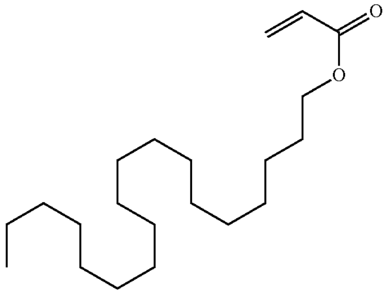

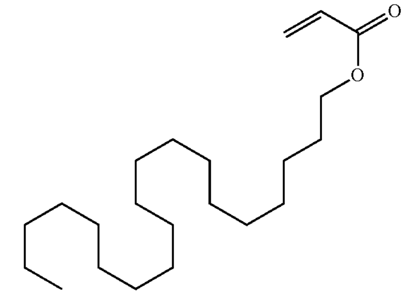
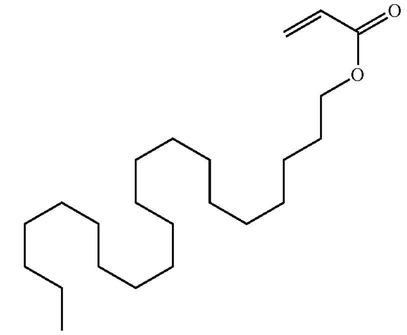
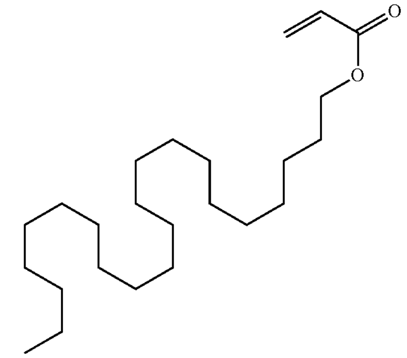
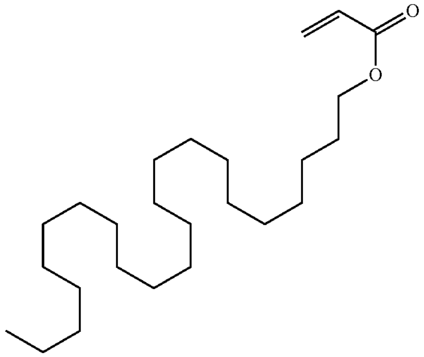
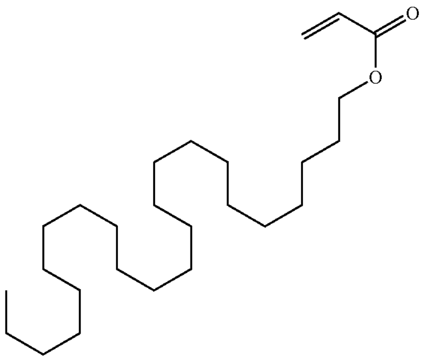
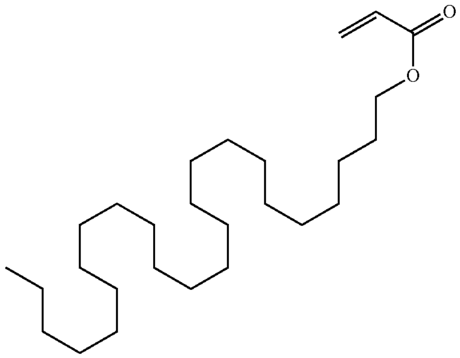
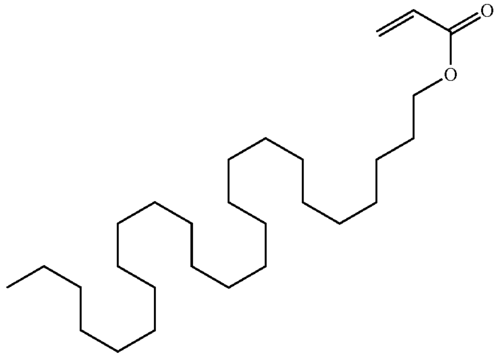
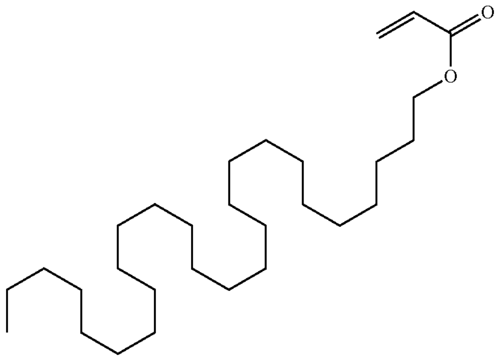
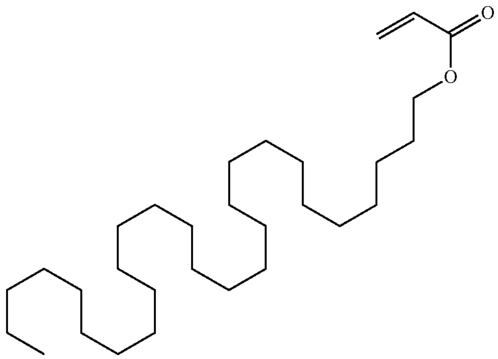

-continued
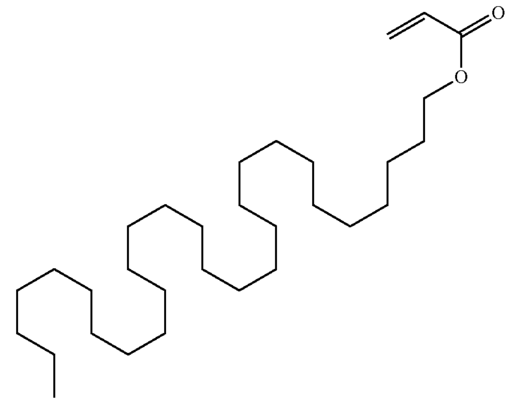
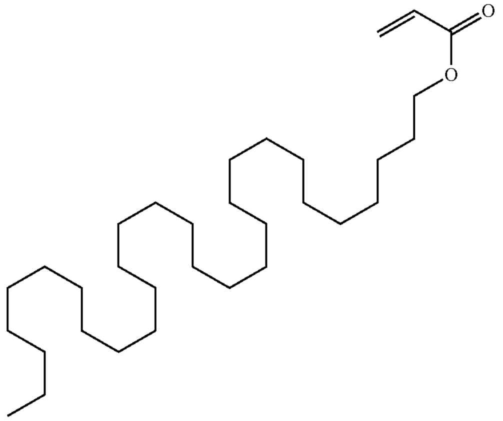
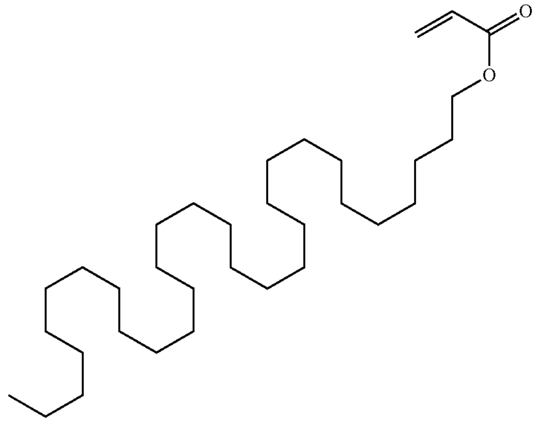
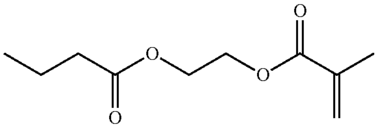
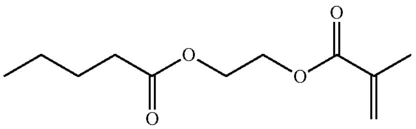
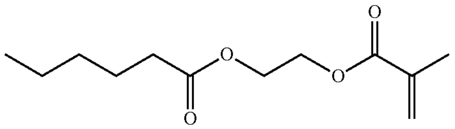
-continued
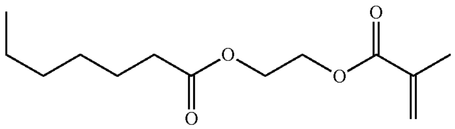
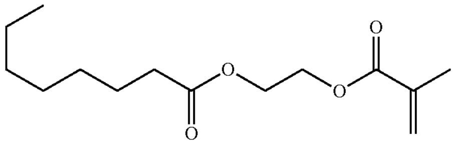
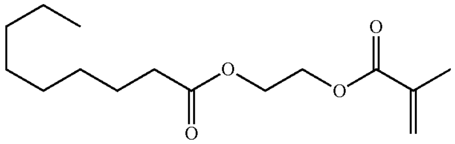
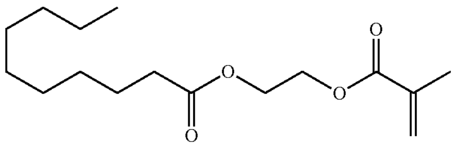
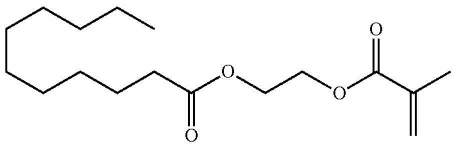
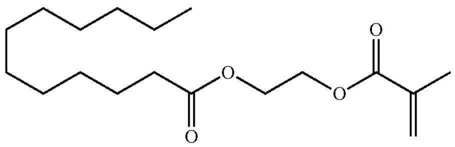
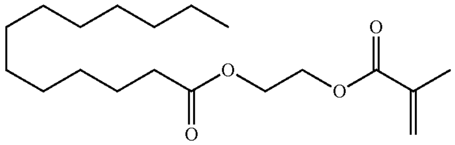
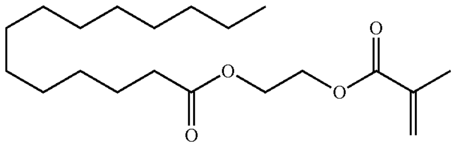
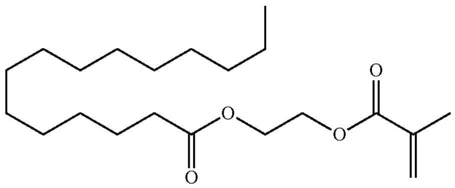
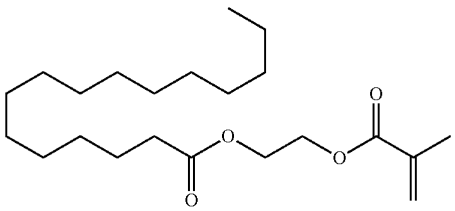

-continued
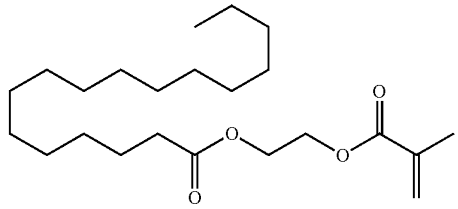
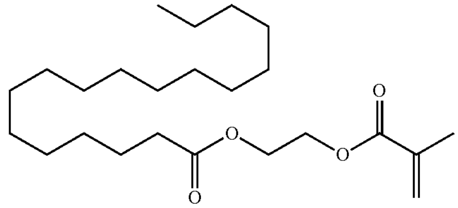
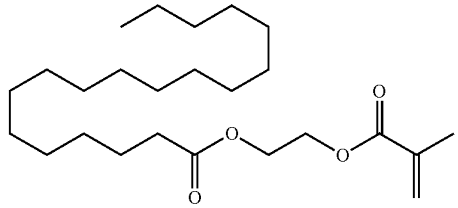
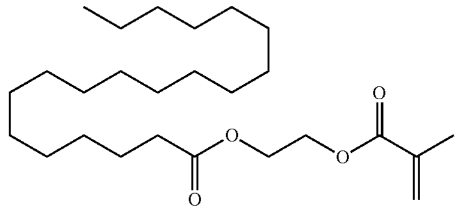
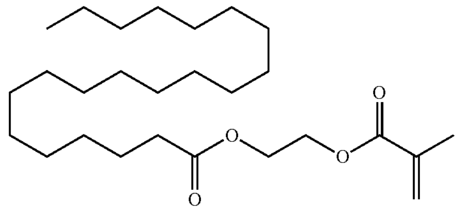
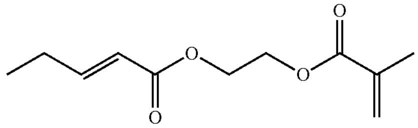
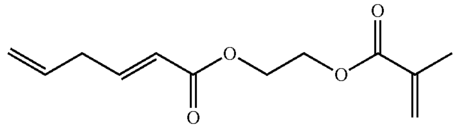
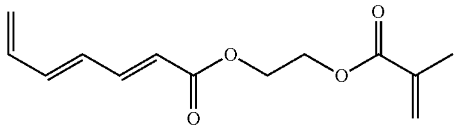
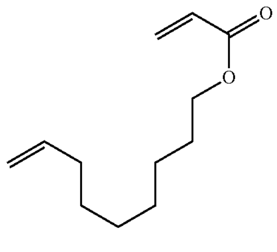
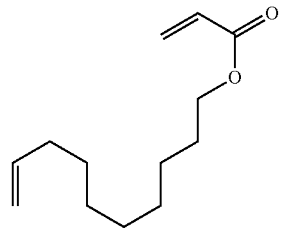
-continued
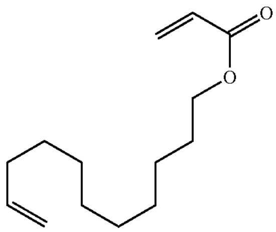
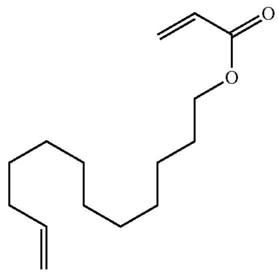
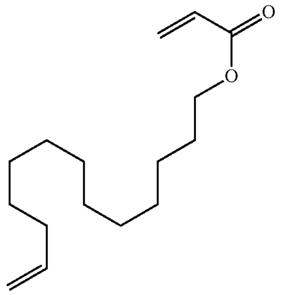
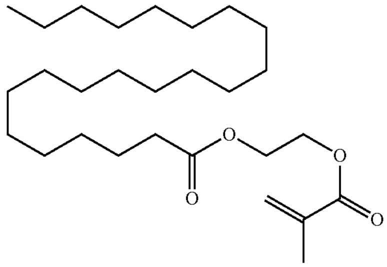
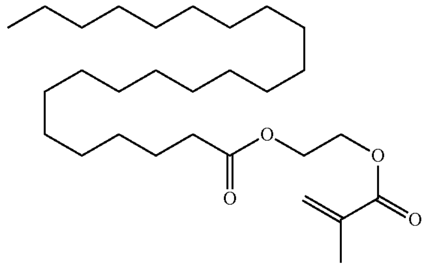
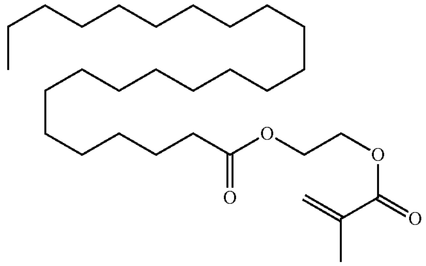
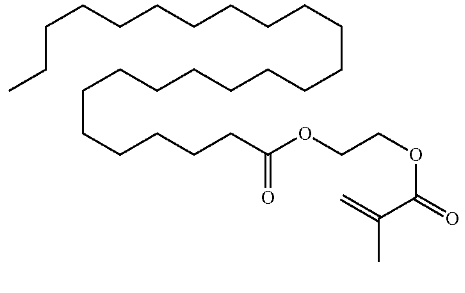

-continued

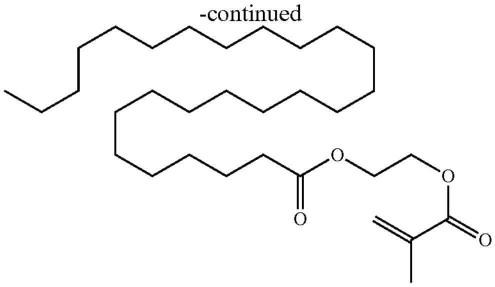

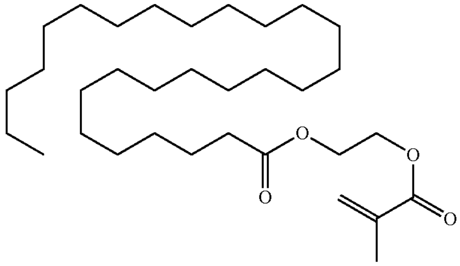

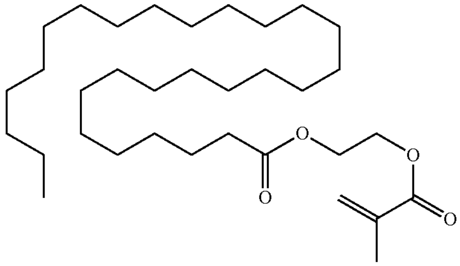

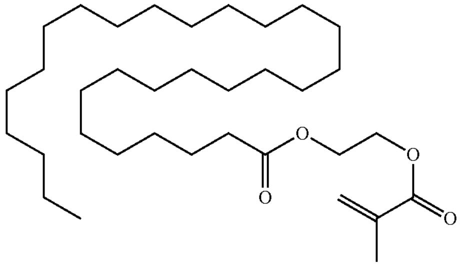

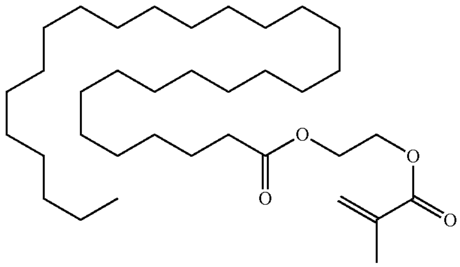

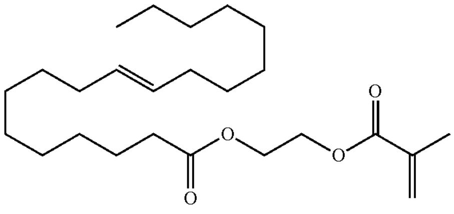

-continued

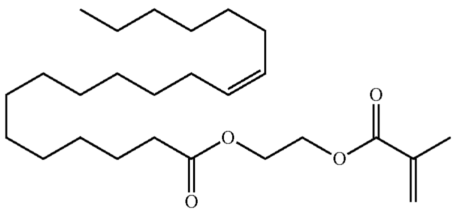

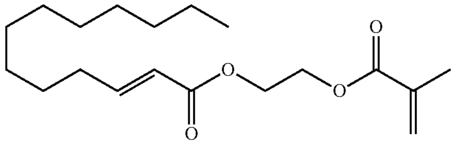

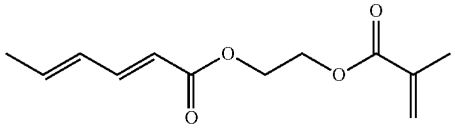

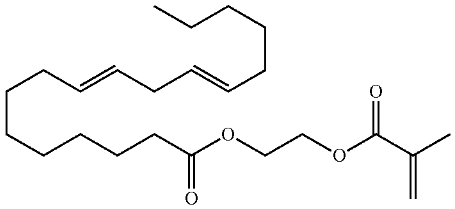

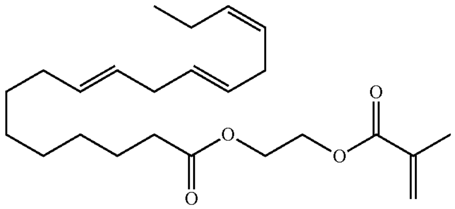

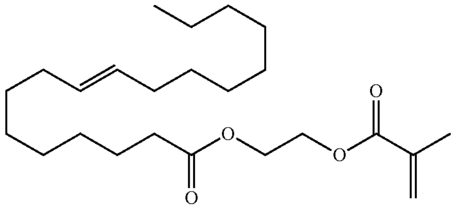

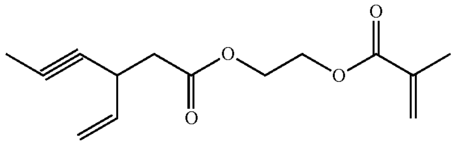

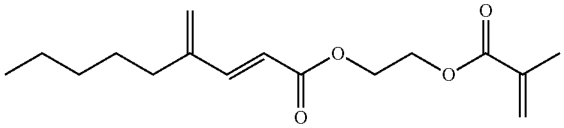

(Repeating Unit-f)

In addition to the repeating units-a1 to -a7, -b1, -c, -d, and -e, it is also possible to copolymerize a crosslinkable repeating unit-f in the component (A) of the inventive bio-electrode composition. Examples of the crosslinkable repeating unit-f include repeating units having an oxirane ring or an oxetane ring. Specific examples of monomers to give the crosslinkable repeating unit-f having an oxirane ring or an oxetane ring include the following.

-continued
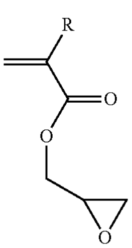
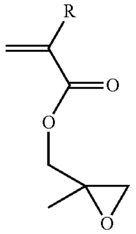
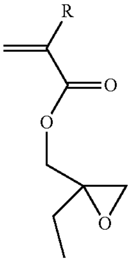
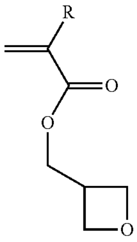
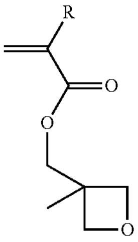
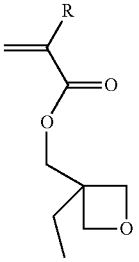
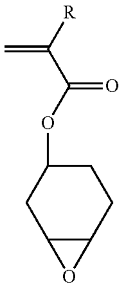
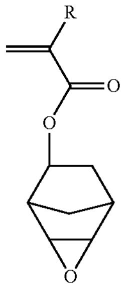
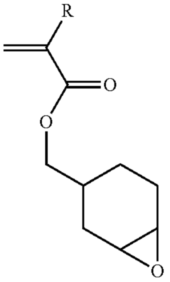
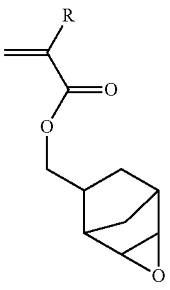
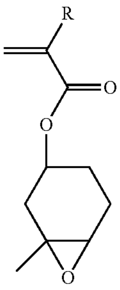
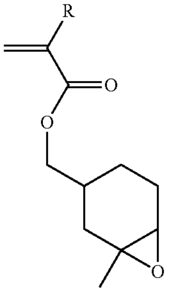
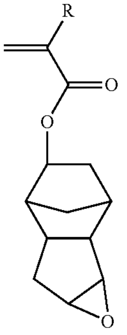
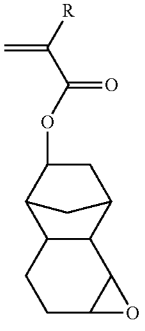
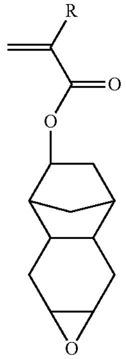
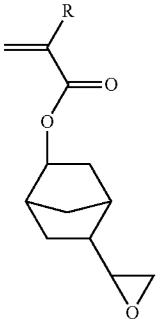
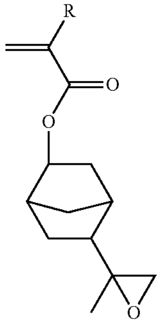
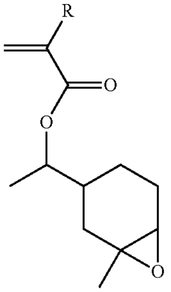
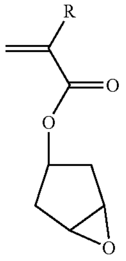
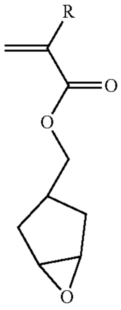
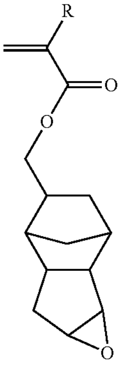
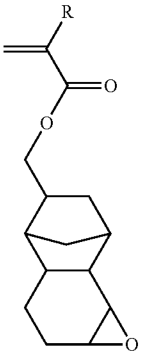
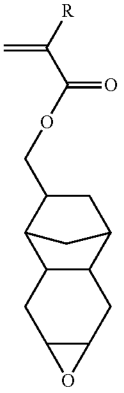
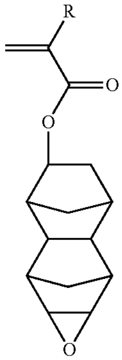
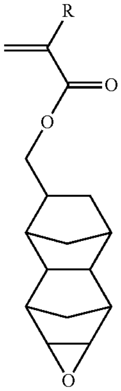
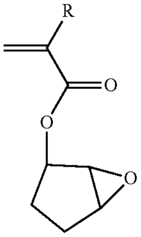
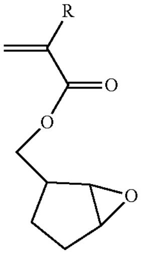
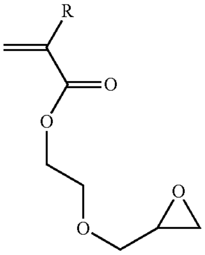
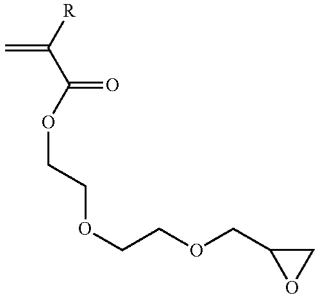
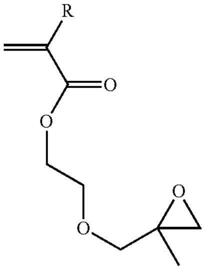

-continued
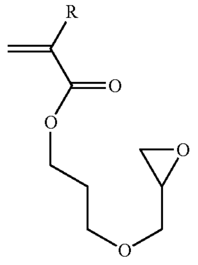
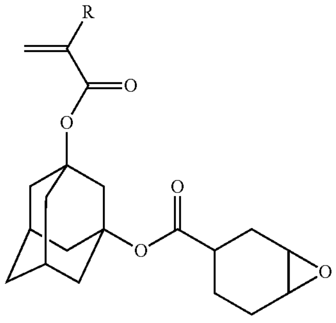
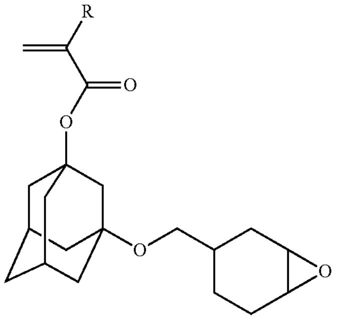
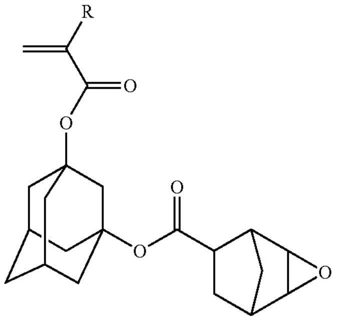
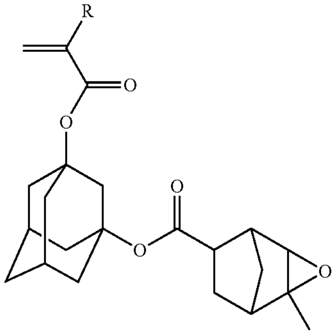
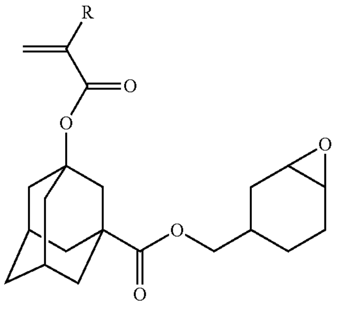
-continued
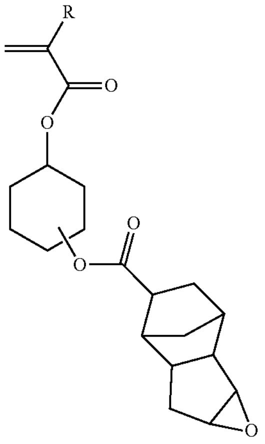
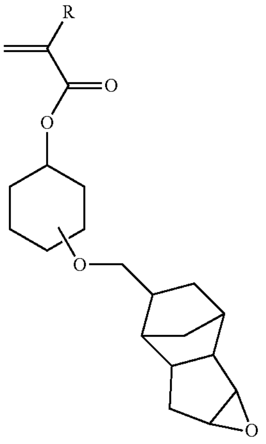
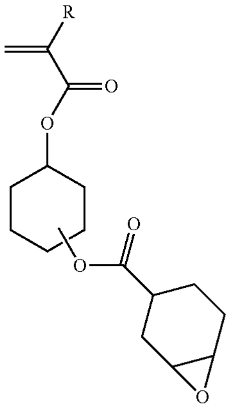
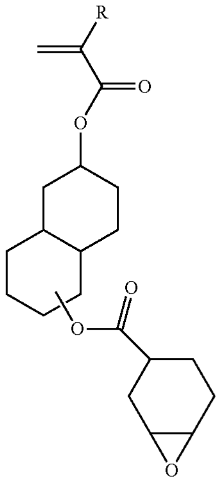
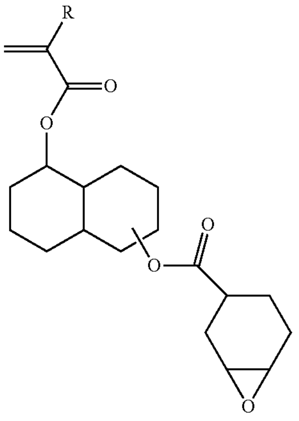
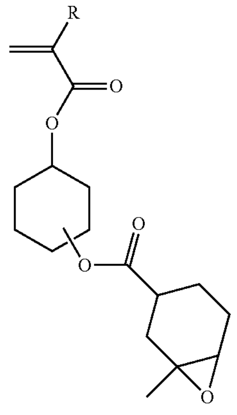

-continued
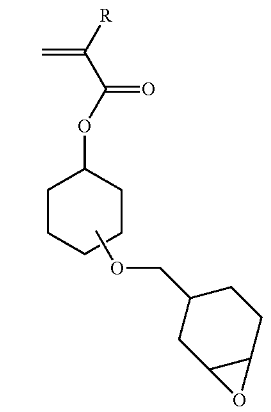
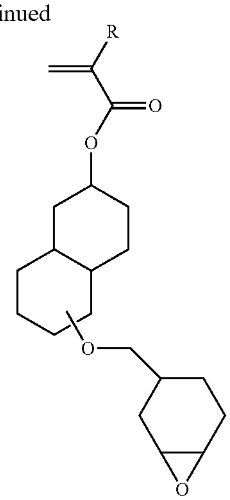
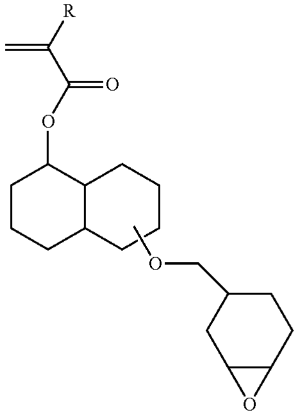
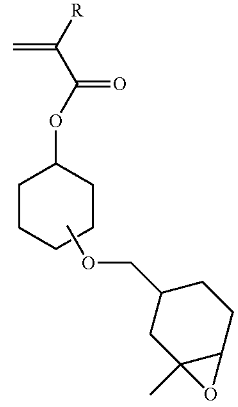
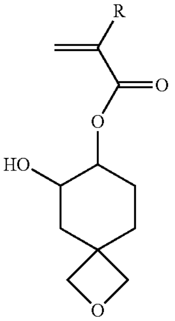
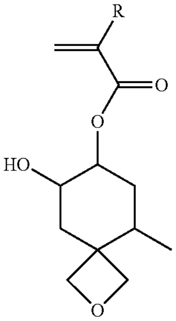
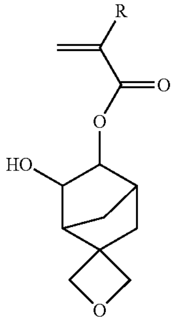
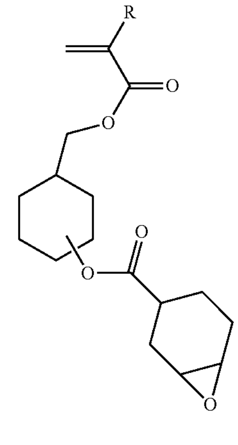
In the formulae, R represents a hydrogen atom or a methyl group.
(Repeating Unit-g)
In addition to the repeating unit(s) selected from the above-described -a1 to -a7, -b1, and -c to -f, the component (A) of the inventive bio-electrode composition can also have a repeating unit-g having silicon. Specific examples include the following.
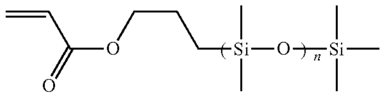
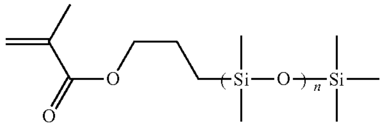
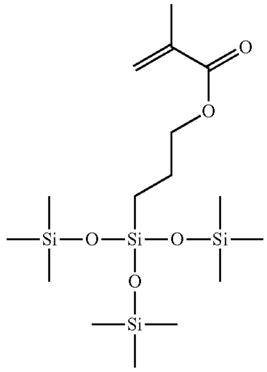
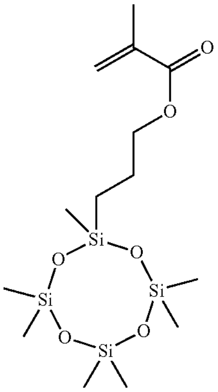
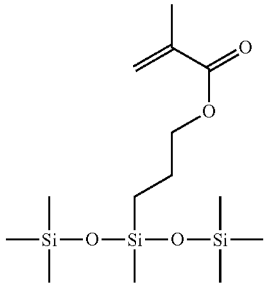
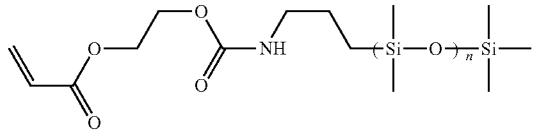
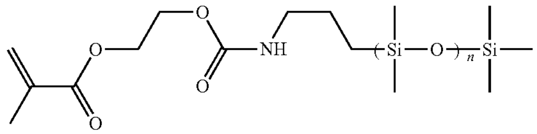
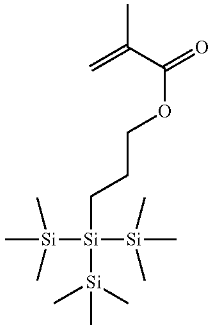
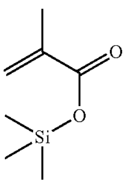

-continued
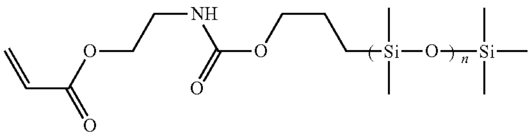
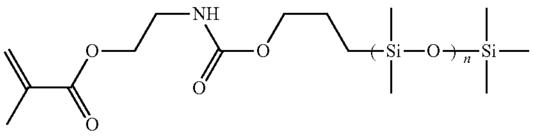
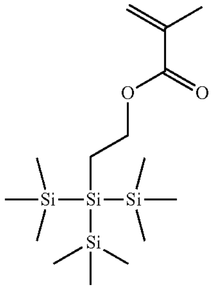
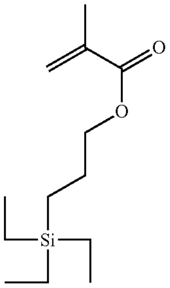
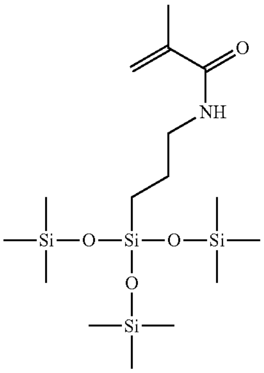
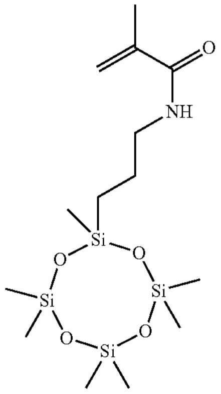
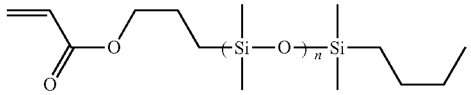
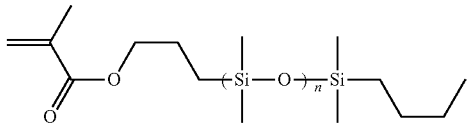
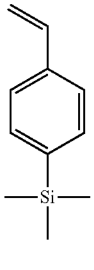
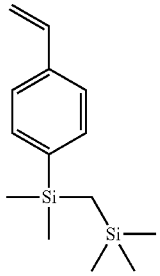
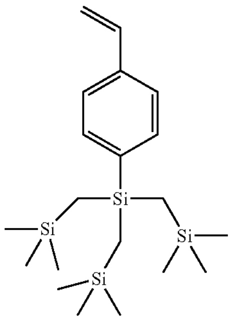
-continued
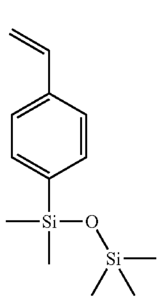
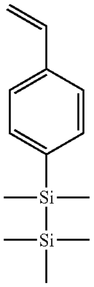
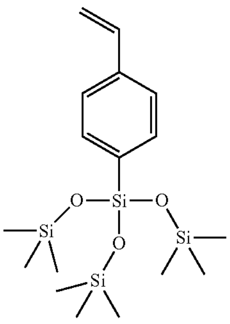
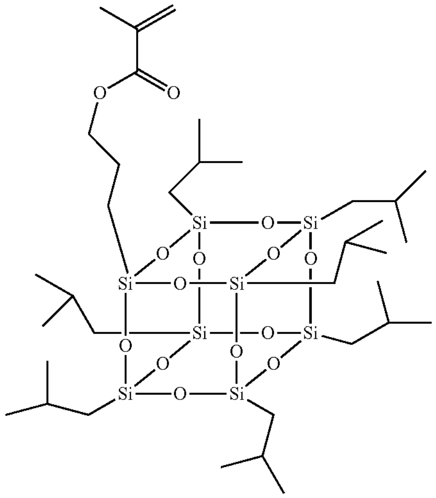
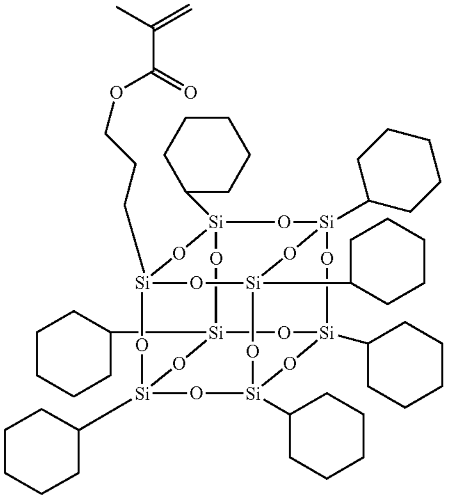

-continued
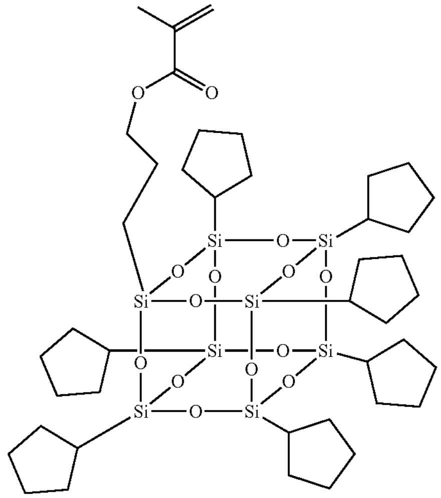
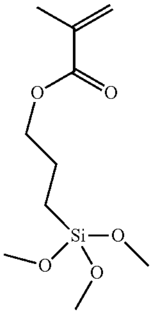
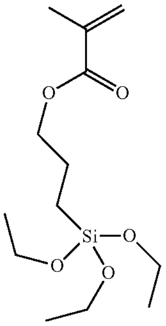
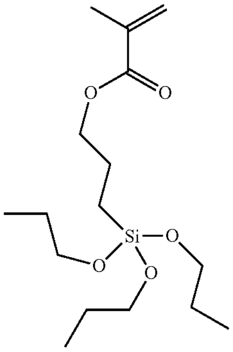
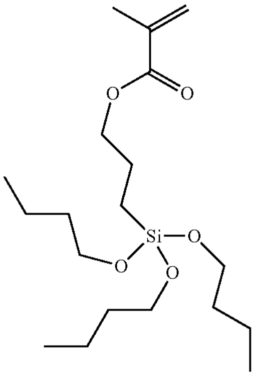
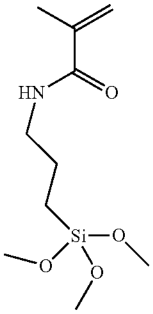
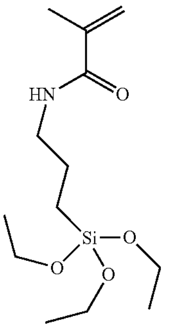
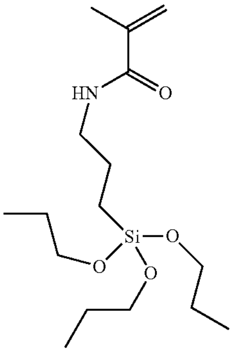
-continued
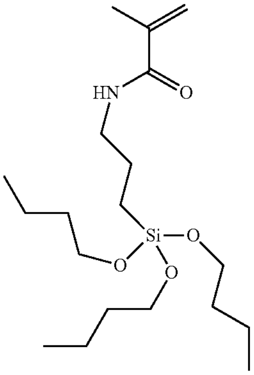
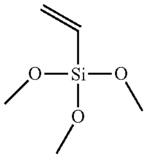
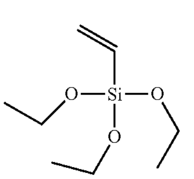
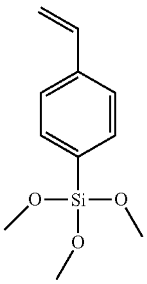
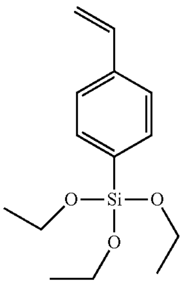
(Repeating Unit-h)
In addition to the repeating unit(s) selected from the above-described -a1 to -a7, -b1, and -c to -g, the component (A) of the inventive bio-electrode composition can also have a repeating unit-h having fluorine. Specific examples of a monomer to give the repeating unit-h having fluorine include the following.
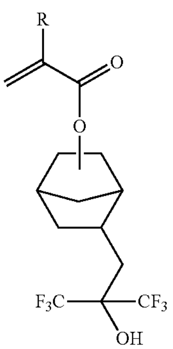
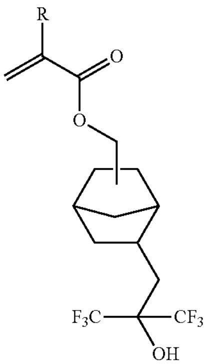
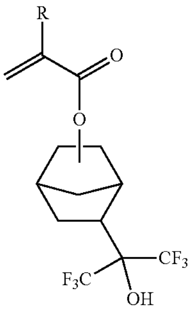
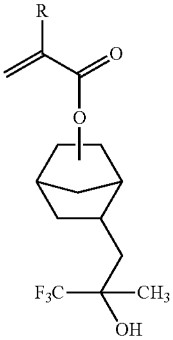

-continued
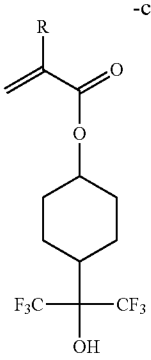
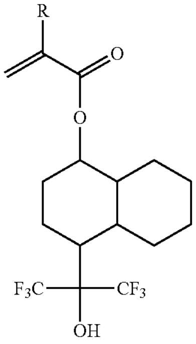
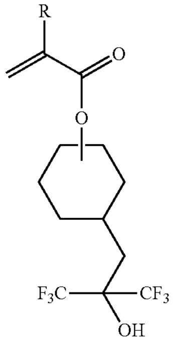
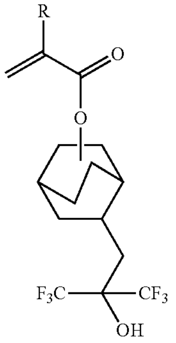
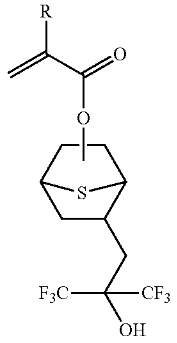
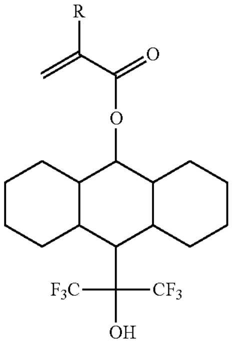
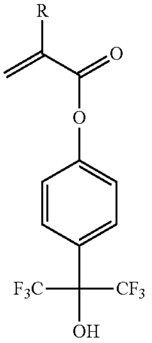
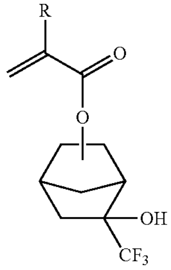
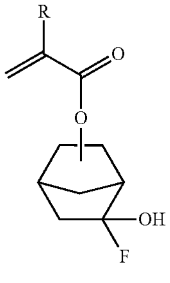
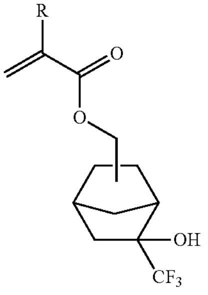
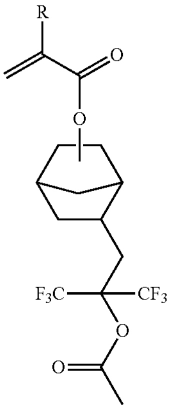
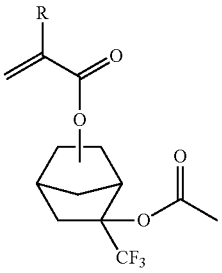
-continued
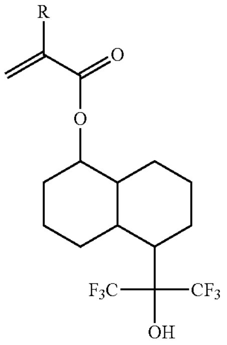
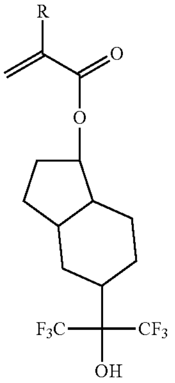
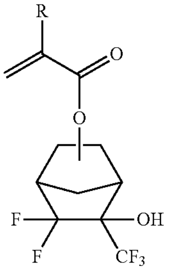
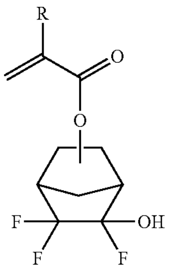
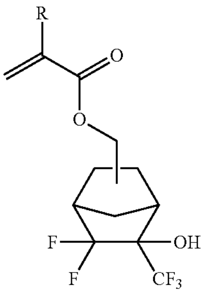
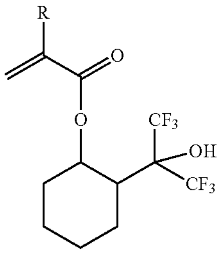
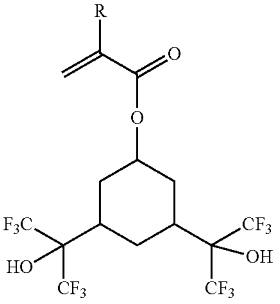
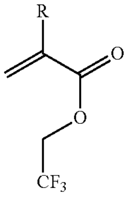
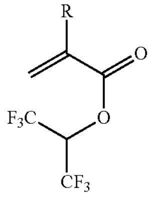
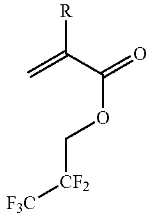
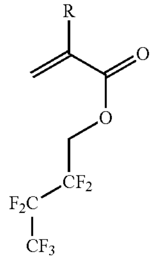
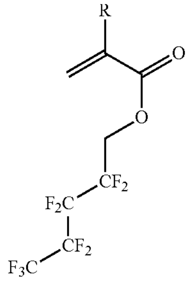
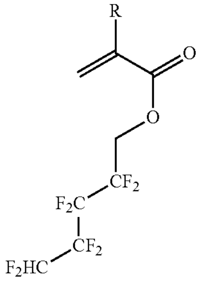

-continued
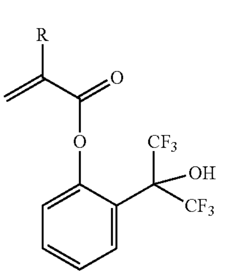
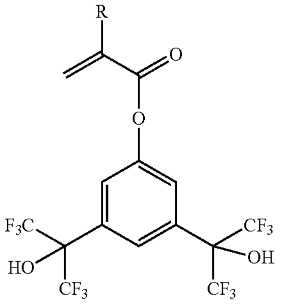
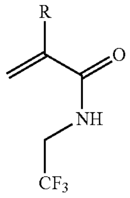
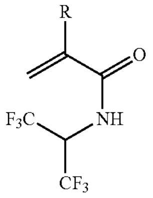
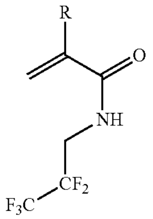
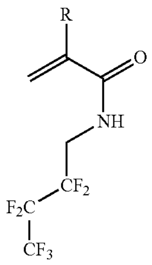
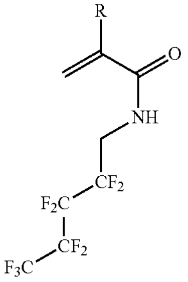
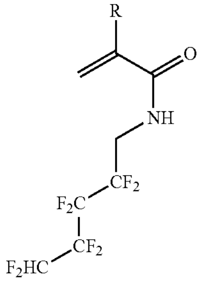
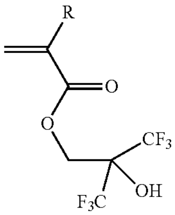
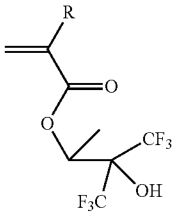
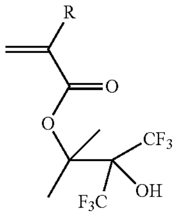
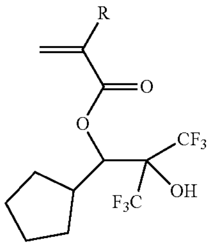
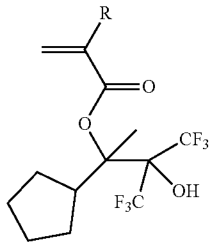
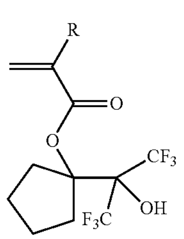
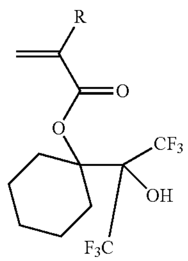
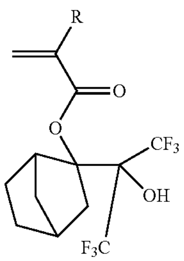
-continued
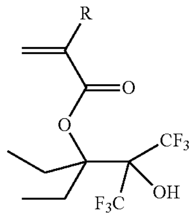
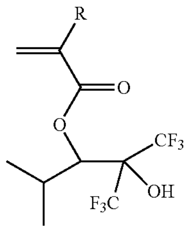
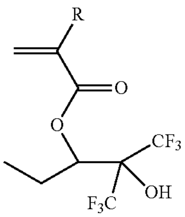
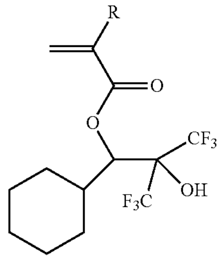
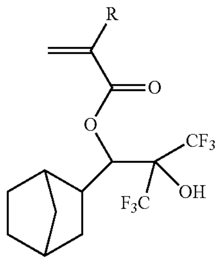
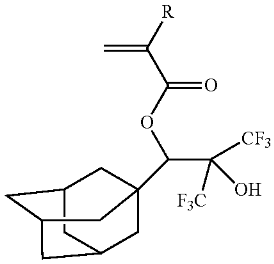
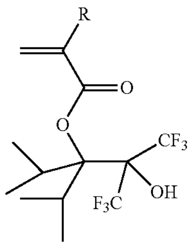
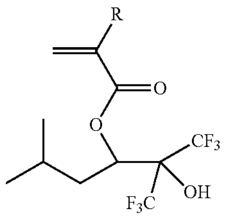
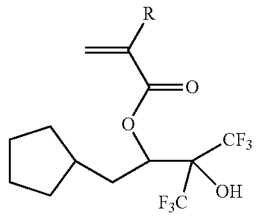
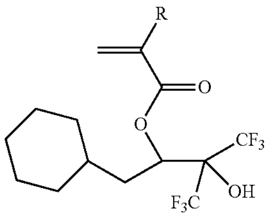
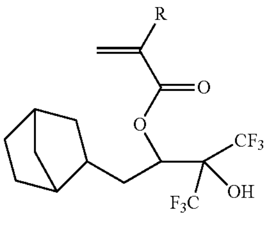
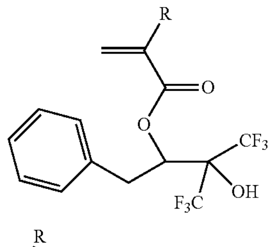
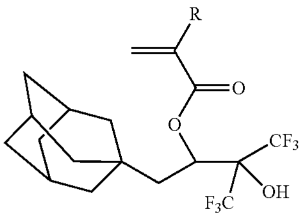

-continued
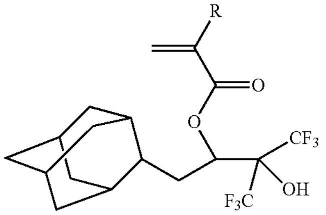
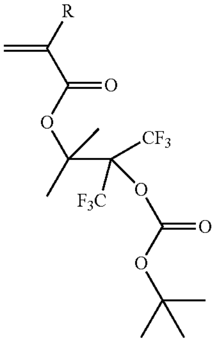
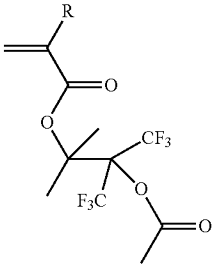
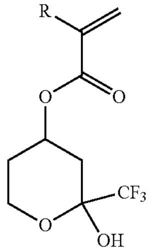
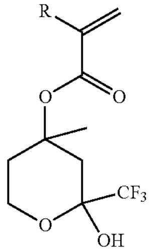
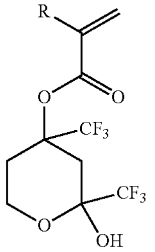
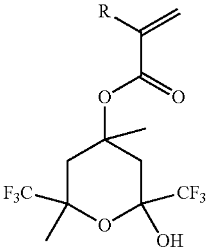
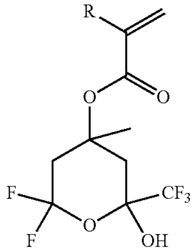
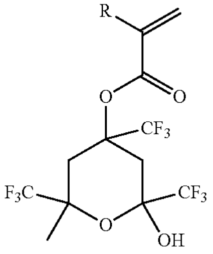
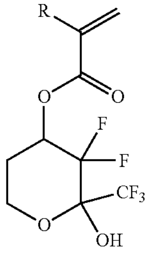
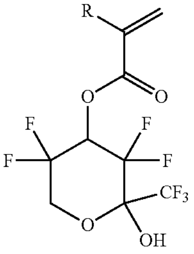
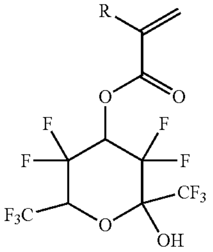
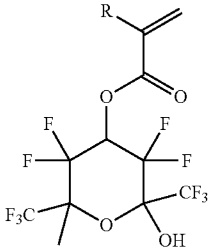
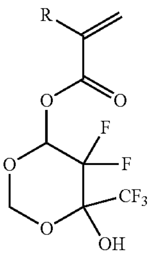
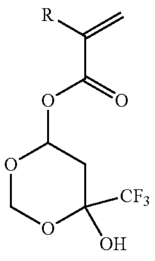
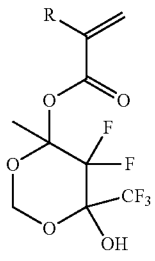
-continued
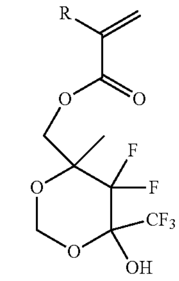
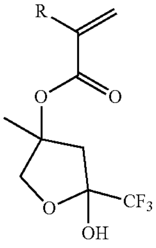
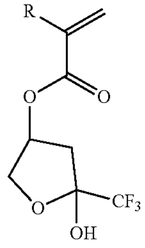
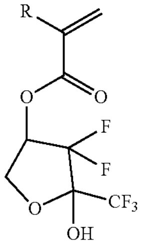
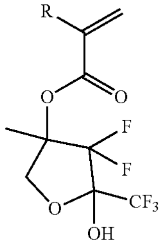
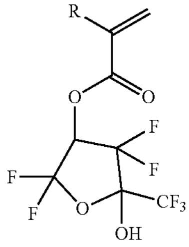
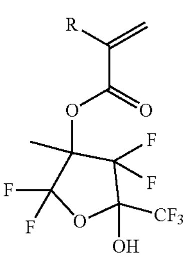
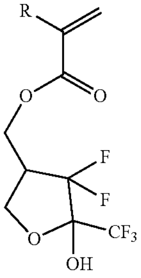
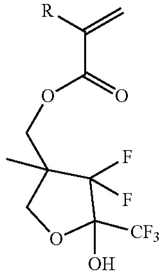
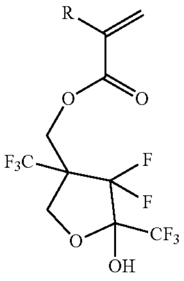
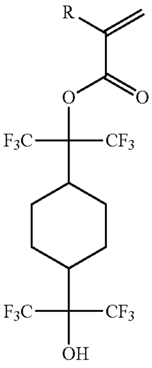
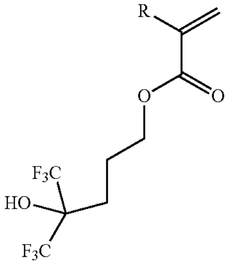
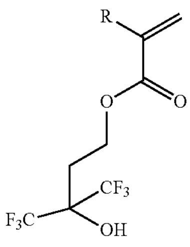
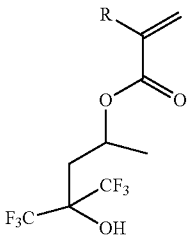
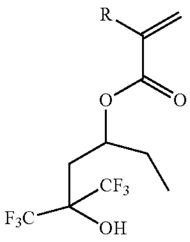

-continued
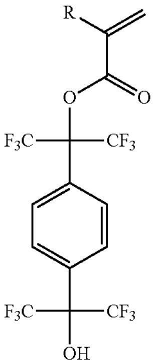
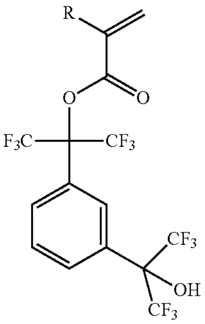
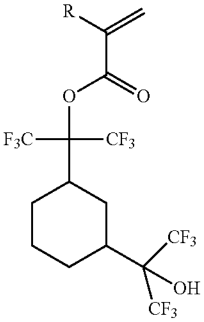
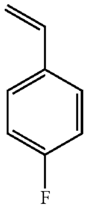
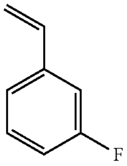
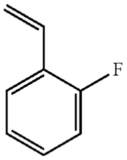
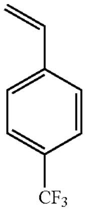
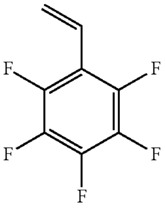
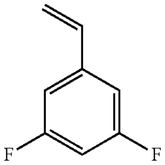
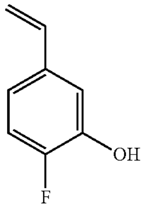
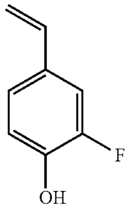
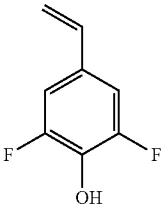
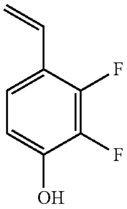
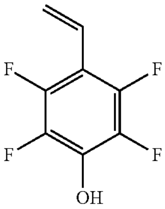
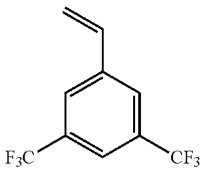
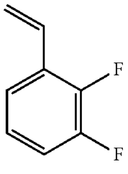
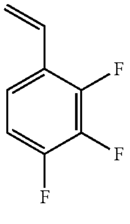
-continued
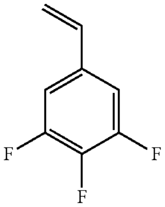
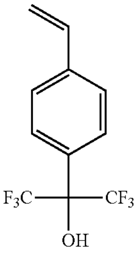
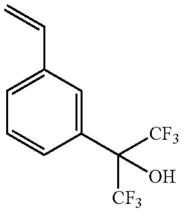
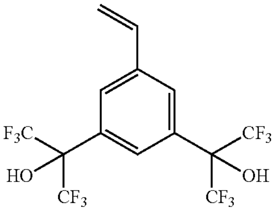
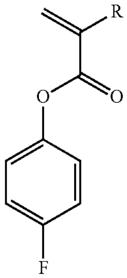
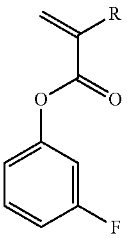
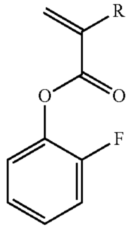
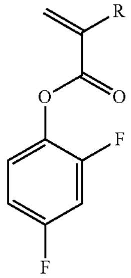
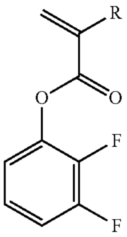
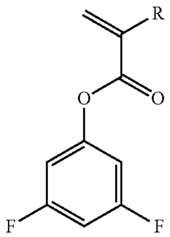
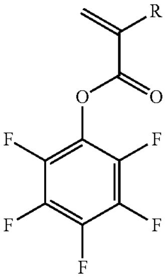
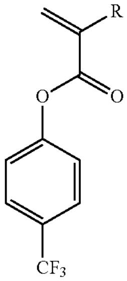
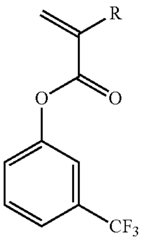
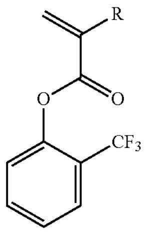
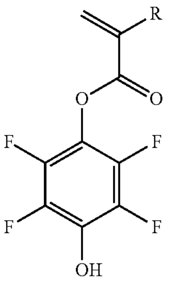
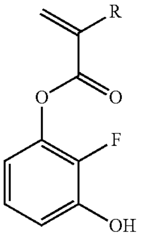
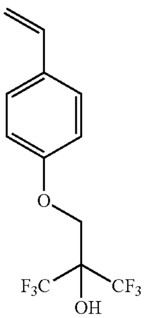
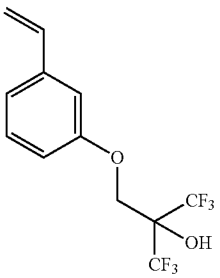

-continued

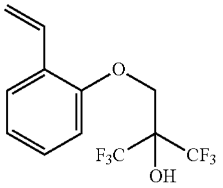
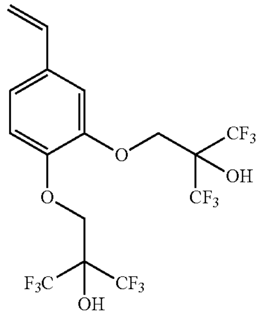
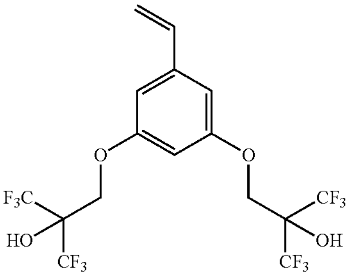
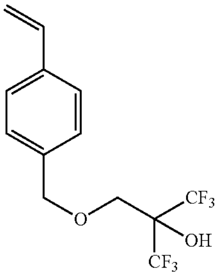
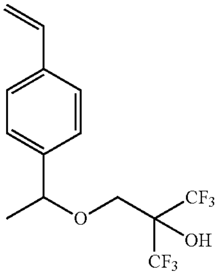
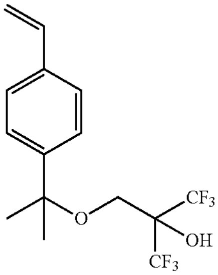
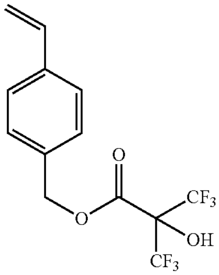
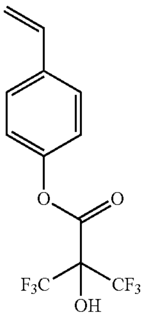
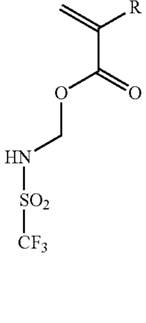
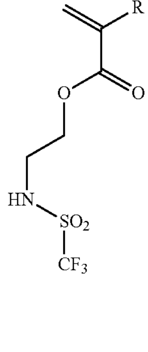
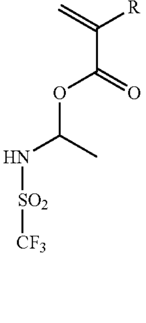

-continued

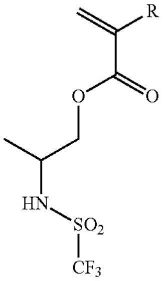
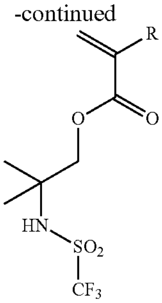
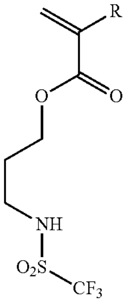
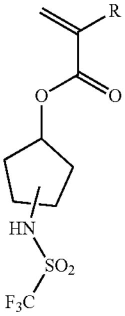
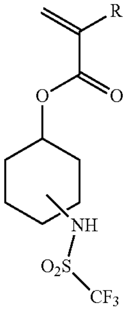
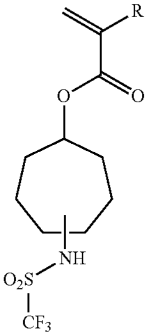
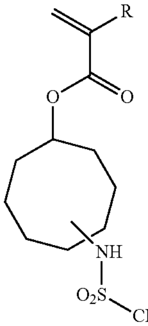
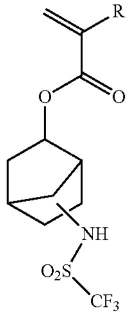
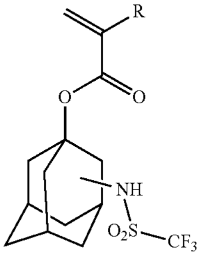
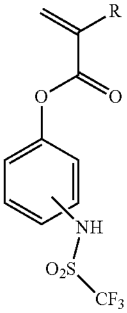
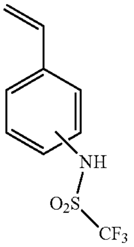

In the formulae, R represents a hydrogen atom or a methyl group.

As one method for synthesizing the component (A) ionic polymer material, a copolymer ionic polymer material can be obtained, for example, by a method in which desired monomer(s) among the monomers to give the repeating units-a1 to -a7, -b1, -c, -d, -e, -f, -g and -h undergo heat polymerization in an organic solvent to which a radical polymerization initiator is added.

Examples of the organic solvent used in the polymerization include toluene, benzene, tetrahydrofuran, diethyl ether, dioxane, etc. Examples of the radical polymerization initiator include 2,2'-azobisisobutyronitrile (AIBN), 2,2'-azobis (2,4-dimethylvaleronitrile), dimethyl 2,2-azobis(2-methylpropionate), benzoyl peroxide, lauroyl peroxide, etc. The heating temperature is preferably 50 to 80° C., and the reaction time is preferably 2 to 100 hours, more preferably 5 to 20 hours.

Here, the proportions of the repeating units-a1 to -a7, -b1, -c, -d, -e, -f, -g, and -h in the component (A) ionic polymer material can be 0≤a1<1.0, 0≤a2<1.0, 0≤a3<1.0, 0≤a4<1.0, 0≤a5<1.0, 0≤a6<1.0, 0≤a7<1.0, 0≤a1+a2+a3+a4+a5+a6+a7<1.0, 0<b1<1.0, 0≤c<1.0, 0≤d<1.0, 0≤e<0.9, 0≤f<0.9, 0≤g<0.9, and 0≤h<0.9; preferably 0≤a1≤0.9, 0≤a2≤0.9, 0≤a3≤0.9, 0≤a4≤0.9, 0≤a5≤0.9, 0≤a6≤0.9, 0≤a7≤0.9, 0.01≤a1+a2+a3+a4+a5+a6+a7≤0.99, 0.01≤b1≤0.9, 0≤c≤0.8, 0≤d≤0.8, 0≤e<0.8, 0≤f<0.8, 0≤g<0.8, and 0≤h<0.8; more preferably 0≤a1≤0.8, 0≤a2≤0.8, 0≤a3≤0.8, 0≤a4≤0.8, 0≤a5≤0.8, 0≤a6≤0.8, 0≤a7≤0.8, 0.02≤a1+a2+a3+a4+a5+a6+a7≤0.95, 0.05≤b1≤0.8, 0≤c≤0.7, 0≤d≤0.5, 0≤e<0.3, 0≤f<0.7, 0≤g<0.7, and 0≤<0.7.

Incidentally, for example, a1+a2+a3+a4+a5+a6+a7+b1+c+d+e+f+g+h=1 means that the total amount of the repeating units-a1, -a2, -a3, -a4, -a5, -a6, -a7, -b1, -c, -d, -e, -f, -g, and -h is 100 mol % based on the total amount of all the repeating units in the polymer compound containing the repeating units-a1, -a2, -a3, -a4, -a5, -a6, -a7, -b1, -c, -d, -e, -f, -g, and -h; and a1+a2+a3+a4+a5+a6+a7+b1+c+d+e+f+g+h<1 means that the total amount of the repeating units-a1, -a2, -a3, -a4, -a5, -a6, -a7, -b1, -c, -d, -e, -f, -g, and -h is less than 100 mol % based on the total amount of all the repeating units, indicating that the polymer compound contains another repeating unit(s) besides the repeating units-a1, -a2, -a3, -a4, -a5, -a6, -a7, -b1, -c, -d, -e, -f, -g, and -h.

Regarding the molecular weight of the component (A) ionic polymer material, the weight-average molecular weight is preferably 500 or more, more preferably 1,000 or more and 1,000,000 or less, and further preferably 2,000 or more and 500,000 or less. Regarding the ionic monomer (residual monomer) that is not incorporated into the component (A) ionic polymer material after the polymerization, if the amount is small, the residual monomer can be prevented from permeating into skin in a biocompatibility test and from causing allergy. Accordingly, it is preferable to decrease the amount of residual monomers. The amount of residual monomers is preferably 10 parts by mass or less based on 100 parts by mass of the entire component (A) ionic polymer material. In addition, one kind of the component (A) may be used, or two or more kinds which differ in molecular weight, dispersity, and constitutive polymerizable monomer may be used in mixture. The molecular weight (Mw) is determined by gel permeation chromatography (GPC) using tetrahydrofuran (THF) as an eluent.

As the component (A) ionic polymer material, the inventive composition preferably contains a polymer having a repeating unit-b1 having a nitro group copolymerized in addition to at least one repeating unit selected from the repeating units-a1 to -a7 shown by the following general formula (2)'.

(2)' a1

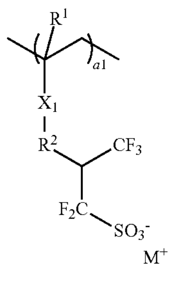

-continued a2

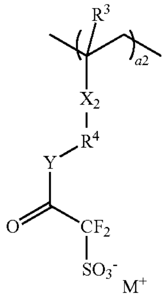

a3

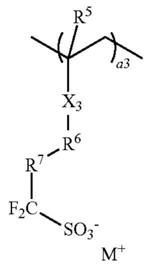

a4

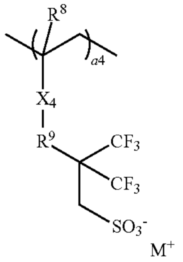

a5

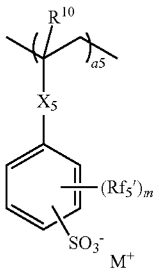

a6

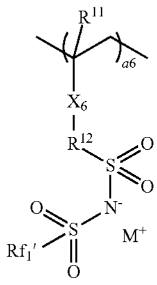

-continued a7

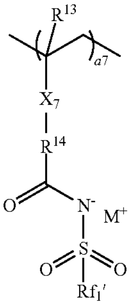

b1

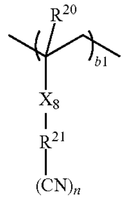

In the formulae, $R^{1\ to\ 14}$, $R^{20}$, $R^{21}$, $X_{1\ to\ 8}$, a1 to a7, b1, $Rf_1$', $Rf_5$', "m", "n", and $M^+$ are as defined above.

In the inventive bio-electrode composition, the component (A) is blended in an amount of preferably 0.1 to 300 parts by mass, more preferably 1 to 200 parts by mass, based on 100 parts by mass of the component (B) described below. Additionally, one kind of the component (A) may be used, or two or more kinds thereof may be used in mixture.

[(B) Resin]

The inventive bio-electrode composition can further contain a resin as a component (B). The resin (B) contained in the inventive bio-electrode composition is a component that is made compatible with the ionic polymer material (A) (salt) to prevent elution of the salt. This component also serves to hold an electric conductivity improver such as a metal powder, a carbon powder, a silicon powder, and a lithium titanate powder, and further enhance adhesiveness. When the ionic polymer material (A) has sufficient adhesiveness, the resin (B) is not necessarily needed. Note that the resin may be any resin other than the above-described component (A), and is preferably either or both of a thermosetting resin and a photo-curable resin, particularly preferably one or more resins selected from the group consisting of silicone-based, acrylic-based, and urethane-based resins: that is, a silicone resin, a (meth)acrylate resin, and a urethane resin. Furthermore, the resin is preferably adhesive, and preferably includes a silicone resin having an $SiO_{4/2}$ unit and an $R_xSiO_{(4-x)/2}$ unit. Here, R represents a substituted or unsubstituted monovalent hydrocarbon group having 1 to 10 carbon atoms, and "x" represents a number in a range of 2.5 to 3.5.

Examples of the adhesive silicone-based resin include an addition reaction-curable (addition-curable) type and a radical crosslinking reaction-curable (radical curable) type. As the addition reaction-curable type, it is possible to use one that contains diorganosiloxane having an alkenyl group(s), an MQ resin having $R_3SiO_{1/2}$ and $SiO_{42}$ units, organohydrogenpolysiloxane having multiple SiH groups, a platinum catalyst, an addition-reaction inhibitor, and an organic solvent, for example, described in JP 2015-193803A. As the radical crosslinking reaction-curable type, it is possible to use one that contains diorganopolysiloxane with or without an alkenyl group, an MQ resin having $R_3SiO_{1/2}$ and $SiO_{4/2}$ units, organic peroxide, and an organic solvent, for example, described in JP 2015-193803A. Here, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanols, and improves adhesive strength when contained, but does not bind to the polysiloxane in molecular level because it is not crosslinkable. The adhesive strength can be increased by integrating the polysiloxane and the resin as described above.

The silicone-based resin may contain modified siloxane that has a functional group selected from the group consisting of an amino group, an oxirane group, an oxetane group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring. The addition of the modified siloxane improves dispersibility of the component (A) in the ionic polymer material. The modified siloxane may be modified at any part such as one terminal, both terminals, or a side chain of the siloxane.

As the adhesive acrylic-based resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adhesive urethane-based resin, it is possible to use one having a urethane bond with a polyether bond, a polyester bond, a polycarbonate bond, or a siloxane bond described in JP 2016-065238A, for example.

In the inventive bio-electrode composition, the resin (B) preferably has high compatibility with the component (A) to prevent lowering of the electric conductivity due to separation of the component (A) from the living body contact layer. In the inventive bio-electrode composition, the resin (B) preferably has high adhesion to the electro-conductive base material to prevent peeling of the living body contact layer from the electro-conductive base material. In order to increase the adhesion to the electro-conductive base material and the compatibility with the salt, the use of a resin with high polarity is effective. Examples of such a resin include resins having one or more moieties selected from an ether bond, an ester bond, an amide bond, an imide bond, a urethane bond, a thiourethane bond, and a thiol group: a polyacrylic resin, a polyamide resin, a polyimide resin, a polyurethane resin, a polythiourethane resin; etc. On the other hand, the living body contact layer is to be contacted with a living body, thereby being susceptible to perspiration. Accordingly, in the inventive bio-electrode composition, the resin (B) preferably has high repellency and is hardly hydrolyzed. To make the resin be highly repellent and hardly hydrolyzed, the use of a silicon-containing resin is effective.

The silicon atom-containing polyacrylic resin includes a polymer that has a silicone main chain and a polymer that has a silicon atom(s) on the side chain, either of which can be suitably used. As the polymer that has a silicone main chain, siloxane, silsesquioxane, or the like having a (meth) acrylpropyl group can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680B, for example. Such polyamide silicone resins can be synthesized by combining, for example, a silicone or non-silicone compound having amino groups at both terminals and a non-silicone or silicone compound having carboxy groups at both terminals.

It is also possible to use polyamic acid before cyclization thereof, which is obtained by reacting carboxylic anhydride and amine. The carboxy group of the polyamic acid may be crosslinked by using a crosslinking agent such as an epoxy type and an oxetane type. It is also possible to esterify the carboxy group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Examples of the silicon atom-containing polyurethane resin include polyurethane silicone resins. Such polyurethane silicone resins can be crosslinked through urethane bond by blending a compound having isocyanate groups at both terminals and a compound having a hydroxy group(s) at the terminal(s), followed by heating. In this case, a silicon atom(s) (siloxane bond) have to be contained in either or both of the compound having isocyanate groups at both terminals and the compound having a hydroxy group(s) at the terminal(s). Alternatively, polysiloxane and a urethane (meth)acrylate monomer can be blended and photo-crosslinked as described in JP 2005-320418A. It is also possible to photo-crosslink a polymer having both of a siloxane bond(s) and a urethane bond(s), with the terminal having a (meth)acrylate group(s). Particularly, a material having a polyurethane main chain with a silicone chain on a side chain as described in JP 2018-123304A and JP 2019-070109A is preferable because of the properties of high strength and high stretchability.

The silicon atom-containing polythiourethane resin can be obtained by reaction of a compound having a thiol group(s) and a compound having an isocyanate group(s), provided that at least one of them contains a silicon atom(s). The resin can also be photo-cured if (meth)acrylate groups are contained at the terminals.

The silicone-based resin can be improved in compatibility with the foregoing salt by adding modified siloxane that has a functional group selected from the group consisting of an amino group, an oxirane group, an oxetane group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring, in addition to the diorganosiloxane having an alkenyl group(s), the MQ resin having $R^3SiO_{1/2}$ and $SiO_{4/2}$ units, and the organohydrogenpolysiloxane having multiple SiH groups.

The diorganosiloxane having an alkenyl group(s) and the organohydrogenpolysiloxane having multiple SiH groups can be crosslinked through an addition reaction with a platinum catalyst.

Examples of the platinum catalyst include platinum-based catalysts such as chloroplatinic acid, alcohol solution of chloroplatinic acid, reaction product of chloroplatinic acid and alcohol, reaction product of chloroplatinic acid and an olefin compound, reaction product of chloroplatinic acid and vinyl group-containing siloxane, a platinum-olefin complex, and a complex of platinum and vinyl group-containing siloxane; platinum group metal-based catalysts such as a rhodium complex and a ruthenium complex; etc. These catalysts may be used after being dissolved or dispersed in alcohol solvent, hydrocarbon solvent, or siloxane solvent.

Note that the platinum catalyst is contained in an amount within preferably 5 to 2,000 ppm, particularly preferably 10 to 500 ppm, based on 100 parts by mass of the resin in the components (A) and (B).

In the inventive bio-electrode composition, the component (B) is preferably contained in an amount of 0 to 2000 parts by mass, more preferably 10 to 1000 parts by mass based on 100 parts by mass of the component (A) ionic polymer material. Furthermore, one kind of each of the components (A) and (B) may be used, or two or more kinds may be used in mixture.

When the addition-curable silicone resin is used, an addition-reaction inhibitor may be added. This addition-reaction inhibitor is added as a quencher to prevent the action of the platinum catalyst in the solution and under a low temperature circumstance after forming the coating film and before heat curing. Specific examples of the addition-reaction inhibitor include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, 1,1,3,3-tetramethyl-1,3-divinyldisiloxane, etc.

The addition-reaction inhibitor is preferably contained in an amount of 0 to 10 parts by mass, particularly preferably 0.05 to 3 parts by mass based on 100 parts by mass of the component (B) resin.

When the component (B) has a double bond capable of radical crosslinking, it is effective to add a radical generator. Examples of radical generators include photoradical generators and thermal-radical generators.

Examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthene-9-one, diphenyl(2,4,6-trimethylbenzoyl)phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

The curing can also be performed by adding a radical generator of a heat decomposition type. Examples of the thermal-radical generator include 2,2'-azobis(isobutyronitrile), 2,2'-azobis(2,4-dimethylvaleronitrile), 2,2'-azobis(2-methylbutyronitrile), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dicumyl peroxide, etc.

Note that the radical generator is preferably contained in an amount of 0.1 to 50 parts by mass based on 100 parts by mass of the resin in the components (A) and (B).

As described below, the living body contact layer is a cured product of the bio-electrode composition. By curing the bio-electrode composition, the resulting living body contact layer has favorable adhesion to both skin and the electro-conductive base material. The curing means is not particularly limited, and common means can be used, including crosslinking reaction by either or both of heat and light, or with an acid catalyst or a base catalyst, for example. The crosslinking reaction can be performed, for example, by appropriately selecting methods described in "Kakyou hannou handbook (handbook of crosslinking reaction)", Chapter 2, pages 51-371, Yasuharu Nakayama, Maruzen Publishing Co., Ltd. (2013).

[Ionic Polymer]

The inventive bio-electrode composition can contain an ionic polymer besides the component (A). As repeating units for the ionic polymer, those shown in the general formula (2) can be used. The ionic polymer is preferably contained in an amount of 0.1 to 100 parts by mass based on 100 parts by mass of the resin in the components (A) and (B).

[(C) Carbon Material and/or Metal Powder]

The inventive bio-electrode composition can further contain a carbon material and/or a metal powder as a component (C).

[Metal Powder]

The inventive bio-electrode composition may also contain a metal powder in order to improve electron conductivity. The metal powder can be one or more metal powders selected from the group consisting of gold, silver, platinum, copper, tin, titanium, nickel, aluminum, tungsten, molybdenum, ruthenium, chromium, and indium. The metal powder is preferably added in an amount of 1 to 50 parts by mass based on 100 parts by mass of the resin in the components (A) and (B).

As the kind of the metal powder, gold, silver, and platinum are preferable from the viewpoint of electric conductivity. Silver, copper, tin, titanium, nickel, aluminum, tungsten, molybdenum, ruthenium, and chromium are preferable from the viewpoint of cost. From the viewpoint of biocompatibility, noble metals are preferable. From a comprehensive viewpoint including the above, silver is the most preferable.

The metal powder may have any shape, such as a spherical shape, a disk shape, a flaky shape, and a needle shape. The addition of flaky powder brings the highest electric conductivity and is preferable. The metal powder is preferably a flake having relatively low density and large specific surface area with a size of 100 μm or less, a tapped density of not more than 5 $g/cm^3$, and a specific surface area of not less than 0.5 $m^2/g$. The size of the metal powder was determined using a scanning microscope (SEM). The tapped density was determined by the method described in JIS Z 2512: 2012. The specific surface was determined by the method described in JIS Z 8830: 2013.

[Carbon Material]

A carbon material can be contained as an electric conductivity improver. Examples of the carbon material include carbon black, graphite, carbon nanotube, carbon fiber, graphene, etc. The carbon nanotube may be either single layer or multilayer, and the surface may be modified with an organic group(s). The carbon material is preferably one or both of carbon black and carbon nanotube. The carbon material is preferably contained in an amount of 1 to 50 parts by mass based on 100 parts by mass of the resin in the components (A) and (B).

[Silicon Powder]

The inventive bio-electrode composition may contain a silicon powder to enhance ion reception sensitivity. Examples of the silicon powder include powders of silicon, silicon monoxide, or silicon carbide. The particle size of the powder is preferably smaller than 100 μm, more preferably 1 μm or less. Since finer particles have a larger surface area, the resulting bio-electrode can receive a larger amount of ions and has higher sensitivity. The silicon powder is preferably contained in an amount of 1 to 50 parts by mass based on 100 parts by mass of the resin in the components (A) and (B). The particle size of the powder was determined using an SEM.

[Lithium Titanate Powder]

The inventive bio-electrode composition may contain a lithium titanate powder to enhance ion reception sensitivity. Examples of the lithium titanate powder include powders containing a compound shown by molecular formulae $Li_2TiO_3$, $LiTiO_2$, or $Li_4Ti_5O_{12}$ with a spinel structure. The lithium titanate powder preferably has a spinel structure. It is also possible to use carbon-incorporated lithium titanate particles. The particle size of the powder is preferably smaller than 100 μm, more preferably 1 μm or less. Since finer particles have a larger surface area, the bio-electrode can receive a larger amount of ions, and has higher sensitivity. The aforementioned powders may be composite powders with carbon. The lithium titanate powder is preferably contained in an amount of 1 to 50 parts by mass based on 100 parts by mass of the resin in the components (A) and (B).

[Crosslinking Agent]

The inventive bio-electrode composition may contain an epoxy-type crosslinking agent. This crosslinking agent is a compound having multiple epoxy groups or oxetane groups in one molecule. The amount of the crosslinking agent to be contained can be 1 to 30 parts by mass based on 100 parts by mass of the resin in the components (A) and (B).

[Crosslinking Catalyst]

The inventive bio-electrode composition may also contain a catalyst for crosslinking the epoxy groups or the oxetane groups. As this catalyst, those described in paragraphs [0027] to [0029] of JP 2019-503406A can be used. The catalyst can be contained in an amount of 0.01 to 10 parts by mass based on 100 parts by mass of the resin in the components (A) and (B).

[Ionic Additive]

The inventive bio-electrode composition may contain an ionic additive to enhance the ionic conductivity. In consideration of biocompatibility, examples of the ionic additive include sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, betaines, and salts disclosed in JP 2018-044147A, JP 2018-059050A, JP 2018-059052A, and JP 2018-130534A. The ionic additive can be contained in an amount of 0 to 10 parts by mass based on 100 parts by mass of the resin in the components (A) and (B).

[(D) Organic Solvent]

In addition, the inventive bio-electrode composition may contain an organic solvent as a component (D). Specific examples of the organic solvent include: aromatic hydrocarbon solvents, such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; aliphatic hydrocarbon solvents, such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.$0^{2,7}$]undeca-4-ene, n-dodecane, n-tridecane, n-pentadecane, n-hexadecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffins; ketone solvents, such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvents, such as 3-methoxybutanol, 3-methyl-3-methoxybutanol, 1-methoxy-2-propanol, and 1-ethoxy-2-propanol; ether solvents, such as propylene glycol monomethyl ether, ethylene glycol monomethyl ether, propylene glycol monoethyl ether, ethylene glycol monoethyl ether, propylene glycol dimethyl ether, diethylene glycol monomethyl ether, diethylene glycol monoethyl ether, diethylene glycol monopropyl ether, diethylene glycol monobutyl ether, diethylene glycol monopentyl ether, diethylene glycol monoheptyl ether, diethylene glycol diethyl ether, diethylene glycol dipropyl ether, diethylene glycol dibutyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, and anisole; ester solvents, such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactone solvents, such as γ-butyrolactone; etc.

Note that the organic solvent is preferably contained in an amount of 10 to 50,000 parts by mass based on 100 parts by mass of the resin in the components (A) and (B).

In addition, the inventive bio-electrode composition may contain water. The water is preferably contained in an amount of 10 to 50,000 parts by mass based on 100 parts by mass of the resin in the components (A) and (B).

[Other Additives]

The inventive bio-electrode composition can also be mixed with silica particles, polyether silicone, and polyglycerin silicone. Silica particles have hydrophilic surfaces and favorable compatibility with the hydrophilic ion polymer, polyether silicone, and polyglycerin silicone. Therefore, in a hydrophobic silicone adhesive, silica particles can improve the dispersibility of the ion polymer, polyether silicone, and polyglycerin silicone in a hydrophobic silicone adhesive. The silica particles may be either dry type or wet type, and both can be used favorably.

[Silicone Compound Having Polyglycerin Structure]

The inventive bio-electrode composition may also contain a silicone compound having a polyglycerin structure in order to improve the moisture-holding property of the film and improve the ionic conductivity and the sensitivity to ions released from the skin. The silicone compound having a polyglycerin structure is preferably contained in an amount of 0.01 to 100 parts by mass, more preferably 0.5 to 60 parts by mass based on 100 parts by mass of the resin in the components (A) and (B). One kind of the silicone compound having a polyglycerin structure may be used, or two or more kinds may be used in mixture.

The silicone compound having a polyglycerin structure is preferably shown by any of the following general formulae (4)' and (5)'.

(4)'

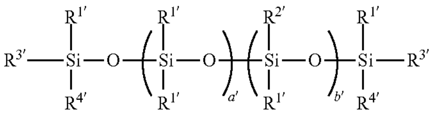

(4)'-1

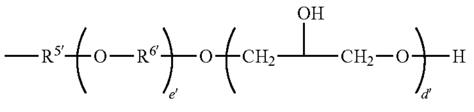

(4)'-2

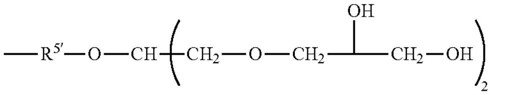

(5)'

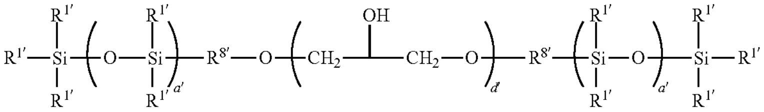

(6)'

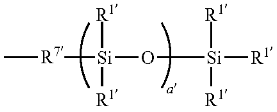

In the formulae, each $R^{1'}$ is identical to or different from one another, and independently represents a hydrogen atom, a phenyl group, a linear or branched alkyl group having 1 to 50 carbon atoms, or a silicone chain shown by the general formula (6)', and optionally contains an ether group. $R^{2'}$ represents a group having a polyglycerin group structure shown by the general formula (4)'-1 or (4)'-2. Each $R^{3'}$ is identical to or different from the other, and independently represents the $R^{1'}$ group or the $R^{2'}$ group. Each $R^{4'}$ is identical to or different from the other, and independently represents the $R^{1'}$ group, the $R^{2'}$ group, or an oxygen atom. When $R^{4'}$ represents an oxygen atom, the two $R^{4'}$ moieties bond to each other and optionally constitute an ether group to form a ring together with silicon atoms. Each a' is identical to or different from one another and represents 0 to 100, b' represents 0 to 100, and a'+b' is 0 to 200. Nevertheless, when b' is 0, at least one $R^{3'}$ is the $R^{2'}$ group. $R^{5'}$ represents an alkylene group having 2 to 10 carbon atoms or an aralkylene group having 7 to 10 carbon atoms. $R^{6'}$, $R^{7'}$, and $R^{8'}$ each represent an alkylene group having 2 to 6 carbon atoms, but $R^{7'}$ may represent an ether group. c' represents 0 to 20. d' represents 1 to 20.

Examples of such a silicone compound having a polyglycerin structure include the following.

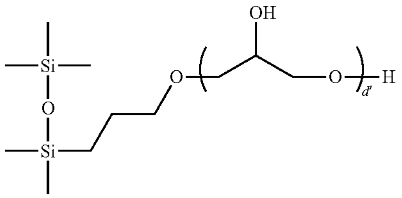

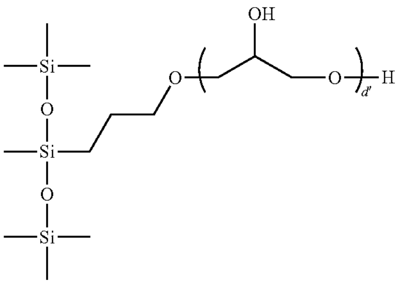

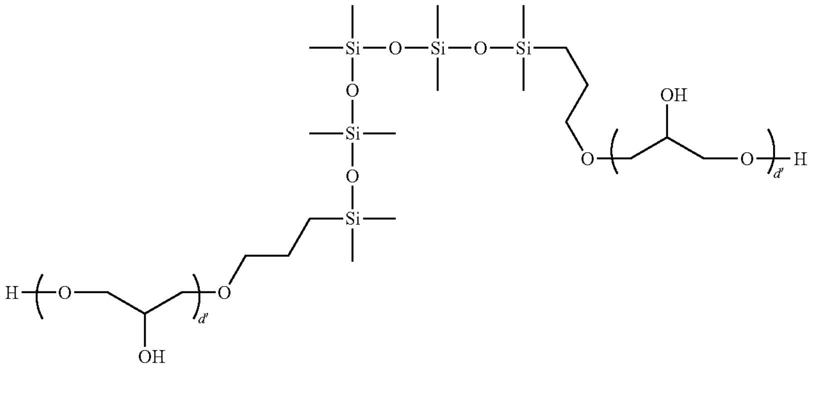

-continued
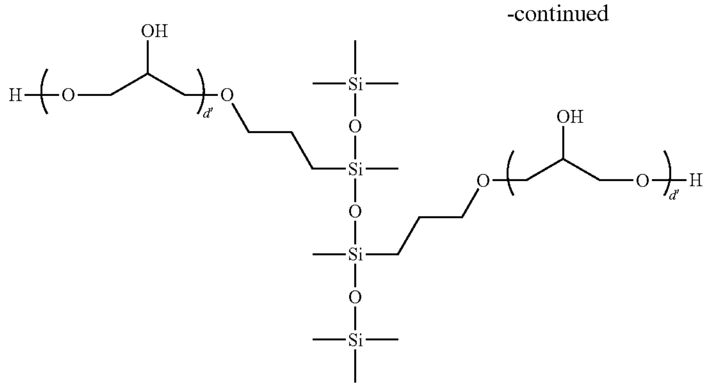
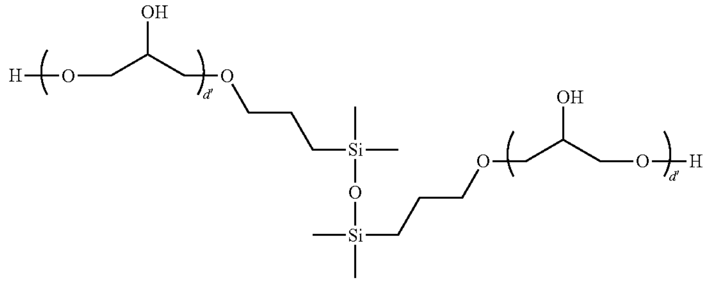
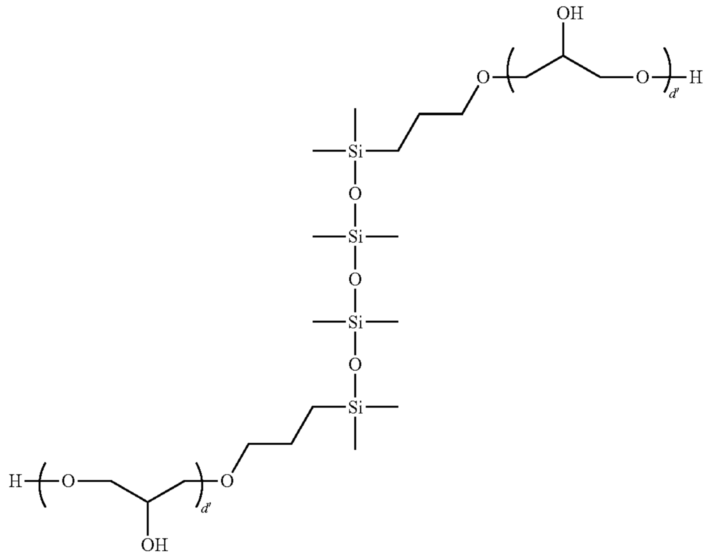
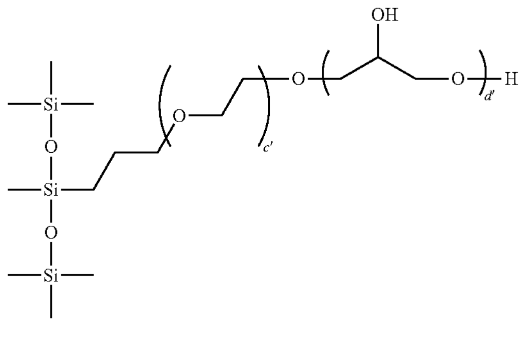
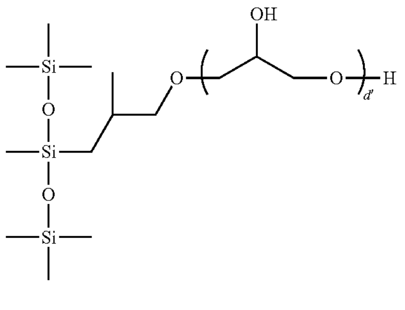

-continued
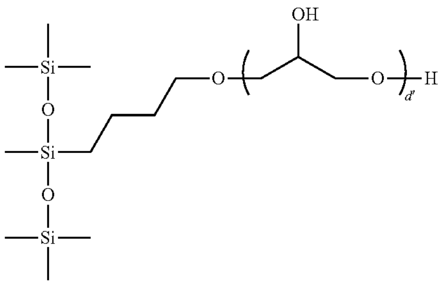
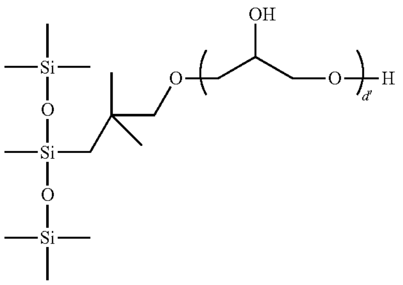
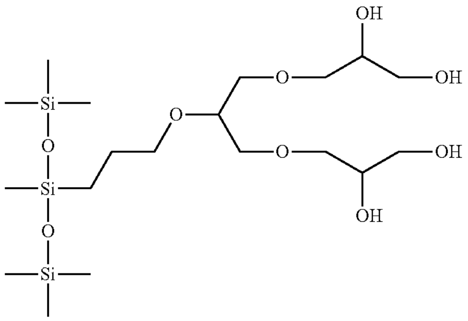
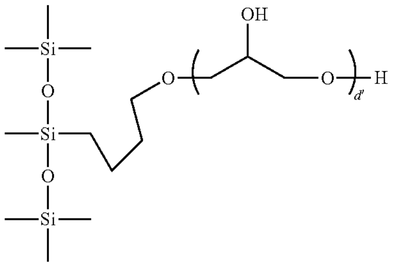
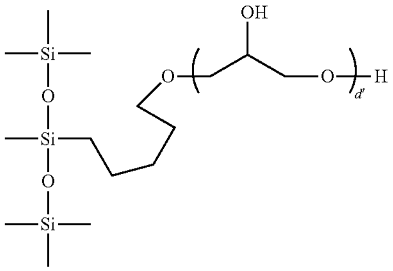
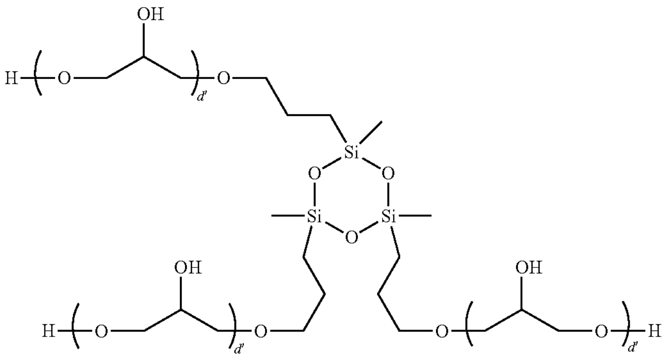
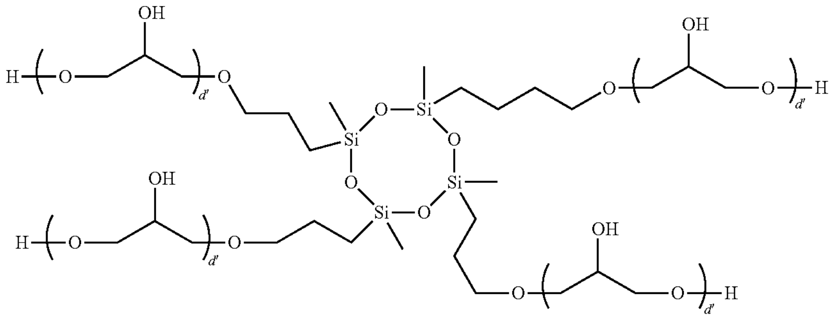
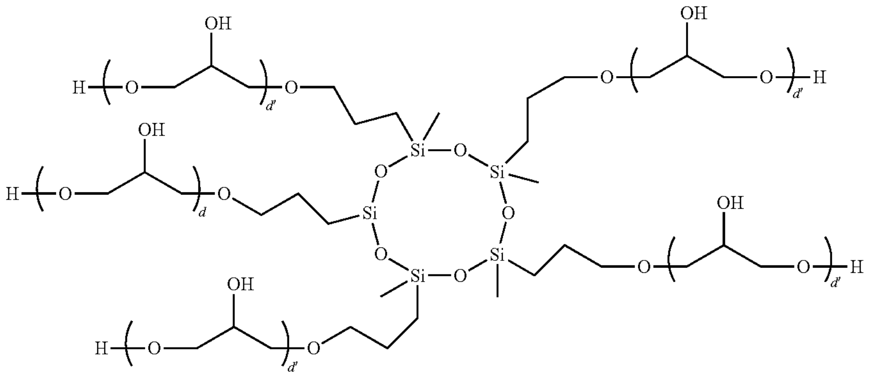

-continued
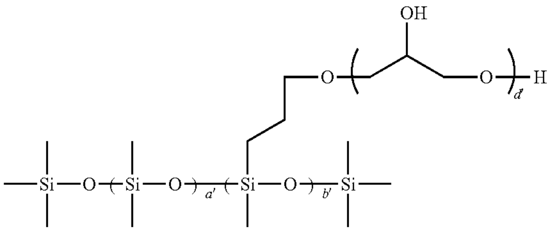
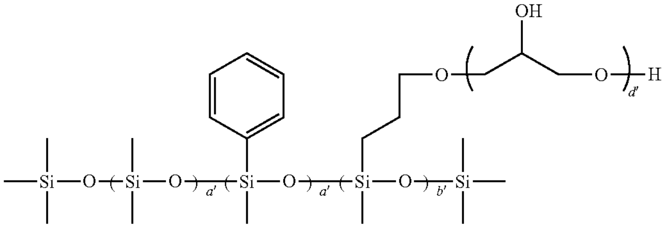
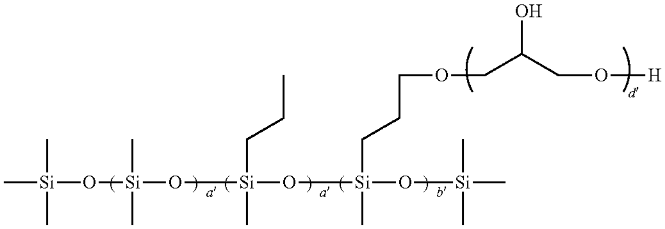
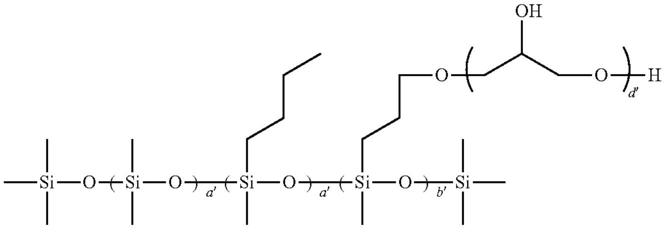
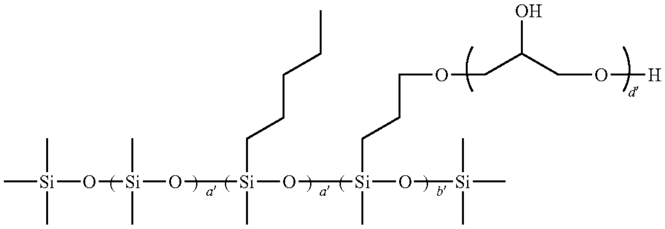
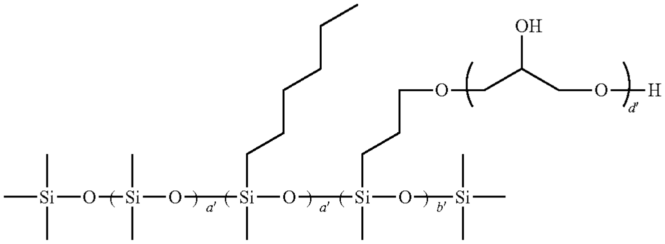
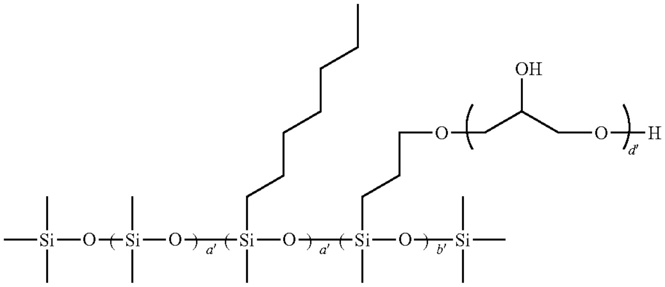

-continued
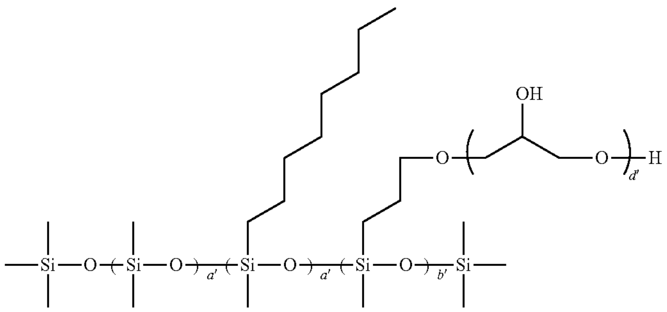
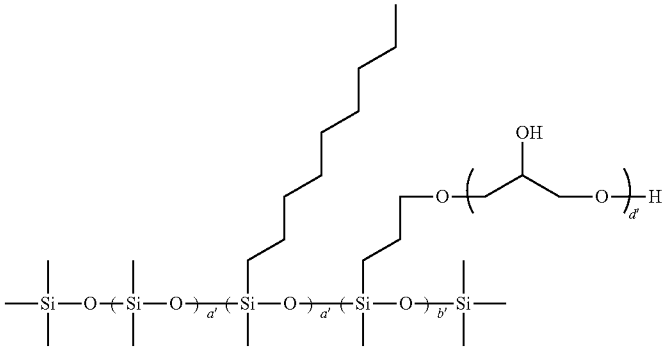
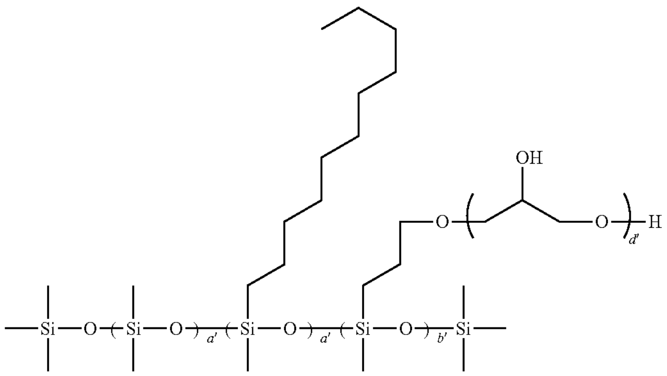
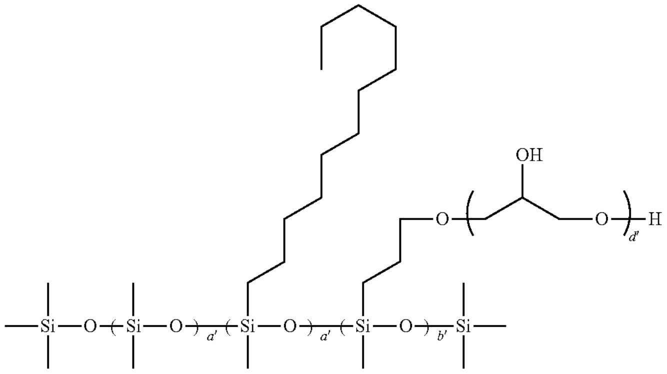

-continued
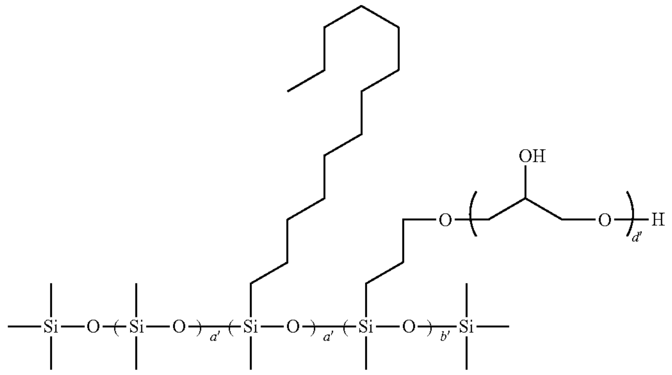
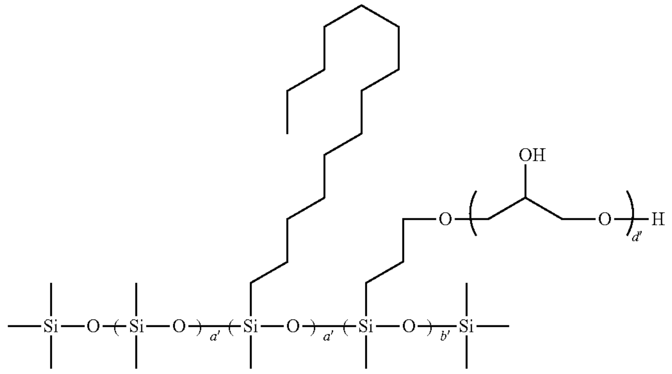
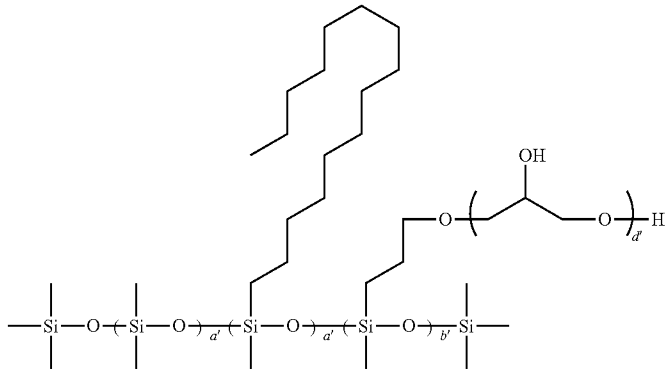
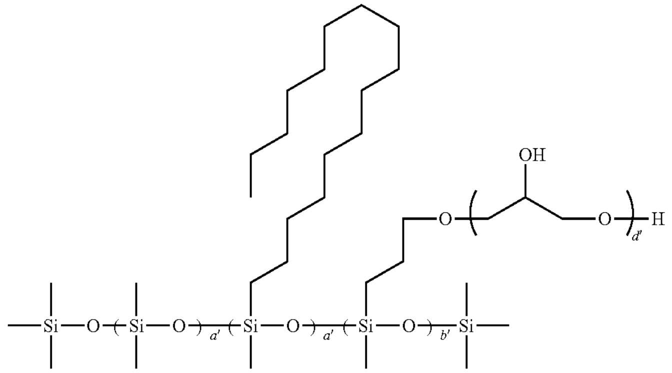

-continued
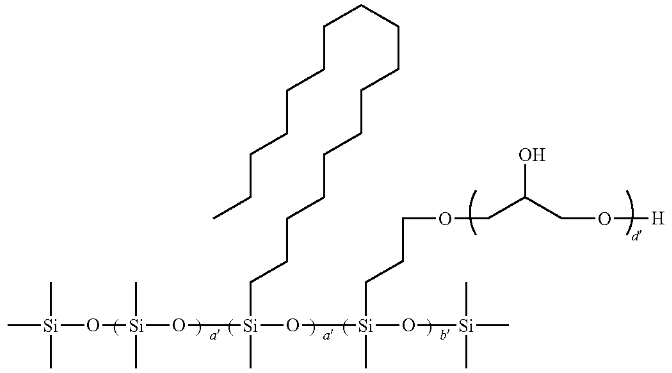
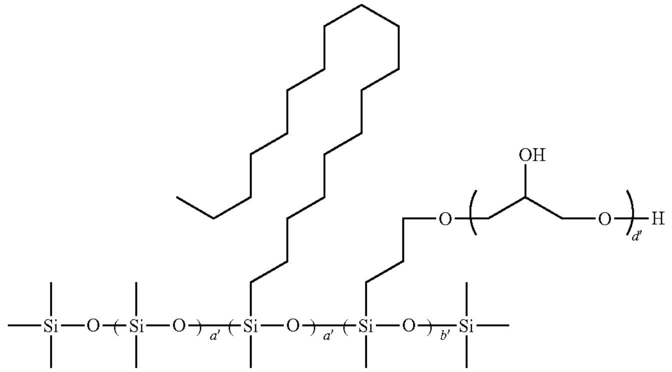
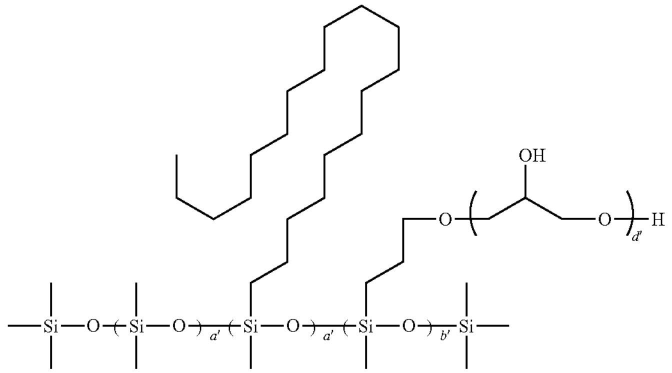
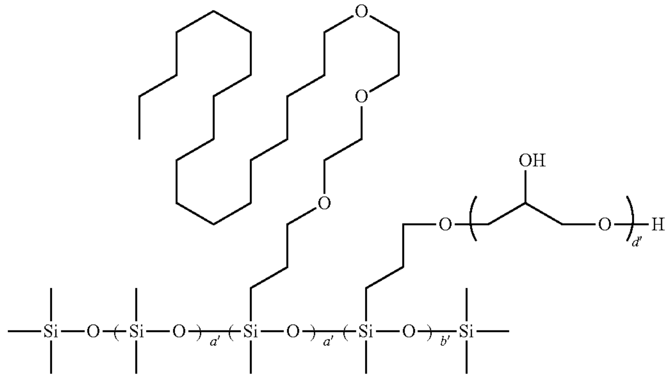

-continued
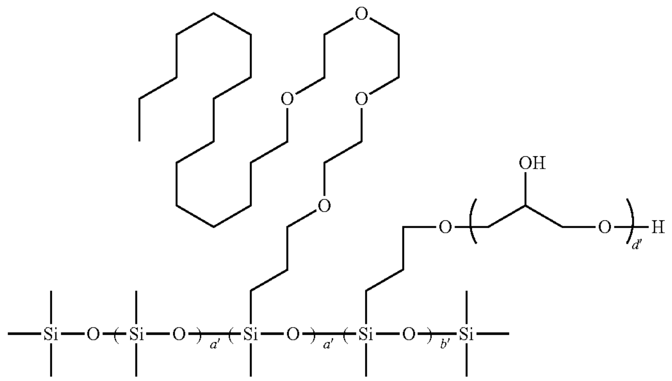
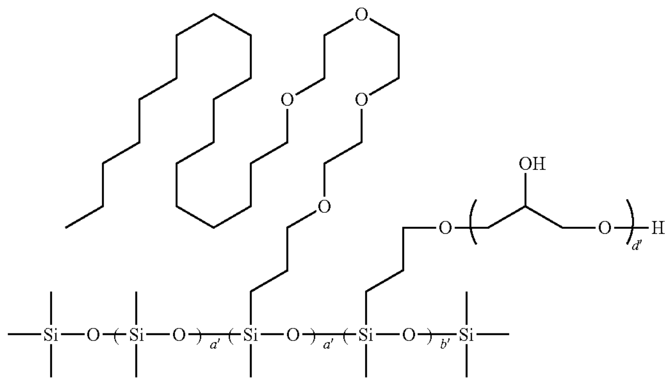
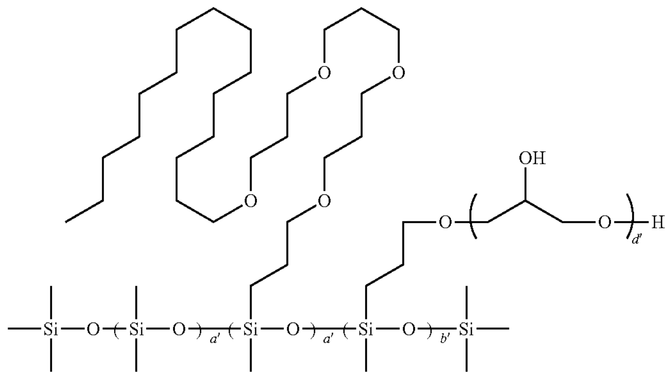
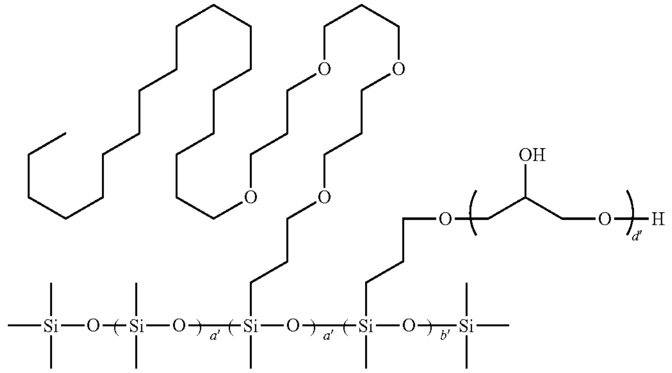

-continued
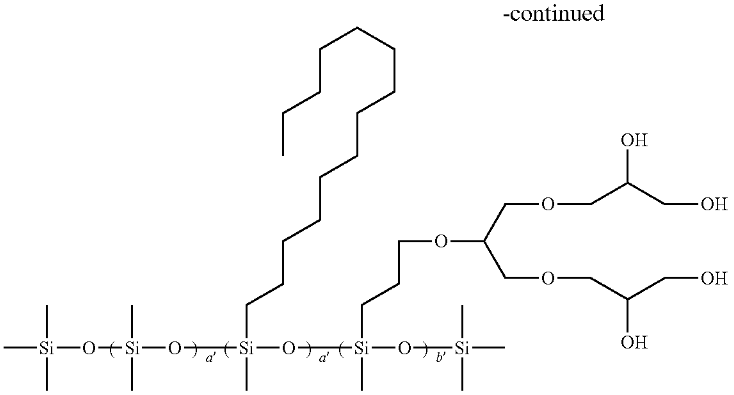
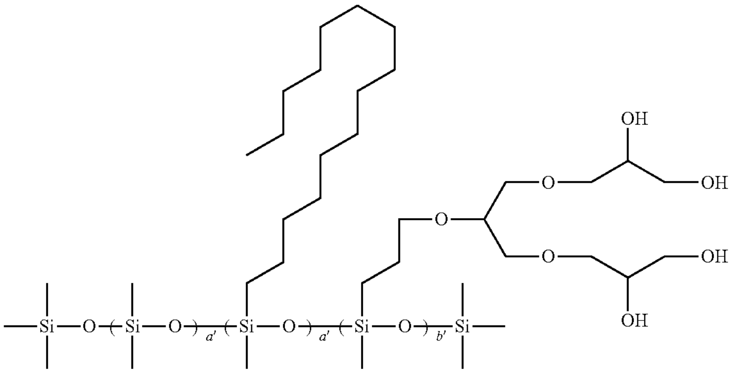
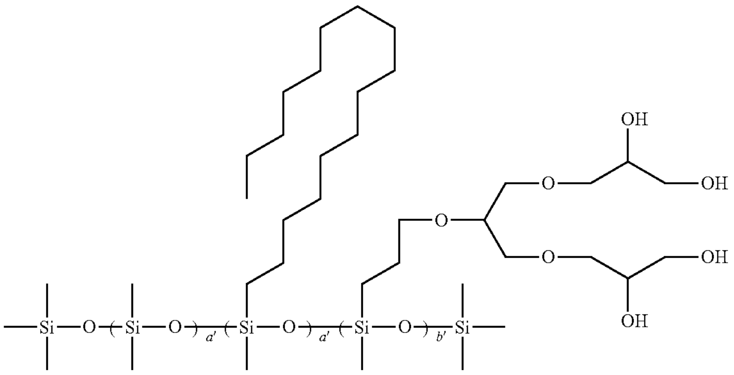
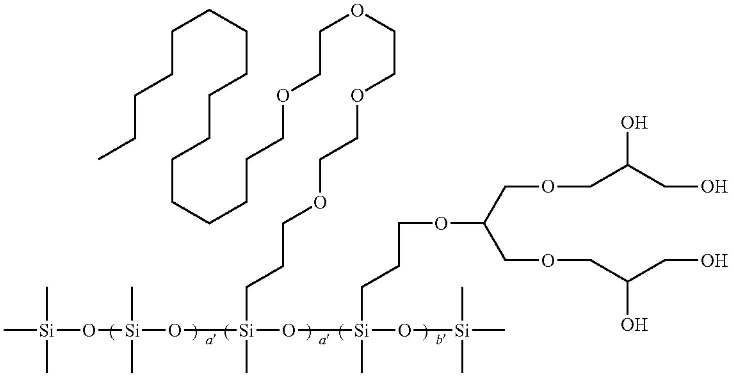

-continued
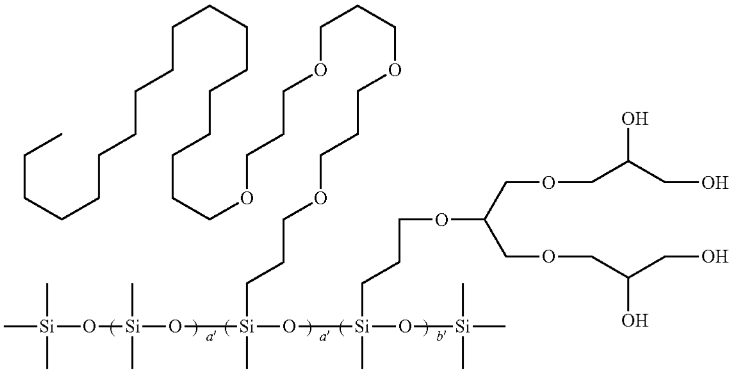
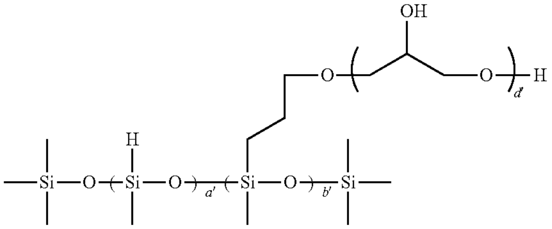
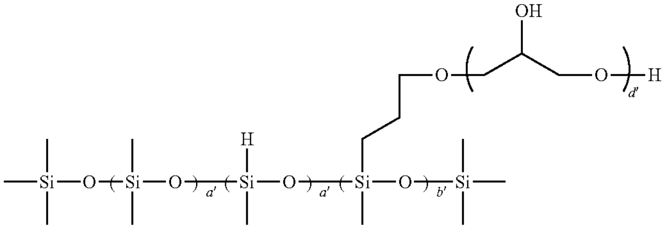
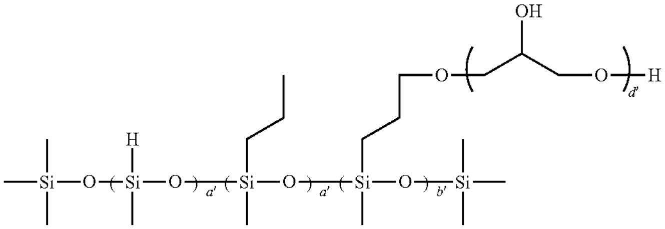
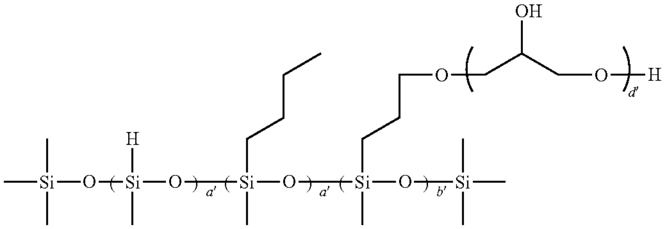
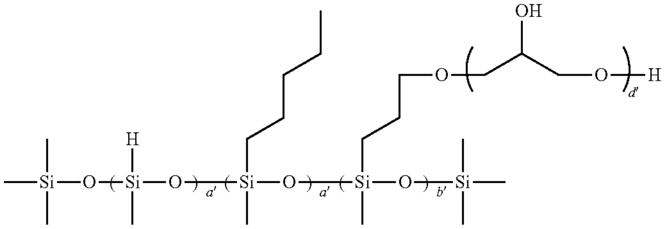

-continued
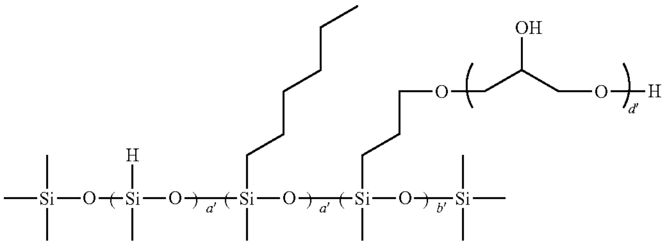
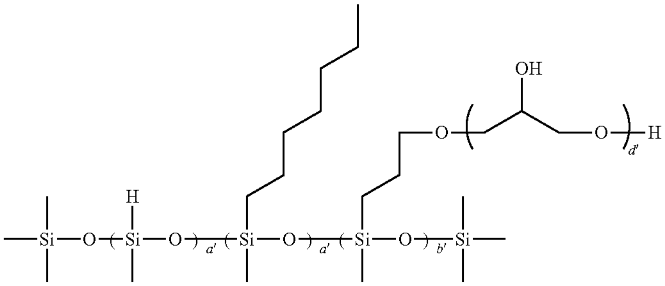
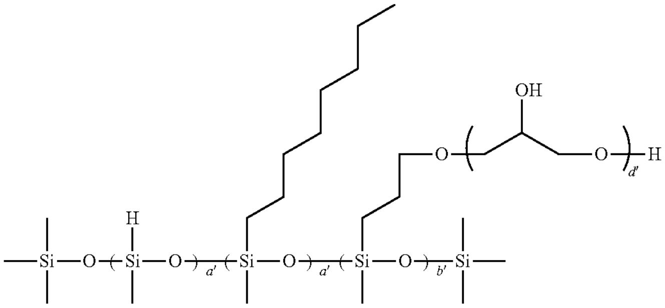
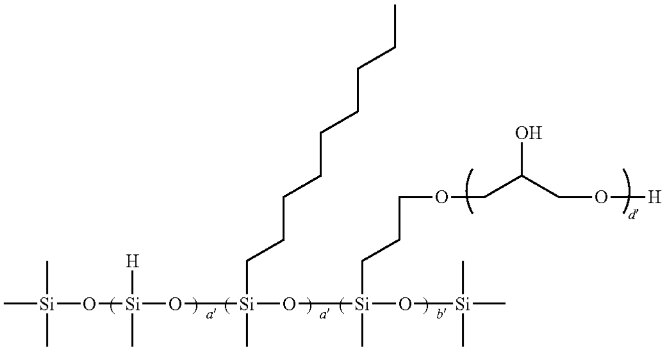
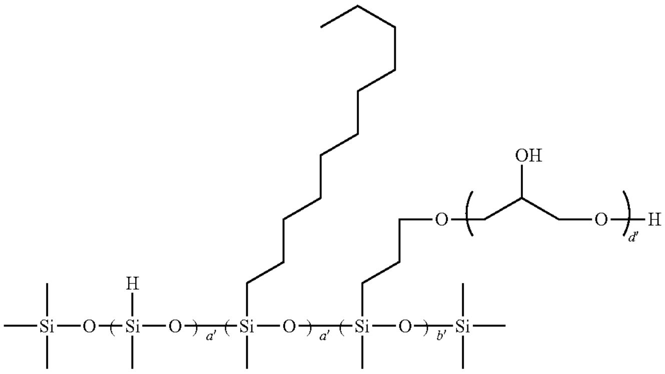

-continued
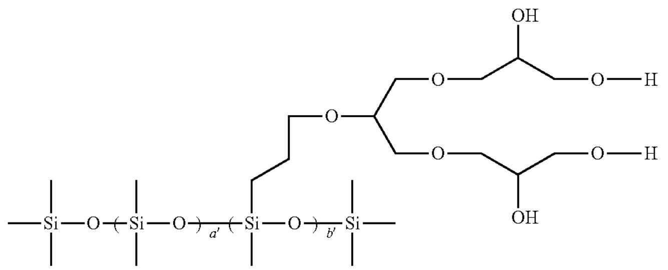
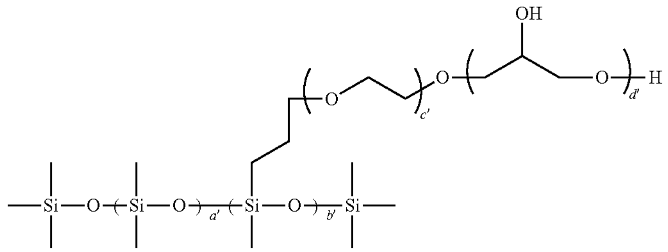
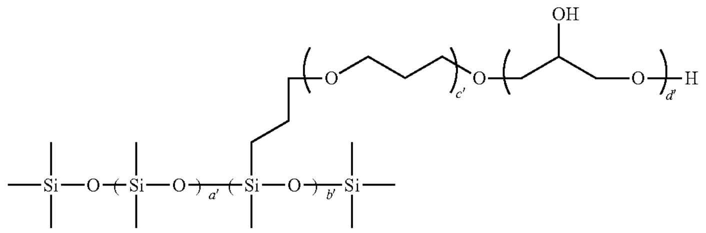
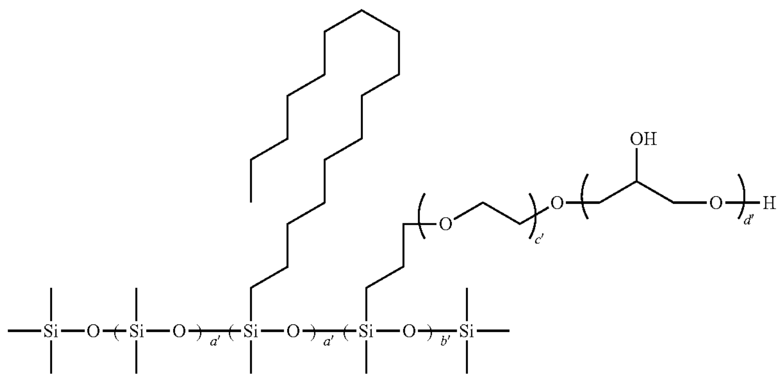
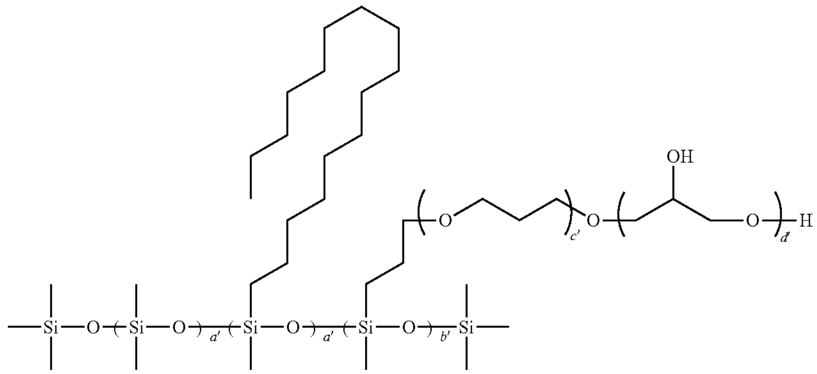

-continued
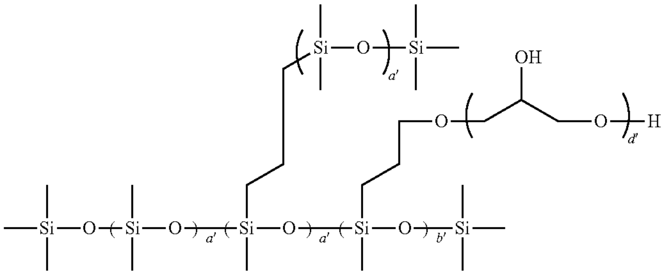
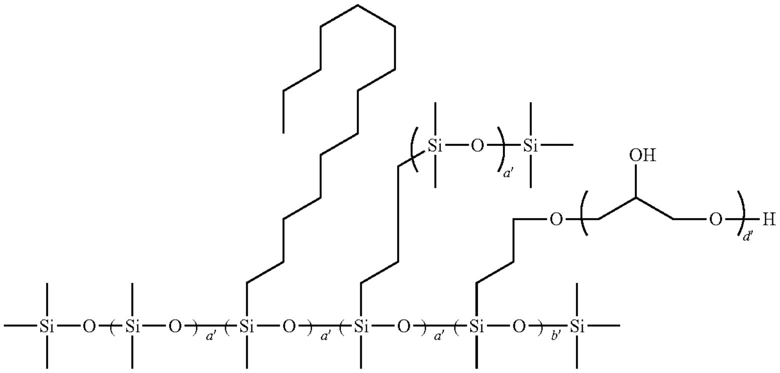
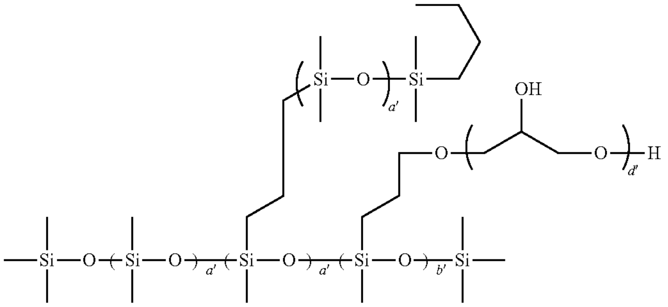
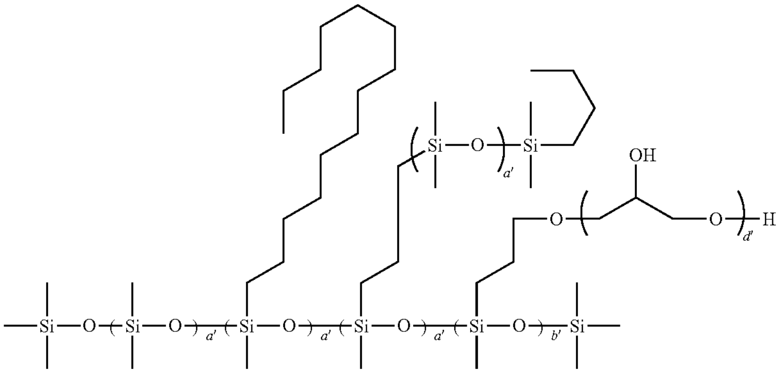
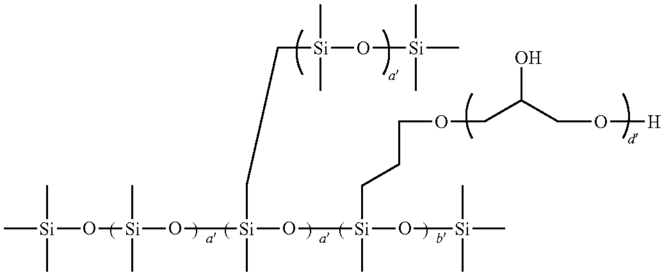

-continued
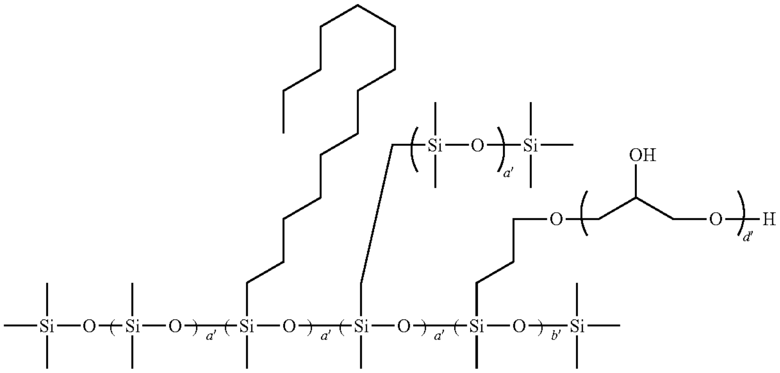
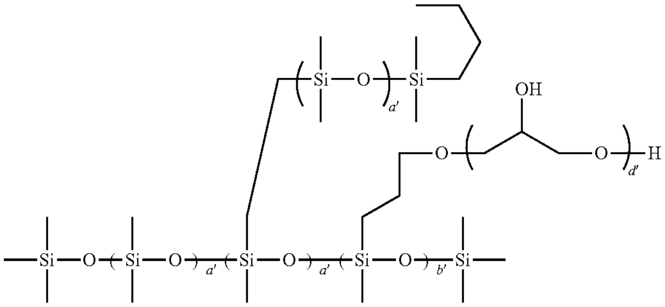
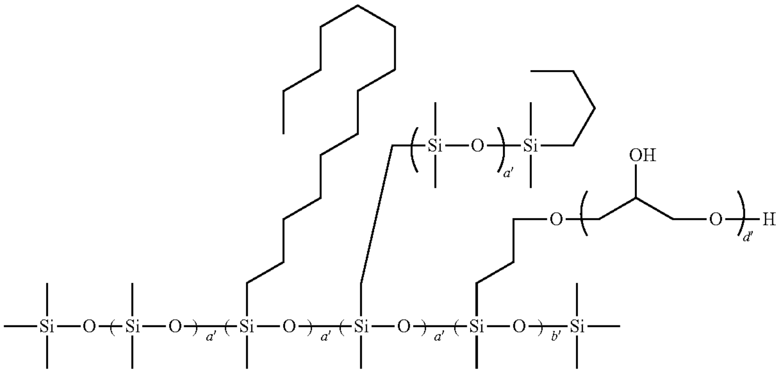
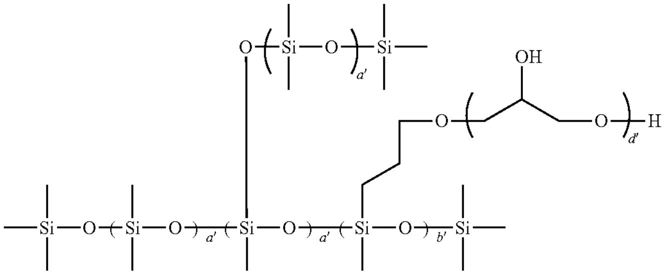
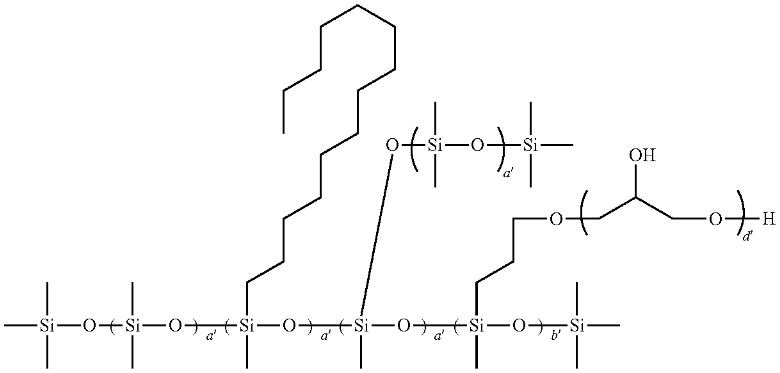

-continued
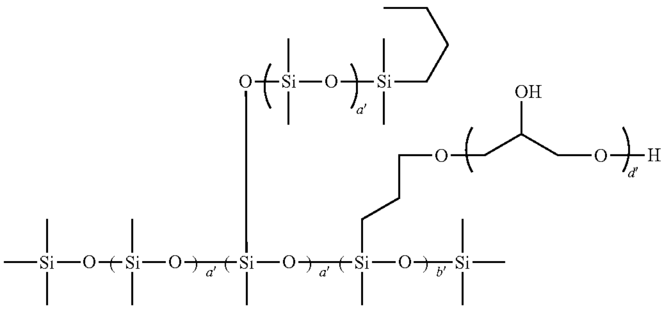
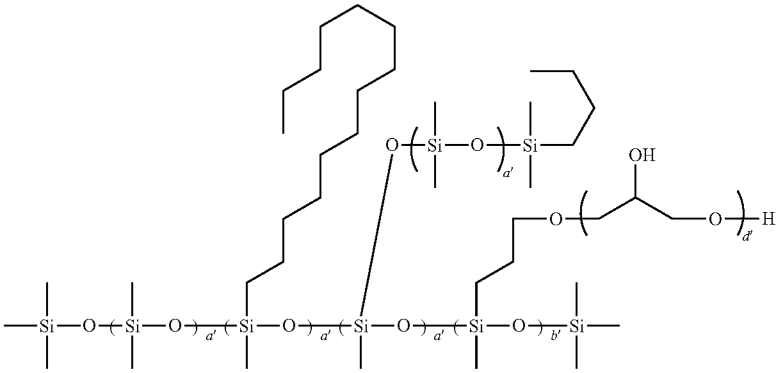
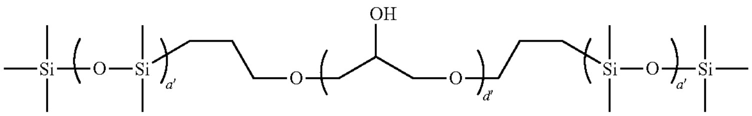
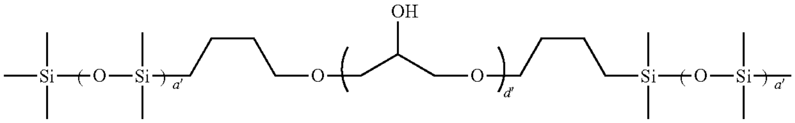
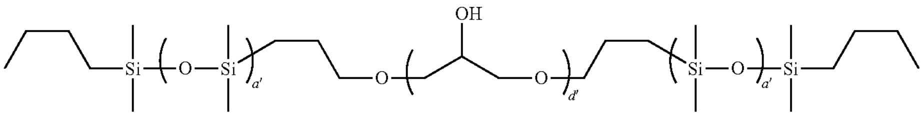
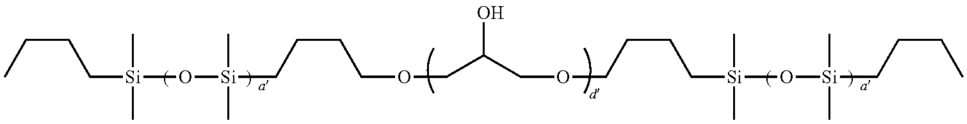
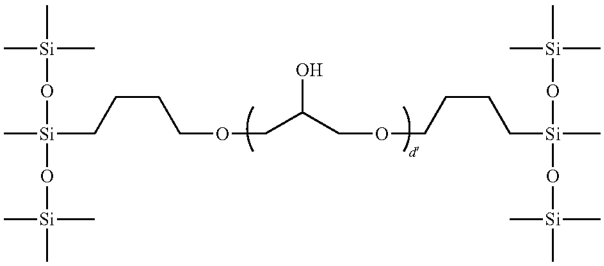
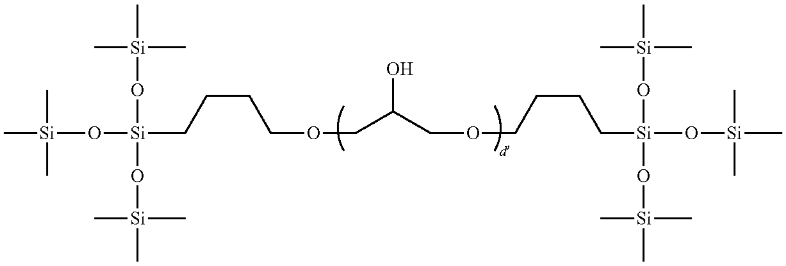

In the formulae, a', b', c', and d' are as defined above.

When such a silicone compound having a polyglycerin structure is incorporated, the resulting bio-electrode composition is capable of forming a living body contact layer that can exhibit more excellent moisture-holding property and consequently exhibit more excellent sensitivity to ions released from skin.

As has been described above, the inventive bio-electrode composition makes it possible to form a living body contact layer for a bio-electrode that is highly adhesive and has sufficient adhesiveness even when detached from the skin and then reattached, capable of efficiently conducting electric signals from skin to a device (i.e., excellent in electric conductivity), free from a risk of causing allergies even when the bio-electrode is attached to skin for a long period (i.e., excellent in biocompatibility), light-weight, manufacturable at low cost, and free from significant reduction in the electric conductivity even when the bio-electrode is wetted with water or dried. Moreover, it is possible to further enhance the electric conductivity by adding a carbon material, and it is possible to manufacture a bio-electrode with particularly high adhesive strength and high stretchability by combining the inventive bio-electrode composition with a resin having adhesion and stretchability. Further, the stretchability and adhesion to skin can be enhanced with an additive and so forth. The stretchability and adhesion can also be controlled by appropriately adjusting the composition of the resin and the thickness of the living body contact layer.

<Bio-Electrode>

The present invention also provides a bio-electrode including an electro-conductive base material and a living body contact layer formed on the electro-conductive base material, the living body contact layer being a cured product of the inventive bio-electrode composition described above.

Hereinafter, the inventive bio-electrode will be described in detail with reference to the drawings, but the present invention is not limited thereto.

FIG. 1 is a schematic sectional view showing an example of the inventive bio-electrode. In FIG. 1, a bio-electrode 1 has an electro-conductive base material 2 and a living body contact layer 3 formed on the electro-conductive base material 2. The living body contact layer 3 is formed from a cured product of the inventive bio-electrode composition. The living body contact layer 3 is, for example, a composite material of an ionic polymer material 5 and a silicone having a T unit and a Q unit. The living body contact layer 3 can further contain an electro-conductive powder 4 and a resin 6 other than the composite material of the ionic polymer material 5 and the silicone having the T unit and the Q unit. Hereinbelow, with reference to FIGS. 1 and 2, the living body contact layer 3 is described as a layer in which the electro-conductive powder 4 and the composite material of the ionic polymer material 5 and the silicone having the T unit and the Q unit are dispersed in the resin 6. Nevertheless, the inventive bio-electrode is not limited to this embodiment.

When the bio-electrode 1 as shown in FIG. 1 is used, the living body contact layer 3 (i.e., the layer in which the electro-conductive powder 4 and the composite material of the ionic polymer material 5 and the silicone having the T unit and the Q unit are dispersed in the resin 6) is brought into contact with a living body 7 as shown in FIG. 2. Electric signals are picked from the living body 7 through the electro-conductive powder 4 and the composite material of the ionic polymer material 5 and the silicone having the T unit and the Q unit, and then conducted to a sensor device or the like (not shown) via the electro-conductive base material 2. As described above, the inventive bio-electrode is capable of achieving both electric conductivity and biocompatibility by using the above-described composite material of the ionic polymer material and the silicone having the T unit and the Q unit, and obtaining electric signals from skin stably in high sensitivity because the contact area with the skin is kept constant since the bio-electrode also has adhesiveness.

Hereinafter, each component of the inventive bio-electrode will be described more specifically.

[Electro-Conductive Base Material]

The inventive bio-electrode has an electro-conductive base material. This electro-conductive base material is usually connected electrically with a sensor device etc., and conducts electrical signals picked from a living body through the living body contact layer to the sensor device etc.

The electro-conductive base material is not particularly limited, as long as it has electric conductivity. The electro-conductive base material preferably contains one or more selected from the group consisting of gold, silver, silver chloride, platinum, aluminum, magnesium, tin, tungsten, iron, copper, nickel, stainless steel, chromium, titanium, carbon, and electro-conductive polymer, for example.

The electro-conductive base material may be a hard electro-conductive substrate, an electro-conductive film having flexibility, a cloth with the surface being coated with electro-conductive paste, a cloth into which electro-conductive polymer is kneaded, or the like without being limited to particular substrates. The electro-conductive base material may be flat, uneven, or mesh-form of woven metal wires, and can be appropriately selected in accordance with the use of the bio-electrode, and so forth.

[Living Body Contact Layer]

The inventive bio-electrode has a living body contact layer formed on the electro-conductive base material. This living body contact layer is a part to be actually in contact with a living body when using the bio-electrode, and has electric conductivity and adhesion. The living body contact layer is a cured product of the inventive bio-electrode composition described above; that is, an adhesive resin layer formed from a cured composition containing: the component (A); and as necessary, the component (B), the component (C), the component (D), and the other component(s).

The living body contact layer preferably has an adhesive strength in a range of 0.01 N/25 mm or more and 20 N/25 mm or less. The adhesive strength is commonly measured by the method described in JIS Z 0237, in which a metal substrate such as a stainless steel (SUS) substrate or a polyethylene terephthalate (PET) substrate can be used as a base material. Alternatively, human skin can be used for measuring. Human skin has lower surface energy than metals and various plastics, and the energy is as low as that of Teflon (registered trademark). It is hard to make the layer adhere to human skin.

The living body contact layer of the bio-electrode has a thickness of preferably 1 μm or more and 5 mm or less, more preferably 2 μm or more and 3 mm or less. When the living body contact layer is thinner, the adhesive strength lowers, but the flexibility is improved, the weight decreases and the compatibility with skin is improved. The thickness of the living body contact layer can be selected based on the balance of adhesion and texture to the skin.

The inventive bio-electrode may be additionally provided with an adhesive film on the living body contact layer as in conventional bio-electrodes (e.g., the bio-electrode described in JP 2004-033468A) in order to prevent the bio-electrode from peeling off from a living body during use. When the adhesive film is provided separately, the adhesive film may be formed by using a raw material for the adhesive film such as an acrylic type, a urethane type, and a silicone type. Particularly, the silicone type is suitable because of: the high oxygen permeability, which enables dermal respiration while the electrode is attached to the skin; the high water repellency, which suppresses lowering of adhesion due to perspiration; and the low irritation to skin. It is to be noted that the inventive bio-electrode does not necessarily require this adhesive film that is provided separately, because peeling off from a living body can be prevented by adding a tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to employ ones described in JP 2004-033468A.

As described above, since the inventive bio-electrode includes the living body contact layer formed from the cured product of the above-described inventive bio-electrode composition, the inventive bio-electrode is capable of efficiently conducting electric signals from skin to a device (i.e., excellent in electric conductivity), does not cause allergies even after long-period attachment to skin (i.e., excellent in biocompatibility), is light-weight and manufacturable at low cost, and prevents significant reduction in the electric conductivity even when wetted with water or dried. In addition, it is possible to further improve the electric conductivity by adding an electro-conductive powder, and it is possible to manufacture a bio-electrode with particularly high adhesive strength and high stretchability by combining the inventive bio-electrode composition with a resin having adhesion and stretchability. Further, the stretchability and adhesion to skin can be improved with an additive and so forth. The stretchability and adhesion can also be controlled by appropriately adjusting the composition of the resin and the thickness of the living body contact layer. Accordingly, the inventive bio-electrode as described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, the method including:

applying the inventive bio-electrode composition onto the electro-conductive base material; and curing the bio-electrode composition to form the living body contact layer.

Note that the electro-conductive base material etc. used in the inventive method for manufacturing a bio-electrode may be the same as those described above.

The method for applying the bio-electrode composition onto the electro-conductive base material is not particularly limited. Examples of the suitable method include dip coating, spray coating, spin coating, roll coating, flow coating, doctor coating, screen printing, flexographic printing, gravure printing, inkjet printing, etc.

The method for curing the resin is not particularly limited and can be appropriately selected based on the kind of the components (A) and (B) used for the bio-electrode composition. For example, the bio-electrode composition is preferably cured by either or both of heat and light. The foregoing bio-electrode composition can also be cured by adding a catalyst in advance to generate acid or base to the bio-electrode composition, which causes a crosslinking reaction.

The heating temperature is not particularly limited and may be appropriately selected based on the kind of the components (A) and (B) used for the bio-electrode composition, but is preferably about 50 to 250° C., for example.

When the heating and light irradiation are combined, it is possible to perform the heating and the light irradiation simultaneously, to perform the light irradiation and then the heating, or to perform the heating and then the light irradiation. It is also possible to perform air-drying to evaporate the solvent before heating the coating film.

Water droplets may be attached to the surface of the cured film; alternatively, the film surface may be sprayed with water vapor or mist. These treatments improve the compatibility with skin, and enable quick collection of biological signals. Water mixed with alcohol can be used to reduce the size of the droplets of the water vapor or mist. The film surface may be wetted by bringing an absorbent cotton or cloth containing water into contact therewith.

The water for making the surface of the cured film wet may contain a salt. The water-soluble salt mixed with the water is selected from the group consisting of sodium salts, potassium salts, calcium salts, magnesium salts, and betaines.

Specifically, the water-soluble salt can be a salt selected from the group consisting of sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaines. It should be noted that the component (A) described above is excluded from the water-soluble salt.

More specific examples of the water-soluble salt include, besides the aforementioned examples, sodium acetate, sodium propionate, sodium pivalate, sodium glycolate, sodium butyrate, sodium valerate, sodium caproate, sodium enanthate, sodium caprylate, sodium pelargonate, sodium caprate, sodium undecylate, sodium laurate, sodium tridecylate, sodium myristate, sodium pentadecylate, sodium palmitate, sodium margarate, sodium stearate, sodium benzoate, disodium adipate, disodium maleate, disodium phthalate, sodium 2-hydroxybutyrate, sodium 3-hydroxybutyrate, sodium 2-oxobutyrate, sodium gluconate, sodium methanesulfonate, sodium 1-nonanesulfonate, sodium 1-decanesulfonate, sodium 1-dodecanesulfonate, sodium 1-undecanesulfonate, sodium cocoyl sethionate, sodium lauroyl methylalanine, sodium methyl cocoyl taurate, sodium cocoyl glutamate, sodium cocoyl sarcosinate, sodium lauroyl methyl taurate, lauramidopropyl betaine, potassium isobutyrate, potassium propionate, potassium pivalate, potassium glycolate, potassium gluconate, potassium methanesulfonate, calcium stearate, calcium glycolate, calcium gluconate, calcium 3-methyl-2-oxobutyrate, and calcium methanesulfonate. The term betaines is a general term for inner salts. Specific examples thereof include amino acid compounds in each of which three methyl groups are added to an amino group. More specific examples include trimethylglycine, carnitine, and proline betaines.

The water-soluble salt can further contain a monohydric alcohol or polyhydric alcohol having 1 to 4 carbon atoms. The alcohol is preferably selected from the group consisting of ethanol, isopropyl alcohol, ethylene glycol, diethylene glycol, triethylene glycol, glycerin, polyethylene glycol, polypropylene glycol, polyglycerin, diglycerin, and a silicone compound having a polyglycerin structure. More preferably, the silicone compound having a polyglycerin structure is shown by the general formulae (4)' to (5)'.

In the pretreatment methods with the aqueous solution containing the water-soluble salt, the cured bio-electrode film can be wetted by a spraying method, a droplet-dispensing method, etc. The bio-electrode film can also be wetted under a high-temperature, high-humidity condition like sauna. To prevent drying after the wetting, a protective film can be further stacked on the permeated layer to cover the surface. Since the protective film needs to be removed immediately before the bio-electrode is attached to skin, the protective film may be coated with a release agent, or a peelable fluorine resin film may be used as the protective film. For long-time storage, the dry electrode covered with the peelable film is preferably sealed in a bag that is covered with aluminum etc. To prevent drying in the bag covered with aluminum, it is preferable to include water therein, too.

Before the inventive bio-electrode is attached to skin, the skin may be moisturized with water, alcohol, etc., or the skin may be wiped with a cloth or absorbent cotton containing water, alcohol, etc. The water and the alcohol may contain the above-described salts.

As has been described above, the inventive method for manufacturing a bio-electrode makes it possible to manufacture the inventive bio-electrode easily and at low cost, with the bio-electrode being excellent in electric conductivity and biocompatibility, light-weight, and capable of preventing significant reduction in the electric conductivity even when wetted with water or dried.

EXAMPLE

Hereinafter, the present invention will be specifically described with reference to Examples and Comparative Examples, but the present invention is not limited thereto.

Ionic polymers 1 to 22, which were blended as ionic materials (conductive materials) in bio-electrode solutions, were synthesized as follows. First, 30 mass % solutions of respective monomers in cyclopentanone were introduced into a reaction vessel and mixed. The reaction vessel was cooled to −70° C. under a nitrogen atmosphere, and subjected to vacuum degassing and nitrogen blowing three times. After raising the temperature to room temperature, azobisisobutyronitrile (AIBN) was added thereto as a polymerization initiator in an amount of 0.02 moles per 1 mole of all the monomers. The mixture was warmed to 60° C. and then allowed to react for 15 hours. After drying the solvent, the composition of the resulting polymer was identified by 1H-NMR. The molecular weight (Mw) and the dispersity (Mw/Mn) of the obtained polymer were determined by gel permeation chromatography (GPC) using tetrahydrofuran (THF) as a solvent. Thus synthesized Ionic polymers 1 to 22 having a nitro group are shown below.

Ionic Polymer 1
Mw=16, 200
Mw/Mn=1.66

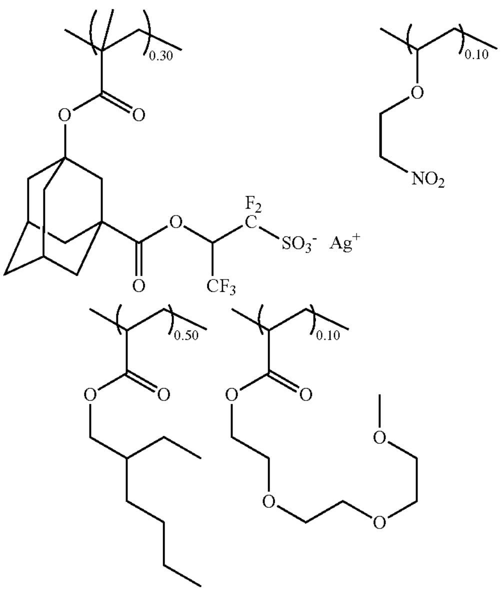

Ionic Polymer 2
Mw=26, 700
Mw/Mn=1.79

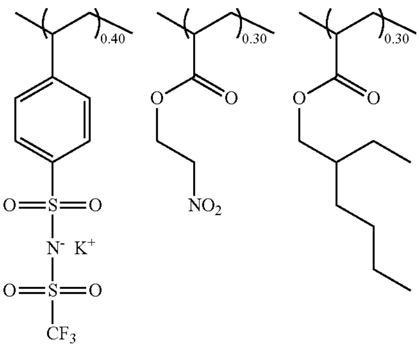

Ionic Polymer 3
Mw=32, 300
Mw/Mn=1.94

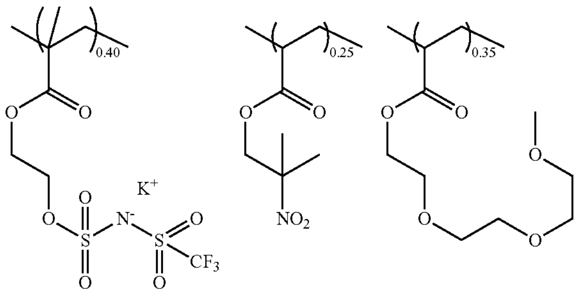

Ionic Polymer 4
Mw=36, 400
Mw/Mn=2.01
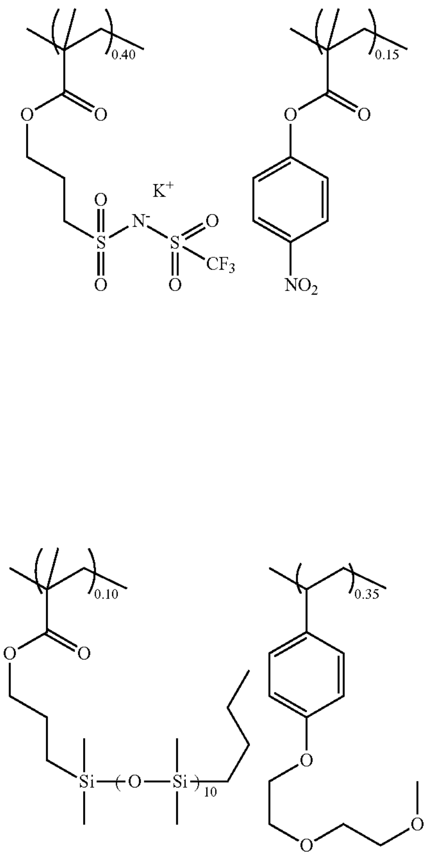
The repeating number in each formula shows the average value.
Ionic Polymer 5
Mw=28, 500
Mw/Mn=2.11
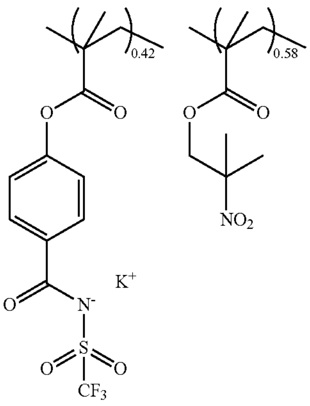
Ionic Polymer 6
Mw=30, 300
Mw/Mn=1.95
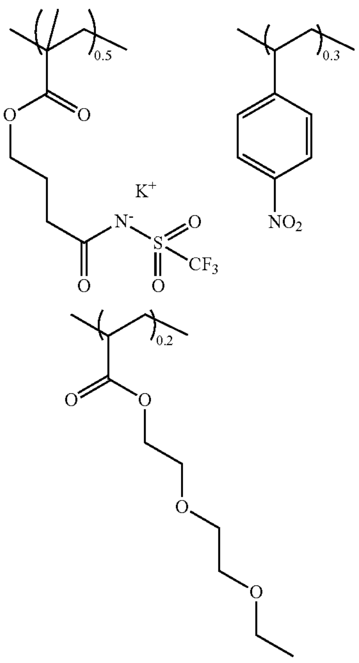
Ionic Polymer 7
Mw=22, 800
Mw/Mn=1.84
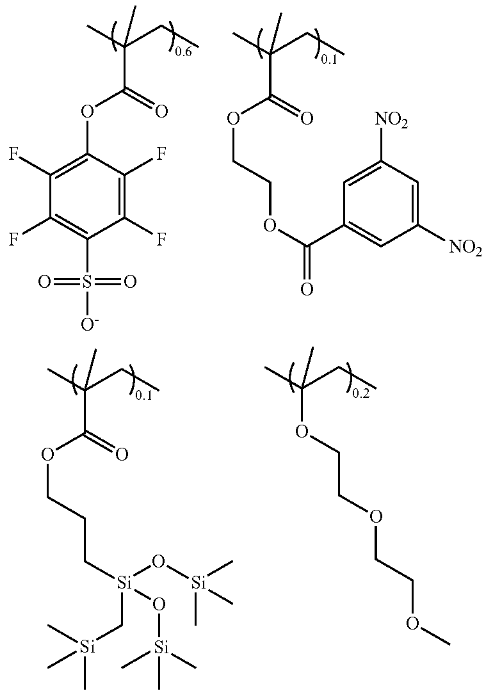

-continued
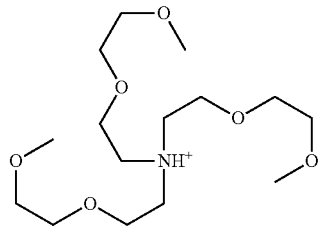
Ionic Polymer 8
Mw=25, 400
Mw/Mn=1.85
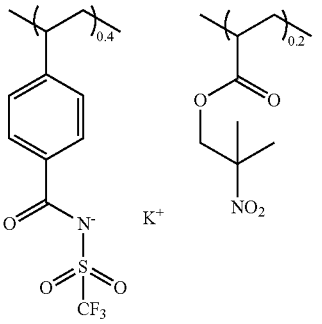
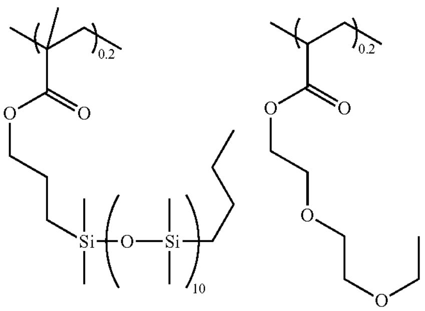
The repeating number in each formula shows the average value.
Ionic Polymer 9
Mw=22, 500
Mw/Mn=1.76
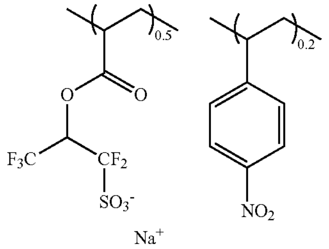
-continued
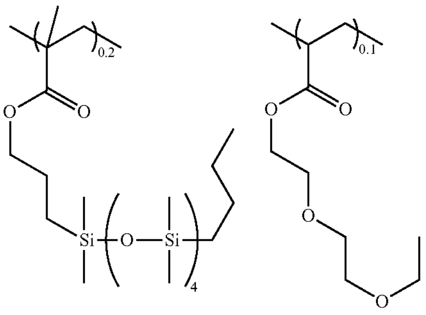
The repeating number in each formula shows the average value.
Ionic Polymer 10
Mw=26, 900
Mw/Mn=1.92
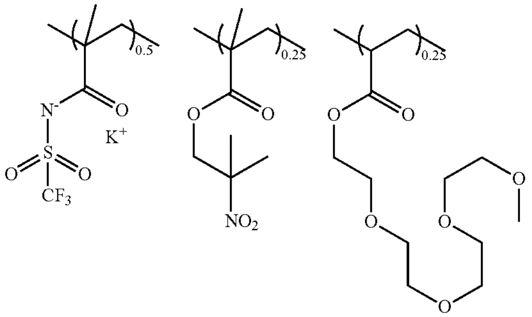
Ionic Polymer 11
Mw=25, 800
Mw/Mn=1.68
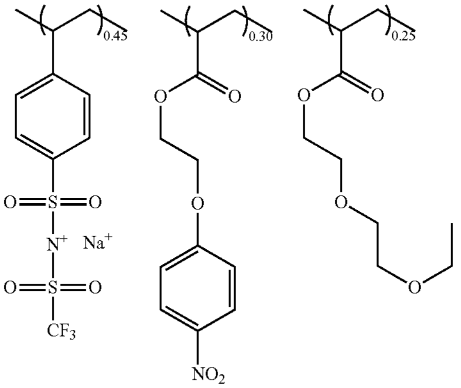

Ionic Polymer 12
Mw=25, 500
Mw/Mn=1.89
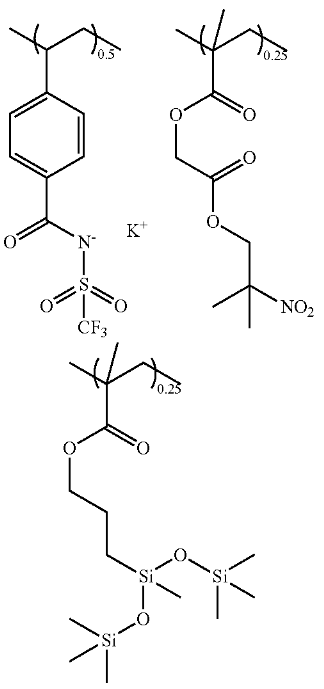
Ionic Polymer 13
Mw=29, 300
Mw/Mn=1.93
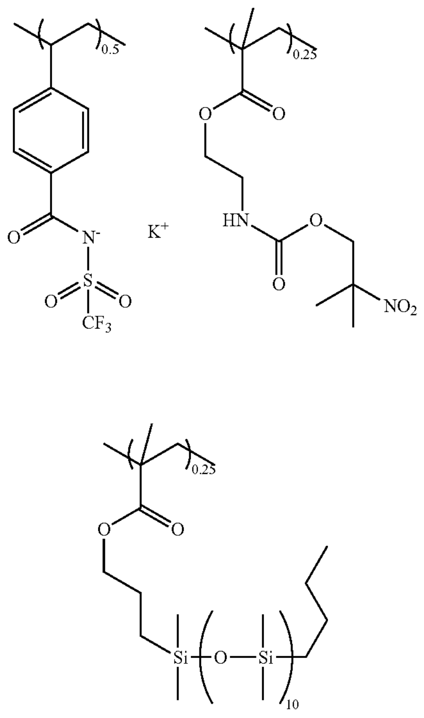
The repeating number in each formula shows the average value.
Ionic Polymer 14
Mw=27, 700
Mw/Mn=1.98
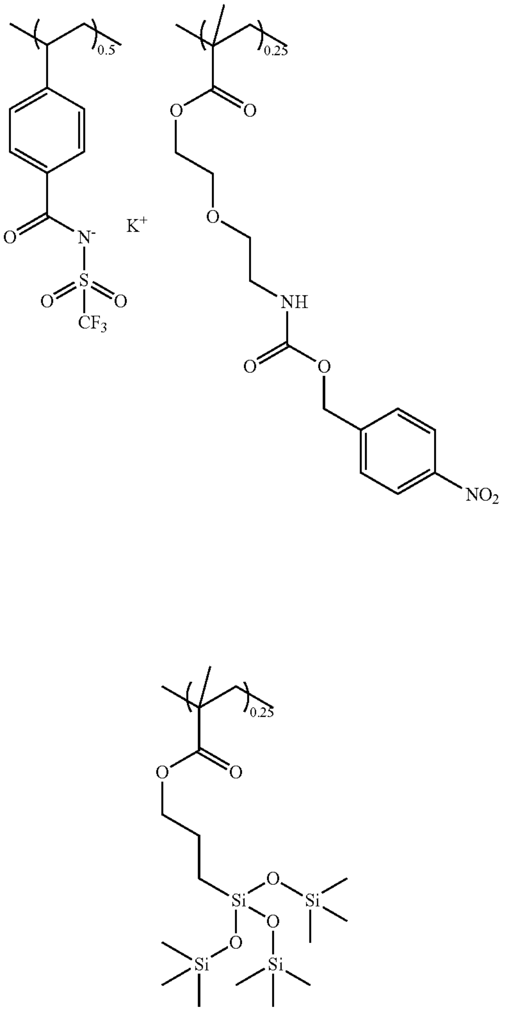
Ionic Polymer 15
Mw=23, 200
Mw/Mn=1.79
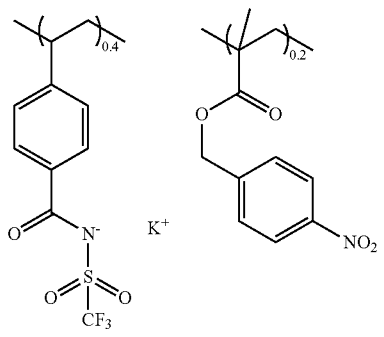

-continued
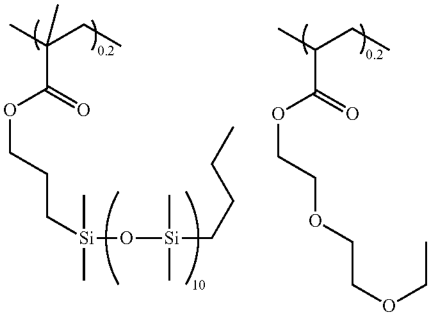
The repeating number in each formula shows the average value.
Ionic Polymer 16
Mw=21, 800
Mw/Mn=1.73
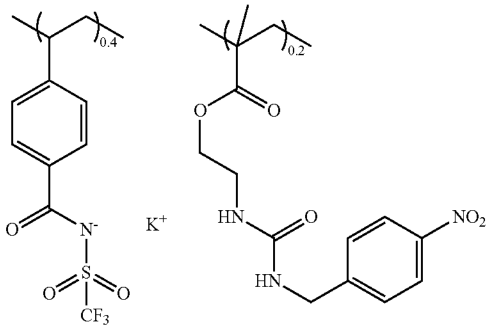
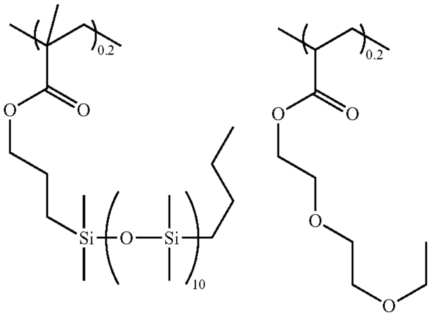
The repeating number in each formula shows the average value.
Ionic Polymer 17
Mw=24, 400
Mw/Mn=1.94
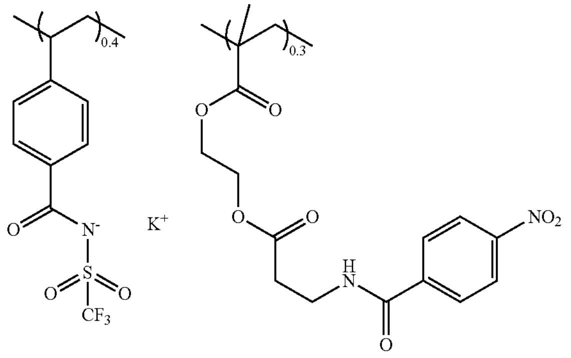
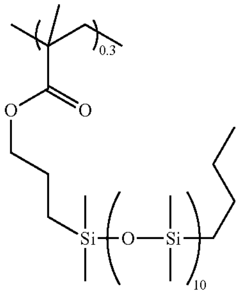
The repeating number in each formula shows the average value.
Ionic Polymer 18
Mw=26, 600
Mw/Mn=1.96
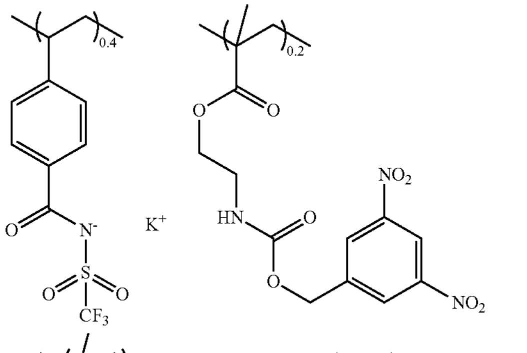
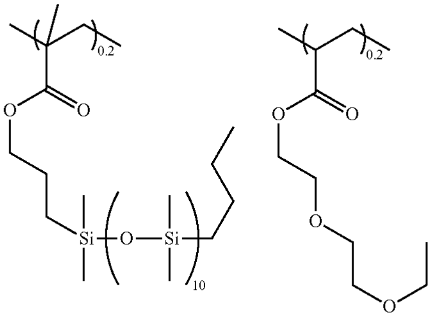

The repeating number in each formula shows the average value.

Ionic Polymer 19

Mw=23, 700

Mw/Mn=1.99

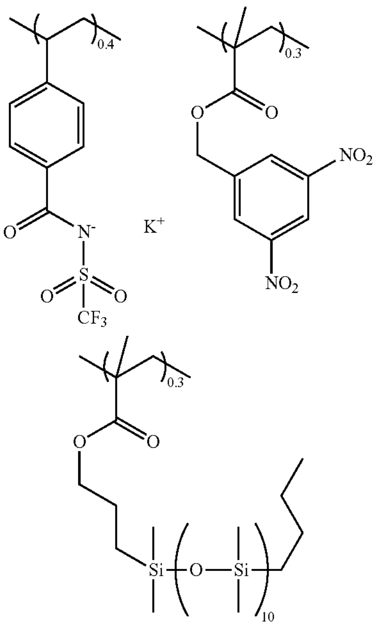

The repeating number in each formula shows the average value.

Ionic Polymer 20

Mw=34, 500

Mw/Mn=2.09

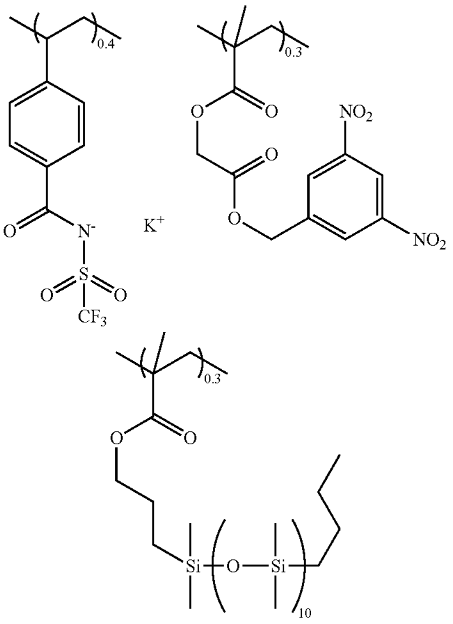

The repeating number in each formula shows the average value.

Ionic Polymer 21 Mw=38, 100 Mw/Mn=2.04

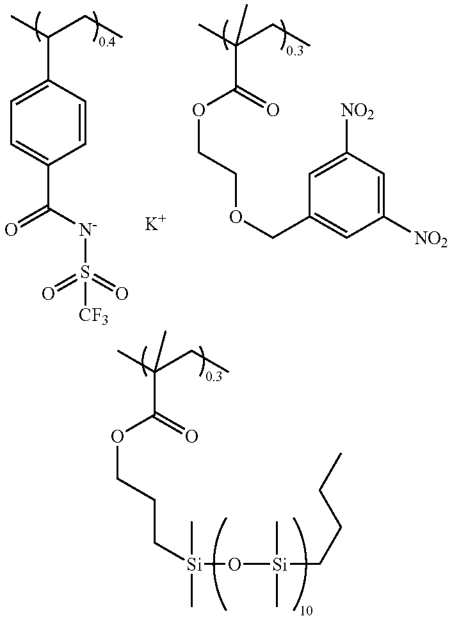

The repeating number in each formula shows the average value.

Ionic Polymer 22

Mw=36,000

Mw/Mn=2.01

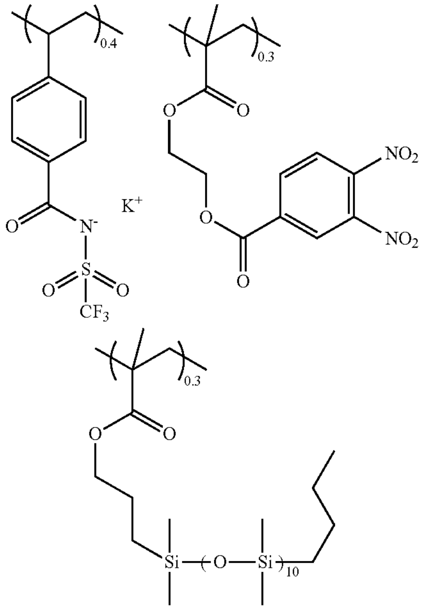

The repeating number in each formula shows the average value.

Blending ionic polymer 1 and Comparative ionic polymers 1 and 2 for the Comparative Examples are shown below.

Blending Ionic Polymer 1

Mw=39, 100

Mw/Mn=1.91

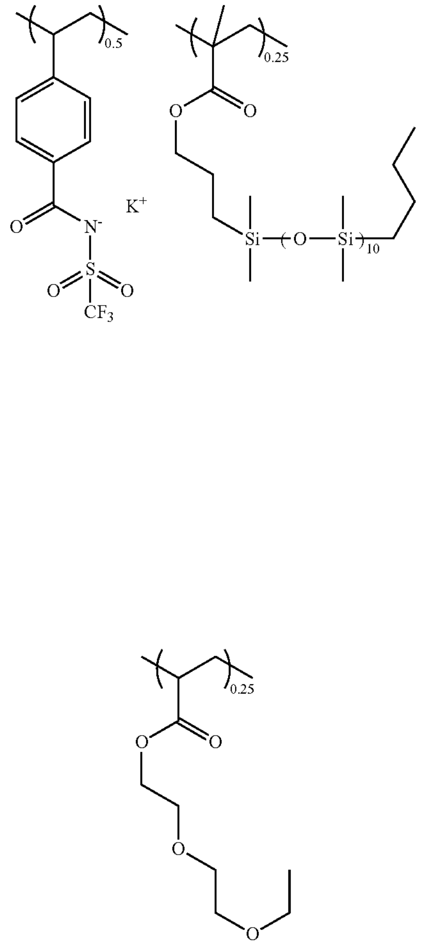

The repeating number in each formula shows the average value.

Comparative Ionic Polymer 1

Mw=26, 900

Mw/Mn=1.99

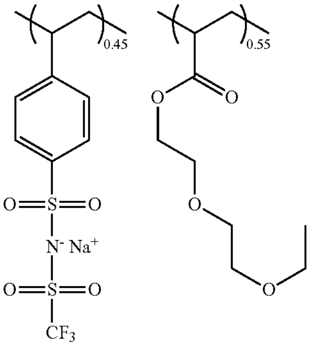

Comparative Ionic Polymer 2

Mw=26, 500

Mw/Mn=1.85

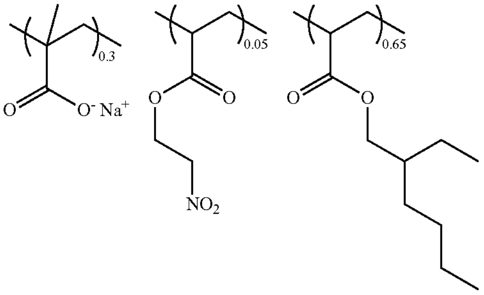

Siloxane compounds 1 to 4, which were blended as silicone-based resins into the bio-electrode solutions, are shown below.

(Siloxane Compound 1)

Siloxane compound 1 was vinyl group-containing polydimethylsiloxane having an alkenyl group-content of 0.007 mol/100 g in which the terminals of molecular chain were capped with $SiMe_2Vi$ groups, the 30% solution of the vinyl group-containing polydimethylsiloxane in toluene having a viscosity of 27,000 mPa-s.

(Siloxane Compound 2)

Siloxane compound 2 was a 60% solution of polysiloxane of MQ resin composed of an $Me_3SiO_{1/2}$ unit and an $SiO_{4/2}$ unit ($Me_3SiO_{1/2}$ unit/$SiO_{4/2}$ unit=0.8) in toluene.

(Siloxane Compound 3)

Siloxane compound 3 was polydimethylsiloxane-bonded MQ resin obtained by heating a solution (composed of 40 parts by mass of vinyl group-containing polydimethylsiloxane having an alkenyl group-content of 0.007 mol/100 g in which the terminals of molecular chain were capped with OH, with the 30% solution in toluene having a viscosity of 42,000 mPa-s; 100 parts by mass of a 60% solution of polysiloxane of MQ resin composed of an $Me_3SiO_1/2$ unit and an $SiO_{4/2}$ unit ($Me_3SiO_{1/2}$ unit/$SiO_4/2$ unit=0.8) in toluene; and 26.7 parts by mass of toluene) with refluxing for 4 hours, followed by cooling.

(Siloxane Compound 4)

As methylhydrogensilicone oil, KF-99 manufactured by Shin-Etsu Chemical Co., Ltd. was used.

Silicone pendant urethane (meth)acrylate 1, which was blended into a bio-electrode solution, is shown below.

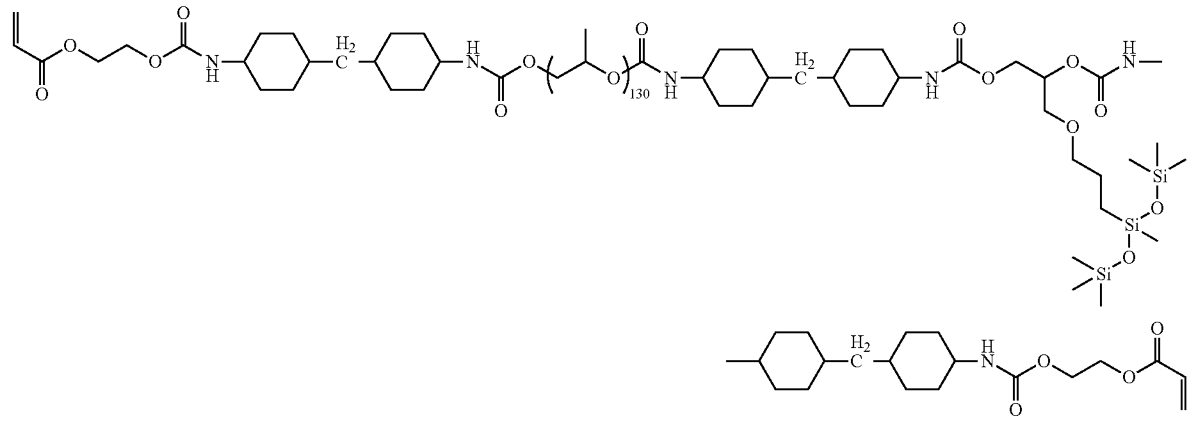
Silicone pendant urethane (meth)acrylate 1
Mw 24800 Mw/Mn 2.65
The repeating number in the formula shows the average value.
Acrylic polymer 1, which was blended into a bio-electrode solution as an acrylic-based resin, is shown below.
Acrylic Polymer 1
Mw=129,000
Mw/Mn=2.45
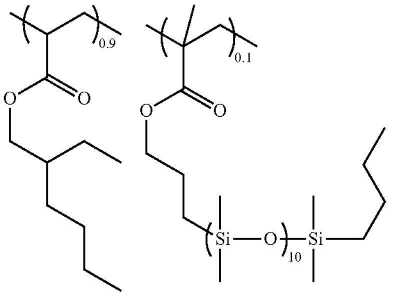
The repeating number in each formula shows the average value.
Polyglycerin-silicone compound 1 is shown below.
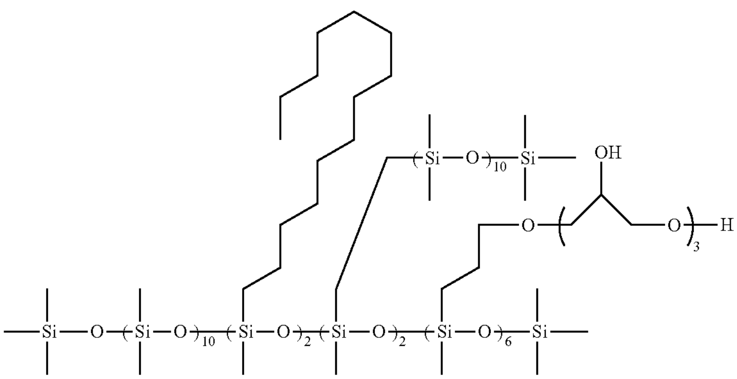

Organic solvents blended into the bio-electrode solutions are shown below.

EDE: diethylene glycol diethyl ether

ISOPAR G: isoparaffin base solvent manufactured by Standard Sekiyu CO., LTD.

ISOPAR M: isoparaffin base solvent manufactured by Standard Sekiyu CO., LTD.

The lithium titanate powder, silver flakes, radical generator, platinum catalyst, and electric conductivity improver (carbon black, multilayer carbon nanotube, and graphite) blended into the bio-electrode solutions as additives are shown below.

Lithium titanate powder, spinel: with the size of 200 nm or less manufactured by Sigma-Aldrich Co., LLC.

Silver flakes: with the average size of 10 μm manufactured by Sigma-Aldrich Co., LLC.

Radical generator: IRGACURE TPO manufactured by BASF SE Platinum catalyst: CAT-PL-50T manufactured by Shin-Etsu Chemical Co., Ltd.

Carbon black: DENKA BLACK Li-400 manufactured by Denka Co., Ltd.

Multilayer carbon nanotube: with the diameter of 110 to 170 nm and length of 5 to 9 μm manufactured by Sigma-Aldrich Co., LLC.

Graphite: with the diameter of 20 μm or less manufactured by Sigma-Aldrich Co., LLC.

Examples 1 to 22, Comparative Examples 1 and 2

According to the compositions shown in Tables 1, 2, and 3, the ionic polymers, resins, organic solvents, and additives (radical generator, platinum catalyst, and electric conductivity improver) were blended to prepare bio-electrode solutions (Bio-electrode solutions 1 to 22 and Comparative bio-electrode solutions 1 and 2).

TABLE 1

| Bio-electrode solution | Ionic polymer (parts by mass) | Resin (parts by mass) | Organic solvent (parts by mass) | Additive (parts by mass) |
|---|---|---|---|---|
| Bio-electrode solution 1 | Ionic polymer 1 (20) | Siloxane compound 1 (40) Siloxane compound 2 (100) Siloxane compound 4 (3) | ISOPAR G (60) cyclopentanone (47) | CAT-PL-50T (0.7) lithium titanate powder (12) silver flakes (8) |
| Bio-electrode solution 2 | Ionic polymer 2 (20) | Siloxane compound 3 (126) Siloxane compound 4 (3) | n-octane (40) n-decane (20) cyclopentanone (47) | CAT-PL-50T (1.5) carbon black (8) |
| Bio-electrode solution 3 | Ionic polymer 3 (20) | Siloxane compound 3 (126) Siloxane compound 4 (3) | n-octane (40) n-dodecane (20) cyclopentanone (47) | CAT-PL-50T (1.5) carbon black (8) |
| Bio-electrode solution 4 | Ionic polymer 4 (20) | Siloxane compound 3 (126) Siloxane compound 4 (3) | n-octane (50) n-tridecane (10) cyclopentanone (47) | CAT-PL-50T (1.5) carbon black (8) |
| Bio-electrode solution 5 | Ionic polymer 5 (4) Blending ionic polymer 1 (4) | Siloxane compound 3 (126) Siloxane compound 4 (3) | n-decane (30) n-octane (30) cyclopentanone (23) | CAT-PL-50T (1.5) carbon black (12) Polyglycerin-silicone compound 1 (8) |

TABLE 1-continued

| Bio-electrode solution | Ionic polymer (parts by mass) | Resin (parts by mass) | Organic solvent (parts by mass) | Additive (parts by mass) |
|---|---|---|---|---|
| Bio-electrode solution 6 | Ionic polymer (10) | Siloxane compound 3 (126) Siloxane compound 4 (3) | ISOPAR G (95) cyclopentanone (23) | CAT-PL-50T (1.5) multilayer carbon nanotube (5) |
| Bio-electrode solution 7 | Ionic polymer 7 (20) | Silicone pendant urethane (meth) acrylate 1 (80) | EDE (60) cyclopentanone (47) | IRGACURE TPO (1) lithium titanate powder (5) |
| Bio-electrode solution 8 | Ionic polymer 8 (10) | Acrylic polymer 1 (80) | EDE (60) cyclopentanone (47) | Polyglycerin-silicone compound 1 (5) |
| Bio-electrode solution 9 | Ionic polymer 9 (20) | Siloxane compound 3 (126) Siloxane compound 4 (3) | ISOPAR M (60) cyclopentanone (47) | CAT-PL-50T (1.5) carbon black (8) |
| Bio-electrode solution 10 | Ionic polymer 10 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |
| Bio-electrode solution 11 | Ionic polymer 11 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |
| Bio-electrode solution 12 | Ionic polymer 12 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |
| Bio-electrode solution 13 | Ionic polymer 13 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |
| Bio-electrode solution 14 | Ionic polymer 14 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |
| Bio-electrode solution 15 | Ionic polymer 15 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |

TABLE 2

| Bio-electrode solution | Ionic polymer (parts by mass) | Resin (parts by mass) | Organic solvent (parts by mass) | Additive (parts by mass) |
|---|---|---|---|---|
| Bio-electrode solution 16 | Ionic polymer 16 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |

TABLE 2-continued

| Bio-electrode solution | Ionic polymer (parts by mass) | Resin (parts by mass) | Organic solvent (parts by mass) | Additive (parts by mass) |
|---|---|---|---|---|
| Bio-electrode solution 17 | Ionic polymer 17 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |
| Bio-electrode solution 18 | Ionic polymer 18 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |
| Bio-electrode solution 19 | Ionic polymer 19 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |
| Bio-electrode solution 20 | Ionic polymer 20 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |
| Bio-electrode solution 21 | Ionic polymer 21 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |
| Bio-electrode solution 22 | Ionic polymer 22 (8) | Siloxane compound 3 (126) Siloxane compound 4 (3) | ISOPAR M (60) cyclopentanone (47) | CAT-PL-50T (1.5) carbon black (12) Polyglycerin-silicone compound 1 (8) |

TABLE 3

| Bio-electrode solution | Ionic polymer (parts by mass) | Resin (parts by mass) | Organic solvent (parts by mass) | Additive (parts by mass) |
|---|---|---|---|---|
| Comparative bio-electrode solution 1 | Comparative ionic polymer 1 (20) | Siloxane compound 1 (40) Siloxane compound 2 (100) Siloxane compound 4 (3) | ISOPAR G (60) cyclopentanone (47) | CAT-PL-50T (1.5) carbon black (8) |
| Comparative bio-electrode solution 2 | Comparative ionic polymer 2 (20) | Siloxane compound 1 (40) Siloxane compound 2 (100) Siloxane compound 4 (3) | ISOPAR G (60) cyclopentanone (47) | CAT-PL-50T (1.5) carbon black (8) |

(Evaluation of Adhesion)

Each of the bio-electrode solutions, except for Bio-electrode solution 7, and Comparative bio-electrode solutions 1 and 2 was respectively applied onto a 100-μm thick polyethylene naphthalate (PEN) substrate by using an applicator. This was air-dried at room temperature for 30 minutes, followed by curing through baking at 120° C. for 10 minutes under a nitrogen atmosphere by using an oven to produce an adhesive film. Bio-electrode solution 7 was applied, air-dried, baked, and then irradiated with 500 mJ/cm$^2$ of light using a 1,000 W xenon lamp under a nitrogen atmosphere to cure a coating film of the composition.

From this adhesive film, a tape having a width of 25 mm was cut out. The tape was pressed to a stainless steel (SUS304) plate and allowed to stand at room temperature for 20 hours. Subsequently, the force (N/25 mm) required for peeling the tape, to which a bio-electrode was attached, from the stainless steel plate was measured at an angle of 180° and a speed of 300 mm/min by using a tensile tester. Table 4 shows the results.

(Measurement of Thickness of Living Body Contact Layer)

On each bio-electrode produced in the evaluation test of adhesion described above, the thickness of the living body contact layer was measured by using a micrometer. Table 4 shows the results.

(Evaluation of Biological Signals)

As shown in FIG. 3, a thermoplastic urethane (TPU) film ST-604 (manufactured by Bemis Associates Inc.) designated by 20 was coated with an electro-conductive paste DOTITE FA-333 (manufactured by Fujikura Kasei Co., Ltd.) by screen printing. The coating film was baked in an oven at 120° C. for 10 minutes to print a keyhole-shaped electro-conductive pattern including a circular portion with a diameter of 2 cm. Then, one of the bio-electrode solutions shown in Tables 1, 2, and 3 was applied onto the circular portion by screen printing. After being air-dried at room temperature for 10 minutes, the coating film was baked using an oven at 125° C. for 10 minutes to evaporate the solvent, and the resultant was cured to prepare bio-electrodes 1. Each bio-electrode 1 included an electro-conductive base material 2 and a living body contact layer 3 formed on the circular portion of the electro-conductive base material 2. The thermoplastic urethane film 20 having the bio-electrodes printed thereon was cut out and pasted on a double-sided tape 21. Thus, three bio-electrode samples 10 were prepared for each of the bio-electrode solutions (FIG. 4).

(Measurement of Biological Signals)

The electro-conductive wiring pattern formed from the electro-conductive paste of each bio-electrode sample was connected to a portable electrocardiograph HCG-901 (manufactured by OMRON HEALTHCARE Co., Ltd.) through an electro-conductive wire. A positive electrode of the electrocardiograph was attached to a location LA in FIG. 5 on a human body, a negative electrode was attached to a location LL, and an earth was attached to a location RA. Immediately after the attachments, the electrocardiogram measurement was started to measure the time until an electrocardiogram waveform including P, Q, R, S, and T waves appeared as shown in FIG. 6. Table 4 shows the results.

TABLE 4

| Example | Bio-electrode solution | Resin thickness (um) | Adhesive strength (N/25 mm) | Time (min.) until ECG signal appeared |
|---|---|---|---|---|
| Example 1 | Bio-electrode solution 1 | 34 | 1.3 | 7 |
| Example 2 | Bio-electrode solution 2 | 40 | 1.4 | 1 |
| Example 3 | Bio-electrode solution 3 | 48 | 1.7 | 1 |
| Example 4 | Bio-electrode solution 4 | 42 | 1.4 | 1 |
| Example 5 | Bio-electrode solution 5 | 41 | 1.2 | 0 |
| Example 6 | Bio-electrode solution 6 | 46 | 1.3 | 0 |
| Example 7 | Bio-electrode solution 7 | 43 | 1.5 | 0 |
| Example 8 | Bio-electrode solution 8 | 49 | 1.6 | 0 |

TABLE 4-continued

| Example | Bio-electrode solution | Resin thick-ness (um) | Adhesive strength (N/25 mm) | Time (min.) until ECG signal appeared |
|---|---|---|---|---|
| Example 9 | Bio-electrode solution 9 | 49 | 2.0 | 1 |
| Example 10 | Bio-electrode solution 10 | 46 | 1.9 | 0 |
| Example 11 | Bio-electrode solution 11 | 52 | 1.8 | 0 |
| Example 12 | Bio-electrode solution 12 | 48 | 1.6 | 0 |
| Example 13 | Bio-electrode solution 13 | 56 | 1.9 | 0 |
| Example 14 | Bio-electrode solution 14 | 58 | 1.8 | 0 |
| Example 15 | Bio-electrode solution 15 | 44 | 1.2 | 0 |
| Example 16 | Bio-electrode solution 16 | 55 | 1.4 | 0 |
| Example 17 | Bio-electrode solution 17 | 48 | 1.6 | 0 |
| Example 18 | Bio-electrode solution 18 | 50 | 1.7 | 0 |
| Example 19 | Bio-electrode solution 19 | 54 | 1.6 | 0 |
| Example 20 | Bio-electrode solution 20 | 59 | 1.7 | 0 |
| Example 21 | Bio-electrode solution 21 | 49 | 1.8 | 0 |
| Example 22 | Bio-electrode solution 22 | 52 | 1.6 | 0 |
| Comparative Example 1 | Comparative bio-electrode solution 1 | 53 | 2.0 | 40 |
| Comparative Example 2 | Comparative bio-electrode solution 2 | 44 | 1.6 | ECG signal did not appear |

As shown in Table 4, adhesion was excellent and biological signals were detected shortly after the attachment to the body in Examples 1 to 22, where the living body contact layer was formed using the inventive bio-electrode composition containing an ionic polymer having nitro group-containing units copolymerized. On the other hand, in Comparative Example 2, where no ionic component having the particular structure was contained, it was not possible to detect biological signals, and in Comparative Example 1, where no nitro groups were contained, it took a long time for the biological signals to appear after the attachment to the skin.

The present description includes the following embodiments.

[1]: A bio-electrode composition comprising an ionic polymer material as a component (A), wherein
the component (A) comprises a polymer having: a repeating unit-a having a structure selected from the group consisting of salts of ammonium, sodium, potassium, and silver formed with any of fluorosulfonic acid, fluorosulfonimide, and N-carbonyl-fluorosulfonamide; and a repeating unit-b having a nitro group.

[2]: The bio-electrode composition of the above [1], wherein the repeating unit-a has a structure shown by any of the following general formulae (1)-1 to (1)-4, (1)-1

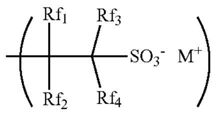

-continued (1)-2

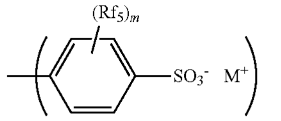

(1)-3

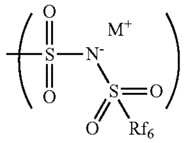

(1)-4

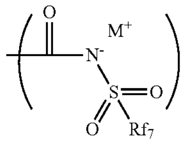

wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom or a linear or branched alkyl group having 1 to 4 carbon atoms, and have at least one fluorine atom; $M^+$ represents an ion selected from the group consisting of an ammonium ion, a sodium ion, a potassium ion, and a silver ion; and "m" represents an integer of 1 to 4.

[3]: The bio-electrode composition of the above [1] or [2], wherein the repeating unit-a comprises at least one repeating unit selected from the group consisting of repeating units-a1 to -a7 shown by the following general formula (2), (2)

a1

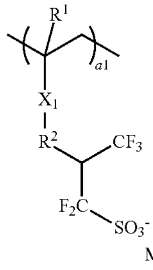

a2

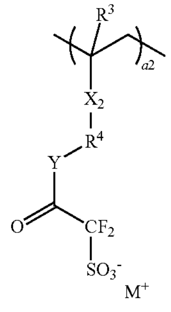

-continued a3

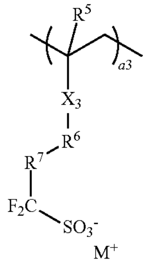

a4

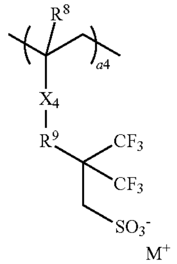

a5

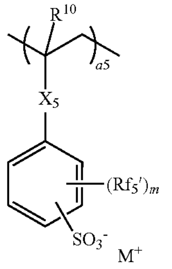

a6

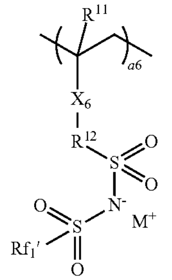

a7

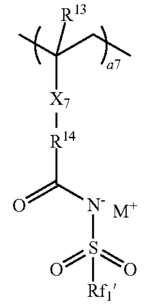

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, $R^{12}$, and $R^{14}$ each independently represent a single bond or a linear, branched, or cyclic hydrocarbon group having 1 to 13 carbon atoms, the hydrocarbon group optionally having either or both of an ester group and an ether group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a —$NR^{19}$— group; $R^{19}$ represents a hydrogen atom or a linear or branched alkyl group having 1 to 4 carbon atoms, and optionally forms a ring together with $R^4$; $Rf_1'$ and $Rf_5'$ each represent a fluorine atom, a trifluoromethyl group, or a linear or branched alkyl group having 1 to 4 carbon atoms, and have at least one fluorine atom; "m" represents an integer of 1 to 4; a1, a2, a3, a4, a5, a6, and a7 satisfy $0 \le a1 < 1.0$, $0 \le a2 < 1.0$, $0 \le a3 < 1.0$, $0 \le a4 < 1.0$, $0 \le a5 < 1.0$, $0 \le a6 < 1.0$, $0 \le a7 < 1.0$, and $0 < a1+a2+a3+a4+a5+a6+a7 < 1.0$; and $M^+$ represents an ion selected from the group consisting of an ammonium ion, a sodium ion, a potassium ion, and a silver ion.

[4]: The bio-electrode composition of the above [3], comprising a polymer having a repeating unit-b1 having a nitro group shown by the following general formula (4) copolymerized in addition to the at least one repeating unit selected from the group consisting of the repeating units-a1 to -a7 shown by the general formula (2), (4)

b1

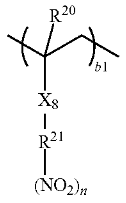

wherein $R^{20}$ represents a hydrogen atom or a methyl group; $X_8$ represents any of a single bond, a phenylene group, a naphthylene group, an ether group, an ester group, and an amide group; $R^{21}$ represents a single bond, a linear, branched, or cyclic alkylene group having 1 to 20 carbon atoms, or a phenylene group, the alkylene group optionally having a hydroxy group, a carboxy group, an ether group, an ester group, a urethane group, a thiourethane group, a carbonate group, an amide group, or a urea bond, and the phenylene group is optionally substituted with a linear or branched alkyl group having 1 to 4 carbon atoms, an alkoxy group, a halogen atom, or a cyano group; and "n" represents 1 or 2 and b1 satisfies $0 < b1 < 1.0$.

[5]: The bio-electrode composition of any one of the above [1] to [4], wherein the component (A) comprises an ammonium ion shown by the following general formula (3) as an ammonium ion for forming the ammonium salts, (3)

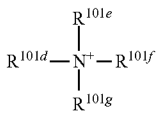

wherein $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the general formula (3) within the ring.

[6]: The bio-electrode composition of any one of the above [1] to [5], further comprising a resin as a component (B).

[7]: The bio-electrode composition of the above [6], wherein the component (B) is at least one resin selected from the group consisting of a silicone resin, a (meth) acrylate resin, and a urethane resin.

[8]: The bio-electrode composition of the above [6] or [7], wherein the component (B) is adhesive.

[9]: The bio-electrode composition of any one of the above [6] to [8], wherein the component (B) comprises a silicone resin having an $SiO_{4/2}$ unit and an $R_xSiO_{(4-x)/2}$ unit, wherein R represents a substituted or unsubstituted monovalent hydrocarbon group having 1 to 10 carbon atoms, and "x" represents a number in a range of 2.5 to 3.5.

[10]: The bio-electrode composition of any one of the above [1] to [9], further comprising a carbon material and/or a metal powder as a component (C).

[11]: The bio-electrode composition of the above [10], wherein the carbon material is one or both of carbon black and carbon nanotube.

[12]: The bio-electrode composition of the above [10] or [11], wherein the metal powder is one or more metal powders selected from the group consisting of gold, silver, platinum, copper, tin, titanium, nickel, aluminum, tungsten, molybdenum, ruthenium, chromium, and indium.

[13]: The bio-electrode composition of the above [12], wherein the metal powder is a silver powder.

[14]: The bio-electrode composition of any one of the above [1] to [13], further comprising an organic solvent as a component (D).

[15]: A bio-electrode comprising an electro-conductive base material and a living body contact layer formed on the electro-conductive base material, wherein the living body contact layer is a cured product of the bio-electrode composition of any one of the above [1] to [14].

[16]: The bio-electrode of the above [15], wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and an electro-conductive polymer.

[17]: A method for manufacturing a bio-electrode having an electro-conductive base material and a living body contact layer formed on the electro-conductive base material, the method comprising:

applying the bio-electrode composition of any one of the above [1] to [14] onto the electro-conductive base material; and curing the bio-electrode composition to form the living body contact layer.

[18]: The method for manufacturing a bio-electrode of the above [17], wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and an electro-conductive polymer.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A bio-electrode composition comprising an ionic polymer material as a component (A), wherein the component (A) comprises a polymer having: a repeating unit-a having a structure selected from the group consisting of salts of ammonium, sodium, potassium, and silver formed with any of fluorosulfonic acid, fluorosulfonimide, and N-carbonyl-fluorosulfonamide; and a repeating unit-b having a nitro group, wherein the repeating unit-a comprises at least one repeating unit selected from the group consisting of repeating units-a1 to -a7 shown by the following general formula (2), wherein the bio-electrode composition comprising a polymer having a repeating unit-b1 having a nitro group shown by the following general formula (4) copolymerized in addition to the at least one repeating unit selected from the group consisting of the repeating units-a1 to -a7 shown by the general formula (2), (2)

a1

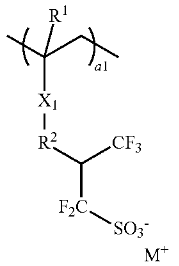

a2

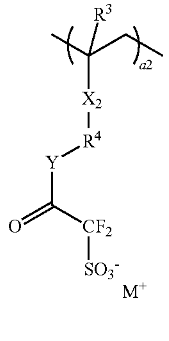

-continued a3

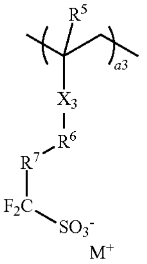

a4

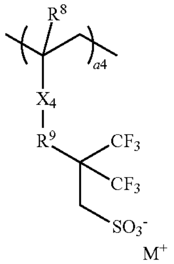

a5

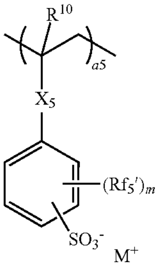

a6

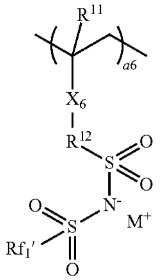

a7

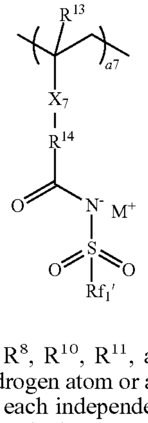

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, $R^{12}$, and $R^{14}$ each independently represent a single bond or a linear, branched, or cyclic hydrocarbon group having 1 to 13 carbon atoms, the hydrocarbon group optionally having either or both of an ester group and an ether group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a —$NR^{19}$— group; $R^{19}$ represents a hydrogen atom or a linear or branched alkyl group having 1 to 4 carbon atoms, and optionally forms a ring together with $R^4$; $Rf_1'$ and $Rf_5'$ each represent a fluorine atom, a trifluoromethyl group, or a linear or branched alkyl group having 1 to 4 carbon atoms, and have at least one fluorine atom; "m" represents an integer of 1 to 4; a1, a2, a3, a4, a5, a6, and a7 satisfy $0 \leq a1 < 1.0$, $0 \leq a2 < 1.0$, $0 \leq a3 < 1.0$, $0 \leq a4 < 1.0$, $0 \leq a5 < 1.0$, $0 \leq a6 < 1.0$, $0 \leq a7 < 1.0$, and $0 \leq a1+a2+a3+a4+a5+a6+a7 < 1.0$; and $M^+$ represents an ion selected from the group consisting of an ammonium ion, a sodium ion, a potassium ion, and a silver ion, (4)

b1

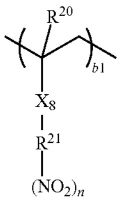

wherein $R^{20}$ represents a hydrogen atom or a methyl group; $X_8$ represents any of a single bond, a phenylene group, a naphthylene group, an ether group, an ester group, and an amide group; $R^{21}$ represents a single bond, a linear, branched, or cyclic alkylene group having 1 to 20 carbon atoms, or a phenylene group, the alkylene group optionally having a hydroxy group, a carboxy group, an ether group, an ester group, a urethane group, a thiourethane group, a carbonate group, an amide group, or a urea bond, and the phenylene group is optionally substituted with a linear or branched alkyl group having 1 to 4 carbon atoms, an alkoxy group, a halogen atom, or a cyano group; and "n" represents 1 or 2 and b1 satisfies $0 < b1 < 1.0$.

2. The bio-electrode composition according to claim 1, wherein the repeating unit-a has a structure shown by any of the following general formulae (1)-1 to (1)-4, (1)-1

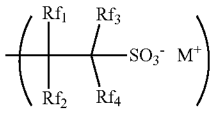

(1)-2

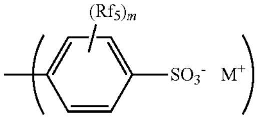

(1)-3

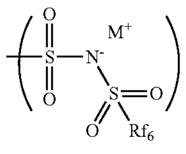

-continued (1)-4

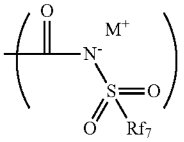

wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom or a linear or branched alkyl group having 1 to 4 carbon atoms, and have at least one fluorine atom; $M^+$ represents an ion selected from the group consisting of an ammonium ion, a sodium ion, a potassium ion, and a silver ion; and "m" represents an integer of 1 to 4.

3. The bio-electrode composition according to claim 1, wherein the component (A) comprises an ammonium ion shown by the following general formula (3) as an ammonium ion for forming the ammonium salts, (3)

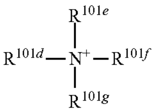

wherein $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the general formula (3) within the ring.

4. The bio-electrode composition according to claim 1, further comprising a resin as a component (B).

5. The bio-electrode composition according to claim 4, wherein the component (B) is at least one resin selected from the group consisting of a silicone resin, a (meth)acrylate resin, and a urethane resin.

6. The bio-electrode composition according to claim 4, wherein the component (B) is adhesive.

7. The bio-electrode composition according to claim 4, wherein the component (B) comprises a silicone resin having an $SiO_{4/2}$ unit and an $R_xSiO_{(4-x)/2}$ unit, wherein R represents a substituted or unsubstituted monovalent hydrocarbon group having 1 to 10 carbon atoms, and "x" represents a number in a range of 2.5 to 3.5.

8. The bio-electrode composition according to claim 1, further comprising at least one of a carbon material and a metal powder as a component (C).

9. The bio-electrode composition according to claim 8, wherein the carbon material (C) is one or both of carbon black and carbon nanotube.

10. The bio-electrode composition according to claim 8, wherein the metal powder (C) is one or more metal powders selected from the group consisting of gold, silver, platinum, copper, tin, titanium, nickel, aluminum, tungsten, molybdenum, ruthenium, chromium, and indium.

11. The bio-electrode composition according to claim 10, wherein the metal powder is a silver powder.

12. The bio-electrode composition according to claim 1, further comprising an organic solvent as a component (D).

13. A bio-electrode comprising an electro-conductive base material and a living body contact layer formed on the electro-conductive base material, wherein the living body contact layer is a cured product of the bio-electrode composition according to claim 1.

14. The bio-electrode according to claim 13, wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and an electro-conductive polymer.

15. A method for manufacturing a bio-electrode having an electro-conductive base material and a living body contact layer formed on the electro-conductive base material, the method comprising:

applying the bio-electrode composition according to claim 1 onto the electro-conductive base material; and curing the bio-electrode composition to form the living body contact layer.

16. The method for manufacturing a bio-electrode according to claim 15, wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and an electro-conductive polymer.

* * * * *